(12) United States Patent
Ghosh et al.

(10) Patent No.: US 8,299,267 B2
(45) Date of Patent: Oct. 30, 2012

(54) (3-HYDROXY-4-AMINO-BUTAN-2-YL) -3-(2-THIAZOL-2-YL-PYRROLIDINE-1-CARBONYL) BENZAMIDE DERIVATIVES AND RELATED COMPOUNDS AS BETA-SECRETASE INHIBITORS FOR TREATING

(75) Inventors: Arun K. Ghosh, West Lafayette, IN (US); Chunfeng Liu, Norman, OK (US); Thippeswamy Devasamudram, Edmond, OK (US); Hui Lei, Edmond, OK (US); Lisa M. Swanson, Oklahoma City, OK (US); Sudha V. Ankala, Edmond, OK (US); John C. Lilly, Norman, OK (US); Geoffrey M. Bilcer, Edmond, OK (US)

(73) Assignees: CoMentis, Inc., South San Francisco, CA (US); Purdue Research Foundation, West Lafayette, IN (US)

( * ) Notice: Subject to any disclaimer, the term of this patent is extended or adjusted under 35 U.S.C. 154(b) by 46 days.

(21) Appl. No.: 12/677,748

(22) PCT Filed: Sep. 24, 2008

(86) PCT No.: PCT/US2008/077537

§ 371 (c)(1),
(2), (4) Date: Apr. 23, 2010

(87) PCT Pub. No.: WO2009/042694

PCT Pub. Date: Apr. 2, 2009

(65) Prior Publication Data

US 2010/0286170 A1    Nov. 11, 2010

Related U.S. Application Data

(60) Provisional application No. 60/974,793, filed on Sep. 24, 2007.

(51) Int. Cl.
| C07D 417/14 | (2006.01) |
| C07D 211/68 | (2006.01) |
| C07D 417/00 | (2006.01) |
| C07D 413/00 | (2006.01) |
| C07D 277/30 | (2006.01) |
| C07D 277/28 | (2006.01) |
| C07D 263/30 | (2006.01) |
| A61K 31/44  | (2006.01) |
| A61K 31/445 | (2006.01) |
| A61K 31/42  | (2006.01) |
| A61K 31/425 | (2006.01) |

(52) U.S. Cl. ........ 548/204; 548/205; 548/235; 546/193; 546/269.7; 546/271.4; 544/405; 514/340; 514/326; 514/255.05; 514/374.2; 514/365

(58) Field of Classification Search ........................ None
See application file for complete search history.

(56) References Cited

U.S. PATENT DOCUMENTS

| 4,801,575 A | 1/1989 | Pardridge |
| 4,861,760 A | 8/1989 | Mazuel et al. |
| 4,911,920 A | 3/1990 | Jani et al. |
| 5,212,162 A | 5/1993 | Missel et al. |
| 5,403,841 A | 4/1995 | Lang et al. |
| 5,728,718 A | 3/1998 | Randad et al. |
| 6,180,603 B1 | 1/2001 | Frey, II |
| 6,287,792 B1 | 9/2001 | Pardridge et al. |
| 6,313,093 B1 | 11/2001 | Frey, II |
| 6,372,250 B1 | 4/2002 | Pardridge |
| 6,545,127 B1 | 4/2003 | Tang et al. |
| 7,214,715 B2 | 5/2007 | Beck et al. |
| 7,244,708 B2 | 7/2007 | Tang et al. |
| 7,335,632 B2 | 2/2008 | Ghosh et al. |
| 7,348,356 B2 | 3/2008 | Coburn et al. |
| 7,504,420 B2 | 3/2009 | Ghosh et al. |
| 7,659,289 B2 | 2/2010 | Ghosh et al. |
| 7,662,816 B2 | 2/2010 | Cumming et al. |
| 7,678,760 B2 | 3/2010 | Tang et al. |
| 2003/0215398 A1 | 11/2003 | Frey, II |
| 2003/0215432 A1 | 11/2003 | Matalon |
| 2003/0216589 A1 | 11/2003 | Gschneidner et al. |
| 2004/0101904 A1 | 5/2004 | Pardridge et al. |
| 2004/0102369 A1 | 5/2004 | Wu et al. |
| 2004/0110928 A1 | 6/2004 | Crisanti et al. |
| 2004/0121947 A1 | 6/2004 | Ghosh et al. |
| 2005/0119227 A1 | 6/2005 | Cumming et al. |

(Continued)

FOREIGN PATENT DOCUMENTS

| WO | WO-89/10134 A1 | 11/1989 |
| WO | WO-95/18104 A1 | 7/1995 |
| WO | WO-96/05309 A2 | 2/1996 |
| WO | WO-96/05309 A3 | 2/1996 |
| WO | WO-02/02505 A2 | 1/2002 |
| WO | WO-02/02505 A3 | 1/2002 |
| WO | WO-02/02505 C1 | 1/2002 |
| WO | WO-02/02512 A2 | 1/2002 |
| WO | WO-02/02512 A3 | 1/2002 |
| WO | WO-02/02518 A2 | 1/2002 |

(Continued)

OTHER PUBLICATIONS

Abbott, N.J. et al. (Mar. 1996). "Transporting Therapeutics Across the Blood-Brain Barrier," *Mol. Med. Today* 2(3):106-113.

(Continued)

*Primary Examiner* — Kamal Saeed
*Assistant Examiner* — Nyeemah A Grazier
(74) *Attorney, Agent, or Firm* — Morrison & Foerster LLP

(57) ABSTRACT

The present invention provides novel beta-secretase inhibitors and methods for their use, including methods of treating of Alzheimer's disease.

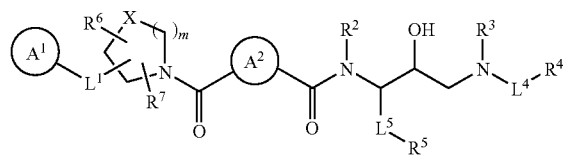

52 Claims, No Drawings

U.S. PATENT DOCUMENTS

| | | |
|---|---|---|
| 2005/0239684 A1 | 10/2005 | Ghosh et al. |
| 2006/0025459 A1 | 2/2006 | Demont et al. |
| 2006/0178383 A1 | 8/2006 | Bischoff et al. |
| 2006/0229309 A1 | 10/2006 | Thompson et al. |
| 2006/0234944 A1 | 10/2006 | Ghosh et al. |
| 2007/0032470 A1 | 2/2007 | Wu et al. |
| 2007/0093523 A1 | 4/2007 | Yang et al. |
| 2007/0117793 A1 | 5/2007 | Ghosh et al. |
| 2007/0213331 A1 | 9/2007 | Dally et al. |
| 2008/0096942 A1 | 4/2008 | Tenbrink et al. |
| 2008/0112946 A1 | 5/2008 | Koelsch et al. |
| 2008/0176939 A1 | 7/2008 | Ghosh et al. |
| 2008/0207527 A1 | 8/2008 | Ghosh et al. |
| 2010/0152138 A1 | 6/2010 | Cumming et al. |

FOREIGN PATENT DOCUMENTS

| | | |
|---|---|---|
| WO | WO-02/02518 A3 | 1/2002 |
| WO | WO-02/02520 A2 | 1/2002 |
| WO | WO-02/02520 A3 | 1/2002 |
| WO | WO-02/053594 A2 | 7/2002 |
| WO | WO-02/064558 A2 | 8/2002 |
| WO | WO-02/064558 A3 | 8/2002 |
| WO | WO-02/053594 A3 | 5/2003 |
| WO | WO-03/039454 A2 | 5/2003 |
| WO | WO-03/039454 A3 | 5/2003 |
| WO | WO-03/040096 A2 | 5/2003 |
| WO | WO-03/040096 A3 | 5/2003 |
| WO | WO-03/050073 A1 | 6/2003 |
| WO | WO-03/072535 A2 | 9/2003 |
| WO | WO-03/072535 C1 | 9/2003 |
| WO | WO-2004/022523 A2 | 3/2004 |
| WO | WO-2004/022523 A3 | 3/2004 |
| WO | WO-2004/043916 A1 | 5/2004 |
| WO | WO-2004/050619 A1 | 6/2004 |
| WO | WO-2004/080376 A2 | 9/2004 |
| WO | WO-2004/080376 A3 | 9/2004 |
| WO | WO-2005/016876 A2 | 2/2005 |
| WO | WO-2005/016876 A3 | 2/2005 |
| WO | WO-2005/030709 A1 | 4/2005 |
| WO | WO-2005/065195 A2 | 7/2005 |
| WO | WO-2005/065195 A3 | 7/2005 |
| WO | WO-2005/108358 A2 | 11/2005 |
| WO | WO-2005/108358 A3 | 11/2005 |
| WO | WO-2005/108391 A1 | 11/2005 |
| WO | WO-2006/002004 A1 | 1/2006 |
| WO | WO-2006/034277 A1 | 3/2006 |
| WO | WO-2006/099352 A1 | 9/2006 |
| WO | WO-2006/110668 A1 | 10/2006 |
| WO | WO-2006/110917 A2 | 10/2006 |
| WO | WO-2006/110917 A3 | 10/2006 |
| WO | WO-2006/126938 A1 | 11/2006 |
| WO | WO-2006/126939 A1 | 11/2006 |
| WO | WO-2007/025596 A1 | 3/2007 |
| WO | WO-2007/047991 A1 | 4/2007 |
| WO | WO-2007/058583 A2 | 5/2007 |
| WO | WO-2007/058583 A3 | 5/2007 |
| WO | WO-2008/036316 A2 | 3/2008 |
| WO | WO-2008/036316 A3 | 3/2008 |
| WO | WO-2009/015369 A2 | 1/2009 |
| WO | WO-2009/015369 A3 | 1/2009 |
| WO | WO-2009/042694 A1 | 4/2009 |
| WO | WO-2010/002994 A1 | 1/2010 |
| WO | WO-2010/042796 A1 | 4/2010 |
| WO | WO-2010/042892 A1 | 4/2010 |
| WO | WO-2010/059953 A1 | 5/2010 |
| WO | WO-2010/065861 A2 | 6/2010 |
| WO | WO-2010/110817 A1 | 9/2010 |
| WO | WO-2011/044057 A1 | 4/2011 |

OTHER PUBLICATIONS

Anderson, R.N. (Oct. 12, 2001). "Deaths: Leading Causes for 1999," *Natl. Vital Stat. Rep.* 49(11):1-87.

Banks, W.A. et al. (Nov./Dec. 1992). "Permeability of the Blood-Brain Barrier to Peptides: An Approach to the Development of Therapeutically Useful Analogs," *Peptides* 13(6):1289-1294.

Begley, D.J. (Feb. 1996). "The Blood-Brain Barrier: Principles for Targeting Peptides and Drugs to the Central Nervous System," *J. Pharm. Pharmacol.* 48(2):136-146.

Berge, S.M. et al. (Jan. 1977). "Pharmaceutical Salts," *J. Pharm. Sci.* 66(1):1-19.

Bertling, W.M. et al. (Jun. 1991). "Use of Liposomes, Viral Capsids, and Nanoparticles as DNA Carriers," *Biotechnol. Appl. Biochem.* 13(3):390-405.

Bickel, U. et al. (Mar. 1, 2001). "Delivery of Peptides and Proteins Through the Blood-Brain Barrier," *Adv. Drug Deliv. Rev.* 46(1-3):247-279.

Bieth, J. (1974). "Some Kinetic Consequences of the Tight Binding of Protein-Proteinase-Inhibitors to Proteolytic Enzymes and Their Application to the Determination of Dissociation Constants," *Bayer-Symposium V "Proteinase Inhibitors", Proceedings of the 2$^{nd}$ International Research Conference on Proteinase Inhibitors*, Grosse Ledder, Fed. Rep. Germany, Oct. 16-20, 1973, pp. 463-469.

Black, K.L. et al. (Nov. 1994). "Enzymatic Barrier Protects Brain Capillaries From Leukotriene $C_4$," *J. Neurosurg.* 81(5):745-751.

Bobo, R.H. et al. (Mar. 15, 1994). "Convection-Enhanced Delivery of Macromolecules in the Brain," *Proc. Natl. Acad. Sci. USA* 91(6):2076-2080.

Bodor, N. et al. (Dec. 18, 1981). "Site-Specific, Sustained Release of Drugs to the Brain," *Science* 214(4527):1370-1372.

Bodor, N. et al. (1995). "Molecular Packaging," Chapter 14 in *Peptide-Based Drug Design: Controlling Transport and Metabolism*, Taylor, M.D. et al. eds., American Chemical Society: Washington, DC, pp. 317-337.

Bodor, N. et al. (Oct.-Dec. 1997). "Drug Targeting via Retrometabolic Approaches," *Pharmacol. Ther.* 76(1-3):1-27.

Brem, H. et al. (Jul./Aug. 1996). "Polymer-Based Drug Delivery to the Brain," *Sci. Med.* 3(4):52-61.

Brem, H. et al. (Jul. 2001). "Biodegradable Polymer Implants to Treat Brain Tumors," *J. Control. Release* 74(1-3):63-67.

Brightman, M. (1992). "Ultrastructure of the Brain Endothelium," Chapter 1 in *Physiology and Pharmacology of the Blood-Brain Barrier. Handbook of Experimental Pharmacology*, Bradbury, M.W.B. ed., Springer-Verlag: Berlin, Germany, pp. 1-22.

Calvo, P. et al. (Aug. 2001). "Long-Circulating PEGylated Polycyanoacrylate Nanoparticles as New Drug Carrier for Brain Delivery," *Pharm. Res.* 18(8):1157-1166.

Chavany, C. et al. (Apr. 1992). "Polyalkylcyanoacrylate Nanoparticles as Polymeric Carriers for Antisense Oligonucleotides," *Pharm. Res.* 9(4):441-449.

Chavany, C. et al. (Sep. 1994). "Adsorption of Oligonucleotides Onto Polyisohexylcyanoacrylate Nanoparticles Protects Them Against Nucleases and Increases Their Cellular Uptake," *Pharm. Res.* 11(9):1370-1378.

Chen, P. et al. (Sep. 24, 1998, e-pub. Sep. 5, 1998). "Strategies to Target Kyotorphin Analogues to the Brain," *J. Med. Chem.* 41(20):3773-3781.

Coloma, M.J. et al. (Mar. 2000). "Transport Across the Primate Blood-Brain Barrier of a Genetically Engineered Chimeric Monoclonal Antibody to the Human Insulin Receptor," *Pharm. Res.* 17(3):266-274.

Cumming, J.N. et al. (Jun. 2007, e-pub. Apr. 25, 2008). "Rational Design of Novel, Potent Piperazinone and Imidazolidinone BACE1 Inhibitors," *Bioorg Med. Chem. Lett.* 18(11):3236-3241.

De Strooper, B. et al. (Jan. 22, 1998). "Deficiency of Presenilin-1 Inhibits the Normal Cleavage of Amyloid Precursor Protein," *Nature* 391:387-390.

Doran, S.E. et al. (May 1995). "Gene Expression From Recombinant Viral Vectors in the Central Nervous System After Blood-Brain Barrier Disruption," *Neurosurg.* 36(5):965-970.

Emerich, D.F. et al. (2001). "The Development of the Bradykinin Agonist Labradimil as a Means to Increase the Permeability of the Blood-Brain Barrier: From Concept to Clinical Evaluation," *Clin. Pharmacokinet.* 40(2):105-123.

Ermolieff, J. et al. (Oct. 10, 2000, e-pub. Sep. 13, 2000). "Proteolytic Activation of Recombinant Pro-memapsin 2 (Pro-β-secretase) Studied With New Fluorogenic Substrates," *Biochemistry* 39(40):1 2450-12456; correction 2000, e-pub. Nov. 23, 2000, *Biochemistry* 39:16263.

Fecik, R.A. et al. (Feb. 24, 2005, e-pub. Jan. 26, 2005). "Chiral DNA Gyrase Inhibitors. 3. Probing the Chiral Preference of the Active Site of DNA Gyrase. Synthesis of 10-Fluoro-6-methyl-6,7-dihyrdo-9-piperazinyl-2H-bezo[α]guinolizin-20-one-3-carboxylic Acid Analogues," *J. Med. Chem.* 48(4):1229-1236.

Fingl, E. et al. (1975). "General Principles," Chapter 1 in *The Pharmacological Basis of Therapeutics*, 5th Edition, Goodman, L.S. et al. eds., Macmillan Publishing Co., Inc: New York, NY, pp. 1-46.

Gennaro, A.R. ed. (1985). *Remington's Pharmaceutical Sciences*, 17th Edition, Mack.Publishing Company: Easton, PA, five pages. (Table of Contents Only.).

Golden, P.L. et al. (Jan. 1997). "Human Blood-Brain Barrier Leptin Receptor. Binding and Endocytosis in Isolated Human Brain Microvessels," *J. Clin. Invest.* 99(1):14-18.

Guo, L. et al. (Aug. 14, 2007). "Targeting Amyloid-β in Glaucoma Treatment," *Proc. Natl. Acad. Sci.* 104(33):13444-13449.

Hah, J.-M. et al. (Apr. 24, 2003, e-pub. Mar. 29, 2003). "Aromatic Reduced Amide Bond Peptidomimetics as Selective Inhibitors of Neuronal Nitric Oxide Synthase," *J. Med. Chem.* 46(9):1661-1669.

Harbaugh, R.E. et al. (Dec. 1988). "Use of Implantable Pumps for Central Nervous System Drug Infusions to Treat Neurological Disease," *Neurosurg.* 23(6):693-698.

Hong, L. et al. (2002, e-pub. Aug. 15, 2002). "Crystal Structure of Mempasin 2 (β-Secretase) in Complex with an Inhibitor OM00-3," *Biochemistry* 41(36):10963-10967.

Hsiao, K. et al. (Oct. 4, 1996). "Correlative Memory Deficits, Aβ Elevation, and Amyloid Plaques in Transgenic Mice," *Science* 274:99-102.

Huang, T.-Y. et al. (1999). "ACNU, MTX and 5-FU Penetration of Rat Brain Tissue and Tumors," *J. Neurooncol.* 45(1):9-17.

Hussain, I. et al. (Jun. 29, 2001). "Prodomain Processing of Asp1 (BACE2) Is Autocatalytic," *J. Biol. Chem.* 276(26):23322-23328.

Huwyler, J. et al. (Nov. 26, 1996). "Brain Drug Delivery of Small Molecules Using Immunoliposomes," *Proc. Natl. Acad. Sci. USA* 93(24):14164-14169.

Huwyler, J. et al. (Sep. 1997). "Receptor Mediated Delivery of Daunomycin Using Immunoliposomes: Pharmacokinetics and Tissue Distribution in the Rat," *J. Pharmcol. Exp. Ther.* 282(3):1541-1546.

Illum, L. (Dec. 2002). "Nasal Drug Delivery: New Developments and Strategies," *Drug Discov. Today* 7(23):1184-1189.

International Search Report mailed on Mar. 2, 2009, for PCT Patent Application PCT/US2008/077537, filed on Sep. 24, 2008, 3 pages.

International Search Report mailed on Dec. 31, 2009, for PCT Patent Application No. PCT/US09/60273, filed on Oct. 10, 2009, 3 pages.

Iserloh, U. et al. (2008, e-pub. Nov. 6, 2007). "Potent Pyrrolidine- and Piperidine-based BACE-1 Inhibitors," *Bioorganic & Medicinal Chemistry Letters* 18:414-417.

Iserloh, U. et al. (2008, e-pub. Oct. 18, 2007). "Discovery of an Orally Efficaceous 4-Phenoxypyrrolidine-based BACE-1 Inhibitor," *Bioorganic & Medicinal Chemistry Letters* 18:418-422.

Kreil, G. et al. (Sep. 1995). "Hyaluronidases—a Group of Neglected Enzymes," *Protein Sci.* 4(9):1666-1669.

Kreuter, J. et al. (Mar. 13, 1995). "Passage of Peptides Through the Blood-Brain Barrier With Colloidal Polymer Particles (Nanoparticles)," *Brain Res.* 674(1):171-174.

Kreuter, J. (Mar. 23, 2001). "Nanoparticulate Systems for Brain Delivery of Drugs," *Adv. Drug Deliv. Rev.* 47(1):65-81.

Kreuter, J. (2002). "Transport of Drugs Across the Blood-Brain Barrier by Nanoparticles," *Curr. Med. Chem.* 2(3):241-249.

Krewson, C.E. et al. (May 22, 1995). "Distribution of Nerve Growth Factor Following Direct Delivery to Brain Interstitium," *Brain Res.* 680(1-2):196-206.

Kroll, R.A. et al. (Apr. 1996). "Increasing Volume of Distribution to the Brain with Intersitial Infusion: Dose, Rather Than Convection, Might Be the Most Important Factor," *Neurosurgery* 38(4):746-754.

Kroll, R.A. et al. (May 1998). "Outwitting the Blood-Brain Barrier for Therapeutic Purposes: Osmotic Opening and Other Means," *Neurosurg.* 42(5):1083-1099.

Kumagai, A.K. et al. (Nov. 5, 1987). "Absorptive-mediated Endocytosis of Cationized Albumin and a β-Endorphin-Cationized Albumin Chimeric Peptide by Isolated Brain Capillaries. Model System of Blood-Brain Barrier Transport," *J. Biol Chem.* 262(31):15214-15219.

Lambert, D.M. (Oct. 2000). "Rationale and Applications of Lipids as Prodrug Carriers," *Eur. J. Pharm. Sci.* 11(Suppl. 2):S15-S27.

Li, J.Y. et al. (Sep. 1999). "Genetically Engineered Brain Drug Delivery Vectors: Cloning, Expression and in Vivo Application of an Anti-Transferrin Receptor Single Chain Antibody-Streptavidin Fusion Gene and Protein," *Protein Engineering* 12(9):787-796.

Lin, X. et al. (Feb. 15, 2000). "Human Aspartic Protease Memapsin 2 Cleaves the β-Secretase Site of 13 -Amyloid Precursor Protein," *Proc. Natl. Acad. Sci. USA* 97(4):1456-1460.

Liu, X. et al. (Feb. 24, 2003). "Synthesis and Preliminary Biological Evaluation of 6-O-[$^{11}$C]-[(methoxymethyl)benzyl]guanines, New Potential PET Breast Cancer Imaging Agents for the DNA Repair Protein AGT," *Bioorg. Med. Chem. Lett.* 13(4):641-644.

Lo, E.H. et al. (Dec. 2001). "Drug Delivery to Damaged Brain," *Brain Res. Rev.* 38(1-2):140-148.

Matsukado, K. et al. (Jul. 1996). "Enhanced Tumor Uptake of Carboplatin and Survival in Glioma-Bearing Rats by Intracarotid Infusion of Bradykinin Analog, RMP-7," *Neurosurgery* 39(1):125-134.

Meyer Zu Reckendorf, W. et al. (1974). "Synthesis of 2,3,4,6-Tetraamino-2,3,4,6-tetradeoxy-D-glucose," *Chem. Ber.* 107:1188-1194, with Certified English Translation, 17 pages.

Miller, G. (Aug. 16, 2002). "Drug Targeting. Breaking Down Barriers," *Science* 297(5584):1116-1118.

Misra, A. et al. (May-Aug. 2003). "Drug Delivery to the Central Nervous System: A Review," *J. Pharm. Pharmaceut. Sci.* 6(2):252-273.

Neuwelt, E.A. ed. (1989). *Implications of the Blood-Brain Barrier and Its Manipulation: Volume 2 Clinical Aspects*, Plenum Press: New York, NY, pp. xvii-xxvi. (Table of Contents Only).

Neuwelt, E.A. et al. (1994). "Therapeutic Dilemma of Disseminated CNS Germinoma and the Potential of Increased Platinum-Based Chemotherapy Delivery With Osmotic Blood-Brain Barrier Disruption," *Pediatr. Neurosurg.* 21(1):16-22.

Neuwelt, E.A. et al. (Nov. 1994). "Effect of Blood-Brain Barrier Disruption on Intact and Fragmented Monoclonal Antibody Localization in Intracerebral Lung Carcinoma Xenografts," *J. Nucl. Med.* 35(11):1831-1841.

Palomino, E. et al. (Mar. 1989). "A Dihydropyridine Carrier System for Sustained Delivery of 2',3'-dideoxynucleosides to the Brain," *J. Med. Chem.* 32(3):622-625.

Pardridge, W.M. (Aug. 1986). "Receptor-Mediated Peptide Transport Through the Blood-Brain Barrier," *Endocrine Rev.* 7(3):314-330.

Pardridge, W.M. et al. (Jun. 1995). "Human Insulin Receptor Monoclonal Antibody Undergoes High Affinity Binding to Human Brain Capillaries in Vitro and Rapid Transcytosis Through the Blood-Brain Barrier in Vivo in the Primate," *Pharm. Res.* 12(6):807-816.

Pardridge, W.M. (Apr. 5,1999). "Vector-Mediated Drug Delivery to the Brain," *Adv. Drug Deliv. Rev.* 36(2,3):299-321.

Pardridge, W.M. (Feb. 2002). "Drug and Gene Targeting to the Brain With Molecular Trojan Horses," *Nat. Rev. Drug Discov.* 1(2):131-139.

Polgár, T. et al. (Jun. 2, 2005, e-pub. May 4, 2005). "Virtual Screening for β-Secretase (BACE-1) Inhibitors Reveals the Importance of Protonation States at Asp32 and Asp228," *J. Med. Chem.* 48(11):3749-3755.

Rapoport, S.I. (Apr. 2000). "Osmotic Opening of the Blood-Brain Barrier: Principles, Mechanism, and Therapeutic Applications," *Cell Mol. Neurobiol.* 20(2):217-230.

Schwarze, S.R. et al. (Sep. 3, 1999). "In Vivo Protein Transduction: Delivery of a Biologically Active Protein Into the Mouse," *Science* 285(5433):1569-1572.

Selkoe, D.J. (Jun. 24, 1999). "Translating Cell Biology into Therapeutic Advances in Alzheimer's Disease," *Nature* 399(6738-Supplemental):A23-A31.

Somogyi, G. et al. (May 11, 1998). "Targeted Drug Delivery to the Brain via Phosphonate Derivatives I. Design, Synthesis and Evaluation of an Anionic Chemical Delivery System for Testosterone," *Int. J. Pharm.* 166(1):15-26.

Stachel, S.J. et al. (2004, e-pub. Nov. 11, 2004). "Structure-Based Design of Potent and Selective Cell-Permeable Inhibitors of Human β-Secretase (BACE-1)," *J. Med. Chem.* 47(26):6447-6450.

Tamai, I. et al. (Jan. 1997). "Structure-Internalization Relationship for Adsorptive-Mediated Endocytosis of Basic Peptides at the Blood-Brain Barrier," *J. Pharmacol. Exp. Ther.* 280(1):410-415.

Thorne, R.G. et al. (Sep. 18, 1995). "Quantitative Analysis of the Olfactory Pathway for Drug Delivery to the Brain," *Brain Res* 692(1-2):278-282.

Thorne, R.G. et al. (2001). "Delivery of Neurotrophic Factors to the Central Nervous System: Pharmacokinetic Considerations," *Clin. Pharmacokinet.* 40(12):907-946.

Urcola, J.H. et al. (2006, e-pub. May 6, 2006). "Three Experimental Glaucoma Models in Rats: Comparison of the Effects of Intraocular Pressure Elevation on Retinal Ganglion Cell Size and Death," *Exp. Eye Research* 83:429-437.

Varghese, J. (Mar. 2006). "Human β-Secretase (BACE) and BACE Inhibitors: Progress Report," *Current Topics in Medicinal Chemistry* 6(6):569-578.

Wender, P.A. et al. (Nov. 21, 2000). "The Design, Synthesis, and Evaluation of Molecules That Enable or Enhance Cellular Uptake: Peptoid Molecular Transporters," *Proc. Natl. Acad. Sci USA* 97(24):13003-13008.

Wu, D. et al. (Oct. 1, 1997). "Drug Targeting of a Peptide Radiopharmaceutical Through the Primate Blood-Brain Barrier in Vivo With a Monoclonal Antibody to the Human Insulin Receptor," *J. Clin. Invest.* 100(7):1804-1812.

Wu, J. et al. (Jul. 2002). "Synthesis and Biological Evaluations of Brain-Targeted Chemical Delivery Systems of [Nva$^2$]-TRH," *J. Pharm. Pharmacol.* 54(7):945-950.

Yamamoto, R. et al. (Nov. 3, 2004). "Neuroprotective Effects of β-Secretase Inhibitors Against Rat Retinal Ganglion Cell Death," *Neuroscience Letters* 370(1):61-64.

Yoshikawa, T. et al. (Nov. 1992). "Biotin Delivery to Brain With a Covalent Conjugate of Avidin and a Monoclonal Antibody to the Transferrin Receptor," *J. Pharmacol. Exp. Ther.* 263(2):897-903.

Zobel, H.-P. et al. (Oct. 1997). "Cationic Polyhexylcyanoacrylate Nanoparticles as Carriers for Antisense Oligonucleotides," *Antisense Nucleic Acid Drug Dev.* 7(5):483-493.

Zordan-Nudo, T. et al. (Dec. 15, 1993). "Effects of Nonionic Detergents on P-Glycoprotein Drug Binding and Reversal of Multidrug Resistance," *Cancer Res.* 53(24):5994-6000.

Bachem (Date Unknown). "M-2485," located at <http://shop.bachem.com/ep6sf/peptides-and-biochemicals/secretase-inhibitors-and-substrates/-secretase-substrates/4034744/prodM2485.html>, last visited on Dec. 8, 2010, 1 page.

International Search Report mailed on Dec. 10, 2009, for PCT Patent Application No. PCT/US09/60269, filed on Oct. 9, 2009, 3 pages.

International Search Report mailed on Mar. 23, 2011, for PCT Patent Application No. PCT/US10/51363, filed on Oct. 4, 2010, 4 pages.

U.S. Appl. No. 13/123,101, filed Apr. 7, 2011, by Bilcer et al.

U.S. Appl. No. 13/309,181, filed Dec. 1, 2011, by Bilcer et al.

U.S. Appl. No. 13/259,091, filed Sep. 22, 2011, by Bilcer et al.

Anonymous. (1965). "IUBMB Enzyme Nomenclature. EC 3.4.23.5," last modified 1986, located at <http://www.chem.qmul.ac.uk/iubmb/enzyme/EC3/4/23/5.html>, last visited on Jun. 30, 2010, 1 page.

Wikipedia.com (Date Unknown). "Beta Secretase," last modified on Apr. 5, 2010, located at <http://en.wikipedia.org/wiki/Beta_secretase>, last visited on Jun. 30, 2010, 3 pages.

Wikipedia.com (Date Unknown). "Cathepsin," last modified on Jun. 30, 2010, located at <http://en.wikipedia.org/wiki/Cathepsin>, last visited on Jun. 30, 2010, 3 pages.

SEQUENCE LISTING

<160> NUMBER OF SEQ ID NOS: 3

<210> SEQ ID NO 1
<211> LENGTH: 12
<212> TYPE: PRT
<213> ORGANISM: Artificial Sequence
<220> FEATURE:
<223> OTHER INFORMATION: Synthetic construct

<400> SEQUENCE: 1

Glu Leu Asp Leu Ala Val Glu Phe Trp His Asp Arg
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic Construct

```
<220> FEATURE:
<221> NAME/KEY: VARIANT
<222> LOCATION: 1
<223> OTHER INFORMATION: Xaa = (7-methoxycoumarin-4-yl)acetyl-Serine
      (MCA-Serine)
<220> FEATURE:
<221> NAME/KEY: VARIANT
<222> LOCATION: 10
<223> OTHER INFORMATION: Xaa= N-Epsilon-(2,4,-dinitrophenyl)-Lysine
      amide

<400> SEQUENCE: 2

Xaa Glu Val Asn Leu Asp Ala Glu Phe Xaa
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic construct

<400> SEQUENCE: 3

Ser Glu Val Asn Leu Asp Ala Glu Phe Lys
1               5                   10
```

(3-HYDROXY-4-AMINO-BUTAN-2-YL) -3-(2-THIAZOL-2-YL-PYRROLIDINE-1-CARBONYL) BENZAMIDE DERIVATIVES AND RELATED COMPOUNDS AS BETA-SECRETASE INHIBITORS FOR TREATING

CROSS REFERENCE TO RELATED APPLICATIONS

This application is a National Phase application under 35 U.S.C. §371 of International Application No. PCT/US2008/077537 filed Sep. 24, 2008, which claims priority benefit of U.S. Provisional Application No. 60/974,793, entitled "Tricyclic Compounds Which Inhibit Beta-Secretase Activity and Methods of Use Thereof" filed Sep. 24, 2007, the disclosures of which are incorporated herein by reference in their entirety.

BACKGROUND OF THE INVENTION

Alzheimer's disease is a progressive mental deterioration in a human resulting, inter alia, in loss of memory, confusion and disorientation. Alzheimer's disease accounts for the majority of senile dementias and is a leading cause of death in adults (Anderson, R. N., *Natl. Vital Stat. Rep.* 49:1-87 (2001), the teachings of which are incorporated herein in their entirety). Histologically, the brain of persons afflicted with Alzheimer's disease is characterized by a distortion of the intracellular neurofibrils and the presence of senile plaques composed of granular or filamentous argentophilic masses with an amyloid protein core, largely due to the accumulation of β-amyloid protein (Aβ) in the brain. Aβ accumulation plays a role in the pathogenesis and progression of the disease (Selkoe, D. J., *Nature* 399: 23-31 (1999)) and is a proteolytic fragment of amyloid precursor protein (APP). APP is cleaved initially by β-secretase followed by γ-secretase to generate Aβ (Lin, X., et al., *Proc. Natl. Acad. Sci. USA* 97:1456-1460 (2000); De Stropper, B., et al., *Nature* 391:387-390 (1998)). Inhibitors of β-secretase are described in U.S. Pat. No. 7,214,715, US 2007/0032470, WO 2006/110/668; WO 2002/02520; WO 2002/02505; WO 2002/02518; WO 2002/02512; WO 2003/040096; WO 2003/072535; WO 2003/050073; WO 2005/030709; WO 2004/050619; WO 2004/080376; WO 2004/043916; WO 2006/110668; Stachel, S. J., *J. Med. Chem.* 47, 6447-6450 (2004); Stachel, S. J., *Bioorg. Med. Chem. Lett.* 16, 641-644 (2006); and Varghese, J., *Curr. Top. Med. Chem.* 6: 569-578 (2006).

There is a need to develop effective compounds and methods for the treatment of Alzheimer's disease. The present invention fulfills these and other needs.

BRIEF SUMMARY OF THE INVENTION

The present invention provides novel β-secretase inhibitor compounds and methods for their use, including methods of treating Alzheimer's disease.

In another aspect of the present invention, the β-secretase inhibitor compounds of the invention can be employed in methods to decrease memapsin 2 activity, decrease hydrolysis of a β-secretase site of a memapsin 2 substrate, and/or decrease the accumulation of β-amyloid protein relative to the amount of memapsin 2 activity, hydrolysis of a β-secretase site, and accumulation of β-amyloid protein, respectively, in the absence of the β-secretase inhibitor.

In another aspect, the present invention provides pharmaceutical compositions comprising a β-secretase inhibitor compound of the invention or a β-secretase inhibitor compound in combination with a pharmaceutically acceptable carrier.

In another aspect of the present invention, the β-secretase inhibitor compounds of the invention can be employed in the treatment of diseases or conditions associated with β-secretase activity, hydrolysis of a β-secretase site of a β-amyloid precursor protein, and/or β-amyloid protein accumulation. Typically, a mammal is treated for the disease or condition. In an exemplary embodiment, the disease is Alzheimer's disease.

In one aspect, the present invention embraces compounds having formula I:

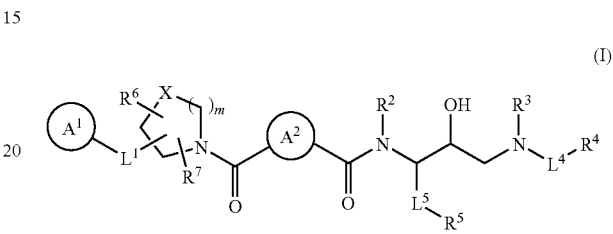

(I)

where
A$^1$ is a substituted or unsubstituted cycloalkyl, substituted or unsubstituted heterocycloalkyl, substituted or unsubstituted aryl, or substituted or unsubstituted heteroaryl;
A$^2$ is a substituted or unsubstituted cycloalkylene, substituted or unsubstituted heterocycloalkylene, substituted or unsubstituted arylene, or substituted or unsubstituted heteroarylene;
X is —CH$_2$—, —O—, —N(R$^8$)—, or —S(O)$_w$—;
or where X is —CH— or —N—, and is the attachment point for R$^6$ or R$^7$;
L$^1$ and L$^5$ are independently a bond, —N(R$^{17}$)—, —S(O)$_q$—, or substituted or unsubstituted alkylene;
L$^4$ is a bond, —C(O)—, —N(R$^{17}$)—, —S(O)$_q$—, or substituted or unsubstituted alkylene;
R$^2$ and R$^3$ are independently hydrogen, —S(O)$_2$R$^{11}$, —C(O)R$^{12}$, —N(R$^8$)R$^9$, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl;
R$^4$ and R$^5$ are independently hydrogen, halogen, —OH, —NO$_2$, —N(R$^8$)R$^9$, —OR$^{10}$, —S(O)$_n$R$^{11}$, —C(O)R$^{12}$, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl;
R$^6$ and R$^7$ are independently hydrogen, halogen, —OH, —NO$_2$, —N(R$^8$)R$^9$, —OR$^{10}$, —S(O)$_n$R$^{11}$, —C(O)R$^{12}$, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl;

$R^8$ is independently hydrogen, —C(O)$R^{13}$, —S(O)$_2$$R^{14}$, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl;

$R^9$ is independently hydrogen, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl;

$R^{10}$ is independently —C(O)$R^{13}$, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl;

$R^{11}$ is independently hydrogen, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl, wherein if n is 2, then $R^{11}$ can also be —$NR^{15}R^{16}$, and wherein if n is 1 or 2, then $R^{11}$ is not hydrogen;

$R^{12}$ and $R^{13}$ are each independently hydrogen, —N($R^{18}$)$R^{19}$, —O$R^{19}$, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl;

$R^{14}$ is independently hydrogen, —N($R^{18}$)$R^{19}$, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl;

$R^{15}$, $R^{16}$, $R^{17}$, $R^{18}$, and $R^{19}$ are each independently hydrogen, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl; and m, n, q, and w are each independently 0, 1, or 2;

or a pharmaceutically acceptable salt, isomer, mixture of isomers, crystalline form, non-crystalline form, hydrate, or solvate thereof.

In one embodiment, the β-secretase inhibitor compound includes any one, any combination, or all of the compounds of Example 3; or a pharmaceutically acceptable salt or solvate thereof. In some embodiments, the compound has a memapsin 2 $K_i$ of less than about 100 nM. In some embodiments, the compound has an apparent memapsin 2 $K_i$ of less than about 100 nM as measured by inhibition of memapsin 2 catalytic activity toward the fluorogenic substrate FS-2 MCA-SEVNLDAEFK-DNP; SEQ ID NO.: 2). In some embodiments, the compound is capable of inhibiting cellular Aβ production with an IC50 of less than about 300 nM. In some embodiments, the compound has a memapsin 1 $K_i$ and/or cathepsin D $K_i$ of greater than about 300 nM. In some embodiments, the compound has an apparent memapsin 1 $K_i$ and/or apparent cathepsin D $K_i$ of greater than about 300 nM, as measured by the substrate peptide $NH_3$-ELDLAVEF-WHDR-$CO_2$ (SEQ ID NO.: 1). In some embodiments, the compound is capable of selectively reducing memapsin 2 catalytic activity relative to memapsin 1 catalytic activity. In some embodiments, the compound is capable of selectively reducing memapsin 2 catalytic activity relative to cathepsin D catalytic activity. In some of these embodiments, the relative reduction is greater than about 5-fold. In other embodiments, the reduction is greater than about 10-fold. In another embodiment, the β-secretase inhibitor compound (a) has a memapsin 2 $K_i$ of less than about 300 nM (or less than about any one of 100 nM, 50 nM, or 10 nM); (b) is capable of inhibiting cellular Aβ production with an IC50 of less than about 1 μM (or less than about any one of 300 nM, 100 nM, 40 nM, or 10 nM); and (c) is capable of selectively reducing memapsin 2 catalytic activity relative to memapsin 1 or cathepsin D catalytic activity by greater than about 5-fold (or greater than about 10-fold, or about 100-fold).

In one embodiment,

In another aspect of the present invention, any one of the β-secretase inhibitor compounds is present in substantially pure form.

In another aspect of the present invention are provided formulations comprising any one of the compounds described herein and a pharmaceutically acceptable carrier. In some embodiments, the formulation is suitable for administration to an individual.

In another aspect of the present invention are provided formulations comprising an effective amount of any one of the compounds described herein and a pharmaceutically acceptable carrier.

In another aspect of the present invention are provided methods of treating Alzheimer's disease in an individual in need thereof, comprising administering to the subject an effective amount of any one of the compounds described herein.

In another aspect of the present invention are provided methods of reducing memapsin 2 catalytic activity, comprising contacting a memapsin 2 protein with an effective amount of any one of the compounds described herein. In some variations, the memapsin 2 beta-secretase is contacted in a cell. In some embodiments, the cell is contacted in vivo. In some embodiments, the cell is contacted in vitro.

In another aspect of the present invention are provided methods of selectively reducing memapsin 2 catalytic activity relative to memapsin 1 catalytic activity, comprising contacting a memapsin 2 protein with an effective amount of a compound of any one of the compounds described herein in the presence of memapsin 1 beta-secretase.

In another aspect of the present invention are provided methods of selectively reducing memapsin 2 catalytic activity relative to cathepsin D catalytic activity, comprising contacting a memapsin 2 protein with an effective amount of a compound of any one of the compounds described herein in the presence of cathepsin D.

In another aspect of the present invention are provided methods of selectively reducing memapsin 2 catalytic activity relative to memapsin 1 catalytic activity and cathepsin D catalytic activity, the method comprising contacting a memapsin 2 protein with an effective amount of a compound of any one of the compounds described herein in the presence of memapsin 1 beta-secretase and cathepsin D.

In another aspect of the present invention are provided methods of treating Glaucoma in an individual in need thereof, comprising administering to the individual an effective amount of any one of the compounds described herein.

In another aspect of the present invention is any one of the compounds described herein for use as a medicament.

Another aspect of the present invention is the use of any one of the compounds described herein for the manufacture of a medicament for the treatment or prevention of a condition characterized by memapsin 2 catalytic activity. In some variations, the condition is Alzheimer's disease.

In another aspect of the present invention are provided kits for the treatment or prevention in an individual with Alzheimer's disease, comprising any one of the compounds described herein; and packaging.

In another aspect of the present invention are provided kits for the treatment or prevention in an individual of a condition mediated by memapsin 2 catalytic activity, comprising any one of the compounds described herein; and packaging.

In another aspect of the present invention are provided kits for the treatment or prevention in an individual with Alzheimer's disease, comprising a formulation described herein; and packaging.

In another aspect of the present invention are provided kits for the treatment or prevention in an individual of a condition mediated by memapsin 2 catalytic activity, comprising a formulation described herein; and packaging.

DETAILED DESCRIPTION OF THE INVENTION

Abbreviations and Definitions

The abbreviations used herein have their conventional meaning within the chemical and biological arts, unless otherwise specified.

Nomenclature of some compounds described herein may be identified using ChemDraw Ultra Version 10.0, available from CambridgeSoft®.

Where substituent groups are specified by their conventional chemical formula, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e. unbranched) or branched chain, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene" by itself or as part of another substituent means a divalent radical derived from an alkyl, as exemplified, but not limited, by —$CH_2CH_2CH_2CH_2$—. Typically, an alkyl (or alkylene) group will have from 1 to 24 carbon atoms. In some embodiments, an alkyl group will have from 1 to 6 carbon atoms. In some embodiments, the alkylene groups are metheylene and methylmethylene.

The term "cycloalkyl" by itself or in combination with other terms, represents, unless otherwise stated, cyclic versions of "alkyl." Additionally, cycloalkyl may contain multiple rings, but excludes aryl and heteroaryl groups. Examples of cycloalkyl include, but are not limited to, cyclopropyl, cyclobutyl, cyclopentyl, cyclohexyl, 1-cyclohexenyl, 3-cyclohexenyl, cycloheptyl, norbornyl, and the like. The term "cycloalkylene" by itself or as part of another substituent means a divalent radical derived from a cycloalkyl, as exemplified, but not limited, by -cyclohexyl-.

The term "heterocycloalkyl," by itself or in combination with other terms, represents a stable saturated or unsaturated cyclic hydrocarbon radical containing of at least one carbon atom and at least one annular heteroatom selected from the group consisting of O, N, P, Si and S, and wherein the nitrogen and sulfur atoms may optionally be oxidized and the nitrogen heteroatom may optionally be quaternized. The heteroatom(s) O, N, P, S and Si may be placed at any interior position of the heterocycloalkyl group or at the position at which the heterocycloalkyl group is attached to the remainder of the molecule. Additionally, heterocycloalkyl may contain multiple rings, but excludes aryl and heteroaryl groups. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The term "heterocycloalkylene" by itself or as part of another substituent means a divalent radical derived from a heterocycloalkyl, as exemplified, but not limited, by

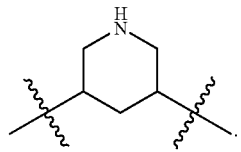

The term "cycloalkyl-alkyl" and "heterocycloalkyl-alkyl" designates an alkyl-substituted cycloalkyl group and alkyl-substituted heterocycloalkyl, respectively, where the alkyl portion is attached to the parent structure. Non-limiting examples include cyclopropyl-ethyl, cyclobutyl-propyl, cyclopentyl-hexyl, cyclohexyl-isopropyl, 1-cyclohexenyl-propyl, 3-cyclohexenyl-t-butyl, cycloheptyl-heptyl, norbornyl-methyl, 1-piperidinyl-ethyl, 4-morpholinyl-propyl, 3-morpholinyl-t-butyl, tetrahydrofuran-2-yl-hexyl, tetrahydrofuran-3-yl-isopropyl, and the like. Cycloalkyl-alkyl and heterocycloalkyl-alkyl also include substituents in which a carbon atom of the alkyl group (e.g., a methylene group) has been replaced by, for example, an oxygen atom (e.g., cyclopropoxymethyl, 2-piperidinyloxy-t-butyl, and the like).

The term "aryl" means, unless otherwise stated, a polyunsaturated, aromatic, hydrocarbon substituent which can be a single ring or multiple rings (e.g., from 1 to 3 rings) which are fused together or linked covalently. Additionally, aryl may contain multiple rings, wherein one or more of the rings can be cylcoalkyl or heterocycloalkyl. Examples of aryl groups include, but are not limited to, phenyl, 1-naphthyl, 2-naphthyl, 4-biphenyl. The term "heteroaryl" refers to aryl groups (or rings) that contain from one to four annular heteroatoms selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Additionally, heteroaryl may contain multiple rings, wherein one or more of the rings can be cylcoalkyl or heterocycloalkyl. Non-limiting examples of heteroaryl groups are 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

The term "arylene" and "heteroarylene" means a divalent radical derived from an aryl and heteroaryl, respectively. Each of the two valencies of arylene and heteroarylene may be located at any portion of the ring (e.g.,

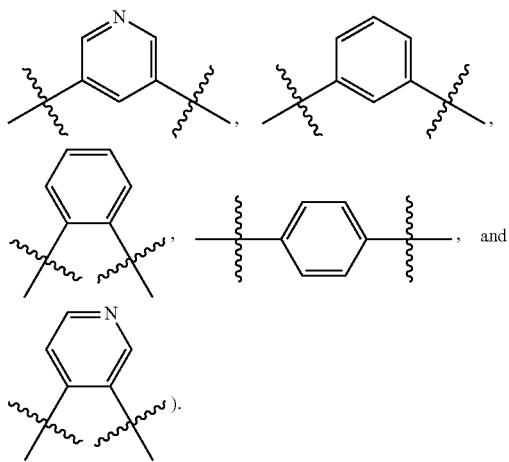

Non-limiting examples of arylene include phenylene, biphenylene, naphthylene, and the like. Examples of heteroarylene groups include, but are not limited to, pyridinylene, oxazolylene, thioazolylene, pyrazolylene, pyranylene, and furanylene.

The term "aralkyl" designates an alkyl-substituted aryl group, where the alkyl portion is attached to the parent structure. Examples are benzyl, phenethyl, phenylvinyl, phenylallyl, pyridylmethyl, and the like. "Heteroaralkyl" designates a heteroaryl moiety attached to the parent structure via an alkyl residue. Examples include furanylmethyl, pyridinylmethyl, pyrimidinylethyl, and the like. Aralkyl and heteroaralkyl also include substituents in which a carbon atom of the alkyl group (e.g., a methylene group) has been replaced by, for example, an oxygen atom (e.g., phenoxymethyl, 2-pyridyloxymethyl, 3-(1-naphthyloxy)propyl, and the like).

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

Each of the above terms (e.g., "alkyl," "cycloalkyl," "heterocycloalkyl," "aryl," "heteroaryl," "cycloalkyl-alkyl," "heterocycloalkyl-alkyl," "aralkyl," and "heteroaralkyl") are meant to include both substituted and unsubstituted forms of the indicated radical. Preferred substituents for each type of substituted radical are provided below.

Substituents for the alkyl radicals (including alkyl portions of cycloalkyl-alkyl, heterocycloalkyl-alkyl, aralkyl, and heteroaralkyl) can be one or more of a variety of groups selected from, but not limited to: —OR', =O, =NR', =N—OR', —NR'R", —SW, -halogen, —SiR'R"R'", —OC(O)R', —C(O)R', —CO₂R', —CONR'R", —OC(O)NR'R", —NR"C(O)R', —NR'—C(O)NR"R'", —NR"C(O)₂R', —NR—C(NR'R"R'")=NR"", —NR—C(NR'R")=NR'", —S(O)R', —S(O)₂R', —S(O)₂NR'R", —NRSO₂R', —CN and —NO₂ in a number ranging from zero to (2 m'+1), where m' is the total number of carbon atoms in such radical. R', R", R'" and R"" each may independently refer to hydrogen, substituted or unsubstituted alkyl, substituted or unsubstituted cycloalkyl, substituted or unsubstituted heterocycloalkyl, substituted or unsubstituted aryl (e.g., aryl substituted with 1-3 halogens), substituted or unsubstituted cycloalkyl-alkyl, substituted or unsubstituted heterocycloalkyl-alkyl, substituted or unsubstituted aralkyl, substituted or unsubstituted heteroaralkyl, alkoxy, or thioalkoxy groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl.

Similar to the substituents described for the alkyl radical, substituents for the aryl and heteroaryl groups (including the aryl and heteroaryl portions of aralkyl and heteroaralkyl, respectively) are varied and are selected from, for example: halogen, —OR', —NR'R", —SR', -halogen, —SiR'R"R'", —OC(O)R', —C(O)R', —CO₂R', —CONR'R", —OC(O) NR'R", —NR"C(O)R', —NR'—C(O)NR"R'", —NR"C (O)₂R', —NR—C(NR'R"R'")=NR"", —NR—C(NR'R") =NR'", —S(O)R', —S(O)₂R', —S(O)₂NR'R", —NRSO₂R', —CN and —NO₂, —R', —N₃, —CH(Ph)₂, fluoro($C_1$-$C_4$) alkoxy, and fluoro($C_1$-$C_4$)alkyl, in a number ranging from zero to the total number of open valences on the aromatic ring system; and where R', R", R'" and R"" are, for example, independently selected from hydrogen, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted cycloalkyl-alkyl, substituted or unsubstituted heterocycloalkyl-alkyl, substituted or unsubstituted aralkyl, or substituted or unsubstituted heteroaralkyl. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-$(CH_2)_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R''')$_d$—, where s and d are independently integers of from 0 to 3, and X' is —O—, —NR'—, —S—, —S(O)—, —S(O)$_2$—, or —S(O)$_2$NR'—. In some embodiments, the substituents R, R', R" and R''' are independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

The terms, "pharmaceutically effective amount," "therapeutically effective amount," "effective amount," and cognates of these terms, as used herein refer to an amount that results in a desired pharmacological and/or physiological effect for a specified condition (e.g., disease, disorder, etc.) or one or more of its symptoms and/or to completely or partially prevent the occurrence of the condition or symptom thereof and/or may be therapeutic in terms of a partial or complete cure for the condition and/or adverse effect attributable to the condition. In reference to conditions mediated by memapsin 2 beta-secretase, a pharmaceutically or therapeutically effective amount comprises an amount sufficient to, among other things, cause antagonism of memapsin 2 beta-secretase. In reference to glaucoma, a pharmaceutically or therapeutically effective amount comprises an amount sufficient to, among other things, decrease intraocular pressure; and/or halt, reverse, and/or diminish the loss of retinal ganglion cells (RGCs). In certain embodiments, the pharmaceutically effective amount is sufficient to prevent the condition, as in being administered to an individual prophylactically.

The "pharmaceutically effective amount" or "therapeutically effective amount" will vary depending on the composition being administered, the condition being treated/prevented, the severity of the condition being treated or prevented, the age and relative health of the individual, the route and form of administration, the judgment of the attending medical or veterinary practitioner, and other factors appreciated by the skilled artisan in view of the teaching provided herein.

When used with respect to methods of treatment/prevention and the use of the compounds and compositions thereof described herein, an individual "in need thereof" may be an individual who has been diagnosed with or previously treated for the condition to be treated. With respect to prevention, the individual in need thereof may also be an individual who is at risk for a condition (e.g., a family history of the condition, life-style factors indicative of risk for the condition, etc.).

In some variations, the individual has been identified as having one or more of the conditions described herein. Identification of the conditions as described herein by a skilled physician is routine in the art and may also be suspected by the individual or others, for example, due to loss of memory in the case of Alzheimer's, exhibiting the symptoms of schizophrenia, etc., and due to loss of vision in the case of Glaucoma.

In some embodiments, the individual has been identified as susceptible to one or more of the conditions as described herein. The susceptibility of an individual may be based on any one or more of a number of risk factors and/or diagnostic approaches appreciated by the skilled artisan, including, but not limited to, genetic profiling, family history, medical history (e.g., appearance of related conditions), lifestyle or habits.

In some embodiments, the individual is a mammal, including, but not limited to, bovine, horse, feline, rabbit, canine, rodent, or primate. In some embodiments, the mammal is a primate. In some embodiments, the primate is a human. In some embodiments, the individual is human, including adults, children and premature infants. In some embodiments, the individual is a non-mammal. In some variations, the primate is a non-human primate such as chimpanzees and other apes and monkey species. In some embodiments, the mammal is a farm animal such as cattle, horses, sheep, goats, and swine; pets such as rabbits, dogs, and cats; laboratory animals including rodents, such as rats, mice, and guinea pigs; and the like. Examples of non-mammals include, but are not limited to, birds, and the like. The term "individual" does not denote a particular age or sex.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19, the content of which is hereby incorporated by reference in its entirety). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates or mixtures thereof including racemic mixtures), succinates, benzoates and salts with amino acids such as glutamic acid. For example, compounds described herein may exist as a citrate salt (e.g., mono citrate, hydrogen citrate, or dihydrogen citrate) and/or a mesylate salt (e.g., dimesylate). These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms (i.e., "solvates"). Compounds of the invention may also include hydrated forms (i.e., "hydrates"). In general, the solvated and hydrated forms are equivalent to unsolvated forms and are encompassed within the scope of the present invention. Certain compounds of the present invention may exist in multiple crystalline or amorphous forms (non-crystalline forms). In general, all physical forms are equivalent for the uses contemplated by the present invention and are intended to be within the scope of the present invention.

Metabolites of the compounds are also embraced by the invention. Metebolites may include primary metabolites and/or secondary metabolites. However, metabolites of substances which occur naturally in subjects are excluded from the claimed compounds of the invention.

As used herein, "isomer" includes all stereoisomers of the compounds referred to in the formulas herein, including enantiomers, diastereomers, as well as all conformers, rotomers, and tautomers. The invention includes all enantiomers of any chiral compound disclosed, in either substantially pure levorotatory or dextrorotatory form, or in a racemic mixture, or in any ratio of enantiomers. For compounds disclosed as an (R)-enantiomer, the invention also includes the (S)-enantiomer; for compounds disclosed as the (S)-enantiomer, the invention also includes the (R)-enantiomer. The invention includes any diastereomers of the compounds referred to in the above formulas in diastereomerically pure form and in the form of mixtures in all ratios.

Unless stereochemistry is explicitly indicated in a chemical structure or chemical name, the chemical structure or chemical name is intended to embrace all possible stereoisomers, conformers, rotomers, and tautomers of the compound depicted. For example, a compound containing a chiral carbon atom is intended to embrace both the (R) enantiomer and the (S) enantiomer. A compound containing multiple chiral carbon atoms (for example, both carbons within the hydroxyethylamine isostere) is intended to embrace all enantiomers and diastereomers (including (R,R), (S,S), (R,S), and (R,S) isomers). When a compound is explicitly indicated in a particular stereochemical arrangement (e.g., 2S,3R for the hydroxyethylamine isostere), the compound may, in other embodiments, be described in another specific stereochemical arrangement (e.g., 2R,3S for the hydroxyethylamine isostere) and/or a mixture of stereochemical arrangements.

A substantially pure compound means that the compound is present with no more than 15% or no more than 10% or no more than 5% or no more than 3% or no more than 1% of the total amount of compound in a different stereochemical form. For instance, substantially pure S,S compound means that no more than 15% or no more than 10% or no more than 5% or no more than 3% or no more than 1% of the total R,R; S,R; and R,S form is present.

A composition may contain the compound as mixtures of such stereoisomers, where the mixture may be enanteomers (e.g., S,S and R,R) or diastereomers (e.g., S,S and R,S or S,R) in equal or unequal amounts. A composition may contain the compound as a mixture of 2 or 3 or 4 such stereoisomers in any ratio of stereoisomers.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are encompassed within the scope of the present invention.

A "transition state isostere," or "isostere," as used herein, is a compound comprising the hydroxyethylamine linking group —CH(OH)—CH$_2$—NH—. This isostere is also referred to herein as a "hydroxyethylamine isostere." The hydroxyethylamine linking group may be found between a pair of natural or non-natural amino acids of a peptide. A hydroxyethylamine group is an isostere of the transition state of hydrolysis of an amide bond.

"Amyloid precursor protein," or "APP," as used herein, refers to a β-amyloid precursor comprising a β-secretase site.

"Memapsin-2," as used herein, refers to proteins identified by National Center for Biotechnology Information ("NCBI") accession number NP_036236 (sometimes referred to as "β-site APP-cleaving enzyme 1" or "BACE-1" or generically as "β-secretase" or "beta-secretase"), including homologs, isoforms and subdomains thereof that retain proteolytic activity. Sequence identities of active memapsin 2 proteins and protein fragments (and nucleic acid coding sequences thereof) have been previously disclosed and discussed in detail in U.S. Application No. 20040121947, and International Application No. PCT/USO2/34324 (Publication No. WO 03/039454), which are herein incorporated by reference for all purposes in their entirety.

"Memapsin-1," as used herein, refers to proteins identified by National Center for Biotechnology Information ("NCBI") accession number NP_036237 (sometimes referred to as "β-site APP-cleaving enzyme 2" or "BACE-2") and/or those previously disclosed and discussed in detail in see U.S. Patent Application Publication No. 20040121947, and International Application No. PCT/USO2/34324 (Publication No. WO 03/039454), incorporated by reference herein in their entirety for all purposes, including homologs, isoforms and subdomains thereof that retain proteolytic activity.

"Cathepsin D," as used herein, refers to proteins identified by Enzyme Structure Database subclass EC 3.4.23.5., including homologs, isoforms and subdomains thereof that retain proteolytic activity.

A "β-secretase site" is an amino acid sequence that is cleaved by an active memapsin 2 or active fragment thereof. Specific β-secretase sites have also been previously set forth and discussed in detail in U.S. Application No. 20040121947, and International Application No. PCT/USO2/34324 (Publication No. WO 03/039454), which are herein incorporated by reference for all purposes in their entirety, and include the Swedish mutation sequence, and the native β-amyloid precursor protein cleavage sequence. Thus, β-secretase inhibitors may be tested for their ability to decrease the hydrolysis of the β-secretase site of a substrate, such as the β-amyloid precursor protein, analogs of β-amyloid precursor protein, or fragments of β-amyloid precursor protein.

A "beta-secretase inhibitor" (i.e. β-secretase inhibitor) refers to a compound capable of reducing the proteolytic activity of memapsin-2 relative to the activity in the absence of inhibitor.

Reference to "about" a value or parameter herein includes (and describes) variations that are directed to that value or parameter per se. For example, description referring to "about X" includes description of "X".

The terms "a" or "an," as used in herein means one or more.

I. β-SECRETASE INHIBITORS

In one aspect, the present invention provides compounds that inhibit (i.e. decrease) the catalytic activity of the β-secretase enzyme (memapsin 2). These compounds may be referred to herein as "compounds of the present invention," "β-secretase inhibitor compounds," or "memapsin 2 β-secretase inhibitors." In this aspect, the compounds have the formula:

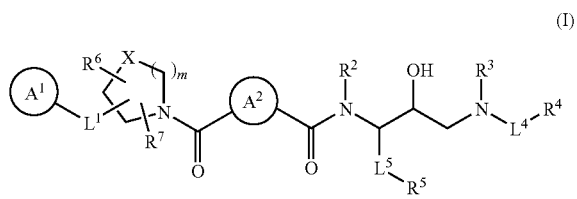

(I)

wherein $A^1$ is a substituted or unsubstituted cycloalkyl, substituted or unsubstituted heterocycloalkyl, substituted or unsubstituted aryl, or substituted or unsubstituted heteroaryl;

$A^2$ is a substituted or unsubstituted cycloalkylene, substituted or unsubstituted heterocycloalkylene, substituted or unsubstituted arylene, or substituted or unsubstituted heteroarylene;

X is $-CH_2-$, $-O-$, $-N(R^8)-$, or $-S(O)_w-$; or where X is $-CH-$ or $-N-$, and is the attachment point for $R^6$ or $R^7$;

$L^1$ and $L^5$ are independently a bond, $-N(R^{17})-$, $-S(O)_q-$, or substituted or unsubstituted alkylene;

$L^4$ is a bond, $-C(O)-$, $-N(R^{17})-$, $-S(O)_q-$, or substituted or unsubstituted alkylene;

$R^2$ and $R^3$ are independently hydrogen, $-S(O)_2R^{11}$, $-C(O)R^{12}$, $-N(R^8)R^9$, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl;

$R^4$ and $R^5$ are independently hydrogen, halogen, $-OH$, $-NO_2$, $-N(R^8)R^9$, $-OR^{10}$, $-S(O)_nR^{11}$, $-C(O)R^{12}$, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl;

$R^6$ and $R^7$ are independently hydrogen, halogen, $-OH$, $-NO_2$, $-N(R^8)R^9$, $-OR^{10}$, $-S(O)_nR^{11}$, $-C(O)R^{12}$, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl;

$R^8$ is independently hydrogen, $-C(O)R^{13}$, $-S(O)_2R^{14}$, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl;

$R^9$ is independently hydrogen, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl;

$R^{10}$ is independently $-C(O)R^{13}$, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl;

$R^{11}$ is independently hydrogen, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl, wherein if n is 2, then $R^{11}$ can also be $-NR^{15}R^{16}$, and wherein if n is 1 or 2, then $R^{11}$ is not hydrogen;

$R^{12}$ and $R^{13}$ are each independently hydrogen, $N(R^{18})R^{19}$, $-OR^{19}$, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl;

$R^{14}$ is independently hydrogen, $-N(R^{18})R^{19}$, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl;

$R^{15}$, $R^{16}$, $R^{17}$, $R^{18}$, and $R^{19}$ are each independently hydrogen, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl; and m, n, q, and w are each independently 0, 1, or 2;

or a pharmaceutically acceptable salt, isomer, mixture of isomers, crystalline form, non-crystalline form, hydrate, or solvate thereof.

In some of these embodiments, $A^1$ is a substituted or unsubstituted cycloalkyl, or substituted or unsubstituted heterocycloalkyl. In other embodiments, $A^1$ is a substituted or unsubstituted cycloalkyl. In other embodiments, $A^1$ is a substituted or unsubstituted heterocycloalkyl. In other embodiments, $A^1$ is a substituted or unsubstituted aryl, or substituted or unsubstituted heteroaryl (e.g., wherein the heteroaryl is attached to $L_1$ at the 1, 2, 3, 4, or 5 position and/or wherein the heteroaryl is substituted at the 1, 2, 3, 4, and/or 5 position(s)). In other embodiments, $A^1$ is a substituted or unsubstituted aryl (e.g., wherein the aryl is substituted at the 1, 2, 3, 4, and/or 5 position(s)). In other embodiments, $A^1$ is a substituted or unsubstituted heteroaryl. In other embodiments, $A^1$ is a substituted or unsubstituted $C_5$-$C_7$ cycloalkyl, substituted or unsubstituted 5 to 7 membered heterocycloalkyl, substituted or unsubstituted 6-membered aryl, or substituted or unsubstituted 5 to 7 membered heteroaryl. In other embodiments, $A^1$ is a substituted or unsubstituted 5-membered heteroaryl.

In other of these embodiments, $A^1$ is a substituted or unsubstituted phenyl, substituted or unsubstituted pyrazolyl, substituted or unsubstituted furanyl, substituted or unsubstituted pyranyl, substituted or unsubstituted imidazolyl, substituted or unsubstituted isoxazolyl, substituted or unsubstituted oxadiazolyl, substituted or unsubstituted oxazolyl, substituted or unsubstituted pyrrolyl, substituted or unsubstituted pyridyl, substituted or unsubstituted pyrimidyl, substituted or unsubstituted pyridazinyl, substituted or unsubstituted thiazolyl, substituted or unsubstituted triazolyl, substituted or unsubstituted thienyl, substituted or unsubstituted dihydrothienopyrazolyl, substituted or unsubstituted thianaphthenyl, substituted or unsubstituted carbazolyl, substituted or unsubstituted benzimidazolyl, substituted or unsubstituted benzothienyl, substituted or unsubstituted benzofuranyl, substituted or unsubstituted indolyl, substituted or unsubstituted quinolinyl, substituted or unsubstituted benzotriazolyl, substituted or unsubstituted benzothiazolyl, substituted or unsubstituted benzooxazolyl, substituted or unsubstituted benzimidazolyl, substituted or unsubstituted isoquinolinyl, substituted or unsubstituted isoindolyl, substituted or unsubstituted acridinyl, substituted or unsubstituted benzoisazolyl, substituted or unsubstituted dimethylhydantoin, substituted or unsubstituted pyrazinyl, substituted or unsubstituted tetrahydrofuranyl, substituted or unsubstituted pyrrolinyl, substituted or unsubstituted pyrrolidinyl, substituted or unsubstituted morpholinyl, substituted or unsubstituted indolyl, substituted or unsubstituted diazepinyl, substituted or unsubstituted azepinyl, substituted or unsubstituted thiepinyl, substituted or unsubstituted piperidinyl, or substituted or unsubstituted oxepinyl.

In other of these embodiments, $A^1$ is a substituted or unsubstituted pyridyl, substituted or unsubstituted phenyl, substituted or unsubstituted thiazolyl (e.g., a substituted or unsubstituted 2-thiazolyl or a substituted or unsubstituted 4-thiazolyl, such as a 2-(4-substituted)thiazolyl or a 4-(2-substituted)thiazolyl), substituted or unsubstituted oxazolyl (e.g., a substituted or unsubstituted 2-oxazolyl or substituted or unsubstituted 4-oxazolyl, such as a 2-(4-substituted)oxazolyl or a 4-(2-substituted)oxazolyl), substituted or unsubstituted imidazolyl, substituted or unsubstituted pyrazolyl, substituted or unsubstituted isoxazolyl, substituted or unsubstituted pyrimidyl, substituted or unsubstituted oxadiazolyl, or substituted or unsubstituted furanyl. In other embodiments, $A^1$ is a substituted or unsubstituted thiazolyl (e.g., a substituted or unsubstituted 2-thiazolyl or a substituted or unsubstituted 4-thiazolyl, such as a 2-(4-substituted)thiazolyl or a 4-(2-substituted)thiazolyl), substituted or unsubstituted oxadiazolyl, or substituted or unsubstituted oxazolyl (e.g., a substituted or unsubstituted 2-oxazolyl or substituted or unsubstituted 4-oxazolyl, such as a 2-(4-substituted)oxazolyl or a 4-(2-substituted)oxazolyl). In other embodiments, $A^1$ is a substituted or unsubstituted pyridyl (e.g., a substituted or unsubstituted 3-pyridyl, such as a 3-(5-substituted)pyridyl). In other embodiments, $A^1$ is a substituted or unsubstituted phenyl (e.g., a 3-substituted phenyl). In other embodiments, $A^1$ is a substituted or unsubstituted thiazolyl (e.g., a substituted or unsubstituted 2-thiazolyl or a substituted or unsubstituted 4-thiazolyl, such as a 2-(4-substituted)thiazolyl or a 4-(2-substituted)thiazolyl). In other embodiments, $A^1$ is a substituted or unsubstituted oxazolyl. In other embodiments, $A^1$ is a substituted or unsubstituted oxadiazolyl. In other embodiments, $A^1$ is a substituted or unsubstituted imidazolyl. In other embodiments, $A^1$ is a substituted or unsubstituted pyrazolyl. In other embodiments $A^1$ is a substituted or unsubstituted isoxazolyl. In other embodiments, $A^1$ is a substituted or unsubstituted pyrimidyl. In other embodiments, $A^1$ is a substituted or unsubstituted furanyl. In other embodiments, $A^1$ is a substituted or unsubstituted pyranyl.

In some embodiments, substituents on $A^1$ include $C_1$-$C_6$ alkyl (e.g., methyl, ethyl, propyl, isopropy) or $C_1$-$C_6$ alkoxy (methoxy, ethoxy, propoxy, isopropoxy, wherein each $C_1$-$C_6$ alkyl and $C_1$-$C_6$ alkoxy is optionally substituted with 1-3 halogens (e.g., $-CF_3$, $-CHF_2$, $-CH_2F$, $-OCH_2F$, $OCHF_2$). In other embodiments, $R^4$ is phenyl, substituted with one or more $-OCH_3$. In other embodiments, $R^4$ is pyridyl, substituted with one or more $-OCH_3$. In some embodiments, $A^1$ is substituted with methyl (e.g., at the 1, 2, 3, or 4 position of $A^1$).

In some of these embodiments, $A^2$ is substituted or unsubstituted arylene, or substituted or unsubstituted heteroarylene. In other embodiments, $A^2$ is substituted or unsubstituted phenylene, substituted or unsubstituted pyridinylene, substituted or unsubstituted oxazolylene, substituted or unsubstituted thioazolylene, substituted or unsubstituted pyrazolylene, substituted or unsubstituted pyranylene, or substituted or unsubstituted furanylene.

In some of these embodiments, $A^2$ has the formula:

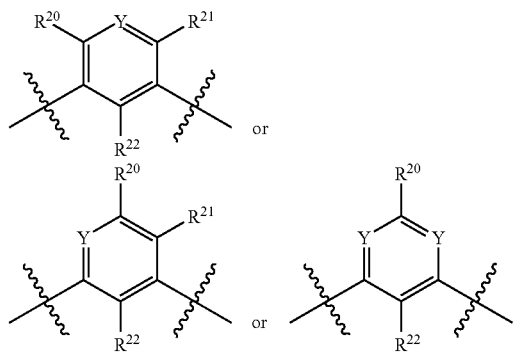

wherein
$R^{20}$, $R^{21}$, and $R^{22}$ are independently hydrogen, $-N(R^{24})R^{25}$, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl; and each Y is independently —N= or —C($R^{23}$)=, wherein $R^{23}$ is hydrogen, halogen, —$NO_2$, —N($R^{24}$)$R^{25}$, —$OR^{26}$, —S(O)$_t R^{27}$, or —C(O)$R^{28}$, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl;

wherein t is an integer from 0 to 2;

$R^{24}$ and $R^{25}$ are independently hydrogen, —C(O)$R^{29}$, or —S($O_2$)$R^{30}$, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl;

wherein $R^{29}$ is independently hydrogen, —N($R^{31}$)$R^{32}$, or —$OR^{33}$, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl;

wherein $R^{31}$, $R^{32}$, and $R^{33}$ are independently hydrogen, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl; and $R^{30}$ is hydrogen, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl;

$R^{26}$ is hydrogen, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl;

$R^{27}$ is —N($R^{34}$)$R^{35}$, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl;

wherein $R^{34}$ and $R^{35}$ are independently hydrogen, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl; and $R^{28}$ is —$OR^{36}$, —N($R^{37}$)$R^{38}$, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl;

wherein $R^{36}$, $R^{37}$, and $R^{38}$ are independently hydrogen, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl.

In other of these embodiments, $A^2$ has the formula:

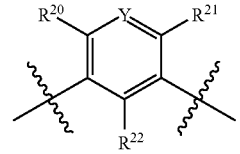

wherein $R^{20}$, $R^{21}$, and $R^{22}$ are as defined above.

In other of these embodiments, $A^2$ has the formula:

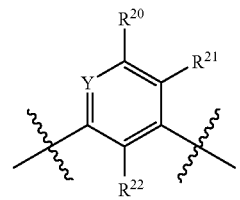

wherein $R^{20}$, $R^{21}$, and $R^{22}$ are as defined above.

In other of these embodiments, $A^2$ has the formula:

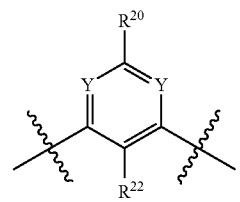

wherein $R^{20}$, $R^{21}$, and $R^{22}$ are as defined above.

In some of these embodiments, $A^2$ has the formula:

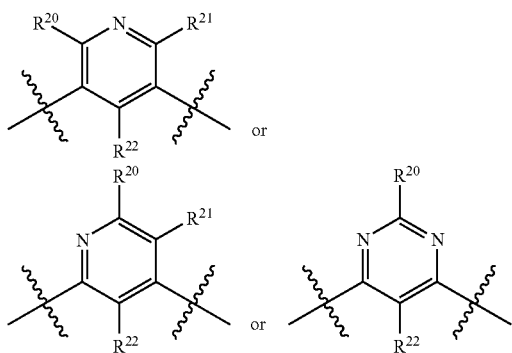

wherein $R^{20}$, $R^{21}$, and $R^{22}$ are as defined above.
In other of these embodiments, $A^2$ has the formula:

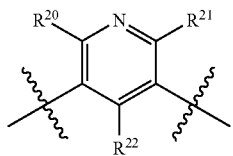

wherein $R^{20}$, $R^{21}$, and $R^{22}$ are as defined above.
In other of these embodiments, $A^2$ has the formula:

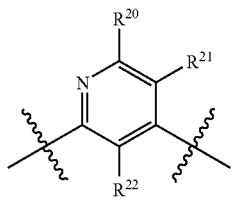

wherein $R^{20}$, $R^{21}$, and $R^{22}$ are as defined above.
In other of these embodiments, $A^2$ has the formula:

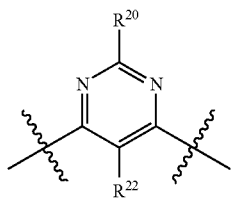

wherein $R^{20}$ and $R^{22}$ are as defined above.

In some of these embodiments, Y is —C($R^{23}$)=. In other embodiments, Y is —N=.

In some of these embodiments, $R^{23}$ is hydrogen, —N($R^{24}$)$R^{25}$, —O$R^{26}$, —S(O)$_r R^{27}$, or —C(O)$R^{28}$. In other embodiments, $R^{23}$ is hydrogen or —N($R^{24}$)$R^{25}$. In other embodiments, $R^{23}$ is hydrogen. In other embodiments, $R^{23}$ is —N($R^{24}$)$R^{25}$. In other embodiments, $R^{23}$ is —O$R^{26}$. In other embodiments, $R^{23}$ is —S(O)$_r R^{27}$. In other embodiments, $R^{23}$ is —C(O)$R^{28}$. In other embodiments, $R^{23}$ is hydrogen, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl.

In other of these embodiments, $R^{23}$ is substituted or unsubstituted alkyl, substituted or unsubstituted cycloalkyl, or substituted or unsubstituted heterocycloalkyl. In other embodiments, $R^{23}$ is substituted or unsubstituted alkyl. In other embodiments, $R^{23}$ is substituted or unsubstituted $C_1$-$C_6$ alkyl. In other embodiments, $R^{23}$ is substituted or unsubstituted cycloalkyl. In other embodiments, $R^{23}$ is substituted or unsubstituted heterocycloalkyl. In other embodiments, $R^{23}$ is methyl. In other embodiments, $R^{23}$ is substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl. In other embodiments, $R^{23}$ is substituted or unsubstituted aryl, substituted or unsubstituted aralkyl, substituted or unsubstituted heteroaryl, or substituted or unsubstituted heteroaralkyl. In other embodiments, $R^{23}$ is substituted or unsubstituted aryl, or substituted or unsubstituted heteroaryl. In other embodiments, $R^{23}$ is substituted or unsubstituted aryl. In other embodiments, $R^{23}$ is substituted or unsubstituted heteroaryl.

In other of these embodiments, $R^{23}$ is a substituted or unsubstituted pyridyl, substituted or unsubstituted phenyl, substituted or unsubstituted thiazolyl, substituted or unsubstituted oxazolyl, substituted or unsubstituted oxadiazolyl, substituted or unsubstituted imidazolyl, substituted or unsubstituted pyrazolyl, substituted or unsubstituted isoxazolyl, substituted or unsubstituted pyrimidyl, or substituted or unsubstituted furanyl. In other embodiments, $R^{23}$ is a substituted or unsubstituted thiazolyl, substituted or unsubstituted oxadiazolyl, or substituted or unsubstituted oxazolyl. In other embodiments, $R^{23}$ is substituted or unsubstituted phenyl. In other embodiments, $R^{23}$ is substituted or unsubstituted pyridyl. In other embodiments, $R^{23}$ is a substituted or unsubstituted thiazolyl. In other embodiments, $R^{23}$ is a substituted or unsubstituted oxazolyl. In other embodiments, $R^{23}$ is a substituted or unsubstituted oxadiazolyl. In other embodiments, $R^{23}$ is a substituted or unsubstituted imidazolyl. In other embodiments, $R^{23}$ is a substituted or unsubstituted pyrazolyl. In other embodiments, $R^{23}$ is a substituted or unsubstituted isoxazolyl. In other embodiments, $R^{23}$ is a substituted or unsubstituted pyrimidyl. In other embodiments, $R^{23}$ is a substituted or unsubstituted furanyl. In other embodiments, $R^{23}$ is a substituted or unsubstituted 2-thiazolyl. In other embodiments, $R^{23}$ is a substituted or unsubstituted 2-oxazolyl.

In some of these embodiments, $R^{24}$ and $R^{25}$ are independently hydrogen, substituted or unsubstituted alkyl, or substituted or unsubstituted heteroalkyl. In other embodiments, $R^{24}$ and $R^{25}$ are independently hydrogen, or substituted or unsubstituted alkyl. In other embodiments, at least one of $R^{24}$ and $R^{25}$ is hydrogen. In other embodiments, $R^{24}$ and $R^{25}$ are hydrogen. In other embodiments, at least one of $R^{24}$ and $R^{25}$ is substituted or unsubstituted alkyl. In other embodiments, $R^{24}$ and $R^{25}$ are independently substituted or unsubstituted alkyl. In other embodiments, at least one of $R^{24}$ and $R^{25}$ is methyl. In other embodiments, $R^{24}$ and $R^{25}$ are independently hydrogen, substituted or unsubstituted alkyl, —C(O)$R^{29}$, or —S(O$_2$)$R^{30}$. In other embodiments, one of $R^{24}$ and $R^{25}$ is —C(O)$R^{29}$ or —S(O$_2$)$R^{30}$. In other embodiments, n one of $R^{24}$ and $R^{25}$ is —C(O)$R^{29}$. In other embodiments, one of $R^{24}$ and $R^{25}$ is —S(O$_2$)R$^{30}$. In other embodiments, $R^{29}$ is independently hydrogen, substituted or unsubstituted alkyl, —N(R$^{31}$)R$^{32}$, or —OR$^{33}$. In other embodiments, $R^{29}$ is independently hydrogen, or substituted or unsubstituted alkyl. In other embodiments, $R^{29}$ is hydrogen. In other embodiments, $R^{29}$ is independently substituted or unsubstituted alkyl. In other embodiments, $R^{29}$ is methyl. In other embodiments, $R^{29}$ is independently —N(R$^{31}$)R$^{32}$, or —OR$^{33}$. In other embodiments, $R^{29}$ is —N(R$^{31}$)R$^{32}$. In other embodiments, $R^{29}$ is —OR$^{33}$.

In some of these embodiments, $R^{31}$, $R^{32}$, and $R^{33}$ are independently hydrogen, or substituted or unsubstituted alkyl.

In some of these embodiments, $R^{30}$ is hydrogen, substituted or unsubstituted alkyl. In other embodiments, $R^{30}$ is substituted or unsubstituted alkyl. In other embodiments, $R^{30}$ is methyl.

In some of these embodiments, $R^{20}$, $R^{21}$, and $R^{22}$ are independently hydrogen, or substituted or unsubstituted $C_1$-$C_{10}$ alkyl. In other embodiments, $R^{20}$, $R^{21}$, and $R^{22}$ are independently hydrogen, or substituted or unsubstituted $C_1$-$C_6$ alkyl. In other embodiments, at least one of $R^{20}$, $R^{21}$, and $R^{22}$ is hydrogen. In other embodiments, $R^{20}$, $R^{21}$, and $R^{22}$ are hydrogen.

In some of these embodiments, $R^{22}$ is hydrogen. In other embodiments, $R^{22}$ is hydrogen; and $R^{20}$ and $R^{21}$ are independently hydrogen, or substituted or unsubstituted $C_1$-$C_6$ alkyl. In other embodiments, $R^{22}$ is hydrogen; and $R^{20}$ and $R^{21}$ are independently hydrogen or methyl. In other embodiments, $R^{22}$ is hydrogen and one of $R^{20}$ and $R^{21}$ is methyl.

In other of these embodiments, at least one of $R^{20}$, $R^{21}$, or $R^{22}$ is —N(R$^{24}$)R$^{25}$. In other embodiments, $R^{20}$ is —N(R$^{24}$)R$^{25}$. In other embodiments, $R^{21}$ is —N(R$^{24}$)R$^{25}$. In other embodiments, $R^{22}$ is —N(R$^{24}$)R$^{25}$.

In some embodiments, $R^{20}$ is a substituted or unsubstituted cycloalkyl, substituted or unsubstituted heterocycloalkyl, a substituted or unsubstituted aryl, or substituted or unsubstituted heteroaryl. In other embodiments, $R^{20}$ is a substituted or unsubstituted aryl. In other embodiments, $R^{20}$ is a substituted or unsubstituted heteroaryl. In other embodiments, $R^{20}$ is a substituted or unsubstituted $C_5$-$C_7$ cycloalkyl, substituted or unsubstituted 5 to 7 membered heterocycloalkyl, substituted or unsubstituted 6 membered aryl, or substituted or unsubstituted 5 to 7 membered heteroaryl.

In some embodiments, $R^{20}$ is a substituted or unsubstituted phenyl, substituted or unsubstituted pyrazolyl, substituted or unsubstituted furanyl, substituted or unsubstituted imidazolyl, substituted or unsubstituted isoxazolyl, substituted or unsubstituted oxadiazolyl, substituted or unsubstituted oxazolyl, substituted or unsubstituted pyrrolyl, substituted or unsubstituted pyridyl, substituted or unsubstituted pyrimidyl, substituted or unsubstituted pyridazinyl, substituted or unsubstituted thiazolyl, substituted or unsubstituted triazolyl, substituted or unsubstituted thienyl, substituted or unsubstituted dihydrothieno-pyrazolyl, substituted or unsubstituted thianaphthenyl, substituted or unsubstituted carbazolyl, substituted or unsubstituted benzimidazolyl, substituted or unsubstituted benzothienyl, substituted or unsubstituted benzofuranyl, substituted or unsubstituted indolyl, substituted or unsubstituted quinolinyl, substituted or unsubstituted benzotriazolyl, substituted or unsubstituted benzothiazolyl, substituted or unsubstituted benzooxazolyl, substituted or unsubstituted benzimidazolyl, substituted or unsubstituted isoquinolinyl, substituted or unsubstituted isoindolyl, substituted or unsubstituted acridinyl, substituted or unsubstituted benzoisazolyl, substituted or unsubstituted dimethylhydantoin, substituted or unsubstituted pyrazinyl, substituted or unsubstituted tetrahydrofuranyl, substituted or unsubstituted pyrrolinyl, substituted or unsubstituted pyrrolidinyl, substituted or unsubstituted morpholinyl, substituted or unsubstituted indolyl, substituted or unsubstituted diazepinyl, substituted or unsubstituted azepinyl, substituted or unsubstituted thiepinyl, substituted or unsubstituted piperidinyl, or substituted or unsubstituted oxepinyl. In other embodiments, $R^{20}$ is a substituted or unsubstituted pyridyl, substituted or unsubstituted phenyl, substituted or unsubstituted thiazolyl, substituted or unsubstituted oxazolyl, substituted or unsubstituted oxadiazolyl, substituted or unsubstituted imidazolyl, substituted or unsubstituted pyrazolyl, substituted or unsubstituted isoxazolyl, substituted or unsubstituted pyrimidyl, or substituted or unsubstituted furanyl. In other embodiments, $R^{20}$ is a substituted or unsubstituted pyridyl, or substituted or unsubstituted phenyl. In other embodiments, $R^{20}$ is a substituted or unsubstituted pyridyl. In other embodiments, $R^{20}$ is a substituted or unsubstituted phenyl.

In some of these embodiments, X is —CH$_2$—, —O—, —N(R$^8$)—, or —S(O)$_w$—. In other embodiments, X is —CH$_2$—. In other embodiments, X is —O—. In other embodiments, X is —N(R$^8$)—. In other embodiments, X is —S(O)$_w$—.

In some of these embodiments, $R^6$ and $R^7$ are independently hydrogen, halogen, —OR$^{10}$, substituted or unsubstituted alkyl, substituted or unsubstituted cycloalkyl, substituted or unsubstituted heterocycloalkyl, substituted or unsubstituted aryl, or substituted or unsubstituted heteroaryl. In other embodiments, $R^6$ and $R^7$ are independently is hydrogen, —OR$^{10}$, or substituted or unsubstituted alkyl. In other embodiments, $R^6$ and $R^7$ are independently hydrogen, or substituted or unsubstituted alkyl. In other embodiments, $R^6$ and $R^7$ are independently hydrogen or —OR$^{10}$. In other embodiments, $R^6$ and $R^7$ are independently hydrogen or —OCH$_3$. In other embodiments, at least one of $R^6$ and $R^7$ is hydrogen. In other embodiments, $R^6$ and $R^7$ are hydrogen. In other embodiments, at least one of $R^6$ and $R^7$ are independently —OR$^{10}$. In other embodiments, at least one of $R^6$ and $R^7$ are independently —OMe.

In some of these embodiments, $R^8$ is hydrogen, substituted or unsubstituted alkyl, substituted or unsubstituted cycloalkyl, substituted or unsubstituted heterocycloalkyl, substituted or unsubstituted aryl, or substituted or unsubstituted heteroaryl. In other embodiments, $R^8$ is hydrogen, or substituted or unsubstituted alkyl. In other embodiments, $R^8$ is hydrogen, or substituted or unsubstituted cycloalkyl. In other embodiments, $R^8$ is hydrogen. In other embodiments, $R^8$ is —C(O)R$^{13}$ or —S(O)$_2$R$^{14}$. In other embodiments, $R^8$ is —C(O)R$^{13}$. In other embodiments, $R^8$ is —S(O)$_2$R$^{14}$.

In some of these embodiments, $R^2$ is hydrogen, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl. In other embodiments, $R^2$ is hydrogen, substituted or unsubstituted alkyl, substituted or unsubstituted cycloalkyl, or substituted or unsubstituted cycloalkyl-alkyl. In other embodiments, $R^2$ is hydrogen or substituted or unsubstituted alkyl. In other embodiments, $R^2$ is hydrogen or substituted or unsubstituted $C_1$-$C_6$ alkyl. In other embodiments, $R^2$ hydrogen. In other embodiments, $R^2$ is substituted or unsubstituted $C_1$-$C_6$ alkyl. In other embodiments, $R^2$ is methyl.

In some of these embodiments, $R^3$ is hydrogen, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl. In other embodiments, $R^3$ is hydrogen, substituted or unsubstituted alkyl, substituted or unsubstituted cycloalkyl, or substituted or unsubstituted cycloalkyl-alkyl. In other embodiments, $R^3$ is hydrogen or substituted or unsubstituted alkyl. In other embodiments, $R^3$ is hydrogen or substituted or unsubstituted $C_1$-$C_6$ alkyl. In other embodiments, $R^3$ hydrogen. In other embodiments, $R^3$ is substituted or unsubstituted $C_1$-$C_6$ alkyl. In other embodiments, $R^3$ is methyl.

In some of these embodiments, $R^4$ is hydrogen. In other embodiments, $R^4$ is —C(O)$R^{12}$. In other embodiments, $R^4$ is a substituted or unsubstituted alkyl, or substituted or unsubstituted cycloalkyl. In other embodiments, $R^4$ is a substituted or unsubstituted alkyl. In other embodiments, $R^4$ is a substituted or unsubstituted cycloalkyl, or substituted or unsubstituted heterocycloalkyl. In other embodiments, $R^4$ is a substituted or unsubstituted cycloalkyl. In other embodiments, $R^4$ is a substituted or unsubstituted heterocycloalkyl. In other embodiments, $R^4$ is a substituted or unsubstituted aryl, or substituted or unsubstituted heteroaryl. In other embodiments, $R^4$ is a substituted or unsubstituted aryl. In other embodiments, $R^4$ is a substituted or unsubstituted heteroaryl. In other embodiments, $R^4$ is a substituted or unsubstituted $C_5$-$C_7$ cycloalkyl, substituted or unsubstituted 5 to 7 membered heterocycloalkyl, substituted or unsubstituted 6 membered aryl, or substituted or unsubstituted 5 to 7 membered heteroaryl.

In other of these embodiments, $R^4$ is a substituted or unsubstituted phenyl (e.g., a 3-substituted phenyl), substituted or unsubstituted pyrazolyl (e.g., a substituted or unsubstituted 3-pyrazolyl, a substituted or unsubstituted 4-pyrazolyl, or a substituted or unsubstituted 5-pyrazolyl such as a 3-(5-substituted)pyrazolyl, a 4-(1-substituted)pyrazolyl, or a 5-(3-substituted)pyrazolyl), substituted or unsubstituted furanyl, substituted or unsubstituted imidazolyl, substituted or unsubstituted isoxazolyl (e.g., a substituted or unsubstituted 3-isoxazolyl or a substituted or unsubstituted 5-isoxazolyl, such as a 3-(5-substituted)isoxazolyl or a 3-(5-substituted)isoxazolyl), substituted or unsubstituted oxadiazolyl, substituted or unsubstituted oxazolyl (e.g., a substituted or unsubstituted 2-oxazolyl or a substituted or unsubstituted 4-oxazolyl, such as a 2-(4-substituted)oxazolyl or a 4-(2-substituted)oxazolyl), substituted or unsubstituted pyrrolyl, substituted or unsubstituted pyridyl (e.g., a substituted or unsubstituted 3-pyridyl, such as a 3-(5-substituted)pyridyl), substituted or unsubstituted pyrimidyl, substituted or unsubstituted pyridazinyl, substituted or unsubstituted thiazolyl (e.g., a substituted or unsubstituted 2-thiazolyl or a substituted or unsubstituted 4-thiazolyl, such as a 2-(4-substituted)thiazolyl or a 4-(2-substituted)thiazolyl), substituted or unsubstituted triazolyl, substituted or unsubstituted thienyl, substituted or unsubstituted dihydrothieno-pyrazolyl, substituted or unsubstituted thianaphthenyl, substituted or unsubstituted carbazolyl, substituted or unsubstituted benzimidazolyl, substituted or unsubstituted benzothienyl, substituted or unsubstituted benzofuranyl, substituted or unsubstituted indolyl, substituted or unsubstituted quinolinyl, substituted or unsubstituted benzotriazolyl, substituted or unsubstituted benzothiazolyl, substituted or unsubstituted benzooxazolyl, substituted or unsubstituted benzimidazolyl, substituted or unsubstituted isoquinolinyl, substituted or unsubstituted isoindolyl, substituted or unsubstituted acridinyl, substituted or unsubstituted benzoisazolyl, substituted or unsubstituted dimethylhydantoin, substituted or unsubstituted pyrazinyl, substituted or unsubstituted tetrahydrofuranyl, substituted or unsubstituted pyrrolinyl, substituted or unsubstituted pyrrolidinyl, substituted or unsubstituted morpholinyl, substituted or unsubstituted indolyl, substituted or unsubstituted diazepinyl, substituted or unsubstituted azepinyl, substituted or unsubstituted thiepinyl, substituted or unsubstituted piperidinyl, or substituted or unsubstituted oxepinyl. In other embodiments, $R^4$ is a substituted or unsubstituted pyridyl, substituted or unsubstituted phenyl, substituted or unsubstituted thiazolyl, substituted or unsubstituted oxazolyl, substituted or unsubstituted oxadiazolyl, substituted or unsubstituted imidazolyl, substituted or unsubstituted pyrazolyl, substituted or unsubstituted isoxazolyl, substituted or unsubstituted pyrimidyl, or substituted or unsubstituted furanyl. In other embodiments, $R^4$ is a substituted or unsubstituted pyridyl, or substituted or unsubstituted phenyl. In other embodiments, $R^4$ is a substituted or unsubstituted pyridyl. In other embodiments, $R^4$ is a substituted or unsubstituted phenyl.

In other of these embodiments, $R^4$ is phenyl (e.g., a 3-substituted phenyl or 3,5-disubstituted phenyl) or pyridyl (e.g., a 3-pyridyl, such as a 3-(5-substituted)pyridyl), substituted with one or more groups selected from halogen (e.g., F, Cl, Br, I), cyano, amido (e.g., methyl amide), hydroxyl, $C_1$-$C_6$ alkyl, and $C_1$-$C_6$ alkoxy; and wherein each $C_1$-$C_6$ alkyl and $C_1$-$C_6$ alkoxy is optionally substituted with 1-3 halogens (e.g., fluoro). In other embodiments, $R^4$ is phenyl, substituted (e.g., at the 3 position and/or the 5 position) with $C_1$-$C_6$ alkyl or $C_1$-$C_6$ alkoxy; and wherein each $C_1$-$C_6$ alkyl and $C_1$-$C_6$ alkoxy is optionally substituted with 1-3 halogens (e.g., fluoro). In other embodiments, $R^4$ is pyridyl (e.g., a 3-pyridyl, such as a 3-(5-substituted)pyridyl), substituted with $C_1$-$C_6$ alkyl (e.g., isopropyl, isobutyl, or $C_1$-$C_6$ alkoxy; and wherein each $C_1$-$C_6$ alkyl and $C_1$-$C_6$ alkoxy is optionally substituted with 1-3 halogens (e.g., fluoro). In other embodiments, $R^4$ is phenyl (e.g., a 3-substituted phenyl or 3,5-disubstituted phenyl) or pyridyl (e.g., a 3-pyridyl, such as a 3-(5-substituted) pyridyl), substituted with one or more groups selected from —$CF_3$, —$CHF_2$, and —$CH_2F$. In other embodiments, $R^4$ is phenyl, substituted (e.g., substituted at the 3 position and/or the 5 position) with one or more groups selected from —$CF_3$, —$CHF_2$, and —$CH_2F$. In other embodiments, $R^4$ is pyridyl (e.g., a 3-pyridyl, such as a 3-(5-substituted)pyridyl), substituted with one or more groups selected from —$CF_3$, —$CHF_2$, and —$CH_2F$. In other embodiments, $R^4$ is phenyl (e.g., a 3-substituted phenyl or 3,5-disubstituted phenyl) or pyridyl (e.g., a 3-pyridyl, such as a 3-(5-substituted)pyridyl), substituted with one or more —$OCH_3$. In other embodiments, $R^4$ is phenyl, substituted (e.g., substituted at the 3 position or the 5 position) with one or more —$OCH_3$. In other embodiments, $R^4$ is pyridyl, substituted with one or more —$OCH_3$.

In some of these embodiments, $R^5$ is hydrogen. In other embodiments, $R^5$ is a substituted or unsubstituted alkyl, or substituted or unsubstituted heteroalkyl. In other embodiments, $R^5$ is a substituted or unsubstituted cycloalkyl, substituted or unsubstituted heterocycloalkyl, substituted or unsubstituted aryl, or substituted or unsubstituted heteroaryl. In other embodiments, $R^5$ is a substituted or unsubstituted cycloalkyl, or substituted or unsubstituted heterocycloalkyl. In other embodiments, $R^5$ is a substituted or unsubstituted aryl, or substituted or unsubstituted heteroaryl. In other embodiments, $R^5$ is substituted or unsubstituted aryl. In other embodiments, $R^5$ is a substituted or unsubstituted heteroaryl. In other embodiments, $R^5$ is phenyl. In other embodiments, $R^5$ is phenyl, optionally substituted with one or more halogens. In other embodiments, $R^5$ is phenyl, optionally substituted with one or more fluoro groups. In other embodiments, $R^5$ is difluorophenyl. In other embodiments, $R^5$ is 3,5-difluorophenyl.

In some of these embodiments, $L^1$ is a bond, or substituted or unsubstituted alkylene. In other embodiments, $L^1$ is $-N(R^{17})-$, $-S(O)_q-$, or substituted or unsubstituted alkylene. In other embodiments, $L^1$ is $-N(R^{17})-$ or $-S(O)_q-$. In other embodiments, $L^1$ is $-N(R^{17})-$. In other embodiments, $L^1$ is $-S(O)_q-$. In other embodiments, $L^1$ is a bond. In other embodiments, $L^1$ is a substituted or unsubstituted alkylene. In other embodiments, $L^1$ is a substituted or unsubstituted $C_1$-$C_6$ alkylene. In other embodiments, $L^1$ is an unsubstituted $C_1$-$C_6$ alkylene. In other embodiments, $L^1$ is methylene.

In some of these embodiments, $L^4$ is a bond, or substituted or unsubstituted alkylene. In other embodiments, $L^4$ is $-N(R^{17})-$, $-S(O)_q-$, or substituted or unsubstituted alkylene. In other embodiments, $L^4$ is $-N(R^{17})-$ or $-S(O)_q-$. In other embodiments, $L^4$ is $-N(R^{17})-$. In other embodiments, $L^4$ is $-S(O)_q-$. In other embodiments, $L^4$ is a bond. In other embodiments, $L^4$ is $-C(O)-$. In other embodiments, $L^4$ is a substituted or unsubstituted alkylene. In other embodiments, $L^4$ is a substituted or unsubstituted $C_1$-$C_6$ alkylene. In other embodiments, $L^4$ is an unsubstituted $C_1$-$C_6$ alkylene. In other embodiments, $L^4$ is a branched unsubstituted $C_2$-$C_6$ alkylene. In other embodiments, $L^4$ is methylmethylene. In other embodiments, $L^4$ is methylene.

In some of these embodiments, $L^5$ is a bond, or substituted or unsubstituted alkylene. In other embodiments, $L^5$ is a bond. In other embodiments, $L^5$ is a substituted or unsubstituted alkylene. In other embodiments, $L^5$ is a substituted or unsubstituted $C_1$-$C_6$ alkylene. In other embodiments, $L^5$ is an unsubstituted $C_1$-$C_6$ alkylene. In other embodiments, $L^5$ is methylene.

In some of these embodiments, m is 0, 1, or 2. In other embodiments, m is 1 or 2. In other embodiments, m is 0. In other embodiments, m is 1. In other embodiments, m is 2.

In some of these embodiments, w is 0 or 2. In other embodiments, w is 0. In other embodiments, w is 2.

In some of these embodiments, n is 0 or 2. In other embodiments, n is 1 or 2. In other embodiments, n is 0. In other embodiments, n is 1. In other embodiments, n is 2.

In some of these embodiments, q is 0 or 2. In other embodiments, q is 1 or 2. In other embodiments, q is 0. In other embodiments, q is 1. In other embodiments, q is 2.

In some embodiments, the present invention embraces compounds of formula I where $A^1$ is a substituted or unsubstituted heteroaryl (e.g., a substituted or unsubstituted 5 membered heteroaryl); $A^2$ is substituted or unsubstituted arylene, or substituted or unsubstituted heteroarylene; X is $-CH_2-$; $L^1$ is a bond; $L^4$, and $L^5$ are independently substituted or unsubstituted alkylene; $R^2$ and $R^3$ are independently hydrogen, or substituted or unsubstituted alkyl; $R^4$ and $R^5$ are independently substituted or unsubstituted aryl, or substituted or unsubstituted heteroaryl; $R^6$ and $R^7$ are hydrogen; and m is 1.

In some embodiments, the present invention embraces compounds of formula I where $A^1$ is a substituted or unsubstituted thiazolyl (e.g., 2-thiazolyl); $A^2$ is substituted or unsubstituted phenyl, X is $-CH_2-$; $L^1$ is a bond; $L^4$, and $L^5$ are independently substituted or unsubstituted alkylene (e.g., methylene); $R^2$ and $R^3$ are hydrogen; $R^4$ substituted or unsubstituted aryl, or substituted or unsubstituted heteroaryl; $R^5$ is substituted or unsubstituted aryl; $R^6$ and $R^7$ are hydrogen; and m is 1.

In some embodiments, the present invention embraces compounds of formula I where $A^1$ is 2-thiazolyl; $A^2$ is

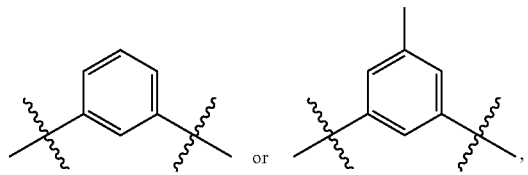

X is $-CH_2-$; $L^1$, $L^4$, and $L^5$ are methylene; $R^2$ and $R^3$ are hydrogen; $R^4$ is substituted or unsubstituted pyridyl (e.g., a substituted or unsubstituted 3-pyridyl, such as a 3-(5-substituted)pyridyl, for example 3-(5-fluoroalkyl)pyridyl), or substituted or unsubstituted phenyl (e.g., a 3-substituted phenyl, such as 3-fluoroalkyl phenyl); $R^5$ is phenyl; $R^6$ and $R^7$ are hydrogen; and m is 1.

In some embodiments, the present invention embraces compounds of formula I having the formula:

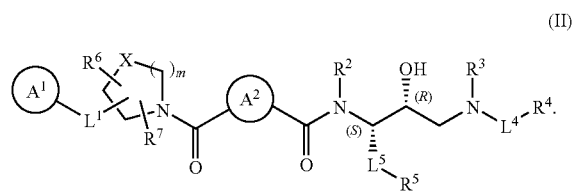

In Formula (II), $A^1$, $A^2$, X, $L^1$, $L^4$, $L^5$, $R^2$, $R^3$, $R^4$, $R^5$, $R^6$, $R^7$ and m are as defined above in the discussion of Formula (I).

In some embodiments, the compounds of the present invention include any one, any combination, or all of the compounds of Table 1.

A. Carrier Moieties

In U.S. Application No. 20040121947, and International Application No. PCT/USO2/34324 (Publication No. WO 03/039454), which are herein incorporated by reference for all purposes, isostere β-secretase inhibitors with and without a carrier moiety were shown to effectively reduce Aβ production in tg2576 mice expressing the Swedish mutation of the human amyloid precursor protein (Hsiao, K., et al., Science 274, 99-102 (1996)). Thus, one of skill in the art will recognize that the compounds of the invention may be administered with or without a carrier moiety.

A "carrier moiety," as used herein, refers to a chemical moiety covalently or non-covalently attached to a β-secretase inhibitor compound of the invention that enhances the ability of the compound to traverse the blood-brain barrier (BBB). The β-secretase inhibitors of the invention may be attached or conjugated to the carrier moiety by covalent interactions (e.g., peptide bonds) or by non-covalent interactions (e.g., ionic bonds, hydrogen bonds, van der Waals attractions). A covalently attached carrier moiety may be attached to any appropriate site on the compounds of the present invention (e.g., a hydroxyl group, amino group, thiol group, carboxylate group). One or more carrier moieties may be used on a compound of the invention. Multiple carrier moieties on a compound may be identical (e.g. multiple peptidyl carrier moieties) or different (e.g, a liphilic carrier moiety and a peptidyl carrier moiety). Attachment of multiple carrier moieties on a compound of the present invention may be identical (e.g., both covalently attached) or different (e.g., one covalently attached and one non-covalently attached).

The blood-brain barrier is a permeability barrier that exists between the extracellular fluid in the brain and the blood in the capillary lumen. The barrier stems from structural differences between the capillaries in the brain and capillaries found in other tissues. Most significant among the structural differences of brain capillaries are the tight junctions between endothelial cells. These specialized tight junctions create a very high trans-endothelial electrical resistance of 1500-2000 ohms/cm$^2$ compared to 3-33 ohms/cm$^2$ in capillary endothelial cells lying outside the brain, reducing the aqueous based para-cellular diffusion observed in other organs (Brightman, M. in Bradbury M W B (ed.) *Physiology and Pharmacology of the blood-brain barrier. Handbook of experimental pharmacology* 103, Springer-Verlag, Berlin, (1992); Lo, E. H., et al., *Brain Res. Rev.*, 38:140-148, (2001)). Thus, in some embodiments, the compounds of the present invention are covalently attached to a carrier moiety (represented by the symbol Y in the formulae above).

Any appropriate carrier moiety may be used in the present invention. Useful carrier moieties include, for example, lipophilic carrier moieties, enzymatic substrate carrier moieties, peptidyl carrier moieties, and nanoparticle carrier moieties. Carrier moieties may also include an oligosaccharide unit or other molecule linked to the compound by phosphoester or lipid-ester or other hydrolyzable bonds which are cleaved by glycosidases, phosphatases, esterases, lipases, or other hydrolases in the lysosomes and endosomes. The carrier moieties may contain guanidine, amino, or imidizole functional groups.

1. Lipophilic Carrier Moieties

Lipophilic carrier moieties increase the overall lipophilicity of a compound, thereby aiding in passage through the BBB. Lipophilicity can be quantified using any suitable approach known in the art. For example, the partition coefficient between octanol and water (log $P_{o/w}$) may be measured thereby indicating the degree of lipophilicity. In some embodiments, the lipophilic carrier moiety has a log $P_{o/w}$ of 1.5-2.5. Lipophilic carrier moieties are widely known in the art and are discussed in detail, for example, in Lambert, D. M., *Eur J Pharm Sci.*, 11:S15-27 (2000). Exemplary lipophilic carrier moieties used to increase the lipophilicity of a compound include modified and unmodified diglycerides, fatty acids, and phospholipids.

Some lipophilic carrier moieties undergo enzyme mediated oxidation after traversing the BBB, resulting in a hydrophilic membrane impermeable form of the carrier moiety that remains trapped behind the BBB (Bodor et al., *Pharmacol Ther* 76:1-27 (1997); Bodor et al., *American Chemical Society*, Washington, D.C. pp 317-337 (1995); Chen et al., *J Med Chem* 41:3773-3781 (1998); Wu et al., *J Pharm Pharmacol* 54:945-950 (2002)). Exemplary lipophilic carrier moieties that undergo enzyme mediated oxidation include 1,4-dihydrotrigonelline (Palomino et al., *J Med Chem*, 32:622-625 (1989)); alkyl phosphonate carrier moieties that have been successfully used to transport testosterone and zidovudine across the blood-brain barrier (Somogyi, G., et al., *Int J Pharm*, 166:15-26 (1998)); and the lipophilic dihydropyridine carrier moieties that are enzymatically oxidized to the ionic pyridinium salt (Bodor et al., *Science*, 214(18):1370-1372 (1981)).

2. Peptidyl Carrier Moieties

Peptidyl carrier moieties are moieties partially or wholly composed of a peptide (including polypeptides, proteins, antibodies, and antibody fragments) used to aid in the transport of compounds across the BBB (Wu et al., *J Clin Invest* 100:1804-1812 (1997); U.S. Pat. No. 4,801,575; Pardridge et al., *Adv Drug Deliv Rev*, 36:299-321 (1999)).

Peptidyl carrier moieties may interact with specific peptide transport systems, receptors, or ligands, that target the corresponding ligand or receptor on an endothelial cell of the BBB. Specific transport systems may include either carrier-mediated or receptor-mediated transport across the BBB (U.S. Pat. App. No. 20040110928). Exemplary peptidyl carrier moieties include insulin (Pardridge et al., *Nat Rev Drug Discov,* 1:131-139 (2002)); small peptides such as enkephalin, thyrotropin-releasing hormone, arginine-vassopressin (Bergley, *J Pharm Pharmacol*, 48:136-146 (1996)), Banks et al., *Peptides*, 13:1289-1294 (1992)), Han et al., *AAPS Pharm. Si.*, 2:E6 (2000)); chimeric peptides such as those described in WO-A-89/10134; amino acid derivatives such as those disclosed in U.S. Pat. App. No. 20030216589; tat peptide (Schwarze, S. R., et al., *Science* 285:1569-1572 (1999); polyarginine peptide (Wender, P. A., et al., *Proc. Natl. Acad. Sci. USA* 97:13003-13008 (2000)); insulin-like-growth factor-1; insulin-like-growth factor-2; transferrin; leptin; low-density lipoprotein (Pardridge, *Nat. Rev. Drug Discov.* 1:131-139 (2002); Colma et al., *Pharm. Res.* 17:266-274 (2000); Pardridge, *Endocrine Rev,* 7:314-330 (1986); Golden, et al., *J Clin Invest,* 99:14-18 (1997); Bickel et al., *Adv. Drug Deliv. Rev.* 46(1-3):247-79 (2001)); and basic fibroblast growth factor (bFGF) (U.S. Pat. App. No. 20040102369).

U.S. Application No. 20040121947, and International Application No. PCT/USO2/34324 (Publication No. WO 03/039454), disclose that confocal microscopic images of cells incubated with a fluorescent tat-conjugated isosteric β-secretase inhibitor showed uneven distribution inside cells. Some high fluorescence intensity was associated with the endosome and lysosome intracellular vesicular structures. This indicated that the tat carrier moiety may have been modified by proteases within the lysosome or endosome resulting in an inhibitor that was unable to exit the lysosomal or endosomal compartment. Lysosomes and endosomes contain many proteases, including hydrolase such as cathepsins A, B, C, D, H and L. Some of these are endopeptidase, such as cathepsins D and H. Others are exopeptidases, such as cathepsins A and C, with cathepsin B capable of both endo- and exopeptidase activity. The specificities of these proteases are sufficiently broad to hydrolyze a tat peptide away from the inhibitor compound, thus, hydrolyzing the carrier peptide away from the isosteric inhibitor. Thus, it has been shown that tat and other carrier peptides may be particularly useful for specific delivery of isosteric inhibitors to lysosomes and endosomes. When administered to a mammal by a mechanism such as injections, the conjugated compound will penetrate cells and permeate to the interior of lysosomes and endosomes. The proteases in lysosomes and endosomes will then hydrolyze tat, thereby preventing to escape from lysosomes and endosomes.

The carrier peptide may be tat or other basic peptides, such as oligo-L-arginine, that are hydrolyzable by lysosomal and endosomal proteases. Specific peptide bonds susceptible for the cleavage of lysosomal or endosomal proteases may be installed, thereby facilitating the removal of the carrier compound from the inhibitor. For example, dipeptides Phe-Phe, Phe-Leu, Phe-Tyr and others are cleaved by cathepsin D.

In one embodiment, the peptidyl carrier molecule includes cationic functional groups, such as the tat-peptide (Schwarze, S. R., et al., *Science* 285: 1569-1572 (1999)), or nine arginine residues (Wender, P. A., et al., *Proc. Natl. Acad. Sci. USA* 97:13003-13008 (2000)). Useful cationic functional groups include, for example, guanidine, amino, and imidazole functional groups. Thus, cationic functional groups also include amino acid side chains such as side chains of lysine, arginine, and histidine residues. In some embodiments, the peptidyl carrier molecule may include from 1-10 cationic functional groups. When a compound of the invention is conjugated or attached to a carrier moiety, the resulting conjugate may be referred to herein as a "Carrier Peptide-Inhibitor" conjugate or "CPI." The CPI conjugate can be administered to an in vitro sample or to a mammal thereby serving as a transport vehicle for a compound or compounds of the invention into a cell in an in vitro sample or in a mammal. The carrier moieties and CPI conjugates result in an increase in the ability of the compounds of the invention to effectively penetrate cells and the blood brain barrier to inhibit memapsin 2 from cleaving APP to subsequently generate Aβ.

Adsorptive-meditated transcytosis (AME) provides an alternative mechanism whereby peptidyl carrier moieties may cross the BBB. AME differs from other forms of transcytosis in that the initial binding of the carrier moiety to the luminal plasma membrane is mediated through either electrostatic interactions with anionic sites, or specific interactions with sugar residues. Uptake through AME is determined by the C-terminal structure and basicity of the carrier moiety. Exemplary adsorptive peptidyl carrier moieties include peptides and proteins with basic isoeletric points (cationic proteins), and some lectins (glycoprotein binding proteins). See Tamai, I., et al., *J. Pharmacol. Exp. Ther.* 280:410-415 (1997); Kumagai, A. K., et al., *J. Biol. Chem.* 262: 15214-15219 (1987).

Peptidyl carrier moieties also include antibody carrier moieties. Antibody carrier moieties are carrier moieties that include an antibody or fragment thereof. Typically, the antibody or antibody fragment is, or is derived from, a monoclonal antibody. Antibody carrier moieties bind to cellular receptors, or transporters expressed on the luminal surface of brain capillary endothelial cells (U.S. Patent App No. 20040101904). Exemplary antibodies, or fragments thereof, include MAb 83-14 that binds to the human insulin receptor (Pardridge et al., *Pharm Res.* 12:807-816 (1995)); anti-transferrin antibody (Li, J. Y., et al., *Protein Engineering* 12:787-796 (1999)); and monoclonal antibodies that mimic an endogenous protein or peptide which is known to cross the BBB as discussed above.

3. Nanoparticle Carrier Moieties

Nanoparticle carrier moieties are solid colloidal carriers generally less than a micron in diameter or length. The compound may be encapsulated in, adsorbed onto, or covalently linked to the surface of the nanoparticle carrier moiety. Nanoparticle carrier moieties have been used to successfully deliver a variety of compounds to the brain, including hexapeptide dalagrin, an enkephalin analog; loperamide; tubocerarine; and doxorubicin (Ambikanandan, et al., *J. Pharm Pharmaceut Sci* 6(2):252-273 (2003)). In addition to aiding transport into the brain, nonionic detergents such as polysorbate-80, which can be used to coat the nanoparticle, may be used to inhibit the efflux pump. Zordan-Nudo, T., et al., *Cancer Res,* 53:5994-6000 (1993). Exemplary materials for the manufacture of nanoparticle carrier moieties include polyalkylcyanoacrylate (PACA) (Bertling et al., *Biotechnol. Appl. Biochem.* 13: 390-405 (1991)); polybutylcyanoacrylate (PBCA) (Chavany et al., *Pharm. Res.* 9: 441-449 (1992)); polybutylcyanoacrylate with the peptide-drug complex absorbed onto the surface and coated with polysorbate 80 (Kreuter, J., et al., *Brain Res,* 674:171-174 (1995), Kreuter, J., *Adv Drug Deliv Rev,* 47:65-81, (2001), Kreuter, J., *Curr Med Chem,* 2:241-249 (2002)); polyisohexylcyanoacrylate (PIHCA) (Chavany et al., *Pharm. Res.* 11: 1370-1378 (1994)); polyhexylcyanoacrylate (PHCA) (Zobel et al., *Antisense Nucleic Acid Drug Dev.* 7:483-493 (1997)); and PEGylated polycyanoacrylate (Pilar, C., et al., *Pharm Res* 18(8):1157-1166 (2001)).

4. Linker Moieties

Linker moieties may be used to attach the carrier moiety to the β-secretase inhibitors of the present invention. For example, steric hinderance between the compound and the carrier can be prevented using polymer technology (e.g., PEGylation) in conjunction with the linker molecule to introduce a long spacer arm (Yoshikawa, T., et al., *J Pharmacol Exp Ther,* 263:897-903, 1992). Linker moieties may be cleavable or non-cleavable.

Cleavable linker molecules include a cleavable moiety. Any appropriate cleavable moiety is useful in the present invention, including for example, phosphoesters, esters, disulfides, and the like. Cleavable moieties also include those moieties capable of being cleaved by biological enzymes, such as peptidases, glycosidases, phosphatases, esterases, lipases, or other hydrolases. Cleavable linker molecules are especially useful where the carrier moiety interferes with the biological activity of the compound. Exemplary cleavable linker molecules include N-succinimidyl-3-2-pyridyldithiopropionate (SPDP), or N-hydrosuccinimide (NHS).

Non-cleavable linker molecules are those that involve the attachment of a carrier moiety to the compound through a linkage that is generally stable to biological conditions and enzymes. Non-cleavable linker molecules are typically used when the carrier moiety does not interfere with the biological activity of the compound. Exemplary non-cleavable linker molecules include thio-ether (e.g., m-maleimidobenzoyl N-hydroxysuccinimide ester (MBS)); amide (e.g., N-hydrosuccinimide (NHS—XX—); extended amide (e.g., N-hydrosuccinimide polyethylene glycol (NHS-PEG); and extended hydrazide linkages (e.g., hydrazide-PEG-biotin-); avidin-biotin; and PEG linkers (Ambikanandan et al., *J. Pharm Pharmaceut Sci* 6(2):252-273 (2003); Pardridge, *Adv Drug Deliv Rev,* 36:299-321 (1999); U.S. Pat. No. 6,287,792).

II. GENERAL SYNTHETIC METHODS

The compounds of the invention are synthesized by an appropriate combination of generally well-known synthetic methods. Techniques useful in synthesizing the compounds of the invention are both readily apparent and accessible to those of skill in the relevant art. The discussion below is offered to illustrate certain of the diverse methods available for use in assembling the compounds of the invention. However, the discussion is not intended to define the scope of reactions or reaction sequences that are useful in preparing the compounds of the present invention.

A method for synthesizing compounds of the invention is by adapting the synthesis for N-((2S,3R)-3-hydroxy-1-phenyl-4-(3-(trifluoromethyl)benzylamino)butan-2-yl)-3-methyl-5-((R)-2-(4-methylthiazol-2-yl)pyrrolidine-1-carbonyl) benzamide (1):

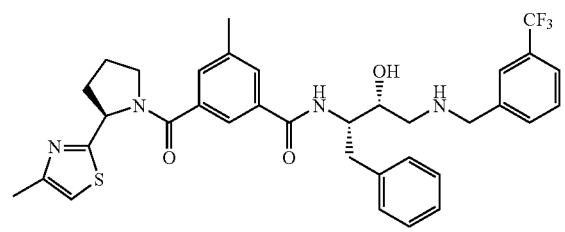

which is shown below in Scheme 1:

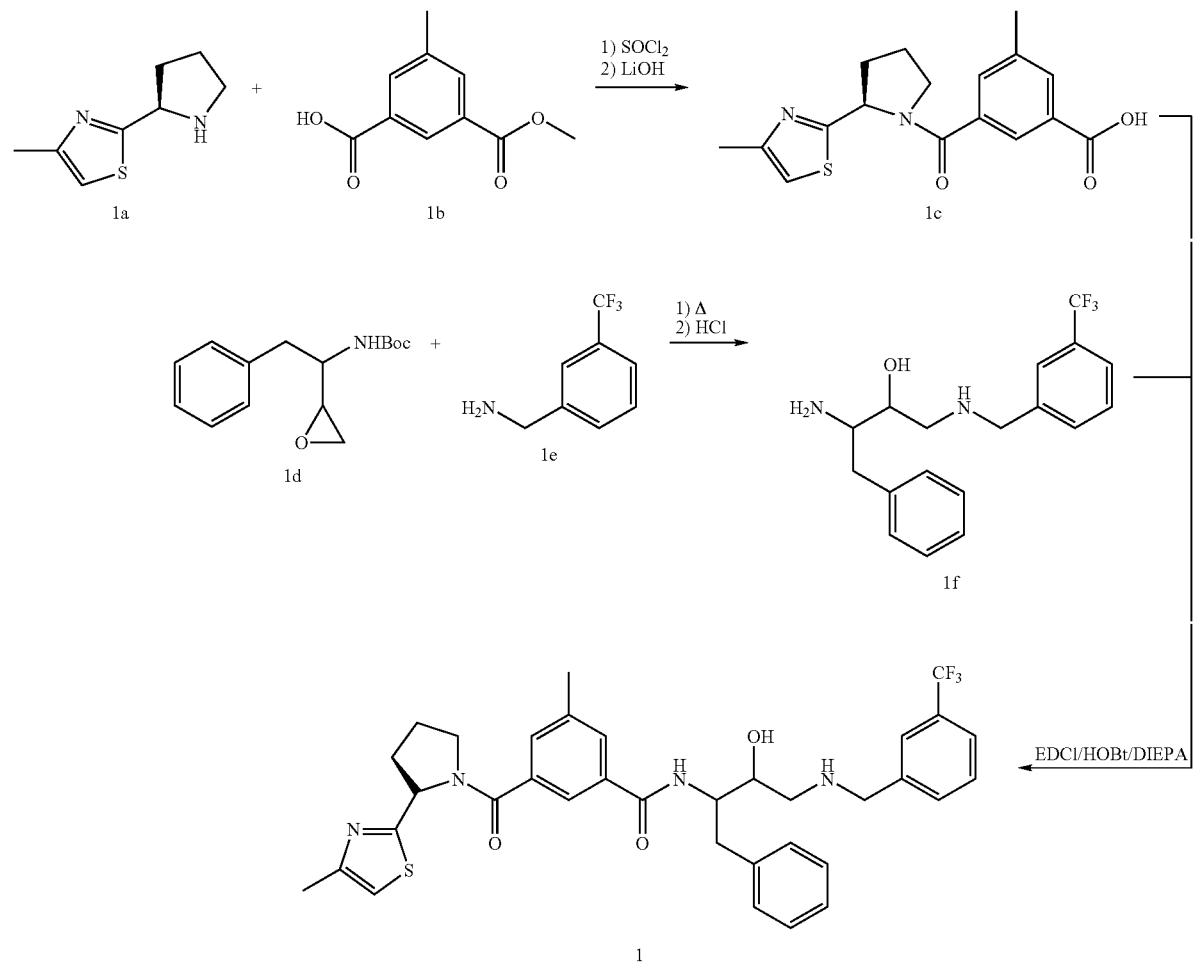

Synthesis of cyclic amine 1a and partially protected isophthalic acid 1b (and related building blocks for variations of the invention) are detailed in the Examples section below. The corresponding isophthalamides may be formed, for example, by coupling a secondary amine 1a with the partially protected isophthalic acid 1b using thionyl chloride ($SOCl_2$) followed by ester hydrolysis under basic conditions (such as LiOH) to generate 1c.

Treatment of the Boc-protected epoxide 1d with an appropriate amine 1e, followed by removal of the Boc protecting group under acidic conditions yields aminoalcohol building block 1f.

Alternatively, as shown in the examples below, epoxides such as 1d may be coupled to an appropriate aldehyde to generate the corresponding amino alcohol. Here the expoxide ring-opening is conducted using ammonia to generate a primary amine which is subsequently coupled to the desired aldehyde under reductive amination conditions (such as $NaBH_3CN$ or $NaB(OAc)_3H$, followed by acid) to generate the desired fragment.

Standard amide coupling of 1f with fragment 1c using common coupling agents (e.g., EDCI with HOBt) under basic conditions gives rise to desired inhibitors, such as 1.

As described in the Examples section below, some inhibitor compounds herein may be synthesized by combining the described fragments in an alternative order. For example, certain inhibitor compounds may be generated by coupling the hydroxyl amine fragment (such as 1f above) with an isophthalic acid fragment (such as 1b), followed by coupling with the secondary amine (such as fragment 1a). The order of coupling various fragments to synthesize the described compounds can be easily determined by the skilled artisan using the teachings provided herein.

III. BETA-SECRETASE INHIBITOR ACTIVITY

To develop useful β-secretase inhibitors, candidate inhibitors capable of selectively decreasing memapsin 2 catalytic activity may be identified in vitro and subsequently tested for their ability to reduce the production of Aβ. The activity of the inhibitor compounds can be assayed utilizing methods known in the art and/or those methods presented herein.

Compounds that decrease memapsin 2 catalytic activity may be identified and tested using biologically active memapsin 2, either recombinant or naturally occurring. Memapsin 2 can be found in native cells, isolated in vitro, or co-expressed or expressed in a cell. Measuring the reduction in the memapsin 2 catalytic activity in the presence of an inhibitor relative to the activity in the absence of the inhibitor may be performed using a variety of methods known in the art.

For example, the compounds may be tested for their ability to cause a detectable decrease in hydrolysis of a β-secretase site of a peptide in the presence of memapsin 2. These data can be expressed, for example, as $K_i$, $K_i$ apparent, $V_i/V_o$, or percentage inhibition. $K_i$ is the inhibition equilibrium constant which indicates the ability of compounds to inhibit a given enzyme (such as memapsin 2, memapsin 1, and/or cathepsin D). Numerically lower $K_i$ values indicate a higher affinity of the compounds of the invention for the enzyme. The $K_i$ value is independent of the substrate, and converted from $K_i$ apparent.

$K_i$ apparent is determined in the presence of substrate according to established techniques (see, for example, Bieth, J., *Bayer-Symposium V: Proteinase Inhibitors*, pp. 463-469, Springer-Verlag, Berlin (1994)). The standard error for the $K_i$ apparent is the error from the nonlinear regression of the $V_i/V_o$ data measured at different concentrations of the compounds of the invention (e.g., between about 10 nM to about 1000 nM) employing well-known techniques (see, for example, Bieth, J., *Bayer-Symposium V: Proteinase Inhibitors*, pp. 463-469, Springer-Verlag, Berlin (1994), Ermolieff, J., et al., *Biochemistry* 39:12450-12456 (2000), the teachings of which are incorporated herein by reference in their entirety). $V_i/V_o$ depicts the ratio of initial conversion velocities of an enzyme substrate (Ermolieff, et al., *Biochemistry* 40:12450-12456 (2000)) by an enzyme in the absence ($V_o$) or presence ($V_i$) of an inhibitor. A $V_i/V_o$ value of 1.0 indicates that a compound does not inhibit the enzyme at the concentration tested. A $V_i/V_o$ value less than 1.0 indicates that a compound of the invention inhibits enzyme activity.

In some embodiments, the compounds described herein (e.g., any compound or group of compounds of Example 3) are capable of reducing memapsin 2 beta-secretase activity. In some embodiments, the compounds have a memapsin 2 beta-secretase $K_i$ and/or $K_i$ apparent (e.g., using any inhibitory assay described herein) of less than about any one of 10 µM, 5 µM, or less than about any one of 750, 500, 400, 300, 200, 100, 50, 25, 10, 5, 2, or 1 nM; or from about 1 to 5, 1 to 10, 1 to 100, 1 to 300, 1 to 500, 1 to 1000, 100 to 500, 200 to 500, 300 to 500, 100 to 750, 200 to 750, 300 to 750, 400 to 750, 500 to 750, 100 to 1000, 250 to 1000, 500 to 1000, or 750 to 1000 nM. In some embodiments, the compounds have a memapsin 2 beta-secretase $K_i$ and/or $K_i$ apparent (e.g., using any inhibitory assay described herein) of less than about 300, 301 to 500, or greater than 501 nM.

Once compounds are identified that are capable of reducing the hydrolysis of a β-secretase site of a peptide in the presence of memapsin 2, the compounds may be further tested for their ability to selectively inhibit memapsin 2 relative to other enzymes. Typically, the other enzyme is a peptide hydrolase, such as memapsin 1 or cathepsin D. Compounds that decrease cathepsin D catalytic activity or memapsin 1 catalytic activity are tested using biologically active enzyme, either recombinant or naturally occurring. Cathepsin D or memapsin 1 catalytic activity can be found in native cells, isolated in vitro, or co-expressed or expressed in a cell. Inhibition by a compound of the invention is measured using standard in vitro or in vivo assays such as those well known in the art or as otherwise described herein.

For example, selectivity of a compound may be measured by determining the extent to which memapsin 2 hydrolyzes a substrate peptide compared to the extent to which the same compound inhibits memapsin 1 and/or cathepsin D cleaving of a β-secretase site of a substrate peptide in the presence of the compound. Exemplary substrate peptides are useful in determining the activity of memapsin 2 includes APP and derivatives thereof, such as FS-2 MCA-SEVNLDAEFK-DNP; SEQ ID NO.: 2) (Bachem Americas, Torrance, Calif.). Exemplary substrate peptides are useful in determining the activity of memapsin 1 and cathepsin D include, for example, peptides which include the sequence ELDLAVEFWHDR (SEQ ID NO.: 1). These substrate peptides can be synthesized using known peptide synthesis methods, e.g., solid-phase peptide synthesis (e.g., FMOC amino acid coupling etc.). These data can be expressed, for example, as $K_i$ apparent, $V_i/V_o$, or percentage inhibition and depict the inhibition of a compound for memapsin 2 catalytic activity relative to memapsin 1 or cathepsin D catalytic activity. For example, if the $K_i$ of a reaction between an inhibitor compound of the invention and memapsin 1 or cathepsin D is 1000 and the $K_i$ of a reaction between an inhibitor compound of the invention and memapsin 2 is 100, the inhibitor compound inhibits the β-secretase activity of memapsin 2 with ten-fold selectivity over memapsin 1 or cathepsin D.

In some embodiments, the compounds described herein (e.g., any compound or group of compounds of Example 3) are capable of selectively reducing memapsin 2 relative to memapsin 1 and/or cathepsin D. In some embodiments, the compounds are capable of selectively reducing memapsin 2 relative to memapsin 1 and/or cathepsin D with greater than about 2-fold selectivity, or greater than about any one of 3, 5, 7, 10, 25, 50, 75, 100, 300, 200, 500, 750, 1000, 2000, 5000, or 10000-fold selectivity. In some embodiments, the compounds have a memapsin 2 beta-secretase $K_i$ and/or $K_i$ apparent (e.g., using any inhibitory assay described herein) of less than about 10 µM, 5 µM, 1 µM, or less than about any one of 750, 500, 400, 300, 200, 100, 50, 25, 10, 5, 2, or 1 nM, or from about any of 1 to 5, 1 to 10, 1 to 100, 1 to 300, 1 to 500, 1 to 1000, 100 to 500, 200 to 500, 300 to 500, 100 to 750, 200 to 750, 300 to 750, 400 to 750, 500 to 750, 100 to 1000, 250 to 1000, 500 to 1000, or 750 to 1000 nM; and have a memapsin 1 and/or cathepsin D $K_i$ and/or $K_i$ apparent of more than about 10 µM, 5 µM, 1 µM, or more than about any one of 750, 500, 400, 300, 200, 100, 50, 25, 10, 5, 2, or 1 nM, or from about any of 1 to 5, 1 to 10, 1 to 100, 1 to 300, 1 to 500, 1 to 1000, 100 to 500, 200 to 500, 300 to 500, 100 to 750, 200 to 750, 300 to 750, 400 to 750, 500 to 750, 100 to 1000, 250 to 1000, 500 to 1000, or 750 to 1000 nM.

Compounds demonstrating the ability to cause a detectable decrease in hydrolysis of a β-secretase site of a peptide in the presence of memapsin 2 (or, in addition, selectivity of action toward memapsin 2), may be tested in cell models or animal models for their ability to cause a detectable decrease in the amount or production of β-amyloid protein (Aβ). For example, isosteric inhibitors of memapsin 2 have been tested for their ability to decrease Aβ production in cultured cells (see U.S. Patent Application Publication No. 20040121947, International Application No. PCT/US02/34324 (Publication No. WO 03/039454), and International Application No. PCT/US06/13342 (Publication No. WO 06/110668, the contents of which are hereby incorporated by reference)). Briefly, inhibitors may be added to a culture of cells (e.g., human embryonic kidney (HEK293) cells, HeLa cells, Chinese hamster ovary cells, or neuroblastoma line M17 cells) stably transfected with a nucleic acid constructs that encode human APP Swedish mutant (or London mutation or double mutant) and, if needed, a nucleic acid construct encoding human memapsin 2. Immunoprecipitation of Aβ followed by SDS-gel electrophoresis allows detection and quantitation of the amount of Aβ produced in the presence and absence of inhibitor.

In addition to cell cultures, animal models may be used to test inhibitors of memapsin 2 for their ability to decrease Aβ production. For example, an animal (e.g., tg2576 mice)

expressing the Swedish mutation of the human amyloid precursor protein (Hsiao, K., et al., *Science* 274, 99-102 (1996) may be injected intraperitoneally with an inhibitor. The plasma may then be collected and Aβ levels determined by capture ELISA (BioSource International, Camarillo, Calif.).

In some embodiments, the compounds described herein (e.g., any compound or group of compounds of Example 3) are capable of reducing cellular Aβ production. In some embodiments, the compounds are capable of reducing cellular Aβ production with a IC50 (e.g., using an Aβ inhibitory assay described herein) of less than about 10 µM, 5 µM, 1 µM, or less than about 750, 500, 400, 300, 200, 100, 50, 25, 10, 5, 2, or 1 nM, or from about 1 to 5, 1 to 10, 1 to 100, 1 to 300, 1 to 500, 1 to 1000, 100 to 500, 200 to 500, 300 to 500, 100 to 750, 200 to 750, 300 to 750, 400 to 750, 500 to 750, 100 to 1000, 250 to 1000, 500 to 1000, or 750 to 1000 nM. In some embodiments, the compounds are capable of reducing cellular Aβ production with a IC50 (e.g., using an Aβ inhibitory assay described herein) of less than 1 µM, between 1 and 5 µM, or greater than 5 µM.

The presence of inhibitors in organs of animal models or within cellular compartments may be ascertained using a fluorescent tag conjugated to the inhibitor and visualization via confocal microscopy (see U.S. Patent Application Publication No. 20040121947, and International Application No. PCT/USO2/34324 (Publication No. WO 03/039454), the contents of which are hereby incorporated by reference in their entireties).

The sample obtained from the mammal can be a fluid sample, such as a plasma or serum sample; or can be a tissue sample, such as a brain biopsy. The amount of β-amyloid protein or a decrease in the production of β-amyloid protein can be measured using standard techniques (e.g., western blotting and ELISA assays).

Further examples of assays for identifying memapsin 2-β-secretase inhibitors are set forth in the Examples section below. Other methods for assaying the activity of memapsin 2, memapsin 1, and cathepsin D and the activity of agents that decrease the activity of these enzymes are known in the art. The selection of appropriate assay methods is well within the capabilities of those of skill in the art, particularly in view of the teaching provided herein.

IV. PHARMACEUTICAL COMPOSITIONS

In another aspect, the present invention provides pharmaceutical compositions comprising a memapsin 2 β-secretase inhibitor compound of the invention or a memapsin 2 β-secretase inhibitor compound in combination with a pharmaceutically acceptable carrier. The pharmaceutical compositions may include optical isomers, diastereomers, or pharmaceutically acceptable salts of the inhibitors disclosed herein. The memapsin 2 β-secretase inhibitor included in the pharmaceutical composition may be covalently attached to a carrier moiety, as described above. Alternatively, the memapsin 2 β-secretase inhibitor included in the pharmaceutical composition is not covalently linked to a carrier moiety.

A "pharmaceutically suitable carrier," as used herein refers to pharmaceutical excipients, for example, pharmaceutically, physiologically, acceptable organic, or inorganic carrier substances suitable for enteral or parenteral application which do not deleteriously react with the extract. Suitable pharmaceutically acceptable carriers include water, salt solutions (such as Ringer's solution), alcohols, oils, gelatins and carbohydrates such as lactose, amylose or starch, fatty acid esters, hydroxymethylcellulose, and polyvinyl pyrrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like which do not deleteriously react with the compounds of the invention.

The compounds of the invention can be administered alone or can be coadministered to the individual. Coadministration is meant to include simultaneous or sequential administration of the compounds individually or in combination (more than one compound). Thus, the preparations can also be combined, when desired, with other active substances related to the treatment of a specified condition (e.g., to reduce metabolic degradation).

A. Formulations

The β-secretase inhibitors of the present invention can be prepared and administered in a wide variety of oral, parenteral and topical dosage forms. Thus, the compounds of the present invention can be administered by injection (e.g., intravenously, intramuscularly, intracutaneously, subcutaneously, intraduodenally, or intraperitoneally). Also, the compounds described herein can be administered by inhalation, for example, intranasally. Additionally, the compounds of the present invention can be administered transdermally. Compounds of the invention may also be administered locally (e.g., ocular administration such as topical eye drops or ointment). It is also envisioned that multiple routes of administration (e.g., intramuscular, oral, transdermal) can be used to administer the compounds of the invention. Accordingly, the present invention also provides pharmaceutical compositions comprising a pharmaceutically acceptable carrier or excipient and one or more compounds of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substance, which may also act as diluents, flavoring agents, binders, preservatives, tablet disintegrating agents, or an encapsulating material.

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampules are convenient unit dosages. The compounds of the invention can also be incorporated into liposomes or administered via transdermal pumps or patches. Pharmaceutical admixtures suitable for use in the present invention are well-known to those of skill in the art and are described, for example, in Pharmaceutical Sciences (17th Ed., Mack Pub. Co., Easton, Pa.) and WO 96/05309, the teachings of both of which are hereby incorporated by reference.

Ocular administration preparations (e.g., in use of glaucoma treatment) include, but are not limited to, formulations in saline, optionally with additional carriers, stabalizers, etc. know to those of skill in the art.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60 and 80; Pluronic F-68, F-84 and P-103; cyclodextrin; polyoxyl 35 castor oil; or other agents known to those skilled in the art. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, combinations of the foregoing, and other agents known to those skilled in the art. Such agents are typically employed at a level between about 0.01% and about 2% by weight. Determination of acceptable amounts of any of the above adjuvants is readily ascertained by one skilled in the art.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

B. Effective Dosages

Pharmaceutical compositions provided by the present invention include compositions wherein the active ingredient is contained in an effective amount, i.e., in an amount effective to achieve its intended purpose. The actual amount effective for a particular application will depend, inter alia, on the condition being treated. For example, when administered in methods to treat Alzheimer's disease, such compositions will contain an amount of active ingredient effective to achieve the desired result (e.g., decreasing β-secretase activity or β-amyloid production). Determination of an effective amount of a compound of the invention is well within the capabilities of those skilled in the art, especially in light of the detailed disclosure herein.

The dosage and frequency (single or multiple doses) administered to a mammal can vary depending upon a variety of factors, including a disease that results in increased activity of memapsin 2 or increased accumulation of β-amyloid protein, whether the mammal suffers from another disease, and its route of administration; size, age, sex, health, body weight, body mass index, and diet of the recipient; nature and extent of symptoms of the disease being treated (e.g., Alzheimer's disease), kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the effective amount can be initially determined from cell culture assays. Target concentrations will be those concentrations of active compound(s) that are capable of reducing the activity of memapsin 2 activity, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring memapsin 2 inhibition and adjusting the dosage upwards or downwards, as described above. Adjusting the dose to achieve maximal efficacy in humans based on the methods described above and other methods as are well-known in the art is well within the capabilities of the ordinarily skilled artisan, particularly in view of the teaching provided herein.

Dosages may be varied depending upon the requirements of the individual and the compound being employed. The dose administered to an individual, in the context of the present invention should be sufficient to affect a beneficial therapeutic response in the individual over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. In one embodiment of the invention, the dosage range is 0.001% to 10% w/v. In another embodiment, the dosage range is 0.1% to 5% w/v.

Additional examples of dosages which can be used are an effective amount within the dosage range of about 0.1 µg/kg to about 300 mg/kg, or within about 1.0 µg/kg to about 40 mg/kg body weight, or within about 1.0 µg/kg to about 20 mg/kg body weight, or within about 1.0 µg/kg to about 10 mg/kg body weight, or within about 10.0 µg/kg to about 10 mg/kg body weight, or within about 100 µg/kg to about 10 mg/kg body weight, or within about 1.0 mg/kg to about 10 mg/kg body weight, or within about 10 mg/kg to about 100 mg/kg body weight, or within about 50 mg/kg to about 150 mg/kg body weight, or within about 100 mg/kg to about 200 mg/kg body weight, or within about 150 mg/kg to about 250 mg/kg body weight, or within about 200 mg/kg to about 300 mg/kg body weight, or within about 250 mg/kg to about 300 mg/kg body weight. Other dosages which can be used are about 0.01 mg/kg body weight, about 0.1 mg/kg body weight, about 1 mg/kg body weight, about 10 mg/kg body weight, about 20 mg/kg body weight, about 30 mg/kg body weight, about 40 mg/kg body weight, about 50 mg/kg body weight, about 75 mg/kg body weight, about 100 mg/kg body weight, about 125 mg/kg body weight, about 150 mg/kg body weight, about 175 mg/kg body weight, about 200 mg/kg body weight, about 225 mg/kg body weight, about 250 mg/kg body weight, about 275 mg/kg body weight, or about 300 mg/kg body weight. Compounds of the present invention may be administered in a single daily dose, or the total daily dosage may be administered in divided dosage of two, three or four times daily.

Utilizing the teachings provided herein, an effective prophylactic or therapeutic treatment regimen can be planned which does not cause substantial toxicity and yet is entirely effective to treat the clinical symptoms demonstrated by the particular individual. This planning should involve the careful choice of active compound by considering factors such as compound potency, relative bioavailability, individual body weight, presence and severity of adverse side effects, preferred mode of administration and the toxicity profile of the selected agent.

C. Kits

Also provided are kits for administration of the compositions described herein (e.g., including the compounds, formulations, and dosage forms described herein).

In certain embodiments the kits may include a dosage amount of at least one composition as disclosed herein. Kits may further comprise suitable packaging and/or instructions for use of the composition. Kits may also comprise a means for the delivery of the composition thereof.

The kits may include other pharmaceutical agents for use in conjunction with the composition described herein. In some variations, the pharmaceutical agent(s) may be one or more anti-psychotic drug. These agents may be provided in a separate form, or mixed with the compounds of the present invention, provided such mixing does not reduce the effectiveness of either the pharmaceutical agent or composition described herein and is compatible with the route of administration. Similarly the kits may include additional agents for adjunctive therapy or other agents known to the skilled artisan as effective in the treatment or prevention of the conditions described herein.

The kits may optionally include appropriate instructions for preparation and administration of the composition, side effects of the composition, and any other relevant information. The instructions may be in any suitable format, including, but not limited to, printed matter, videotape, computer readable disk, optical disc or directions to internet-based instructions.

In another aspect of the invention, kits for treating an individual who suffers from or is susceptible to the conditions described herein are provided, comprising a first container comprising a dosage amount of a composition as disclosed herein, and instructions for use. The container may be any of those known in the art and appropriate for storage and delivery of intravenous composition. In certain embodiments the kit further comprises a second container comprising a pharmaceutically acceptable carrier, diluent, adjuvant, etc. for preparation of the composition to be administered to the individual.

Kits may also be provided that contain sufficient dosages of the inhibitor (including compositions thereof) as disclosed herein to provide effective treatment for an individual for an extended period, such as 1-3 days, 1-5 days, a week, 2 weeks, 3, weeks, 4 weeks, 6 weeks, 8 weeks, 3 months, 4 months, 5 months, 6 months, 7 months, 8 months, 9 months or more.

Kits may also include multiple doses of the composition and instructions for use and packaged in quantities sufficient for storage and use in pharmacies, for example, hospital pharmacies and compounding pharmacies.

The kits may include the composition as described herein packaged in either a unit dosage form or in a multi-use form. The kits may also include multiple units of the unit dose form.

In certain embodiments, are provided the composition described herein in a unit dose form. In other embodiments the compositions may be provided in a multi-dose form (e.g., a blister pack, etc.).

D. Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g., Fingl et al., In: THE PHARMACOLOGICAL BASIS OF THERAPEUTICS, Ch. 1, p. 1, 1975. The exact formulation, route of administration and dosage can be chosen by the individual physician in view of the individual's condition and the particular method in which the compound is used.

V. METHODS OF REDUCING THE ACTIVITY OF MEMAPSIN 2 BETA-SECRETASE

In another aspect of the present invention, the β-secretase inhibitor compounds of the invention can be employed in methods to decrease memapsin 2 activity, decrease hydrolysis of a β-secretase site of a memapsin 2 substrate, and/or decrease the accumulation of β-amyloid protein relative to the amount of memapsin 2 activity, hydrolysis of a β-secretase site, and accumulation of β-amyloid protein, respectively, in the absence of the β-secretase inhibitor.

In an exemplary embodiment, a method of reducing memapsin 2 activity is provided. The method includes contacting a memapsin 2 with a β-secretase inhibitor compound of the present invention. The memapsin 2 may be contacted in any appropriate environment (e.g., in vitro, ex vivo, in vivo). The memapsin 2 activity is decreased relative the amount of activity in the absence of β-secretase inhibitor.

In another exemplary embodiment, a method is provided of selectively reducing memapsin 2 activity using an inhibitor of the present invention. Selective reduction of the activity of memapsin 2 means that memapsin 2 is not only reduced relative to its activity in the absence of inhibitor, but is reduced to a greater extent as compared to the reduction in activity due to inhibitor action against another peptide hydrolase. For example, as described above, the reduction in activity of an enzyme may be expressed in terms of the inhibitory constant ($K_i$). Where an inhibitor selectively reduces the activity of memapsin 2, the $K_i$ of the reaction between an inhibitor compound of the invention and memapsin 2 is less than the $K_i$ of the reaction between an inhibitor compound of the invention and another peptide hydrolase.

In an exemplary embodiment, the $K_i$ of the reaction between an inhibitor compound of the invention and memapsin 2 is at least 2 times less than the $K_i$ of the reaction between an inhibitor compound of the invention and another peptide hydrolase. In another exemplary embodiment, the $K_i$ of the reaction between an inhibitor compound of the invention and memapsin 2 is at least 10 times less than the $K_i$ of the reaction between an inhibitor compound of the invention and another peptide hydrolase. In another exemplary embodiment, the $K_i$ of the reaction between an inhibitor compound of the invention and memapsin 2 is at least 100 times less than the $K_i$ of the reaction between an inhibitor compound of the invention and another peptide hydrolase. In another exemplary embodiment, the $K_i$ of the reaction between an inhibitor compound of the invention and memapsin 2 is at least 1000 times less than the $K_i$ of the reaction between an inhibitor compound of the invention and another peptide hydrolase. In another exemplary embodiment, the $K_i$ of the reaction between an inhibitor compound of the invention and memapsin 2 is at least 10000 times less than the $K_i$ of the reaction between an inhibitor compound of the invention and another peptide hydrolase.

In some related embodiments, the inhibitor selectively reduces the activity of memapsin 2 as compared to memapsin 1. In other related embodiments, the inhibitor selectively reduces the activity of memapsin 2 as compared to cathepsin D.

Thus, the present invention provides methods of selectively reducing the activity of memapsin 2. The method includes contacting a memapsin 2 with a β-secretase inhibitor compound of the present invention. In a related embodiment, the method includes contacting the memapsin 2 with a β-secretase inhibitor in the presence of memapsin 1. In an alternative related embodiment, the method includes contacting the memapsin 2 with a β-secretase inhibitor in the presence of cathepsin D. In yet another related embodiment, the method includes contacting the memapsin 2 with a β-secretase inhibitor in the presence of cathepsin D and memapsin 1.

In some embodiments, the activity of memapsin-2 β-secretase may be determined by measuring the hydrolysis of a β-secretase site of a β-secretase substrate. Thus, the present invention also relates to a method of decreasing the hydrolysis of a β-secretase site of a β-secretase substrate by contacting a memapsin 2 with a β-secretase inhibitor compound of the present invention. In some embodiments, the hydrolysis of a β-secretase site is decreased relative the amount of hydrolysis in the absence of the inhibitor. In other embodiments, the hydrolysis is selectively reduced as compared to hydrolysis by memapsin 1 and/or cathepsin D. Thus, a method of selectively decreasing hydrolysis of a β-secretase site of a β-amyloid precursor protein relative to memapsin 1 and/or cathepsin D in a sample is provided. The method includes contacting a memapsin 2 with a β-secretase inhibitor compound of the present invention.

In another embodiment, the present invention relates to a method of decreasing the amount of β-amyloid protein in a sample by contacting the memapsin 2 with an inhibitor compound of the present invention. The amount of β-amyloid protein in a sample is decreased relative the amount of β-amyloid protein in the sample in the absence of the inhibitor. Thus, the accumulation of β-amyloid protein is thereby decreased.

Memapsin 2 may be contacted in any suitable environment or any suitable sample. For example, memapsin 2 may be contacted in vitro, within a cell, or within a mammal. Typically, in vitro solutions are selected such that the components do not substantially interfere with the enzymatic activity of memapsin 2 (e.g., aqueous solutions). In some embodiments, the in vitro solution includes a biological sample, such as a mammalian sample. Exemplary mammalian samples include plasma or serum samples and tissue samples, such as a brain biopsy. Any appropriate cell or cellular sample may be selected in which to contact the memapsin 2 with the inhibitor. The cell may contain endogenous memapsin 2 or recombinant memapsin 2 as previously described (see U.S. Patent Application Publication No. 20040121947 (the contents of which are hereby incorporated by reference), and International Application No. PCT/USO2/34324 (Publication No. WO 03/039454)). Exemplary cells include human embryonic kidney (HEK293) cells, HeLa cells, Chinese hamster ovary cells, or neuroblastoma line M17 cells Hela cells, 293 cells. In an exemplary embodiment, the compounds of the invention are administered to a mammal to inhibit the hydrolysis of a β-secretase site of a β-amyloid precursor protein (e.g., a mouse, rabbit or human).

VI. METHODS OF TREATING ALZHEIMER'S DISEASE

In another aspect of the present invention, the β-secretase inhibitor compounds of the invention can be employed in the treatment of diseases or conditions associated with β-secretase activity, hydrolysis of a β-secretase site of a β-amyloid precursor protein, and/or β-amyloid protein accumulation. Typically, a mammal is treated for the disease or condition. In an exemplary embodiment, the disease is Alzheimer's disease.

Thus, in some embodiments, the invention provides a method of treating Alzheimer's disease in a mammal comprising the step of administering to the mammal in need thereof an effective amount of the β-secretase inhibitors of the invention. The mammals treated with the inhibitors may be human primates, nonhuman primates or non-human mammals (e.g., rodents, canines). In one embodiment, the mammal is administered a compound of the invention that reduces β-secretase activity (inhibits memapsin 1 and memapsin 2 activity). In another embodiment, the mammal is administered a compound that selectively reduces memapsin 2 activity. In a related embodiment, the compound has minimal or no effect on reducing memapsin 1 activity. Therefore, the present invention also provides a method of treating Alzheimer's disease in a subject in need thereof, the method comprising administering to the subject an effective amount of a β-secretase inhibitor compound. In an exemplary embodiment, the β-secretase inhibitor compound is part of a pharmaceutical formulation, as described above.

The inhibitor compounds of the invention can be employed in the treatment of diseases or conditions associated with β-secretase activity, which can halt, reverse or diminish the progression of the disease or condition, in particular Alzheimer's disease. In addition to compounds that decrease memapsin 2 activity, compounds that selectively reduce memapsin 2 activity are useful to treat diseases or conditions or biological processes associated with memapsin 2 activity rather than diseases or conditions or biological processes associated with both memapsin 2 activity and another peptide hydrolase (such as cathepsin D or memapsin 1).

For example, both memapsin 1 and memapsin 2 cleave amyloid precursor protein (APP) at a β-secretase site to form β-amyloid protein (also referred to herein as Aβ or β-amyloid protein). Thus, both memapsin 1 and memapsin 2 have β-secretase activity (Hussain, I., et al., *J. Biol. Chem.* 276: 23322-23328 (2001)). However, the β-secretase activity of memapsin 1 is significantly less than the β-secretase activity of memapsin 2 (Hussain, I., et al., *J. Biol. Chem.* 276:23322-23328 (2001)). Memapsin 2 is localized in the brain, and pancreas, and other tissues (Lin, X., et al., *Proc. Natl. Acad. Sci. USA* 97:1456-1460 (2000)) and memapsin 1 is localized preferentially in placentae (Lin, X., et al., *Proc. Natl. Acad. Sci. USA* 97:1456-1460 (2000)). Alzheimer's disease is associated with the accumulation of Aβ in the brain as a result of cleaving of APP by β-secretase (also referred to herein as memapsin 2, ASP2 and BACE). Thus, methods employing the compounds which selectively inhibit memapsin 2 activity relative to memapsin 1 activity may be important in the treatment of memapsin 2-related diseases, such as Alzheimer's disease. Selective inhibition of memapsin 2 activity makes the compounds of the invention suitable drug candidates for use in the treatment of Alzheimer's disease.

VII. METHODS OF TREATING GLAUCOMA

In another aspect of the present invention, the β-secretase inhibitor compounds of the invention can be employed in the treatment of diseases associated with vision loss (e.g., glaucoma). In some embodiments, the invention provides a method of treating glaucoma (e.g. closed-angle glaucoma and open-angle glaucoma) in an individual comprising the step of administering to the individual in need thereof an effective amount of the β-secretase inhibitors of the invention. In an exemplary embodiment, the β-secretase inhibitor compound is part of a pharmaceutical formulation, as described above.

In some aspects, the inhibitor compounds of the invention can be employed in the treatment of diseases or conditions associated with β-secretase activity, which can halt, reverse or diminish the progression of glaucoma (e.g. closed-angle glaucoma and open-angle glaucoma). In some embodiments, the inhibitor compounds of the invention can be used to halt, reverse or diminish the loss of retinal ganglion cells (RGCs). In other embodiments, compounds of the inhibition are employed to improve or decrease intraocular pressure (TOP).

Compounds of the invention may be used to treat glaucoma by one of several known routes of administration, including, but not limited to, orally (e.g., in tablet or capsule form), parenterally (e.g., injected into the anterior chamber, intravenous, intramuscular, or subcutaneous), or locally (e.g., topical eye drops or ointment). Compounds of the invention may also be formulated for sustained release during glaucoma treatment.

Additional embodiments for treating glaucoma with compounds of the invention are described by adapting one or more of the methods in Guo, et. al. *Proc. Natl. Acad. Sci.*, 14, 13444-13449 (2007); Yamamoto, et. al., Neuroscience Letters, 370, 61-64 (2004); and/or Urcola et. al., Exp. Eye Research, 83, 429-437 (2006). The content of these applications are hereby incorporated by reference in its entireties.

A. Methods of Administering Beta-Secretase Inhibitors to the CNS

The inhibitor compounds of the present invention may be administered to the CNS through either invasive or non-invasive methods. Non-invasive methods of administration include those methods that do not require the use of a mechanical or physical means to breach the integrity of the blood-brain barrier. Typically, non-invasive methods include the use of immunoliposomes, blood-brain barrier disruption (BBBD), or the olfactory pathway.

Immunoliposomes are liposomes with antibodies or antibody fragments that bind to receptors or transporters expressed on brain capillary endothelial cells attached to the surface of the liposome. An exemplary immunoliposome combines polymer (e.g., PEGylation) technology with that of chimeric peptide technology. For example, the β-secretase inhibitor may be packaged into a unilamellar lipid vesicle containing a $PEG^{2000}$ derivative that contains a reactive groups at one end, for attachment to a complementary reactive group of an antibody or fragment thereof. Complementary reactive groups are well known in the art and, include, for example, amine and activated carboxylic acids, thiols and maleimides, and the like (Ambikanandan et al., *J. Pharm Pharmaceut Sci* 6(2):252-273 (2003); Huwyler et al., *Proc. Natl. Acad. Sci. USA*, 93:14164-14169 (1996); and Huwyler et al., *J Pharmcol Exp Ther.* 282:1541-1546 (1997); and U.S. Pat. No. 6,372,250, all of which are herein incorporated by reference for all purposes in their entirety).

Blood-brain barrier disruption is a temporal loss of the integrity of the tight junctions between endothelial cells that comprise the blood brain barrier. Typically, the compound is administered via systemic or intercarotid injection in conjuction with transient blood-brain barrier disruption (BBBD). Exemplary agents useful for inducing BBBD include solvents such as dimethyl sulfoxide (DMSO); ethanol (EtOH); metals (e.g., aluminum); X-irradiation; induction of pathological conditions (e.g., hypertension, hypercapnia, hypoxia, or ischemia); anti-neoplastic agents (e.g., VP-16, cisplatin, hydroxyurea, fluorouracil and etoposide); or concurrent systemic administration of the convulsant drug metrazol and the anti-convulsant drug pentobarbital (Ambikanandan et al., *J. Pharm Pharmaceut Sci* 6(2):252-273 (2003)); vasoactive leukotrienes (Black et al., *J Neurosurg,* 81(5):745-751 (1994)); intracarotid infusion of bradykinin, histamine, or the synthetic bradykinin analog RMP-7 (Miller et al., *Science* 297: 1116-1118 (2002), Matsukado, et al., *Neurosurgery* 39:125-133 (1996), Abbott, et al., *Mol Med Today* 2:106-113 (1996), Emerich et al., *Clin Pharmacokinet* 40:105-123 (2001)); hyaluronidase (U.S. Patent Application Publication No. 20030215432, Kreil, et al. *Protein Sci.,* 4(9):1666-1669 (1995)); and intercarotid injection of inert hypertonic solutions such as mannitol, or arabinose (Neuwelt, E. A., et al., in Neuwelt E A (ed), *Implications of the Blood Brain Barrier and its Manipulation: Clinical Aspects*. Vol. 2, Plenum Press, New York, (1989), Neuwelt, et al., *J Nucl Med,* 35:1831-1841 (1994), Neuwelt et al., *Pediatr Neurosurg* 21:16-22 (1994), Kroll et al., *Neurosurg,* 42:1083-1099 (1998), Rapoport, *Cell Mol Neurobiol* 20:217-230 (2000), and Doran et al., *Neurosurg* 36:965-970, (1995)).

Olfactory pathway administration is the intranasal delivery of the compound to the olfactory nerves in the upper third of the nasal passages. After intranasal delivery, the compound is transported back along the sensory olfactory neurons to yield significant concentrations in the cerebral spinal fluid (CSF) and olfactory bulb (Thorne et al., *Brain Res,* 692(1-2):278-282 (1995); Thorne et al., *Clin Pharmacokinet* 40:907-946 (2001); Ilium, *Drug Discov Today* 7:1184-1189 (2002); U.S. Pat. No. 6,180,603; U.S. Pat. No. 6,313,093; and U.S. Patent Application Publication No. 20030215398).

Invasive methods of administration are those methods that involve a physical breach of the blood-brain barrier typically through a mechanical or physical means to introduce the compound into the CSF, or directly into the parenchyma of the brain. Typically, invasive methods of administration may include injection or surgical implantation of the compound.

In injection methods, a needle is used to physically breach the BBB and deliver the compound directly into the CSF. Exemplary injection methods include intraventricular, intrathecal, or intralumbar routes of administration and may also involve infusion of the compound through a reservoir external to the body (Krewson et al., *Brain Res* 680:196-206 (1995); Harbaugh et al., *Neurosurg.* 23(6):693-698 (1988); Huang et al., *J Neurooncol* 45:9-17 (1999); Bobo et al., *Proc Natl Acad Sci USA* 91:2076-2082 (1994); Neuwalt et al., *Neurosurg.* 38(4):1129-1145 (1996)).

In surgical implantation methods, the compound is placed directly into the parenchyma of the brain. Exemplary surgical implantation methods may include incorporation of the compound into a polyanhydride wafer placed directly into the interstitium of the brain (Brem et al., *Sci Med* 3(4):1-11 (1996); Brem et al., *J Control Release* 74:63-67 (2001)).

VIII. CRYSTALLIZED COMPLEXES

In another aspect, the present invention provides a crystallized complex containing a memapsin 2 protein and a β-secretase inhibitor of the present invention. Memapsin 2 proteins useful in forming co-crystals with isostere compounds (e.g., memapsin 2 protein fragments, transmembrane proteins, etc.) have been previously discussed in detail (see U.S. Patent Application Publication No. 20040121947, and International Application No. PCT/US02/34324 (Publication No. WO 03/039454)). These memapsin 2 proteins are equally useful in forming crystallized complexes with β-secretase inhibitors of the present invention.

The crystallized complex may be formed employing techniques described in U.S. Patent Application Publication No. 20040121947, and International Application No. PCT/USO2/34324 (Publication No. WO 03/039454). Briefly, a nucleic acid construct encoding the protein is generated, is expressed in a host cell, such as a mammalian host cell (e.g., Hela cell, 293 cell) or a bacterial host cell (e.g., *E. coli*), is purified and is crystallized with a compound or compounds of the invention. The diffraction resolution limit of the crystallized protein can be determined, for example, by x-ray diffraction or neutron diffraction techniques.

In an exemplary embodiment, the crystallized protein may have an x-ray diffraction resolution limit not greater than about 4.0 Å. The crystallized protein may also have an x-ray diffraction resolution limit not greater than about 4.0 Å, about 3.5 Å, about 3.0 Å, about 2.5 Å, about 2.0 Å, about 1.5 Å, about 1.0 Å, or about 0.5 Å. In some embodiments, the crystallized protein may also have an x-ray diffraction resolution limit not greater than about 2 Å. The diffraction resolution limit of the crystallized protein can be determined employing standard x-ray diffraction techniques.

In an other exemplary embodiment, the β-secretase inhibitor of the crystallized complex is in association with said protein at an $S_3'$ binding pocket, an $S_4'$ binding pocket and/or an $S_4$ binding pocket. $S_3'$, $S_4'$, and $S_4$ binding pockets are discussed in detail in U.S. Patent Application Publication No. 20040121947, and International Application No. PCT/USO2/34324 (Publication No. WO 03/039454).

The terms and expressions which have been employed herein are used as terms of description and not of limitation, and there is no intention in the use of such terms and expressions of excluding equivalents of the features shown and described, or portions thereof, it being recognized that various modifications are possible within the scope of the invention claimed. Moreover, any one or more features of any embodiment of the invention may be combined with any one or more other features of any other embodiment of the invention, without departing from the scope of the invention. For example, the features of the β-secretase inhibitors of the present invention are equally applicable to the methods of treating disease states and/or the pharmaceutical compositions described herein. All publications, patents, and patent applications cited herein are hereby incorporated by reference in their entirety for all purposes.

IX. EXAMPLES

Example 1

Preparation of Selected Beta-Secretase Inhibitors and Precursor Compounds

The described synthesis of Beta-Secretase inhibitors and precursor compounds is related to WO 2006/110668, filed on Apr. 10, 2006 and entitled "Compounds Which Inhibit Beta-Secretase Activity and Methods of Use Thereof," the content of which is incorporated herein by reference in its entirety, and particularly with respect to the synthetic methods described therein, e.g., paragraphs 150-153 and paragraphs 215-285; and U.S. Provisional Patent Application No. 60/952,198, filed on Jul. 26, 2007 and entitled "Compounds Which Inhibit Beta-Secretase Activity and Methods of Use Thereof," the content of which is incorporated herein by reference in its entirety, and particularly with respect to the synthetic methods described therein, e.g., paragraphs 83-86 and paragraphs 161-354.

The precursor compounds synthesized below are useful in the methods of making compounds of the present invention provided herein. Using the guidance provided, (for example, in the Exemplary Syntheses of Scheme 1) one skilled in the art will immediately recognize that the exemplified synthesis of the below precursor compounds may be modified using well known techniques and the teaching provided herein to arrive at a wide variety of inhibitor compounds. Certain starting materials described, and some precursor compounds not described, may be commercially available and purchased from, for example, Sigma-Aldrich, Alfa Aesar, or Ryan Scientific.

NMR spectra were collected on a Varian Mercury model VX-300 NMR spectrometer. NMR solvent were purchased from Cambrige Isotope Laboratories.

Solvents used in the synthesis of inhibitor compounds were purchased from Aldrich, VWR, and EMD. Solvents were ACS Reagent Grade or higher, and used without further purification.

Example 1.1

Synthesis of Amine Building Blocks

Example 1.1.1

(4-methylthiazol-2-yl)methanamine

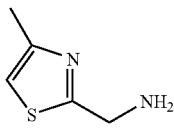

Methylthiazole (1.0 g, 10.1 mmol) in THF at −78° C. was treated with n-BuLi (1.6 M, 7.56 mL) for 30 min, DMF (1.4 mL, 18.2 mmol) was added dropwise. The resulting reaction mixture was warmed to r.t. After the starting material disappeared (by TLC), the reaction mixture was recooled to 0° C. and LAH (0.69 g, 18.5 mmol) was added. The mixture was warmed to r.t. and stirred for 1 h, the reaction was quenched with aqueous $NH_4Cl$, diluted with EtOAc. The organic solution was separated, extracted twice with EtOAc, dried with $Na_2SO_4$, and concentrated. The residue was purified with flash chromatography to give the corresponding alcohol as a light yellow oil. $^1$H-NMR: (300 MHz, $CDCl_3$), d: 6.89 (s, 1H); 4.95 (s, 2H); 2.48 (s, 3H).

Methylthiazole methanol (0.57 g, 4.4 mmol) was treated with mesyl chloride (0.42 mL, 5.4 mmol) and triethyl ethylamine at 0° C. in dichloromethane. The resulting mixture was stirred for 20 minutes followed by quenching with aqueous $NH_4Cl$. Evaporation of the solvent from the organic layer and flash chromatography of the residue afforded the corresponding mesylate as an oil. The mesylate (0.25 g, 1.2 mmol) was then dissolved in DMF and sodium azide (0.62 g, 9.6 mmol) was added. The mixture was heated to reflux for 2 hours followed by cooling and washing with aqueous $NH_4Cl$. Evaporation of the solvent from the organic layer resulted in the corresponding azide. The azide (0.14 g, 0.91 mmol) was dissolved in ethyl acetate, $Pd(OH)_2$ (0.07 g) was added, and the suspension was stirred under a hydrogen atmosphere for 5 hours. The suspension was filtered through Celite. Evaporation of the solvent and flash chromatography of the residue afforded the desired methylthiazole methylamine as a yellow oil. $^1$H-NMR: (300 MHz, $CDCl_3$), d: 6.74 (m, 1H); 4.09 (m, 2H); 2.37 (s, 3H).

Using an alternative synthetic route, $NaBH_4$ (0.75 g, 19.9 mmol, 1.3 eq) was added to a stirred solution of 4-methylthiazole-2-carbaldehyde (Aldrich, 1.7 ml, 2.0 g, 15.3 mmol, 1 eq) in 30 ml anhydrous MeOH at 0° C. After 45 min the solvent was removed in vacuo. The residue was diluted with saturated aqueous $NH_4Cl$ and extracted with EtOAc (×3). The combined organics were washed with brine (×1) and dried over $Na_2SO_4$. The inorganics were filtered off, and the solvent was removed in vacuo. Purification via flash chromatography yielded (4-methylthiazol-2-yl)methanol in quantitative yield.

Diphenylphosphoryl azide (DPPA) (1.2 eq) and 1,8-Diazabicyclo(5.4.0)undec-7-ene (DBU) (1.2 eq) were added to a stirred solution of (4-methylthiazol-2-yl)methanol (1 eq) in 7 ml anh. toluene under Ar. After stirring overnight, the solvent was removed in vacuo. Purification via flash chromatography yielded 2-(azidomethyl)-4-methylthiazole.

2-(azidomethyl)-4-methylthiazole was dissolved in 5 ml MeOH. $Pd(OH)_2$ (20% by wt. on carbon) was added and the mixture was stirred vigorously under $H_2$ overnight. The mixture was filtered through Celite, and the filter cake rinsed with MeOH. The solvent was removed in vacuo yielding (4-methylthiazol-2-yl)methanamine.

Example 1.1.2

1-(pyridin-3-yl)ethanamine

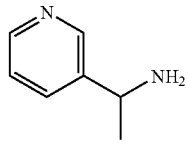

To a solution of 3-acetylpyridine (82.6 mmol) in methanol (200 mL) was added ammonium acetate (1.03 mol) in one portion at room temperature. After the mixture was stirred for 20 min, sodium cyanoborohydride (57.8 mmol) was added. After being stirring for one day, 6 M hydrochloric acid was added. The resulting solution was washed with diethyl ether, and then the aqueous phase was basified to pH=10 with potassium hydroxide. The liberated amine was extracted with chloroform, and the combined organic extracts were dried over anhydrous sodium sulfate. After removal of the solvent under reduced pressure, the crude amine was obtained as a colorless oil, which was further purified by distillation under reduced pressure. $^1$H NMR (300 MHz, $CDCl_3$), d: 8.552 (d, 1H), 8.453 (dd, 1H), 7.678 (m, 1H), 7.206-7.261 (m, 1H), 4.148 (q, 1H), 1.378 (d, 3H).

Example 1.1.3

1-(4-methylthiazol-2-yl)ethylcarbamate

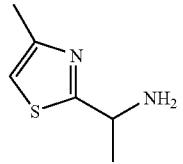

A mixture of Boc-alanine-thioamide (1.39 g, 6.81 mmol), chloroacetone (0.65 mL, 8.18 mmol) and calcium carbonate (1.0 g, 10.22 mmol) were refluxed in ethanol (25 mL) for 4 h. The reaction was cooled to room temperature and quenched with 20 mL of saturated aq. $NaHCO_3$ solution. Ethanol was evaporated under reduced pressure and extracted with ethyl acetate (2×30 mL). The combined organic layers was dried over $Na_2SO_4$ and concentrated. The residue was chromatographed on silica gel (20% ethyl acetate/80% hexane) to yield 48% of the Boc-protected product. The desired 1-(4-methylthiazol-2-yl)ethylcarbamate was then generated by treatment with HCl (in methanol or dioxane) or trifluoroacetic acid in dichloromethane.

Example 1.1.4

(4-isopropylpyridin-2-yl)methanamine

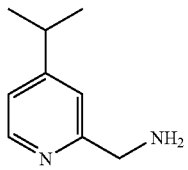

To a stirring mixture of 5.1 g (14.3 mmol) of Ph$_3$PCH$_3$Br in 25 mL of THF at 0° C. was added 11.0 mL of n-BuLi (1.6M in hexanes) dropwise over a period of 20 min. After 1 h, 1.5 g (12.8 mmol) of 1-(pyridin-4-yl)ethanone was added in 20 mL of THF. The mixture was stirred at 0° C. for 1 h and then at r.t for 50 min. The mixture was filtered through a Buchner funnel. Saturated NH$_4$Cl and H$_2$O were added, and the layers were separated. The organic layer was washed with brine, dried over Na$_2$SO$_4$, filtered, and concentrated. Purification by flash silica gel chromatography (54% EtOAc/hexanes) provided the isopropenyl pyridine as a pale yellow liquid.

A mixture of 4-(prop-1-en-2-yl)pyridine and 342 mg of 20% Pd(OH)$_2$ in 15 mL of EtOAc and 10 mL of MeOH was stirred under H$_2$ balloon at r.t. After 24 h, 305 mg of 20% Pd(OH)$_2$ was added, and after 6 h the mixture was filtered through Celite, filtered, and concentrated. The crude product was dissolved in 15 mL of MeOH and 512 mg of 20% Pd(OH)$_2$ was added. The mixture was stirred under H$_2$ balloon for 11.5 h at r.t., filtered through Celite, and concentrated to give the 4-isopropylpyridine which was used without further purification.

A solution of 4-isopropylpyridine and 1.5 mL of 30% H$_2$O$_2$ in 7 mL of AcOH was heated at 135° C. A total of 15.4 mL of H$_2$O$_2$ was added in 4 portions, and the solution was refluxed for 2 h. Chloroform and water were added, the layers were separated, and the aqueous layer was extracted 3 times with CHCl$_3$. The combined extracts were dried over Na$_2$SO$_4$, filtered, and concentrated. Purification by flash silica gel chromatography (5% MeOH/CHCl$_3$) provided 139 mg of the 4-isopropylpyridine N-oxide as an orange oil.

To a stirring solution of 139 mg (1.01 mmol) of 4-isopropylpyridine N-oxide in 10 mL of CH$_2$Cl$_2$ at r.t. was added 160 µL (1.20 mmol) of TMSCN. After 5 min., 100 µL (1.09 mmol) of dimethylcarbamyl chloride was added, and the solution was stirred at r.t. for 16 h. The solution was diluted with chloroform and washed with 20 mL of 10% aqueous K$_2$CO$_3$. The layers were separated, and the aqueous layer was extracted 3 times with CHCl$_3$. The combined extracts were dried over Na$_2$SO$_4$, filtered, and concentrated. Purification by flash silica gel chromatography (30% EtOAc/hexanes) provided 4-isopropylpicolinonitrile with some impurity as a liquid.

To a stirring solution of 149 mg (1.01 mmol) of 4-isopropylpicolinonitrile in 7 mL of THF at 0° C. was added 150 mg (3.95 mmol) of LiAlH$_4$. After about 15 min., 250 mg of LiAlH$_4$ was added, and after about 15 min. the ice bath was removed and stirring was continued with warming to r.t. After 40 min., 400 µL of H$_2$O, 400 µL of 15% NaOH (aq), and 1.2 mL of brine were added in succession. The mixture was stirred for 85 min., filtered through Celite, and conc. to give 143 mg of (4-isopropylpyridin-2-yl)methanamine which was used without further purification.

Example 1.1.5

(6-isopropylpyridin-2-yl)methanamine

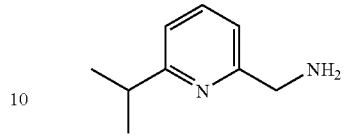

(6-isopropylpyridin-2-yl)methanamine was synthesized from the ketone following the general procedure as described for 4-isopropyl-2-pyridylmethylamine.

Example 1.1.6

(2-isopropylpyridin-4-yl)methanamine

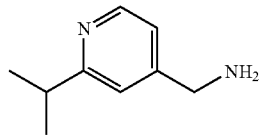

To a solution of 3.1 g (29.8 mmol) of 4-cyanopyridine and 7.7 g (87.4 mmol) of pyruvic acid in 150 mL of CH$_2$Cl$_2$ was added a solution of 150 mL of H$_2$O with 3.0 mL H$_2$SO$_4$ and 9.9 g (43.4 mmol) of (NH$_4$)$_2$S$_2$O$_8$. To this mixture was added 440 mg of AgNO$_3$. Let mixture stir with the light off for 2 h at 40° C. Solid NaOH was added to a pH=8, and the aqueous layer was extracted with CHCl$_3$. The extract was dried over Na$_2$SO$_4$, filtered, and concentrated. Flash silica gel chromatography (10% EtOAc/hexanes) provided 1.81 g colorless solid of the corresponding ketone (2-acetylisonicotinonitrile) with some impurity.

The isopropenyl pyridine (2-(prop-1-en-2-yl)isonicotinonitrile) was synthesized from 2-acetylisonicotinonitrile following the general procedure as described for 4-isopropyl-2-pyridylmethylamine.

A mixture of 154 mg (1.07 mmol) of 2-(prop-1-en-2-yl) isonicotinonitrile and 19.2 mg of 10% Pd/C with 1.7 mL of 1.25 N HCl in 10 mL of MeOH was stirred at r.t. under H$_2$ balloon for 14 h. The mixture was filtered through Celite and concentrated. Saturated NaHCO$_3$ was added, and the mixture concentrated with methanol, filtered through a sintered funnel, and reconcentrated to give 95.1 mg of crude (2-isopropylpyridin-4-yl)methanamine which was used without further purification.

Example 1.1.7 methyl 6-(aminomethyl)-2-methylnicotinate

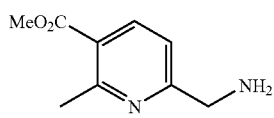

methyl 2-methylnicotinate was synthesized from 2-methylnicotinic acid following the general procedure as described for dimethylpyridine-3,5-dicarboxylate.

methyl 6-cyano-2-methylnicotinate was synthesized from methyl 2-methylnicotinate following the general procedure as described for 4-isopropyl-2-pyridylmethylamine.

methyl 6-(aminomethyl)-2-methylnicotinate was synthesized from methyl 6-cyano-2-methylnicotinate following the general procedure as described for 2-isopropyl-4-pyridylmethylamine.

Example 1.1.8

(2-fluoro-5-isopropylpyridin-3-yl)methanamine

To a stirring mixture of 3.0 g (21.3 mmol) of boronic acid in 60 mL of THF and 30 mL of 2.0 M $Na_2CO_3$ (degassed) was added 1.31 g (1.14 mmol) of $Pd(PPh_3)_4$ followed by 2.8 mL (32.1 mmol) of 2-bromopropene. The mixture was stirred at 40° C. under Ar. After 165 min., 2.0 mL of 2-bromopropene was added and heating was continued for 140 min. Diethyl ether was added, and the layers were separated. The organic layer was dried over $Na_2SO_4$, filtered, and concentrated. 2-fluoro-5-(prop-1-en-2-yl)pyridine was used without further purification.

2-fluoro-5-isopropylpyridine was synthesized from 2-fluoro-5-(prop-1-en-2-yl)pyridine following the general procedure as described for 4-isopropylpyridine.

To a stirring solution of 9.2 mL of LDA (lithium diisopropylamide) (2.0M solution in THF/heptane/ethylbenzene) in 20 mL of THF at −78° C. was added 2-fluoro-5-isopropylpyridine in 40 mL of THF dropwise over a period of 20 min. After 30 min. 4.39 g (17.3 mmol) of iodine in 25 mL of THF was added. After 2 h at −78° C. with the light off, 20 mL of water was added, and the cold bath was removed. Water (80 mL) was added and 9 g of sodium thiosulfate was added in 3 portions. Diethyl ether was added, and the layers were separated. The organic layer was washed with brine, dried over $Na_2SO_4$, filtered, and concentrated. Purification by flash silica gel chromatography (5% $Et_2O$/hexanes) provided 1.83 g of 2-fluoro-3-iodo-5-isopropylpyridine with some impurity.

To a mixture of 2-fluoro-3-iodo-5-isopropylpyridine and 485 mg (4.13 mmol) of $Zn(CN)_2$ in 15 mL of DMF (degassed) was added 360 mg (0.312 mmol) of $Pd(PPh_3)_4$. The mixture was heated at 80° C. under Ar for 19 h. The mixture was diluted with EtOAc, and the organic layer was washed with 10% $NH_4OH$ (2×10 mL), $H_2O$ (3×), and brine. The organic layer was dried over $Na_2SO_4$, filtered, and concentrated. Purification by flash silica gel chromatography (5% $Et_2O$/hexanes) provided 384 mg of pure 2-fluoro-5-isopropylnicotinonitrile as a yellow liquid.

To a stirring solution of 238 mg (1.44 mmol) of 2-fluoro-5-isopropylnicotinonitrile in 7 mL of THF at 0° C. was added 102 mg (2.7 mmol) of $LiAlH_4$. After 20 min., 104 mg of $LiAlH_4$ was added and after 10 min, the mixture was allowed to warm to r.t. and after another 20 min. the mixture was heated to 50-60° C. The reaction did not go to completion after 30 min., and the reaction was then quenched with 200 μL of $H_2O$, 200 μL of 15% NaOH aqueous, and 600 μL of brine were added. EtOAc was added and stirring was continued at r.t. The mixture was filtered through Celite and concentrated.

To a stirring mixture of crude product and 382 mg (1.61 mmol) of $CoCl_2.6H_2O$ in 7 mL of EtOH at 50° C. was added 259 mg (6.85 mmol) of $NaBH_4$ in 2 portions. After 10 min., 56.2 mg of $NaBH_4$ was added. After 2 h at 50° C., 5N HCl was added to a pH=1-2, and the mixture was stirred until the bubbling ceased. The mixture was concentrated, and $NH_4OH$ was added to a pH=8. The aqueous layer was extracted with the extract of (40 mL $CHCl_3$: 5 mL $H_2O$: 5 mL MeOH) 3 times. The combined extracts were dried over $Na_2SO_4$, filtered, and concentrated to give 165 mg of crude (2-fluoro-5-isopropylpyridin-3-yl)methanamine which was used without further purification.

Example 1.1.9

(5-isopentylpyridin-3-yl)methanamine

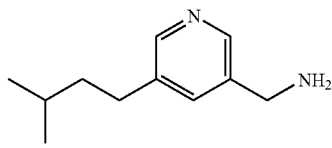

To a stirring mixture of 4.26 g (10.7 mmol) of $Ph_3PCH_2CH(CH_3)_2Br$ in 20 mL of THF 0° C. was added 12.0 mL of n-BuLi (1.6 M in hexanes). The mixture was stirred at 0° C. for 1 h, and then 521 mg (2.82 mmol) of 5-bromonicotinaldehyde in 20 mL of THF was added. After 5-10 min. the bath was removed and stirring was continued with warming to r.t. After 1 h, the reaction was quenched with water and diluted with EtOAc. The organic layer was washed with brine, dried over $Na_2SO_4$, filtered, and concentrated. Purification by flash silica gel chromatography 15% EtOAc/hexanes provided (E)-3-bromo-5-(3-methylbut-1-enyl)pyridine and impurity.

(E)-5-(3-methylbut-1-enyl)nicotinonitrile was synthesized from (E)-3-bromo-5-(3-methylbut-1-enyl)pyridine following the general procedure as described for the 2-fluoro-5-isopropylnicotinonitrile.

To a stirring mixture of 536 mg of cyanide and 789 mg (3.32 mmol) of $CoCl_2.6H_2O$ in 10 mL of EtOH at 50° C. was added 749 mg (19.8 mmol) of $NaBH_4$ in 3 portions. After 2 h at 50° C., 5N HCl was added to a pH=1-2 and stirring was continued until the bubbling ceased. The reaction mixture was concentrated and $NH_4OH$ was added to a pH=9. The aqueous layer was extracted with the extract of (40 mL $CHCl_3$: 5 mL MeOH: 5 mL $H_2O$) (2×). The combined extracts were dried over $Na_2SO_4$, filtered, and concentrated. Crude (5-isopentylpyridin-3-yl)methanamine was used in the next reaction without purification.

Example 1.1.10 benzyl 3-(aminomethyl)-5-isopropylphenylcarbamate

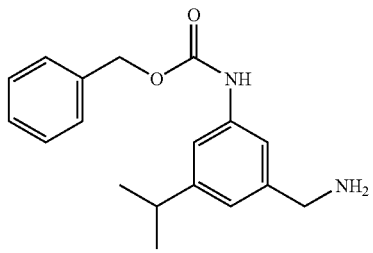

To a stirring mixture of 1.2 g (4.96 mmol) of 2-amino-3-bromo-5-nitrobenzonitrile and 2.8 mL of $H_2SO_4$ in 28 mL of EtOH at 90° C. was added 2.5 g (36.2 mmol) of NaNO$_2$ in several portions. After 13.5 h, EtOAc and H$_2$O were added. The organic layer was washed with H$_2$O and brine, dried over Na$_2$SO$_4$, filtered, and concentrated. Purification by flash silica gel chromatography (5% EtOAc/hexanes) provided 927 mg of 3-bromo-5-nitrobenzonitrile in 82% yield as a yellow solid.

To a stirring solution of 1.8 g of 3-bromo-5-nitrobenzonitrile in 8 mL of EtOH and 8 mL of THF was added 8.8 g (38.6 mmol) of SnCl$_2$.2H$_2$O in several portions. The mixture was allowed to stir at r.t. for 10.5 h and then concentrated. A solution of 2N NaOH (60 mL) was added and stirring continued for 2 h. EtOAc was added, and the layers were separated. The organic layer was washed with H$_2$O and brine. The aqueous layer was reextracted with EtOAc and washed with brine. The combined extracts were dried over Na$_2$SO$_4$, filtered, and concentrated. Purification by flash silica gel chromatography (35% EtOAc/hexanes) provided 965 mg of 3-amino-5-bromobenzonitrile.

To a stirring of 965 mg (4.90 mmol) of 3-amino-5-bromobenzonitrile in 15 mL of CH$_2$Cl$_2$ was added 1.27 g (5.09 mmol) of N-(benzyloxycarbonyloxy)succinimide (followed by 5 mL of CH$_2$Cl$_2$), and 1.5 mL (10.8 mmol) of Et$_3$N. After 27 h, the solution was concentrated and 10 mL of 10% citric acid and EtOAc were added. The layers were separated, and the organic layer was washed with 10 mL of 10% citric acid, 20 mL of H$_2$O, and 10 mL of brine, dried over Na$_2$SO$_4$, filtered, and concentrated. Purification by flash silica gel chromatography (25% EtOAc/hexanes) provided 773 mg of Cbz protected product (benzyl 3-bromo-5-cyanophenylcarbamate) with some impurity.

Benzyl 3-(aminomethyl)-5-bromophenylcarbamate was synthesized from benzyl 3-bromo-5-cyanophenylcarbamate following the general procedure as described for the 3-cyano-5-isopentylpyridine.

A solution of crude benzyl 3-(aminomethyl)-5-bromophenylcarbamate, 1.6 mL (11.5 mmol) of Et$_3$N, and 0.6 mL (2.61 mmol) of Boc$_2$O in 15 mL of MeOH was stirred at r.t. 17 h. The solution was concentrated, water and EtOAc were added, and the layers were separated. The organic layer was washed with H$_2$O and brine, dried over Na$_2$SO$_4$, filtered, and concentrated. Purification by flash silica gel chromatography (15% EtOAc/hexanes) provided the Boc-protected benzyl 3-(aminomethyl)-5-bromophenylcarbamate with some impurity.

A solution of 400 mg of Boc-protected benzyl 3-(aminomethyl)-5-bromophenylcarbamate, 153 mg (1.02 mmol) of potassium isopropenyltrifluoroborate, and 0.4 mL (2.87 mmol) of Et$_3$N in 40 mL of isopropanol and 20 mL of H$_2$O (degassed) was added 42.1 mg (0.0516 mmol) of PdCl$_2$(dppf).CH$_2$Cl$_2$. After heating the solution for 2 h, 100 mL of H$_2$O and EtOAc were added. The organic layer was washed with brine, dried over Na$_2$SO$_4$, filtered, and concentrated. Purification by flash silica gel chromatography (20% EtOAc/hexanes) provided 126 mg of the Boc-protected benzyl 3-(aminomethyl)-5-(prop-1-en-2-yl)phenylcarbamate as a yellow liquid in 66% yield.

The desired benzyl 3-(aminomethyl)-5-isopropylphenylcarbamate was synthesized from the Boc-protected benzyl 3-(aminomethyl)-5-(prop-1-en-2-yl)phenylcarbamate following the general procedure as described above for the 3-cyano-5-isopentylpyridine.

Example 1.1.11

(6-methyl-5-(methylthiomethyl)pyridin-2-yl)methanamine

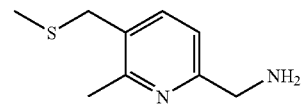

To a stirring solution of 1.05 g of methyl 6-cyano-2-methylnicotinate in 45 mL of MeOH at 0° C. was added 605 mg of NaBH$_4$. During a period of 45 min, 2 portions (a total of 1.26 g) of NaBH$_4$ was added. After 1 h, 1N HCl was added to a pH=7, and the aqueous layer was extracted with CHCl$_3$. The organic layer was dried over Na$_2$SO$_4$, filtered, and concentrated. The crude alcohol (5-(hydroxymethyl)-6-methylpicolinonitrile) was used for the next reaction without further purification.

To a stirring solution of 5-(hydroxymethyl)-6-methylpicolinonitrile in 15 mL of CH$_2$Cl$_2$ was added 0.9 mL (6.46 mmol) of Et$_3$N and 46.0 mg (0.377 mmol) of DMAP at r.t. The solution was cooled to 0° C. and 0.7 mL of MsCl was added. The solution was cooled to 0° C. for 45 min. and 20 mL of H$_2$O, CH$_2$Cl$_2$ and CHCl$_3$ were added. The layers were separated and the organic layer was washed with brine, dried over Na$_2$SO$_4$, filtered, and concentrated. Purification by flash silica gel chromatography ((0.6-1.0) % MeOH/CHCl$_3$) resulted in 919 mg of (6-cyano-2-methylpyridin-3-yl)methyl methanesulfonate as a yellow liquid in 68% yield.

A mixture of 919 mg (4.05 mmol) of (6-cyano-2-methylpyridin-3-yl)methyl methanesulfonate and 360 mg (5.14 mmol) of NaSMe in 15 mL of EtOH was heated at 95° C. for 4 h. Saturated NaHCO$_3$ solution and EtOAc were added, and the layers were separated. The organic layer was washed with brine, dried over Na$_2$SO$_4$, filtered, and concentrated. Purification by flash silica gel chromatography (50% Et$_2$O/hexanes) provided 46.6 mg of 6-methyl-5-(methylthiomethyl)picolinonitrile as a pale yellow solid in 6.4% yield.

(6-methyl-5-(methylthiomethyl)pyridin-2-yl)methanamine was synthesized from 6-methyl-5-(methylthiomethyl)picolinonitrile following the general procedure as described for the 3-cyano-5-isopentylpyridine.

Example 1.1.12

3-(aminomethyl)-5-isopropyl-N,N-dimethylaniline

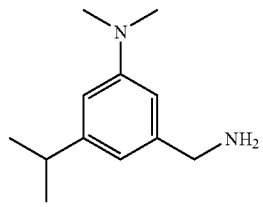

To a stirring suspension of 210 mg (10.6 mmol) of 3-amino-5-bromobenzonitrile in 11 mL of CH$_3$CN and 11 mL of 37% formaldehyde in H$_2$O was added 222 mg (3.53 mmol) of NaCNBH$_3$ followed by about 7 drops of acetic acid to a pH=7. After 1 h 40 min., an additional amount of acetic acid (10 drops) was added. After 15 h, 40 mL of EtOAc and 40 mL of sat. NaHCO₃ was added, and the layers were separated. The organic layer was washed with 25 mL of sat. NaHCO₃ and 25 mL of brine, dried over Na₂SO₄, filtered, and concentrated. Purification by flash silica gel chromatography (10% EtOAc/hexanes) provided 67.4 mg of 3-bromo-5-(dimethylamino)benzonitrile as a yellow solid in 28% yield.

3-(dimethylamino)-5-(prop-1-en-2-yl)benzonitrile was synthesized from 3-bromo-5-(dimethylamino)benzonitrile following the general procedure as described for the Cbz protected Boc aminomethyl bromide.

3-(aminomethyl)-5-isopropyl-N,N-dimethylaniline was synthesized from 3-(dimethylamino)-5-(prop-1-en-2-yl)benzonitrile following the general procedure as described for the 3-cyano-5-isopentylpyridine.

Example 1.1.13

(5-isopropyl-2,6-dimethylpyridin-3-yl)methanamine

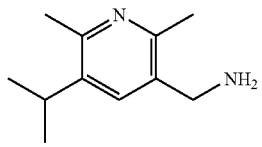

5-(methoxycarbonyl)-2,6-dimethylnicotinic acid was synthesized from 2,6-dimethylpyridine-3,5-dicarboxylic acid following the general procedure as described for the pyridine-3,5-dicarboxylic acid.

A solution of 686 mg of 5-(methoxycarbonyl)-2,6-dimethylnicotinic acid and 8.0 mL of BH₃.THF (1.0 M in THF) in 10 mL of THF was heated to 75° C. for 2.5 h. An aqueous solution of 3 mL of AcOH:H₂O (1:1) was added, and the solution was stirred until the bubbling ceased. Saturated NaHCO₃ was added to a pH=7, and the solution was stirred overnight. EtOAc and H₂O were added, and the layers were separated. The aqueous layer was extracted with 30 mL of EtOAc, and the combined extracts were washed with brine, dried over Na₂SO₄, filtered, and concentrated. Purification by flash silica gel chromatography (3% MeOH/CHCl₃) provided 452 mg of methyl 5-(hydroxymethyl)-2,6-dimethylnicotinate as a pale yellow solid in 71% yield.

To a stirring solution of 5.0 mL of MeMgCl (3.0 M in THF) in 20 mL of THF at 0° C. was added 452 mg (2.31 mmol) of methyl 5-(hydroxymethyl)-2,6-dimethylnicotinate in 40 mL of THF dropwise over a period of about 25 min. The solution was stirred at 0° C. for 45 min. and then at rt. for about 2.5 h. Another portion of MeMgCl (4 mL) was added and stirring was continued for about 2 h 20 min. Saturated NH₄Cl solution (60 mL), 15 mL of H₂O, and EtOAc were added, and the layers were separated. The aqueous layer was extracted with EtOAc (2×), and the combined extracts were washed with brine (60 mL), dried over Na₂SO₄, filtered, and concentrated. 2-(5-(hydroxymethyl)-2,6-dimethylpyridin-3-yl)propan-2-ol (313 mg) was used for the next reaction without further purification.

To a stirring solution of 2-(5-(hydroxymethyl)-2,6-dimethylpyridin-3-yl)propan-2-ol in 10 mL of CH₂Cl₂ was added 1.5 mL of SO₂Cl₂. After 11 h at r.t., the solution was concentrated and CH₂Cl₂ and 10 mL of sat. NaHCO₃ solution were added, and the layers were separated. The organic layer was washed with brine, dried over Na₂SO₄, filtered, and concentrated. Purification by flash silica gel chromatography (20% Et₂O/hexanes) provided 96.5 mg of the desired 3-(chloromethyl)-2,6-dimethyl-5-(prop-1-en-2-yl)pyridine as a mixture.

A mixture of 96.5 mg of the 3-(chloromethyl)-2,6-dimethyl-5-(prop-1-en-2-yl)pyridine and 86.8 mg (1.34 mmol) of NaN₃ in 3 mL of DMF was heated at 70° C. for 4 h. Water and EtOAc were added, and the layers were separated. The organic layer was washed with H₂O (2×) and then with brine. It was dried over Na₂SO₄, filtered, and concentrated to give the crude azide (3-(azidomethyl)-2,6-dimethyl-5-(prop-1-en-2-yl)pyridine) which was used without further purification.

A mixture of crude 3-(azidomethyl)-2,6-dimethyl-5-(prop-1-en-2-yl)pyridine and 10.2 mg of 10% Pd/C in 6 mL of MeOH was stirred at r.t. under H₂ balloon. After 3 h the mixture was filtered through Celite and concentrated to provide (2,6-dimethyl-5-(prop-1-en-2-yl)pyridin-3-yl)methanamine.

To a solution of crude (2,6-dimethyl-5-(prop-1-en-2-yl)pyridin-3-yl)methanamine and 120 mg (0.505 mmol) of CoCl₂.6H₂O in 5 mL of EtOH at 50° C. was added 115 mg of NaBH₄ in 2 portions. After 2 h, 5N HCl was added to a pH=1 and stirring was continued until the bubbling ceased. The mixture was concentrated, and NH₄OH was added to pH=9. Some water was added, and the aqueous layer was extracted with the extract of (40 mL CHCl₃: 5 mL MeOH: 5 mL H₂O). The combined extracts were dried over Na₂SO₄, filtered, and concentrated to give the crude (5-isopropyl-2,6-dimethylpyridin-3-yl)methanamine which was used without further purification.

Example 1.1.14

(6-methyl-5-(methylsulfonylmethyl)pyridin-2-yl)methanamine

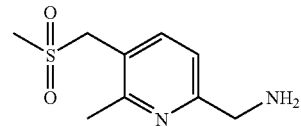

To a stirring solution of 1.5 g of methyl 2-methylnicotinate in 20 mL of THF at 0° C. was added 844 mg of LiAlH₄. After 20 min., 0.84 mL of H₂O, 0.84 mL of 15% aqueous NaOH, and 2.5 mL of brine. EtOAc was added, the ice bath removed, and stirring was continued for 1 h. The mixture was filtered through Celite and concentrated to give 889 mg of crude (2-methylpyridin-3-yl)methanol which was used without further purification.

To a stirring solution of crude (2-methylpyridin-3-yl)methanol in 20 mL of CH₂Cl₂ was added 2.2 mL of SO₂Cl₂. After 17 h the solution was concentrated and CH₂Cl₂ and saturated NaHCO₃ were added. The layers were separated, and the organic layer was washed with brine, dried over Na₂SO₄, filtered, and concentrated. Purification by flash silica gel chromatography (1% MeOH/CHCl₃) provided 1.18 g of 3-(chloromethyl)-2-methylpyridine as yellow-orange oil.

A mixture of 3-(chloromethyl)-2-methylpyridine and 619 mg (8.83 mmol) of NaSMe in 10 mL of EtOH was heated at 95° C. for 6 h. Saturated NaHCO₃ (10 mL) and EtOAc were added, and the layers were separated. The organic layer was washed with brine, dried over Na₂SO₄, filtered, and concentrated. Purification by flash silica gel chromatography (1%

MeOH/CHCl₃) provided 801 mg of 2-methyl-3-(methylthiomethyl)pyridine as a brown liquid in 72% yield.

A solution of 801 mg (5.26 mmol) of 2-methyl-3-(methylthiomethyl)pyridine and 5 mL of 30% H₂O₂ in 5 mL of AcOH was heated at 120° C. After 2 h, 3 mL of 30% H₂O₂ was added, and after about 3.5 h, the solution was concentrated. The solution was diluted with CHCl₃ and H₂O, the layers were separated, and the organic layer was extracted with the extract of (40 mL CHCl₃: 5 mL MeOH: 5 mL H₂O) The combined extracts were dried over Na₂SO₄, filtered, and concentrated. Purification by flash silica gel chromatography (10 mL MeOH/100 mL CHCl₃) provided 2-methyl-3-(methylsulfonylmethyl)pyridine N-oxide as a pale yellow solid in about 60% yield.

6-methyl-5-(methylsulfonylmethyl)picolinonitrile was synthesized from 2-methyl-3-(methylsulfonylmethyl)pyridine N-oxide following the general procedure as described for the 4-isopropyl-2-pyridylmethylamine.

(6-methyl-5-(methylsulfonylmethyl)pyridin-2-yl)methanamine was synthesized from 6-methyl-5-(methylsulfonylmethyl)picolinonitrile following the general procedure as described above for the 3-cyano-5-isopentylpyridine.

Example 1.1.15

(2,6-diisopropylpyridin-4-yl)methanamine

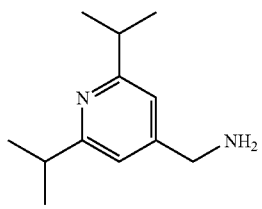

A solution of 1.14 g (6.2 mmol) of chelidamic acid hydrate (4-oxo-1,4-dihydropyridine-2,6-dicarboxylic acid) and about 10 g of PBr₅ was heated at 90° C. under a CaCl₂ drying tube for 3.5 h. Chloroform (125 mL) was added, the mixture was filtered, and to the solution in a 500 mL round bottom flask was added 30 mL of MeOH dropwise over a period of 1 h. After 1 h, 120 mL of saturated NaHCO₃ was added, and the layers were separated. The organic layer was washed with brine, dried over Na₂SO₄, filtered, and concentrated. Crude dimethyl 4-bromopyridine-2,6-dicarboxylate (1.72 g) was used without further purification.

2,2'-(4-bromopyridine-2,6-diyl)dipropan-2-ol was synthesized from dimethyl 4-bromopyridine-2,6-dicarboxylate following the general procedure as described for 2,6-dimethyl 3,5-pyridyl derivative.

A solution of 1.45 g (5.28 mmol) of 2,2'-(4-bromopyridine-2,6-diyl)dipropan-2-ol and 585 mg (6.53 mmol) of CuCN in 20 mL of DMF was heated at 150° C. After about 20.5 h, 40 mL of H₂O and EtOAc was added, and the mixture was filtered through a Buchner funnel. The layers were separated, and the organic layer was washed with water (3×30 mL) and brine (30 mL). The organic layer was dried over Na₂SO₄, filtered, and concentrated. Purification by flash silica gel chromatography (1% MeOH/CHCl₃) provided 373 mg of 2,6-bis(2-hydroxypropan-2-yl)isonicotinonitrile as a pale orange solid in 32% yield.

2,6-di(prop-1-en-2-yl)isonicotinonitrile was synthesized from 2,6-bis(2-hydroxypropan-2-yl)isonicotinonitrile following the general procedure as described for 2,6-dimethyl 3,5-pyridyl.

(2,6-diisopropylpyridin-4-yl)methanamine was synthesized from 2,6-di(prop-1-en-2-yl)isonicotinonitrile following the general procedure as described for 3-cyano-5-isopentylpyridine.

Example 1.1.16

(3-(benzyloxy)-5-isopropylphenyl)methanamine

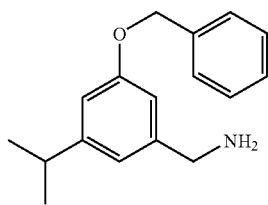

A mixture of 1.98 g (9.42 mmol) of dimethyl 5-hydroxyisophthalate, 3.0 g (21.7 mmol) of K₂CO₃, and 1.8 mL (15.1 mmol) of BnBr in 30 mL of DMF was heated at 60° C. After 17.5 h, the mixture was filtered through cotton, the solution was diluted with CHCl₃ and the organic layer washed with water, and brine. The organic layer was dried over Na₂SO₄, filtered, and concentrated. Purification by flash silica gel chromatography (15% EtOAc/hexanes) resulted in 2.64 g of dimethyl 5-(benzyloxy)isophthalate as a colorless solid in 93% yield.

1-(azidomethyl)-3-(benzyloxy)-5-(prop-1-en-2-yl)benzene was synthesized from dimethyl 5-(benzyloxy)isophthalate following the general procedure as described for 2,6-dimethyl 3,5-pyridyl.

A solution of 392 mg (1.35 mmol) of 1-(azidomethyl)-3-(benzyloxy)-5-(prop-1-en-2-yl)benzene and 525 mg (2.00 mmol) of PPh₃ in 5 mL of THF and 0.5 mL of H₂O was stirred at r.t. for 19 h. The solution was concentrated, diluted with EtOAc, dried over Na₂SO₄, filtered, and concentrated. Crude (3-(benzyloxy)-5-(prop-1-en-2-yl)phenyl)methanamine was used for the next reaction without purification.

The Boc protected (3-(benzyloxy)-5-(prop-1-en-2-yl)phenyl)methanamine was synthesized from (3-(benzyloxy)-5-(prop-1-en-2-yl)phenyl)methanamine following the general procedure as described for the Cbz protected Boc aminomethyl bromide.

tert-butyl 3-(benzyloxy)-5-isopropylbenzylcarbamate was synthesized from the Boc protected (3-(benzyloxy)-5-(prop-1-en-2-yl)phenyl)methanamine following the general procedure as described for 3-cyano-5-isopentylpyridine.

A solution of tert-butyl 3-(benzyloxy)-5-isopropylbenzylcarbamate and 15.0 mL of 1.25 M HCl in MeOH was stirred at r.t. for 3.5 h. The solution was concentrated, and saturated NaHCO₃ was added to a pH=7-8. The aqueous layer was extracted with the extract of (40 mL CHCl₃: 5 mL MeOH: 5 mL H₂O) (2×). The combined extracts were dried over Na₂SO₄, filtered, and concentrated to give 221 mg of crude (3-(benzyloxy)-5-isopropylphenyl)methanamine which was used for the next reaction without further purification.

Example 1.1.17

N-(3-(aminomethyl)-5-isopropylphenyl)methanesulfonamide

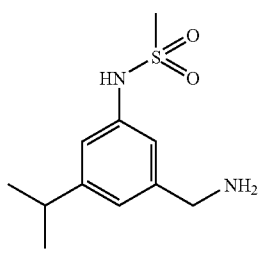

To a stirring solution of 502 mg of 3-amino-5-bromobenzonitrile in 6 mL of $CH_2Cl_2$ and 2 mL of pyridine at 0° C. was added 0.2 mL (2.57 mmol) of MsCl at 0° C. The ice bath was removed and stirring was continued at r.t. for 6.5 h. The solution was concentrated and EtOAc and 20 mL of $H_2O$ were added. The organic layer was washed with 15 mL of brine and water, dried over $Na_2SO_4$, filtered, and concentrated. Purification by flash silica gel chromatography (35% EtOAc/hexanes) provided 617 mg of N-(3-bromo-5-cyanophenyl)methanesulfonamide as a colorless solid in 88% yield.

N-(3-cyano-5-(prop-1-en-2-yl)phenyl)methanesulfonamide was synthesized from N-(3-bromo-5-cyanophenyl)methanesulfonamide following the general procedure as described for the Cbz protected Boc aminomethyl bromide.

N-(3-(aminomethyl)-5-isopropylphenyl)methanesulfonamide was synthesized from N-(3-cyano-5-(prop-1-en-2-yl)phenyl)methanesulfonamide following the general procedure as described above for the 3-cyano-5-isopentylpyridine.

Example 1.1.18 benzyl 3-(aminomethyl)-5-isopropylphenylmethyl)carbamate

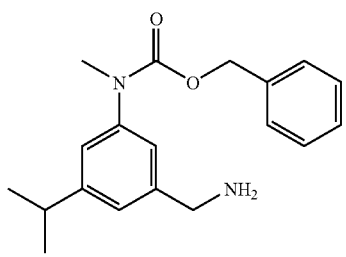

To a stirring solution of 773 mg (2.33 mmol) of benzyl 3-bromo-5-cyanophenylcarbamate in 10 mL of THF at 0° C. was added 231 mg of NaH (60% dispersion in mineral oil). After 1 h, 300 µL (4.82 mmol) of methyl iodide was added, the ice bath was removed, and the red mixture was stirred at r.t. with the light off. After 17 h, saturated $NH_4Cl$, $H_2O$, and EtOAc were added and the layers separated. The organic layer was washed with brine, dried over $Na_2SO_4$, filtered, and concentrated. Purification by flash silica gel chromatography (5% EtOAc/hexanes) provided 195 mg of benzyl 3-bromo-5-cyanophenyl(methyl)carbamate in 24% yield.

benzyl 3-cyano-5-(prop-1-en-2-yl)phenyl(methyl)carbamate was synthesized from benzyl 3-bromo-5-cyanophenyl(methyl)carbamate following the general procedure as described for the Cbz protected Boc aminomethyl bromide.

benzyl 3-(aminomethyl)-5-isopropylphenyl(methyl)carbamate was synthesized from the isopropenylbenzonitrile following the general procedure as described for 3-cyano-5-isopentylpyridine.

Example 1.1.19 methyl 3-(aminomethyl)-5-(N-methylmethylsulfonamido)benzoate

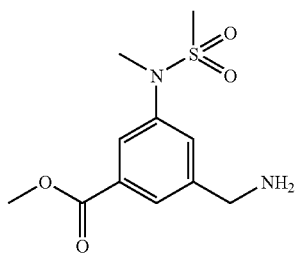

methyl 3-(hydroxymethyl)-5-(N-methylmethylsulfonamido)benzoate was synthesized from 3-(methoxycarbonyl)-5-(N-methylmethylsulfonamido)benzoic acid following the general procedure as described for the 2,6-dimethyl 3,5-pyridyl derivative.

To a stirring solution of 130 mg (0.475 mmol) of methyl 3-(hydroxymethyl)-5-(N-methylmethylsulfonamido)benzoate in 7 mL of toluene and 4 mL of THF was added 120 µL of diphenyl phosphoryl azide (DPPA). The solution was cooled to 0° C. and 86 µL (0.568 mmol) of 1,8-diazabicyclo[5.4.0]-undec-7-ene (DBU) was added. The ice bath was removed, and stirring was continued with warming to room temperature. After about 16 h, the solution was diluted with EtOAc and $H_2O$, and 1N HCl was added to a pH=8. The organic layer was washed with brine and dried over $Na_2SO_4$. After filtration and concentration, the crude product was purified by flash silica gel chromatography (50% EtOAc/hexanes) to give 151 mg of methyl 3-(azidomethyl)-5-(N-methylmethylsulfonamido)benzoate as a yellow oil.

The desired product was synthesized from methyl 3-(azidomethyl)-5-(N-methylmethylsulfonamido)benzoate following the general procedure as described for 3-cyano-5-isopentylpyridine.

Example 1.1.20

(1-tert-butyl-5-methyl-1H-pyrazol-4-yl)methanamine

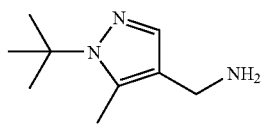

A stirred solution of diethylaminomethylene ethyl acetoacetate (552 mg, 2.8 mmol, see R. A. Fecik, P. Devasthale, S. Pillai, A. Keschavarz-Shokri, L. Sehn, and L. A. Mitscher; *J. Med. Chem.* 2005, 48, 1229) and tert-butyl hydrazine hydrochloride (387 mg, 3.1 mmol) in EtOH (5 mL) was heated to reflux for 15 h. The reaction mixture was cooled to room temperature and concentrated under reduced pressure. The residue was dissolved in EtOAc and saturated aqueous NaHCO₃. The layers were separated and the aqueous layer was extracted with EtOAc (2×10 mL). The combined organic layer was washed with brine, dried with Na₂SO₄ and concentrated under reduced pressure to provide ethyl 1-tert-butyl-5-methyl-1H-pyrazole-4-carboxylate (560 mg, 96%) as a yellow oil.

4-(azidomethyl)-1-tert-butyl-5-methyl-1H-pyrazole was generated from ethyl 1-tert-butyl-5-methyl-1H-pyrazole-4-carboxylate according to a procedure similar to that described for the 2,6 dimethyl 3,5-pyridyl derivative, then reduced to the crude primary amine, following procedures described herein.

Example 1.1.21

(1-(2-methoxyethyl)-5-methyl-1H-pyrazol-4-yl)methanamine

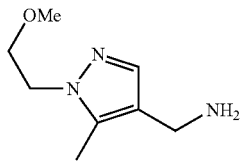

Ethyl 1-(2-hydroxyethyl)-5-methyl-1H-pyrazole-4-carboxylate (376 mg, 67%) was synthesized from diethylaminomethylene ethyl acetoacetate (509 mg, 2.8 mmol) and 2-hydroxyethyl hydrazine (0.30 mL, 4.1 mmol) following the general procedure for ethyl 1-tert-butyl-5-methyl-1H-pyrazole-4-carboxylate as described (see R. A. Fecik, P. Devasthale, S. Pillai, A. Keschavarz-Shokri, L. Sehn, and L. A. Mitscher; *J. Med. Chem.* 2005, 48, 122). To a stirred solution of NaH (91 mg, 2.3 mmol) in THF (5 mL) was added ethyl 1-(2-hydroxyethyl)-5-methyl-1H-pyrazole-4-carboxylate (376 mg, 1.9 mmol) in THF (1 mL) at 0° C. followed by MeI (0.18 mL, 2.9 mmol). The resulting mixture was stirred for 15 h and quenched with saturated aqueous NH₄Cl. The layers were separated and the aqueous layer was extracted with EtOAc (3×3 mL). The combined organic layer was dried over Na₂SO₄ and concentrated under reduce pressure. The residue was purified by column chromatography to provide ethyl 1-(2-methoxyethyl)-5-methyl-1H-pyrazole-4-carboxylate (249 mg, 62%) as a yellow oil.

4-(azidomethyl)-1-(2-methoxyethyl)-5-methyl-1H-pyrazole was generated from ethyl 1-(2-methoxyethyl)-5-methyl-1H-pyrazole-4-carboxylate according to a procedure similar to that described for the 2,6 dimethyl 3,5-pyridyl derivative, then reduced to the crude primary amine, following procedures described herein.

Example 1.1.22

(3-cyclopropylphenyl)methanamine

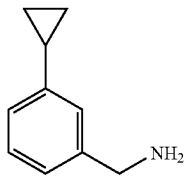

To a solution of tert-butyl 3-bromobenzylcarbamate (572 mg, 2 mmol), cyclopropyl boronic acid (223 mg, 2.6 mmol), potassium phosphate (1.49 g, 7.0 mmol) and tricyclohexyl phosphine (56 mg, 0.2 mmol) in toluene (9 mL) and water (0.45 mL) under a nitrogen atmosphere was added palladium acetate (22 mg, 0.1 mmol). The mixture was heated at 100° C. for 3 h and then cooled to rt. Water (20 mL) was added and the mixture extracted with EtOAc (2×30 mL), the combined organic extracts were washed with brine (20 mL), dried over Na₂SO₄ and concentrated in vacuo. Crude product was purified by column chromatography (15% EtOAc in hexanes) afforded tert-butyl 3-cyclopropylbenzylcarbamate as a colorless oil in 93% yield. (3-cyclopropylphenyl)methanamine was then generated by removing the Boc protecting group by treatment with HCl (in methanol or dioxane) or trifluoroacetic acid in dichloromethane.

Example 1.1.23

(5-(prop-1-en-2-yl)pyridin-3-yl)methanamine

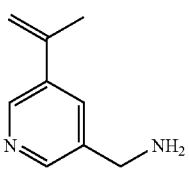

A solution of potassium isopropenyl trifluoroborate (464 mg, 3.13 mmol), PdCl₂(dppf).CH₂Cl₂ (153 mg, 0.06 mmol), tert-butyl (5-bromopyridin-3-yl)methylcarbamate (900 mg, 3.13 mmol) and triethylamine (475 mg, 4.69 mmol) in i-PrOH—H₂O (2:1, 30 mL) was heated under reflux in a nitrogen atmosphere. The reaction mixture was heated at reflux for 4 h, then cooled to rt and diluted with water (40 mL) followed by extraction with diethylether. The organic layers were combined and washed with brine, dried over sodium sulfate and then filtered. The solvent was removed under vacuum, and the crude product was purified by silica gel chromatography (eluting with 45% EtOAc/hexanes) to afford tert-butyl (5-(prop-1-en-2-yl)pyridin-3-yl)methylcarbamate as a white solid in 85% yield. (5-(prop-1-en-2-yl)pyridin-3-yl)methanamine was then generated by removal of the Boc protecting group by treatment with HCl (in methanol or dioxane) or trifluoroacetic acid in dichloromethane.

Example 1.1.24

(5-cyclopropylpyridin-3-yl)methanamine

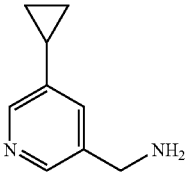

To a solution of tert-butyl (5-bromopyridin-3-yl)methylcarbamate (496 mg, 2 mmol), cyclopropyl boronic acid (223 mg, 2.6 mmol), potassium phosphate (1.49 g, 7.0 mmol) and tricyclohexyl phosphine (56 mg, 0.2 mmol) in toluene (9 mL) and water (0.45 mL) under a nitrogen atmosphere was added palladium acetate (22 mg, 0.1 mmol). The mixture was heated at 100° C. for 3 h and then cooled to rt. Water (20 mL) was added and the mixture extracted with EtOAc (2×30 mL), the combined organic extracts were washed with brine (20 mL), dried over Na$_2$SO$_4$ and concentrated in vacuo. Crude product was purified by column chromatography (50% EtOAc in hexanes) afforded tert-butyl (5-cyclopropylpyridin-3-yl)methylcarbamate in 60% yield. (5-cyclopropylpyridin-3-yl)methanamine was then generated by removal of the Boc protecting group by treatment with HCl (in methanol or dioxane) or trifluoroacetic acid in dichloromethane.

Example 1.1.25

(4-methoxypyrimidin-2-yl)methanamine

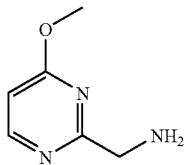

To the 2,4-dichloropyrimidine (1 g, 6.71 mmol) in MeOH (11 mL), NaOMe (362 mg, 6.71 mmol) was added and the reaction mixture was stirred at rt for 0.5 h. Then 15 mL of ether was added and the precipitate was filtered off. Solvent was removed from the reaction mixture and the crude product containing 2-chloro-4-methoxypyrimidine was carried further without any purification.

2-chloro-4-methoxypyrimidine (500 mg, 3.45 mmol) was combined with zinc cyanide (242 mg, 2.07 mmol) and tetrakis (triphenylphosphne)palladium (0) (159 mg, 0.14 mmol) in DMF (10 mL) and the slurry was heated at 80° C. under nitrogen for 6 h. The mixture was cooled to rt, diluted with EtOAc (50 mL) and washed twice with 2N ammonium hydroxide (50 mL). The EtOAc solution was washed with brine (20 mL) and concentrated in vacuo to provide the crude mixture. The crude was then purified by column chromatography (10% EtOAc in hexanes) to afford 4-methoxypyrimidine-2-carbonitrile in 50% yield.

To 4-methoxypyrimidine-2-carbonitrile (370 mg) in MeOH (5 mL), aqueous ammonium hydroxide (1 mL) and Raney Nickel (catalytic) were added and the reaction mixture was hydrogenated at 55 psi for 2 h. Then the reaction mixture was filtered and solvent evaporated to afford (4-methoxypyrimidin-2-yl)methanamine, which was carried to next step without purification.

Example 1.1.26

(4-methylpyrimidin-2-yl)methanamine

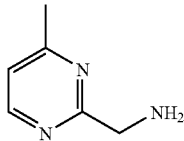

MeMgCl (3M solution in THF, 4.47 mL, 13.42 mmol) was added dropwise to a stirred solution of the 2,4-dichloropyrimidine (2 g, 13.42 mmol) and Fe(acac)$_3$ (1.37 g, 3.9 mmol) in THF (40 mL) under argon at 0° C. and the resulting reaction mixture was stirred at 0° C. for 8 h. The reaction mixture was diluted with water and extracted with EtOAc. Evaporation of the organic phase followed by column chromatography on a silica gel (eluting with 25% EtOAc/hexanes) to afford 2-chloro-4-methylpyrimidine in 50% yield.

2-chloro-4-methylpyrimidine pyrimidine (725 mg, 5.62 mmol) was combined with zinc cyanide (396 mg, 3.37 mmol) and tetrakis (triphenylphosphne)palladium (0) (716 mg, 0.562 mmol) in DMF (10 mL) and the slurry was heated at 110° C. under nitrogen for 0.5 h. The mixture was cooled to rt, diluted with EtOAc (70 mL) and washed twice with 2N ammonium hydroxide (50 mL). The EtOAc solution was washed with brine (20 mL) and concentrated in vacuo to provide the crude mixture. The crude was then purified by column chromatography (30% EtOAc in hexanes) to afford 4-methylpyrimidine-2-carbonitrile in 67% yield.

4-methylpyrimidine-2-carbonitrile (450 mg) in MeOH (5 mL), aqueous ammonium hydroxide (1 mL) and Raney Nickel (catalytic) were added and the reaction mixture was hydrogenated at 55 psi for 2 h. Then the reaction mixture was filtered and solvent evaporated to afford (4-methylpyrimidin-2-yl)methanamine, which was carried to next step without purification.

Example 1.1.27

(5-(trifluoromethyl)pyridin-3-yl)methanamine

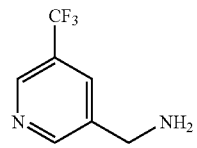

3-bromo-5-(trifluoromethyl)pyridine (1.0 g, 4.42 mmol, 1 eq) was dissolved in 20 mL anhydrous DMF. The solution was degassed by bubbling through with Ar. Zn(CN)$_2$ (0.312 g, 2.65 mmol, 0.6 eq) and Pd(PPh$_3$)$_4$ were added, and the resulting solution was heated to 80° C. with stirring overnight. The reaction was cooled to room temperature and diluted with Et$_2$O, NH$_4$OH (28%) was added with stirring and the layers were separated. The organic layer was washed with water (×3), brine (×1), and dried over Na$_2$SO$_4$. The inorganics were filtered off, and the reaction mixture was concentrated in vacuo. Purification via flash chromatography on silica gel yielded 0.310 g (1.95 mmol, 44% yield) of 5-(trifluoromethyl)nicotinonitrile.

5-(trifluoromethyl)nicotinonitrile (0.31 g, 1.95 mmol, 1 eq) and CoCl$_2$.6H$_2$O (0.23 g, 0.97 mmol, 0.5 eq) were dissolved in 10 mL EtOH. The flask was fitted with a reflux condenser and heated to 50° C. under Ar. NaBH$_4$ (0.22 g, 5.85 mmol, 3 eq) was added in 2 batches and the mixture was stirred at 50° C. for 2 h. The mixture was then cooled to room temperature and 5 N HCl was added to pH=1-2. The reaction was stirred until the bubbling stopped and NH$_4$OH (28%) was added to pH=9. The mixture was then concentrated in vacuo and the residue was extracted with CHCl$_3$/MeOH/water (8:1: 1) (×2). The combined extracts were dried over Na$_2$SO$_4$. The inorganics were filtered off, and the solvent was removed in vacuo yielding 0.1 g (0.61 mmol, 31% yield) of (5-(trifluoromethyl)pyridin-3-yl)methanamine.

Example 1.1.28

3-(aminomethyl)-N,N-dimethylaniline

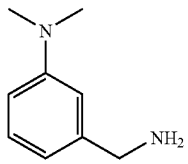

(Boc)₂O (1.06 mL, 1.0 g, 4.62 mmol, 1.1 eq) was added to a stirred solution of 3-(aminomethyl)aniline (0.512 g, 4.2 mmol, 1 eq) and Et₃N (1.3 mL, 0.94 g, 9.24 mmol, 2.2 eq) in 5 mL anhydrous MeOH at 0° C. under Ar. The solution was stirred at 0° C. to room temperature overnight. The solvent was removed in vacuo. The residue was dissolved in EtOAc, washed with water (×2), brine (×1), and dried over Na₂SO₄. The inorganics were filtered off, and the solvent was removed in vacuo. Purification via flash chromatography on silica gel yielded 0.8746 g (3.9 mmol, 94% yield) of tert-butyl 3-aminobenzylcarbamate.

CH₂O (aq. 37%, 1.57 mL, 21.1 mmol, 10 eq) was added to a stirred solution of tert-butyl 3-aminobenzylcarbamate (0.47 g, 2.1 mmol, 1 eq) in 10 mL CH₃CN. The resulting solution was treated with NaBH₃CN (0.42 g, 6.3 mmol, 3 eq) followed by the dropwise addition of HOAc to pH=7. The solution was stirred for 1 h adding HOAc occasionally to keep the pH close to 7. The reaction was concentrated in vacuo and the resulting residue was diluted with sat. NaHCO₃ and extracted into EtOAc (×1). The organic layer was washed with water (×3), brine (×1), and dried over Na₂SO₄. The inorganics were filtered off, and the solvent removed in vacuo. Purification via flash chromatography on silica gel yielded 0.39 g (1.6 mmol, 74% yield) of tert-butyl 3-(dimethylamino)benzylcarbamate.

3-(aminomethyl)-N,N-dimethylaniline was then generated by removal of the Boc protecting group by treatment with HCl (in methanol or dioxane) or trifluoroacetic acid in dichloromethane.

Example 1.1.29

N-methyl-1-(5-methylthiazol-2-yl)methanamine

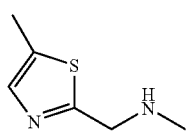

To a solution of BuLi (1.6 M in hexanes, 12.6 mL, 20.2 mmol) in 25 mL of diethyl ether at −78° C., was added a solution of 5-methylthiazole (2.0 g, 20.2 mmol) in ether (6 mL), drop-wise and stirred at −78° C. for 1.5 h. A solution of DMF (2.33 mL, 30.3 mmol in ether (5 mL) was added at once and the reaction mixture was allowed to warm to room temperature and stirred overnight. Ice was added to the reaction mixture followed by the slow addition of 4N HCl. The mixture was taken up in a separating funnel, ether added (30 mL) and shaken. The organic layer was discarded. The aqueous layer was brought to pH ~7.5 with solid NaHCO₃ and extracted with ether twice. The ether layer was dried over Na₂SO₄ and concentrated, and the resulting crude 5-methylthiazole-2-carbaldehyde (1.6 g) was carried over to the next-step without purification.

Ti (OⁱPr)₄ (1.3 eq) was added with stirring to MeNH₂ (2.0 M in MeOH, 3 eq) under Ar. After 5 min. 5-methylthiazole-2-carbaldehyde (1 eq) was added, and the solution was stirred for 1-2 h. The reaction was cooled to 0° C. and NaBH₄ (1.3 eq) was added. The solution was stirred at 0° C. to room temperature overnight. After quenching the reaction with water the mixture was filtered through Celite to remove the white ppt. MeOH was removed in vacuo and the residue was diluted with EtOAc. The resulting solution was washed with water (×3), brine (×1), and dried over Na₂SO₄. The inorganic material was filtered off, and the solvent was removed in vacuo to give the crude product. Purification via column chromatography yielded N-methyl-1-(5-methylthiazol-2-yl)methanamine in 80-85% yield.

Example 1.1.30

N-((4-methylthiazol-2-yl)methyl)ethanamine

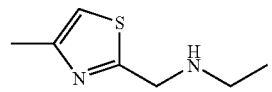

N-((4-methylthiazol-2-yl)methyl)ethanamine was prepared following a similar procedure as N-methyl-1-(5-methylthiazol-2-yl)methanamine using EtNH₂.

Example 1.1.31

N-((4-methylthiazol-2-yl)methyl)propan-1-amine

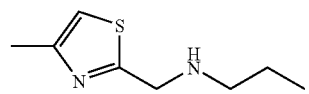

N-((4-methylthiazol-2-yl)methyl)propan-1-amine was prepared following a similar procedure as N-methyl-1-(5-methylthiazol-2-yl)methanamine using n-propylamine.

Example 1.1.32

N-((4-methylthiazol-2-yl)methyl)propan-2-amine

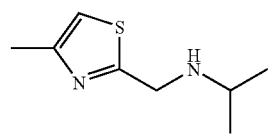

N-((4-methylthiazol-2-yl)methyl)propan-2-amine was prepared following a similar procedure as N-methyl-1-(5-methylthiazol-2-yl)methanamine using isopropylamine.

Example 1.1.33

N-((4-methylthiazol-2-yl)methyl)cyclopropanamine

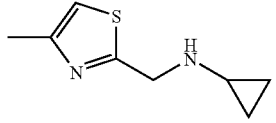

N-((4-methylthiazol-2-yl)methyl)cyclopropanamine was prepared following a similar procedure as N-methyl-1-(5-methylthiazol-2-yl)methanamine using cyclopropanamine.

Example 1.1.34

1-(4,5-dimethylthiazol-2-yl)-N-methylmethanamine

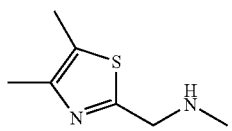

1-(4,5-dimethylthiazol-2-yl)-N-methylmethanamine was prepared following a similar procedure as N-methyl-1-(5-methylthiazol-2-yl)methanamine from 4,5-dimethylthiazole-2-carboxyaldehyde.

Example 1.1.35

2-((4-methylthiazol-2-yl)methylamino)ethanol

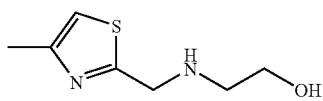

Ti(O$^i$Pr)$_4$ (3.4 mL, 3.3 g, 11.7 mmol, 1.3 eq) was added to a stirred solution of ethanolamine in 10 mL anhydrous MeOH under Ar. After 10 min, 4-methylthiazole-2-carbaldehyde (1 mL, 1.18 g, 9 mmol, 1 eq) was added. After 1 h the reaction was cooled to 0° C. and the NaBH$_4$ (0.44 g, 11.7 mmol, 1.3 eq) was added. The reaction was stirred at 0° C. to room temperature overnight. The reaction was quenched with water, and a white ppt formed. The mixture was filtered through Celite, and the MeOH removed in vacuo. The residue was diluted with EtOAc, washed with water (×3), brine (×1), and dried over Na$_2$SO$_4$. The inorganics were filtered off, and the solvent was removed in vacuo yielding 1.14 g (7.2 mmol, 80% yield) of the crude product 2-((4-methylthiazol-2-yl)methylamino)ethanol, which was used without further purification.

Example 1.1.36

(3-methylisoxazol-5-yl)methanamine

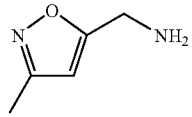

A solution of 321 mg (2.27 mmol) of 2-(3-methylisoxazol-5-yl)acetic acid, 0.5 mL (2.32 mmol) of diphenylphosphorylazide (DPPA), and 0.35 mL (2.51 mmol) of triethylamine in 30 mL of distilled tert-butyl alcohol was refluxed for 13.5 h. The solution was concentrated, and the crude residue was dissolved in EtOAc. The organic layer was washed with 1N HCl (3×10 mL) and saturated NaHCO$_3$ solution (3×10 mL). The organic layer was dried over sodium sulfate, filtered, concentrated. Purification by flash silica gel chromatography (28% EtOAc/hexanes) provided 50 mg (10% yield) of the protected amine as a pale yellow solid. (3-methylisoxazol-5-yl)methanamine was then generated by removal of the Boc protecting group by treatment with HCl (in methanol or dioxane) or trifluoroacetic acid in dichloromethane.

Example 1.1.37

(3-(methoxymethyl)phenyl)methanamine

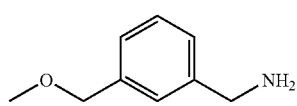

1,3-phenylenedimethanol was converted to (3-(methoxymethyl)phenyl)methanol using the procedure found in the following reference: Liu, Xuan; Zheng, Qi-Huang; Fei, Xiangshu; Wang, Ji-Quan; Ohannesian, David W.; Erickson, Leonard C.; Stone, K. Lee; Hutchins, Gary D.; Bioorg. Med. Chem. Lett. 2003, 13, 641-644. (3-(methoxymethyl)phenyl)methanol was converted to the target molecule following standard reactions including formation of the azide with DPPA and reduction.

Example 1.1.38

N-(3-(aminomethyl)phenyl)acetamide

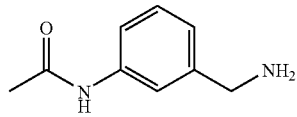

To a stirred solution of tert-butyl 3-aminobenzylcarbamate (Hah, Jung-Mi; Martasek, Pavel; Roman, Linda J.; Silverman, Richard B.; J. Med. Chem.; 2003, 46, 1661-1669) (287 mg, 1.29 mmol) in CH₂Cl₂ (10 mL) at 0° C. was added Et₃N (0.27 mL, 2.0 mmol) and acetyl chloride (0.10 mL, 1.4 mmol) and the resulting solution was warmed up to room temperature slowly. After further stirring of 4 h, the reaction was quenched with saturated aqueous NH₄Cl. The layers were separated and the aqueous layer was extracted with CH₂Cl₂ (2×20 mL). The combined organic layer was washed with H₂O, brine, dried with Na₂SO₄ and concentrated under reduced pressure. The residue oil was purified by column chromatography (60% EtOAc in hexanes) to provide tert-butyl 3-acetamidobenzylcarbamate (123.1 mg, 36%). N-(3-(aminomethyl)phenyl)acetamide was then generated by removal of the Boc protecting group by treatment with HCl (in methanol or dioxane) or trifluoroacetic acid in dichloromethane.

Example 1.1.39

3-(aminomethyl)-N-methylaniline

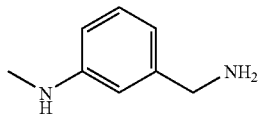

Tert-butyl 3-aminobenzylcarbamate was converted to tert-butyl 3-(methylamino)benzylcarbamate following standard reductive amination conditions using formaldehyde and sodium cyanoborohydride. 3-(aminomethyl)-N-methylaniline was then generated by removal of the Boc protecting group by treatment with HCl (in methanol or dioxane) or trifluoroacetic acid in dichloromethane.

Example 1.1.40

(5-(benzyloxy)pyridin-3-yl)methanamine

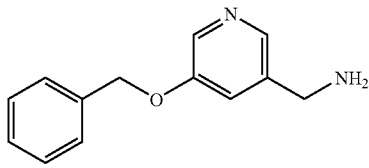

A mixture of 818 mg (5.34 mmol) of 5-hydroxynicotinic acid, 1.70 g (12.3 mmol) of K₂CO₃, and 1.0 mL (8.41 mmol) of benzyl bromide in 25 mL of DMF was heated at 60° C. under Ar for 16 h. The mixture was filtered through cotton, and the residue was dissolved in CHCl₃. The organic layer was washed with water (2×30 mL), brine (30 mL), dried over Na₂SO₄, filtered, and concentrated. Purification by flash silica gel chromatography provided 363 mg of methyl 5-(benzyloxy)nicotinate in 28% yield as an orange oil.

To a stirring solution of 363 mg (1.49 mmol) of methyl 5-(benzyloxy)nicotinate in 10 mL of THF at 0° C. was added 141 mg (3.71 mmol) of LiAlH₄. The ice bath was removed, and after 55 min., 20.5 mg of LiAlH₄ was added. After 40 min., the reaction was quenched by adding successively 160 μL of H₂O, 160 μL of 15% aqueous NaOH, and 480 μL of brine. Purification by flash silica gel chromatography (2 mL MeOH/100 mL CHCl₃) provided 250 mg of (5-(benzyloxy)pyridin-3-yl)methanol (yellow oil) in 78% yield.

To a stirring solution of 250 mg (1.17 mmol) of (5-(benzyloxy)pyridin-3-yl)methanol in 8 mL of toluene was added 310 μL (1.44 mmol) of DPPA. The mixture was cooled to 0° C. and 210 μL (1.44 mmol) of 1,8-diazabicyclo[5.4.0]-undec-7-ene] (DBU) was added. The ice bath was removed, and stirring was continued with warming to room temperature. After about 20 h, the solution was diluted with EtOAc, and 1N HCl was added to a pH between 7 and 8. The organic layer was washed with water (2×15 mL) and brine (15 mL) and dried over Na₂SO₄. After filtration and concentration, the crude product was purified by flash silica gel chromatography (56-60% EtOAc/hexanes) to give 181 mg (65% yield) of 3-(azidomethyl)-5-(benzyloxy)pyridine as a colorless oil.

To a stirring solution of 181 mg of 3-(azidomethyl)-5-(benzyloxy)pyridine in 6 mL of THF at 0° C. was added 80.6 mg (2.12 mmol) of LiAlH₄. The ice bath was removed and stirring was continued with warming to r.t. After 30 min. the reaction was quenched by adding successively 160 μL of H₂O, 160 μL of 15% aqueous NaOH, and 480 μL of brine. The mixture was filtered through Celite and concentrated. The crude product was used for the next reaction without further purification.

Example 1.1.41

(5-methylpyridin-3-yl)methanamine

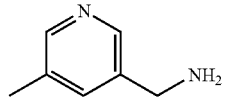

To stirring solution of 233 mg (1.70 mmol) of 5-methylnicotinic acid (synthesized following the general procedure for 5-fluoro-isophthalic acid) in 30 mL of THF at 0° C. was added 181 mg (4.76 mmol) of LiAlH₄. After 25 min., the reaction was quenched by adding successively 180 μL of H₂O, 180 μL of 15% aqueous NaOH, and 540 μL of brine. The mixture was filtered through Celite and concentrated to give 87 mg of (5-methylpyridin-3-yl)methanol which was used for the next reaction without further purification.

(5-methylpyridin-3-yl)methanamine was synthesized from (5-methylpyridin-3-yl)methanol following the general procedure as described for the nicotinic acid benzyl ether derivative.

Example 1.1.42

(6-methylpyridin-2-yl)methanamine

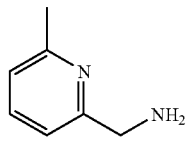

Diphenylphosphoryl azide (DPPA) (0.74 mL, 0.9 g, 3.4 mmol, 1.2 eq) and 1,8-Diazabicyclo(5.4.0)undec-7-ene (DBU) (0.508 mL, 0.52 g, 3.4 mmol, 1.2 eq) were added to a stirred solution of the (6-methylpyridin-2-yl)methanol (0.35 g, 2.8 mmol, 1 eq) in 7 mL anh. toluene under Ar. After stirring overnight, the solvent was removed in vacuo. Purification via flash chromatography yielded 0.47 g (3.2 mmol, 113% yield of the crude product. The crude was dissolved in 5 mL MeOH. Pd(OH)$_2$ (20% by wt. on carbon, 0.040 g) was added, and the mixture was stirred vigorously under H$_2$ overnight. The mixture was filtered through Celite, and the filter cake rinsed with MeOH. The solvent was removed in vacuo yielding 0.4948 g of crude (6-methylpyridin-2-yl)methanamine.

Example 1.1.43

(5-methoxypyridin-3-yl)methanamine

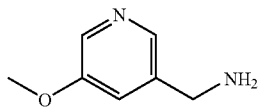

(5-methoxypyridin-3-yl)methanamine was synthesized from the hydroxynicotinate following the general procedure as described for the nicotinic acid benzyl ether derivative.

Example 1.1.44

(1H-indol-7-yl)methanamine

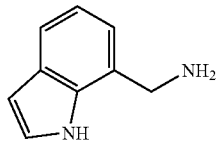

1H-indole-7-carbaldehyde (1 g, 6.9 mmol) in EtOH (30 mL), hydroxylamine (527 mg, 7.6 mmol) in water (10 mL) was added followed by 50% NaOH (1.38 g in 1.38 mL water) was added. After refluxing for 2 h, ethanol was removed under reduced pressure. Resultant slurry was extracted with ethylacetate. Organic layer was washed with water, brine and dried. Crude residue was column chromatographed on a silica gel eluting with (30% EtOAc/hexanes) to afford (Z)-1H-indole-7-carbaldehyde oxime in 80% yield.

(Z)-1H-indole-7-carbaldehyde oxime (100 mg, 0.60 mmol) in MeOH (5 mL), Pd(OH)$_2$ (50 mg) was added and stirred under hydrogen atmosphere (balloon pressure) for 4 h. Reaction mixture was then filtered and solvent evaporated to yield (1H-indol-7-yl)methanamine in quantitative yield.

Example 1.1.45

(3-tert-butylphenyl)methanamine

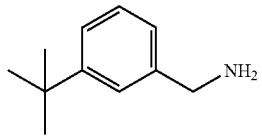

To 3-tert-butylphenol (3 g, 20 mmol) in pyridine (11 mL, 140 mmol) at 0° C., triflic anhydride (4.06 mL, 24 mmol) was added and stirred at 0° C. for 1 h. Then the reaction mixture was allowed to come to rt and stirred at rt for 4 h. Then the reaction mixture was diluted with ether, washed with water. Organic layers were collected washed with dilute HCl, water, brine and dried over anhydrous sodium sulfate. Volatiles were removed on a rotavap under reduced pressure. The crude 3-tert-butylphenyl trifluoromethanesulfonate was carried to the next step without any further purification.

To a solution of 3-tert-butylphenyl trifluoromethanesulfonate (1.5 g, 6.70 mmol) in DMF (10 mL), zinc cyanide (1.57 g, 13.40 mmol) was added. The reaction mixture was heated to 120° C. for 4 h. Then reaction mixture was cooled, diluted with ether (2500 mL) and washed twice with 2N ammonium hydroxide (50 mL). The ether solution was washed with brine (20 mL) and concentrated in vacuo to provide the crude mixture. The crude was then purified by column chromatography (5% EtOAc in hexanes) to afford 3-tert-butylbenzonitrile in 75% yield.

To 3-tert-butylbenzonitrile (400 mg) in MeOH (5 mL), aqueous ammonium hydroxide (1 mL) and Raney Nickel (catalytic) were added and the reaction mixture was hydrogenated at 50 psi for 2 h. Then the reaction mixture was filtered and solvent evaporated. (3-tert-butylphenyl)methanamine was used without any purification.

Example 1.1.46

2-(aminomethyl)-6-tert-butylphenol

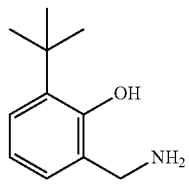

To a stirred solution of hydroxylamine hydrochloride (437 mg, 6.3 mmol) in CH$_3$CN at 0° C. was added Et$_3$N and 3-tert-butyl-2-hydroxybenzaldehyde (1.02 g, 5.7 mmol). The reaction mixture was warmed up to room temperature and stirred for 24 h. The solvent was removed and the residue was dissolved in EtOAc and H$_2$O. The layers were separated and the aqueous layer was extracted with EtOAc (2×20 mL). The combined organic layer was washed with brine, dried with Na$_2$SO$_4$ and concentrated under reduced pressure to provide 3-tert-butyl-2-hydroxybenzaldehyde oxime (1.01 g, 92%) as a pale yellow solid.

3-tert-butyl-2-hydroxybenzaldehyde oxime (550 mg, 2.9 mmol) in EtOAc (10 mL) and MeOH (10 mL) was hydrogenated at balloon pressure in the presence of 10% Pd on carbon (100 mg) for 15 h. The reaction mixture was filtered over celite and concentrated. The residue was dissolved in EtOAc and 0.5 N HCl (10 mL). The layers were separated and the aqueous layer was treated with 1N NaOH solution until pH=9. The resulting aqueous layer was extracted with CHCl$_3$ (3×10 mL). The combined CHCl$_3$ was washed with brine, dried with Na$_2$SO$_4$ and concentrated under reduced pressure to provide to desired product (123 mg, 23%).

Example 1.1.47

(5-tert-butyl-2-(tert-butyldimethylsilyloxy)phenyl)methanamine

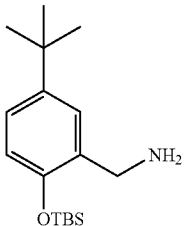

To a stirred solution of 5-tert-butyl-2-hydroxybenzaldehyde (570 mg, 3.2 mmol) in DMF (5 mL) was added imidazole (435 mg, 6.4 mmol) and TBSCl (576 mg, 3.8 mmol). The reaction mixture was stirred for 15 h and quenched with saturated aqueous NH$_4$Cl. The resulting mixture was extracted with EtOAc (2×20 mL). The combined organic layer was washed with H$_2$O, brine, dried with Na$_2$SO$_4$ and concentrated under reduced pressure to provide 5-tert-butyl-2-(tert-butyldimethylsilyloxy)benzaldehyde (1.07 g, quantitative).

(5-tert-butyl-2-(tert-butyldimethylsilyloxy)phenyl)methanamine was generated from 5-tert-butyl-2-(tert-butyldimethylsilyloxy)benzaldehyde using a similar procedure to the described synthesis of 2-(aminomethyl)-6-tert-butylphenol.

Example 1.1.48

(2-fluoro-6-methoxyphenyl)methanamine

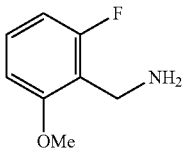

(2-fluoro-6-methoxyphenyl)methanamine was synthesized from 2-fluoro-6-methoxybenzaldehyde using a similar procedure to the described synthesis of 2-(aminomethyl)-6-tert-butylphenol.

Example 1.1.49

(3-(2-methyl-1,3-dioxolan-2-yl)phenyl)methanamine

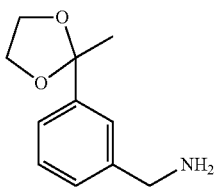

A stirred solution of 3-acetylbenzonitrile (1.05 g, 7.2 mmol), ethylene glycol (0.81 mL, 14.5 mmol) and TsOH (0.65 g, 7.2 mmol) was heated at reflux with a Dean-Stark for 15 h during which time the reaction became dark brown suspension. The reaction mixture was cooled to room temperature and diluted with saturated aqueous NaHCO$_3$. The layers were separated and the aqueous layer was extracted with EtOAc (2×20 mL). The combined organic layer was washed with brine, dried with Na$_2$SO$_4$ and concentrated under reduced pressure. The residue was purified by column chromatography (10% EtOAc in hexanes) to provide 3-(2-methyl-1,3-dioxolan-2-yl)benzonitrile (1.08 g, 79%).

To a stirred solution of LiAlH$_4$ (114 mg, 3.6 mmol) in ether at 0° C. was added 3-(2-methyl-1,3-dioxolan-2-yl)benzonitrile (0.57 g, 3.0 mmol). The reaction mixture was stirred for 4 h and quenched with H$_2$O (0.2 mL), 20% NaOH (0.2 mL), brine (0.6 mL). The resulting mixture was stirred for 1 h and filtered over celite and concentrated. The residue was purified by column chromatography (10% MeOH in CHCl$_3$) to provide (3-(2-methyl-1,3-dioxolan-2-yl)phenyl)methanamine (334 mg, 57%).

The ethylene ketal protecting group can be removed following amide coupling using standard conditions known in the art to generate the desired ketone derivative.

Example 1.1.50

(R)-1-(4-methyloxazol-2-yl)ethanamine

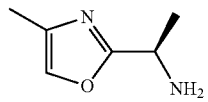

To a solution of L-Serine methyl ester hydrochloride (5.0 g, 32.0 mmol), in CH$_2$Cl$_2$ (150 mL) at 0° C., were added Et$_3$N (4.88 mL, 35.2 mmol), Boc-D-Alanine (6.06 g, 32 mmol), and DCC (7.26 g, 35.2 mmol) sequentially. The reaction was allowed to warm to room temperature and stirred overnight. All the solvent was evaporated and the residue was triturated with ethyl acetate and the precipitate was filtered off. The filtrate was concentrated under low pressure and chromatographed on silica gel (70% ethyl acetate/30% chloroform) to yield 86% of methyl 2-((R)-2-(tert-butoxycarbonylamino)propanamido)-3-hydroxypropanoate.

Deoxo-fluor™ (Bis-(2-methoxy)amino sulfur trifluoride, 1.4 mL, 7.6 mmol) was added drop-wise to a solution of methyl 2-((R)-2-(tert-butoxycarbonylamino)propanamido)-3-hydroxypropanoate (2.0 g, 6.9 mmol) in CH$_2$Cl$_2$ (50 mL) at −20° C. The solution was stirred for 30 min and BrCCl$_3$ (2.45 mL, 24.8 mmol) was added drop-wise. The reaction was stirred at 2-3° C., for 8 h., quenched with sat. aq. NaHCO$_3$ solution and extracted with ethyl acetate. The organic layer was concentrated and chromatographed on silica gel (30% ethyl acetate/70% hexanes) to yield 65% of (R)-methyl 2-(1-(tert-butoxycarbonylamino)ethyl)oxazole-4-carboxylate.

To a solution of (R)-methyl 2-(1-(tert-butoxycarbonylamino)ethyl)oxazole-4-carboxylate (3.07 g, 11.37 mmol) in THF (25 mL) at 0° C., was added LiBH$_4$ (17.0 mL, 2.0M in THF, 34.0 mmol). The reaction was allowed to warm to room temperature and stirred for 3 h. Ethyl acetate (11 mL) was added drop-wise and stirred for 30 min. The reaction was cooled to 0° C. and 17 mL of 1N HCl was added drop-wise and diluted with 30 mL of water. The mixture was then extracted with ethyl acetate, dried on Na$_2$SO$_4$, concentrated, and chromatographed on silica gel (3% MeOH/97% chloroform) to yield 84% of (R)-tert-butyl 1-(4-(hydroxymethyl)oxazol-2-yl)ethylcarbamate.

To a solution of TPP (873 mg, 3.33 mmol) in $CH_2Cl_2$ (10 mL), was added $I_2$ (845 mg, 3.33 mmol), and stirred for 10 min. Imidazole (227 mg, 3.33 mmol) was added and stirred for an additional 10 min and then a solution of (R)-tert-butyl 1-(4-(hydroxymethyl)oxazol-2-yl)ethylcarbamate (537 mg, 2.22 mmol) in $CH_2Cl_2$ (15 mL) was added. After 2 h, the reaction mixture was washed successively with sat. aq. $NaHCO_3$, aq. $Na_2S_2O_3$, dried on $Na_2SO_4$ and concentrated under low pressure. The residue was chromatographed on silica gel (20% ethyl acetate/80% hexanes) to yield 84% of (R)-tert-butyl 1-(4-(iodomethyl)oxazol-2-yl)ethylcarbamate.

To a solution of (R)-tert-butyl 1-(4-(iodomethyl)oxazol-2-yl)ethylcarbamate (660 mg, 1.87 mmol) in HMPA (10 mL), was added $NaCNBH_3$ (470 mg, 7.5 mmol). The reaction was stirred for 4 h. and poured into ice-cold water and extracted with hexanes. The organic layer was dried on $Na_2SO_4$, concentrated, and chromatographed on silica gel (10% ethyl acetate/90% hexanes) to yield 38% of (R)-tert-butyl 1-(4-methyloxazol-2-yl)ethylcarbamate.

(R)-1-(4-methyloxazol-2-yl)ethanamine was then generated by removal of the Boc protecting group by treatment with HCl (in methanol or dioxane) or trifluoroacetic acid in dichloromethane.

Example 1.1.51

(4-methyloxazol-2-yl)methanamine

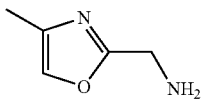

(4-methyloxazol-2-yl)methanamine was generated using a procedure similar to the synthesis of (R)-1-(4-methyloxazol-2-yl)ethanamine using Boc-glycine as starting material.

Example 1.1.52

(5-isopropylpyridin-3-yl)methanamine

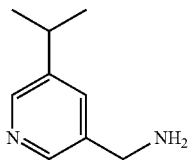

Methyl 5-bromonicotinate was reduced to (5-bromopyridin-3-yl)methanol using $LiAlH_4$ under conditions well known in the art. (5-bromopyridin-3-yl)methanol was transformed to (5-isopropylpyridin-3-yl)methanamine similar to the procedures described for methyl 3-(aminomethyl)-5-(N-methylmethylsulfonamido)benzoate and benzyl 3-(aminomethyl)-5-isopropylphenyl(methyl)carbamate.

Example 1.1.53

5-(aminomethyl)-N,N-dimethylpyridin-3-amine

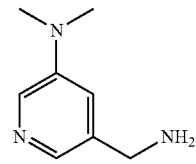

5-methyl 5-aminonicotinate was generated from pyridine-3,5-dicarboxylic acid following procedures well know in the art and synthesis described herein. To a stirring solution of 5-methyl 5-aminonicotinate (283 mg, 1.86 mmol) in 19 mL of $CH_3CN$ and 19 mL of 37% formaldehyde in $H_2O$ was added 353 mg (5.62 mmol) of $NaCNBH_3$, and 50 drops of acetic acid. The solution was stirred at r.t. for 18.5 h and 40 mL of EtOAc and 40 mL of sat. $NaHCO_3$ solution were added. The layers were separated, and the organic layer was washed with 25 mL of sat. $NaHCO_3$ and 25 mL of brine, dried over $Na_2SO_4$, filtered, and concentrated. Purification by flash silica gel chromatography (0.5% $MeOH/CHCl_3$) resulted in 124 mg of methyl 5-(dimethylamino)nicotinate as a yellow oil in 37% yield.

Methyl 5-(dimethylamino)nicotinate was then transformed to 5-(aminomethyl)-N,N-dimethylpyridin-3-amine using a procedure similar to the synthesis of (5-isopropylpyridin-3-yl)methanamine described herein.

Example 1.1.54

(6-(trifluoromethyl)pyridin-3-yl)methanamine

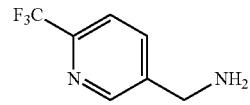

A mixture of (6-(trifluoromethyl)pyridin-3-yl)methanol (2.0 g, 11.3 mmol) and diphenyl phosphorazidate (2.93 mL, 14 mmol) was dissolved in dry toluene (20 mL). The mixture was cooled to 0° C. under Argon, and neat DBU (2.1 mL, 14 mmol) was added. The reaction mixture was stirred for 2 h at 0° C. and then at rt for 16 h. The resulting two-phase mixture was washed with water and extracted with EtOAc. The combined organic layer was concentrated in vacuo and purified by silica gel chromatography afford 5-(azidomethyl)-2-(trifluoromethyl)pyridine (2.3 g, quantitative yield) of a light yellow oil: $^1H$ NMR (300 MHz, $CDCl_3+CD_3OD$), d: 8.686 (m, 1H), 7.853 (m, 1H), 7.723 (d, J=8.1 Hz, 1H), 4.518 (s, 2H).

5-(azidomethyl)-2-(trifluoromethyl)pyridine (2.6 g, 12.86 mmol) in THF at −78° C. was added LAH (0.54 g, 14.2 mmol). The resulting mixture was stirred for 15 min. and warmed to room temperature for one hour. Then the reaction was quenched with saturated aqueous $NH_4Cl$ and stirred for a couple of hours. Anhydrous $Na_2SO_4$ was added to make the mixture clear two phases, filtered and washed with EtOAc. The combined organic solution was concentrated to provide (6-(trifluoromethyl)pyridin-3-yl)methanamine as a red syrup (2.1 g). $^1H$ NMR (300 MHz, $CDCl_3+CD_3OD$), d: 8.729 (s, 1H), 7.928 (d, J=9.1 Hz, 1H), 7.706 (d, J=9.1 Hz, 1H), 4.054 (s, 2H).

Example 1.1.55

N-methyl-1-(4-methylthiazol-2-yl)methanamine

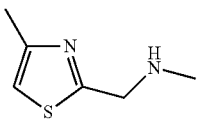

Ti(O$^i$PR)$_4$ (1.3 eq) was added with stirring to MeNH$_2$ (2.0 M in MeOH, 3 eq) at 0° C. under Ar. After 15 min. 4-methylthiazole-2-carbaldehyde (1 eq) was added, and the solution was stirred for 2-3 h. NaBH$_4$ (1.4 eq, in batches if large scale) was added and stirred at 0° C. to RT overnight, followed by solvent removal in vacuo. The residue was diluted with water/CH$_2$Cl$_2$, and a white ppt formed. The mixture was then filtered through Celite to remove the white ppt and the layers were separated. The aqueous layer was extracted with CH$_2$Cl$_2$ (×3) and the combined organics were dried over Na$_2$SO$_4$. The inorganics were filtered off, and the solvent was removed in vacuo to give the crude product. Purification via column chromatography yielded the pure product in 80-90% yield.

Example 1.1.56

(3-methyl-1,2,4-oxadiazol-5-yl)methanamine

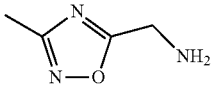

To a stirred solution of acetonitrile (5 mL, 95 mmol) in a 4:1 mixture of EtOH and water (180 mL) were added NaOH (4.26 g, 107 mmol) and hydroxylamine hydrochloride (7.1 g, 0.1 mmol) and the reaction was refluxed for 24 h. It was then concentrated under reduced pressure. The white solid was dissolved in 150 mL of absolute EtOH and filtered to remove the inorganic salts. Concentration of the filtrate gave a crude white solid, which was recrystallized form isopropanol to obtain 3.2 g of (Z)—N'-hydroxyacetimidamide.

To a stirred suspension of molecular sieves 3A° in anhydrous THF (200 mL) was added (Z)—N'-hydroxyacetimidamide (900 mg, 10.0 mmol) and stirred for 15 min. NaH (1.3 g, 32.0 mmol) wad added and the reaction was stirred for 45 min. Then Glycine methyl ester (1.89 g, 10 mmol) was added and the reaction was refluxed overnight, cooled filtered over celite and concentrated. The residue was dissolved in CH$_2$Cl$_2$, washed with water, dried on Na$_2$SO$_4$ and concentrated. The residue was purified by column chromatography (40% EtOAc in hexanes) to provide 460 mg of tert-butyl (3-methyl-1,2,4-oxadiazol-5-yl)methylcarbamate.

tert-butyl (3-methyl-1,2,4-oxadiazol-5-yl)methylcarbamate was converted into (3-methyl-1,2,4-oxadiazol-5-yl)methanamine using standard deprotection protocol of Boc group with TFA.

Example 1.1.57

(5-methyl-1,2,4-oxadiazol-3-yl)methanamine

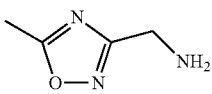

To a stirred solution of N-Boc-2-aminoacetonitrile (3.0 g, 19.21 mmol) in a 4:1 mixture of EtOH and water (25 mL) were added NaOH (860 mg, 21.5 mmol) and hydroxylamine hydrochloride 9 1.44 g, 20.7 mmol) and the reaction was stirred for 30 h. All the solvent was evaporated under reduced pressure. The solid was dissolved in water and the aqueous layer was extracted with EtOAc. The combined organic layers were dried on Na$_2$SO$_4$ and concentrated to provide 1.8 g of (Z)-tert-butyl 2-amino-2-(hydroxyimino)ethylcarbamate.

To a stirred solution of (Z)-tert-butyl 2-amino-2-(hydroxyimino)ethylcarbamate (945 mg, 5 mmol) and EtOAc (2.0 mL, 20.0 mmol) in EtOH (100 mL) was added a solution of NaOEt in EtOH (13 mL, 50.0 mmol) and refluxed for 6 h. The reaction mixture was cooled and all the solvent was evaporated under reduced pressure. The residue was dissolved in water and the aqueous layer was extracted with EtOAc. The combined organic layers were dried on Na$_2$SO$_4$ and concentrated to provide 1.0 g of tert-butyl (5-methyl-1,2,4-oxadiazol-3-yl)methylcarbamate.

tert-butyl (5-methyl-1,2,4-oxadiazol-3-yl)methylcarbamate was converted into (5-methyl-1,2,4-oxadiazol-3-yl)methanamine using standard deprotection protocol of Boc group with TFA.

Example 1.1.58

3-(aminomethyl)-N,N-diethylaniline

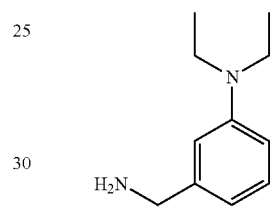

Acetaldehyde (0.52 ml, 0.4 g, 9.08 mmol, 5 eq) was added to a stirred solution of tert-butyl 3-aminobenzylcarbamate (derived from 3-(aminomethyl)aniline (TCI America)) in 11 ml CH$_3$CN/H$_2$O (10:1) at 0° C. After 5 min NaBH$_3$CN (0.3 g, 4.54 mmol, 2.5 eq) was added. The reaction was adjusted to pH 7 with HOAc and stirred at 0° C. for 5 min. The ice-bath was removed and the reaction was stirred at room temperature for 45 min. The solvent was removed in vacuo. The residue was diluted with saturated aqueous NaHCO$_3$ and extracted with EtOAc (×2). The combined organics were washed with water (×3), brine (×1), and dried over Na$_2$SO$_4$. The inorganics were filtered off, and the solvent was removed in vacuo. Purification via flash chromatography yielded 0.3875 g (1.4 mmol, 77% yield) of tert-butyl 3-(diethylamino)benzylcarbamate.

MeOH.HCl (1.25 M, 11 ml, 13.9 mmol, 10 eq) was added to a flask charged with tert-butyl 3-(diethylamino)benzylcarbamate (0.3875 g, 1.4 mmol, 1 eq) at 0° C. under Ar. After stirring for 1.5 h at 0° C. the ice-bath was removed. After stirring at room temperature for 6 h, the solvent was removed in vacuo. The residue was stirred with saturated aqueous NaHCO$_3$ for 30 min and extracted with CH$_2$Cl$_2$ (×2). The combined organics were dried over Na$_2$SO$_4$. The inorganics were filtered off, and the solvent was removed in vacuo to yield 0.191 g (1.07 mmol, 77% yield) of the product.

Example 1.1.59

3-(aminomethyl)-N-methylaniline

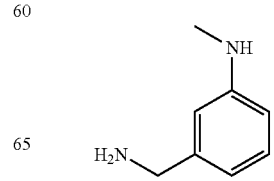

A stirred solution of the starting tert-butyl 3-aminobenzylcarbamate (0.925 g, 4.16 mmol, 1 eq, derived from 3-(aminomethyl)aniline (TCI America)) in 10 ml anhydrous DMF under Ar was treated with benzyl bromide (0.54 ml, 0.78 g, 4.58 mmol, 1.1 eq) and Et₃N (0.75 ml, 0.55 g, 1.3 eq). After stirring for 48 h the reaction was diluted with water and extracted with EtOAc (×2). The combined organics were washed with water (×4), brine (×1), and dried over Na₂SO₄. The inorganics were filtered off, and the solvent was removed in vacuo. Purification via flash chromatography yielded 0.3937 g (1.26 mmol, 30% yield) of tert-butyl 3-(benzylamino)benzylcarbamate.

CH₂O (aq, 37%) (0.112 ml, 0.12 g, 1.51 mmol, 2 eq) was added to a stirred solution of tert-butyl 3-(benzylamino)benzylcarbamate (0.2353 g, 0.753 mmol, 1 eq) in 5 ml CH₃CN. After 10 min NaBH₃CN (0.0615 g, 0.98 mmol, 1.3 eq) was added. The reaction was adjusted to pH 7 with HOAc. After 2 h the solvent was removed in vacuo. The residue was diluted with saturated aqueous NaHCO₃/EtOAc, and the layers were separated. The organic layer was washed with water (×3), brine (×1), and dried over Na₂SO₄. The inorganics were filtered off, and the solvent was removed in vacuo to yield 0.2482 g (0.76 mmol, 100% yield) of tert-butyl 3-(benzyl(methyl)amino)benzylcarbamate.

20% Pd(OH)₂ 0.076 g) was added to a stirred suspension of tert-butyl 3-(benzyl(methyl)amino)benzylcarbamate (0.248 g, 0.76 mmol, 1 eq) in 10 ml EtOH. A H₂ balloon was added. After stirring overnight the mixture was filtered through Celite. The filter cake was rinsed with EtOAc (×3). The organics were combined and the solvent was removed in vacuo to yield tert-butyl 3-(methylamino)benzylcarbamate.

3-(aminomethyl)-N-methylaniline was generated from tert-butyl 3-(methylamino)benzylcarbamate by using a standard deprotection protocol of Boc group described herein.

Example 1.1.60

3-(aminomethyl)-5-methoxy-N,N-dimethylaniline

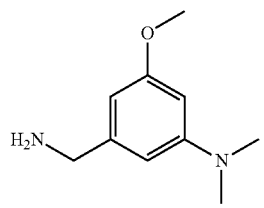

SOCl₂ (3.4 ml, 5.61 g, 47.1 mmol, 5 eq) was added dropwise to a stirred solution of 3,5-dinitrobenzoic acid (2.0 g, 9.43 mmol, 1 eq, Aldrich) in 20 ml anhydrous MeOH at 0° C. under Ar. The reaction was stirred at 0° C. to room temperature overnight. The solvent was removed in vacuo, and the residue was dissolved in EtOAc. The organic layer was washed with saturated aqueous NaHCO₃ (×2), water (×3), brine (×1), and dried over Na₂SO₄. The inorganics were filtered off, and the solvent was removed in vacuo yielding 2.12 g (9.38 mmol, 99% yield) of methyl 3,5-dinitrobenzoate.

methyl 3,5-dinitrobenzoate (1.5 g, 6.63 mmol, 1 eq) in 10 ml anhydrous MeOH under Ar was heated to reflux at 85° C. LiOMe (1.0 M in MeOH, 13.3 ml, 13.3 mmol, 2 eq) was added to the refluxing solution. After 4 h the reaction was cooled to room temperature, and the mixture was adjusted to pH 3 with concentrated HCl. The solvent was removed in vacuo and the residue was dissolved in EtOAc. The organic layer was washed with saturated aqueous NaHCO₃ (×2), water (×3), brine (×1), and dried over Na₂SO₄. The inorganics were filtered off, and the solvent was removed in vacuo. Purification via flash chromatography yielded 0.7705 g (3.70 mmol, 56% yield) of methyl 3-methoxy-5-nitrobenzoate.

Lithium aluminum hydride (0.1116 g, 2.94 mmol, 1.5 eq) was added to a stirred solution of methyl 3-methoxy-5-nitrobenzoate (0.408 g, 1.96 mmol, 1 eq) in 10 ml anhydrous Et₂O at 0° C. under Ar. The reaction was stirred at 0° C. to room temperature overnight. Starting material was still present after stirring overnight. Additional LAH (0.1116 g, 2.94 mmol, 1.5 eq) was added. After 2 h the reaction was quenched with water. The reaction was diluted with saturated aqueous NaHCO₃ and extracted with EtOAc (×2). The combined organics were washed with brine (×1) and dried over Na₂SO₄. The inorganics were filtered off, and the solvent was removed in vacuo. Purification via flash chromatography yielded 0.2463 g (1.33 mmol, 68% yield) of (3-methoxy-5-nitrophenyl)methanol.

Diphenylphosphoryl azide (0.316 ml, 0.4 g, 1.46 ml, 1.1 eq) and 1,8-Diazabicyclo(5.4.0)undec-7-ene (0.219 ml, 0.22 g, 1.46 mmol, 1.1 eq) were added to a stirred solution of (3-methoxy-5-nitrophenyl)methanol in 10 ml anhydrous toluene under Ar. After stirring overnight the solvent was removed in vacuo. Purification via flash chromatography yielded 0.278 g (1.34 mmol, 100% yield) of 1-(azidomethyl)-3-methoxy-5-nitrobenzene.

10% Pd/C (0.028 g) was added to a stirred solution of 1-(azidomethyl)-3-methoxy-5-nitrobenzene in 10 ml MeOH. A H₂ balloon was added. After stirring overnight the mixture was filtered through Celite. The filter cake was rinsed with EtOAc (×3). The organics were removed in vacuo. The residue was dissolved water and extracted with Et₂O (×1). The water was removed in vacuo to yield 0.161 g (1.06 mmol, 100% yield) of the crude 3-(aminomethyl)-5-methoxyaniline which was used without purification.

Et₃N (0.3 ml, 0.2 g, 2.12 mmol, 2 eq) and (Boc)₂O (0.24 ml, 0.23 g, 1.06 mmol, 1 eq) were added sequentially to a stirred solution of 3-(aminomethyl)-5-methoxyaniline (0.161 g, 1.06 mmol, 1 eq) in 10 ml anhydrous MeOH at 0° C. under Ar. After stirring at 0° C. to room temperature overnight the solvent was removed in vacuo. The residue was dissolved in EtOAc, washed with water (×3), brine (×1), and dried over Na₂SO₄. The inorganics were filtered off, and the solvent was removed in vacuo. Purification via flash chromatography yielded 0.0975 g (0.39 mmol, 36% yield) of tert-butyl 3-amino-5-methoxybenzylcarbamate with some impurity.

CH₂O (aq, 37%) (0.12 ml, 0.127 g, 1.56 mmol, 4 eq) was added to a stirred solution of tert-butyl 3-amino-5-methoxybenzylcarbamate (0.0975 g, 0.39 mmol, 1 eq) in 5 ml CH₃CN. After 10 min NaBH₃CN (0.056 g, 0.897 mmol, 2.3 eq) was added. The reaction was adjusted to pH 7 with HOAc. After stirring overnight the reaction was diluted with Et₂O/water and the layers were separated. The organic layer was washed with saturated aqueous NaHCO₃ (×2), water (×3), brine (×1), and dried over Na₂SO₄. The inorganics were filtered off, and the solvent was removed in vacuo. Purification via flash chromatography yielded 0.0638 g (0.228 mmol, 58% yield) of tert-butyl 3-(dimethylamino)-5-methoxybenzylcarbamate.

3-(aminomethyl)-5-methoxy-N,N-dimethylaniline was generated from tert-butyl 3-(dimethylamino)-5-methoxybenzylcarbamate by using a standard deprotection protocol of Boc group described herein.

Example 1.1.61

(3-methoxy-5-nitrophenyl)methanamine

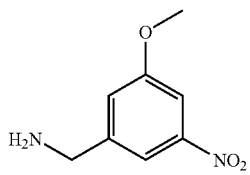

PPh₃ (0.0707 g, 0.27 mmol, 1.1 eq) was added to a stirred solution of 1-(azidomethyl)-3-methoxy-5-nitrobenzene (synthesis described herein) in 5 ml THF. After 5 min 1 ml of water was added, and the reaction was stirred overnight. The solvent was removed in vacuo. The residue was dissolved in EtOAc and extracted with 1N HCl (×1). The aqueous layer was adjusted to pH>8 with 1N NaOH and extracted with EtOAc (×1). This organic fraction was washed with brine (×1) and dried over Na₂SO₄. The inorganics were filtered off, and the solvent was removed in vacuo to yield 0.030 g (0.16 mmol, 67% yield) of the product.

Example 1.1.62

5-(aminomethyl)-N1,N1,N3,N3-tetramethylbenzene-1,3-diamine

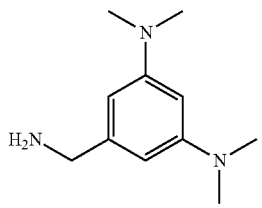

20% Pd(OH)₂ (0.13 g) was added to a stirred suspension of 3,5-dinitrobenzonitrile (0.50 g, 2.59 mmol, 1 eq, Aldrich) in 10 ml EtOH. A H₂ balloon was added. After stirring over the weekend the mixture was filtered through Celite. The filter cake was rinsed with EtOH (×3). The organics were removed in vacuo. The residue was stirred in CHCl₃ and the resulting mixture was filtered (×3). The CHCl₃ fractions were combined, and the solvent was removed in vacuo to yield crude 3,5-diaminobenzonitrile.

CH₂O (aq, 37%) (0.68 ml, 0.7412 g, 9.08 mmol, 6 eq) was added to a stirred solution of 3,5-diaminobenzonitrile (0.2076 g, 1.51 mmol, 1 eq) in 10 ml CH₃CN. After 10 min NaBH₃CN (0.45 g, 6.8 mmol, 4.5 eq) was added. The reaction was adjusted to pH 7 with HOAc. After stirring overnight the solvent was removed in vacuo. The residue was dissolved in EtOAc, washed with saturated aqueous NaHCO₃ (×2), water (×3), brine (×1), and dried over Na₂SO₄. The inorganics were filtered off, and the solvent was removed in vacuo. Purification via flash chromatography yielded 0.1145 g (0.59 mmol, 39% yield) of 3,5-bis(dimethylamino)benzonitrile.

NaBH₄ (0.067 g, 1.77 mmol, 3 eq) was added to a stirred solution of 3,5-bis(dimethylamino)benzonitrile (0.1145 g, 0.59 mmol, 1 eq) and CoCl₂.6H₂O (0.0161 g, 0.059 mmol, 10 mol %) in 5 ml EtOH at 50° C. After 2 h the reaction was not complete. Additional NaBH₄ (0.0245 g, 0.64 mmol, 1.1 eq) was added. After 2 h the reaction was cooled to room temperature and 3 N HCl was added to pH=1-2. After stirring for 1 h the reaction was concentrated in vacuo. The residue was extracted with EtOAc (×2). The aqueous layer was adjusted to pH=8-9 with 1 N NaOH. The water was removed in vacuo. The residue was stirred with CHCl₃, filtered through Celite, and dried over Na₂SO₄. The inorganics were filtered off, and the solvent was removed in vacuo yielding 0.0807 g (0.22 mmol, 37% yield) of the product.

Example 1.1.63

4-(aminomethyl)-6-methoxypyrimidin-2-amine

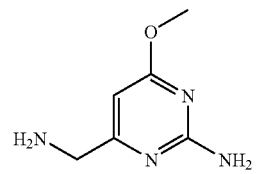

NaH (60% dispersion in oil, 0.201 g, 5.02 mmol, 2 eq) was added to a stirred solution of 4-chloro-6-methoxypyrimidin-2-amine (0.400 g, 2.51 mmol, 1 eq, Aldrich) and MeI (0.5 ml, 1.07 g, 7.52 mmol, 3 eq) in 2 ml anhydrous DMF at 0° C. After 1 h the reaction was quenched with water and diluted with EtOAc. The layers were separated. The organic layer was washed with water (×3), brine (×1), and dried over Na₂SO₄. The inorganics were filtered off, and the solvent was removed in vacuo. Purification via flash chromatography yielded 0.180 g (0.96 mmol, 38% yield) of 4-chloro-6-methoxy-N,N-dimethylpyrimidin-2-amine.

A solution of 4-chloro-6-methoxy-N,N-dimethylpyrimidin-2-amine (0.350 g, 2.19 mmol, 1 eq) in 10 ml anhydrous DMF was degassed with Ar for 5 min. Zn(CN)₂ (0.155 g, 1.32 mmol, 0.6 eq) and Pd(PPh₃)₄ (0.253 g, 0.219 mmol, 10 mol %) were added and the mixture was heated to 95° C. After 23 h the reaction was cooled to room temperature and the mixture was diluted with Et₂O and NH₄OH (28%). After stirring for 1 h the layers were separated. The organic layer was washed with water (×3), brine (×1), and dried over Na₂SO₄. The inorganics were filtered off, and the solvent was removed in vacuo. Purification via flash chromatography yielded 0.214 g (1.43 mmol, 65% yield) of 2-amino-6-methoxypyrimidine-4-carbonitrile.

10% Pd/C (0.010 g) was added to a stirred solution of 2-amino-6-methoxypyrimidine-4-carbonitrile (0.107 g, 0.71 mmol, 1 eq) in 4 ml HOAc. A H₂ balloon (20 psi) was added. After 2 h the mixture was filtered through Celite. The filter cake was rinsed with MeOH. The organics were combined and the solvent was removed in vacuo. 1 N NaOH was added to pH>8 and the solvent was removed in vacuo. The residue was stirred in EtOAc (30 ml) and saturated aqueous NaHCO₃ (1 ml). After 30 min Na₂SO₄ was added and the mixture was stirred for 10 min. The inorganics were filtered off, and the solvent was removed in vacuo yielding 0.1044 g (0.68 mmol, 95% yield) of the product.

Example 1.1.64

1-(5-isopropylpyridin-3-yl)ethanamine

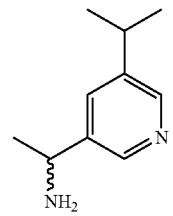

A stirred solution of 1-(5-bromopyridin-3-yl)ethanone (600 mg, 3.0 mmol), potassium isopopenyltrifluoroborate (148 mg, 3.0 mmol), and Et$_3$N (1.25 mL, 9.0 mmol) in $^i$PrOH (20 mL) and H$_2$O (10 mL) was degassed with argon for 10 min and then PdCl2 (dppf).CH$_2$Cl$_2$ (74 mg, 0.09 mmol) was added and the reaction mixture was heated to reflux for 5 h. The solution was cooled to room temperature and diluted with Ether and H$_2$O. The layers were separated and the aqueous layer was extracted with Ether (2×50 mL). The combined organic layer was washed with brine, dried with Na$_2$SO$_4$ and concentrated under reduced pressure. The residue was purified by column chromatography (30% EtOAc in hexanes) to provide 460 mg of 1-(5-(prop-1-en-2-yl)pyridin-3-yl)ethanone.

To a stirred solution of 1-(5-(prop-1-en-2-yl)pyridin-3-yl)ethanone (460 mg, 2.86 mmol) in 95% EtOH was added a solution of NH$_2$OH.HCl (1.19 g, 17.14 mmol) in a mixture of water (5.8 mL) and 10% NaOH (5.8 mL) and refluxed for 2.5 h. All solvent was removed. The residue was dissolved in CHCl$_3$, washed with water, dried with Na$_2$SO$_4$ and concentrated under reduced pressure to yield 400 mg of crude 1-(5-(prop-1-en-2-yl)pyridin-3-yl)ethanone oxime.

To a stirred solution of 1-(5-(prop-1-en-2-yl)pyridin-3-yl)ethanone oxime (400 mg) in MeOH.HCl (1.25M, 8 mL) was added 10% Pd/C (40 mg) and stirred under hydrogen atmosphere for 4 h. The catalyst was filtered off and the residue was dissolved in 5 mL of 25% aqueous NH$_3$ and extracted with CHCl$_3$ and the organic layer was washed with brine, dried with Na$_2$SO$_4$ and concentrated under reduced pressure. The residue was purified by column chromatography (10% MeOH/90% CHCl$_3$ spiked with 0.25% of Et$_3$N) to provide 155 mg of the product.

Example 1.1.65

(R)-1-(5-(prop-1-en-2-yl)pyridin-3-yl)ethanamine

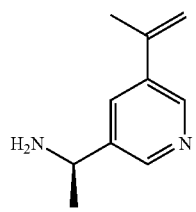

To a stirred solution of 1-(5-bromopyridin-3-yl)ethanone (5.0 g, 25.0 mmol) in anhydrous MeOH (50 mL) at 0° C., was added NaBH$_4$ (1.32 g, 35.0 mmol) and the reaction was allowed to warm to room temperature. All solvent was removed. The residue was dissolved in cold water and extracted with EtOAc (2×70 mL). The combined organic layers was dried with Na$_2$SO$_4$ and concentrated under reduced pressure. The residue was purified by column chromatography (40% EtOAc in hexanes) to provide 4.555 g of 1-(5-bromopyridin-3-yl)ethanol.

To a stirred solution of 1-(5-bromopyridin-3-yl)ethanol (2.0 g) in anhydrous Et$_2$O (50 mL) at 0° C., was vinyl acetate (2 mL), 4A° molecular sieves (2.0 g), Lipase immobilized from *Candida Antarctica* (200 mg) and the reaction was stirred for 16 h. The catalyst and molecular sieves were filtered off and the solvent was concentrated under reduced pressure. The residue was purified by column chromatography (30% EtOAc in hexanes) to provide 1.0 g of (S)-1-(5-bromopyridin-3-yl)ethanol and 1.18 g of (R)-1-(5-bromopyridin-3-yl)ethyl acetate.

A stirred solution of (S)-1-(5-bromopyridin-3-yl)ethanol (950 mg, 4.7 mmol), potassium isopopenyltrifluoroborate (730 mg, 4.94 mmol), and Et$_3$N (1.95 mL, 14.1 mmol) in $^i$PrOH (30 mL) and H$_2$O (15 mL) was degassed with argon for 10 min and then PdCl2 (dppf).CH$_2$Cl$_2$ (192 mg, 0.24 mmol) was added and the reaction mixture was heated to reflux for 4 h. The solution was cooled to room temperature and diluted with Ether and H$_2$O. The layers were separated and the aqueous layer was extracted with Ether (2×50 mL). The combined organic layer was washed with brine, dried with Na$_2$SO$_4$ and concentrated under reduced pressure. The residue was purified by column chromatography (60% EtOAc in hexanes) to provide 520 mg of (S)-1-(5-(prop-1-en-2-yl)pyridin-3-yl)ethanol.

DPPA (0.55 mL, 2.55 mmol) was added to (S)-1-(5-(prop-1-en-2-yl)pyridin-3-yl)ethanol (347 mg, 2.13 mmol) in toluene (5 mL) and the reaction is cooled to 0° C. DBU (0.38 mL, 2.55 mmol) was added, the reaction was allowed to warm to room temperature and stirred overnight, diluted with EtOAc and washed with water. The organic layer was dried with Na$_2$SO$_4$ and concentrated under reduced pressure. The residue was purified by column chromatography (35% EtOAc in hexanes) to provide 340 mg of (R)-3-(1-azidoethyl)-5-(prop-1-en-2-yl)pyridine.

To a stirred solution of (R)-3-(1-azidoethyl)-5-(prop-1-en-2-yl)pyridine (340 mg) in MeOH.HCl (1.25M, 10 mL) was added 10% Pd/C (50 mg) and stirred under hydrogen atmosphere for 12 h. The catalyst was filtered off and the residue was dissolved in 5 mL of 25% aqueous NH$_3$ and extracted with CHCl$_3$ and the organic layer was washed with brine, dried with Na$_2$SO$_4$ and concentrated under reduced pressure. The residue was purified by column chromatography (10% MeOH/90% CHCl$_3$ spiked with 0.25% of Et$_3$N) to provide 246 mg of (R)-1-(5-(prop-1-en-2-yl)pyridin-3-yl)ethanamine.

Example 1.1.66

(S)-1-(5-(prop-1-en-2-yl)pyridin-3-yl)ethanamine

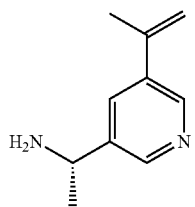

To a stirred solution of (R)-1-(5-bromopyridin-3-yl)ethyl acetate (1.21 g, 4.96 mmol, synthesis described herein) in MeOH (20 mL), was added K$_2$CO$_3$ (1.37 g, 9.92 mmol) and the reaction was stirred for 1 h. All the solvent was removed, the residue was dissolved in cold water and extracted with EtOAc (2×50 mL), to provide 1.0 g of crude (R)-1-(5-bromopyridin-3-yl)ethanol.

(R)-1-(5-bromopyridin-3-yl)ethanol was transformed into (S)-1-(5-(prop-1-en-2-yl)pyridin-3-yl)ethanamine following same chemistry as described for (R)-1-(5-(prop-1-en-2-yl)pyridin-3-yl)ethanamine.

Example 1.1.67

(3-isopropyl-5-(methylsulfonyl)phenyl)methanamine

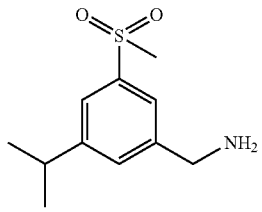

To a stirring slurry of 3.2 g (25.4 mmol) of $Na_2SO_3$ and 6.2 g (73.8 mmol) of $NaHCO_3$ in 20 mL of $H_2O$ at 75° C. was added 5.0 g (24.4 mmol) of 3,5-dimethylbenzene-1-sulfonyl chloride in several portions. After 2 h at 75° C., 3.5 g (37.0 mmol) of chloroacetic acid was added in portions followed by 1.5 g (37.5 mmol) of NaOH in 3 mL of $H_2O$. The mixture was stirred at 135° C. for 13 h, and 3 N HCl was added to a pH=1. A colorless precipitate formed, and the mixture was filtered through a Buchner funnel to provide 3.8 g of 1,3-dimethyl-5-(methylsulfonyl)benzene in 84% yield.

To a stirring mixture of 5.2 g (28.2 mmol) of 1,3-dimethyl-5-(methylsulfonyl)benzene in 25 mL of pyridine and 50 mL of $H_2O$ was added 27 g of $KMnO_4$ in 9, 3 g portions at 120° C. After the mixture was stirred at 120° C. overnight, the mixture was filtered hot through a Buchner funnel. The solution was washed with $CHCl_3$ about 2-3 times and acidified to a pH=1-2. The colorless precipitate of 5-(methylsulfonyl)isophthalic acid that formed was filtered through a Buchner funnel and used in the next reaction without further purification.

To a stirring mixture of 3.5 g (14.3 mmol) of 5-(methylsulfonyl)isophthalic acid in 60 mL of MeOH was added 11.5 mL (158 mmol) of $SOCl_2$ dropwise over a period of about 30 minutes. After 39 h, the solution was concentrated and sat. $NaHCO_3$ and $CHCl_3$ were added. The extract was dried over $Na_2SO_4$, filtered, and concentrated. The dimethyl 5-(methylsulfonyl)isophthalate product was used in the next reaction without further purification.

To a stirring solution of 4.57 g (16.8 mmol) of dimethyl 5-(methylsulfonyl)isophthalate in 100 mL of THF and 100 mL of MeOH was added 671 mg (16.8 mmol) of NaOH in 17 mL of water. The solution was allowed to stir at r.t. for 29.5 h and then concentrated. The aqueous layer was washed with $CHCl_3$ (2×) and then acidified to pH=1 with 1 N HCl. A precipitate formed, and the mixture was filtered through a Buchner funnel. The colorless solid of 3-(methoxycarbonyl)-5-(methylsulfonyl)benzoic acid (2.85 g-62% yield) was used without further purification.

The corresponding azide, methyl 3-(azidomethyl)-5-(methylsulfonyl)benzoate, was synthesized from 3-(methoxycarbonyl)-5-(methylsulfonyl)benzoic acid following the general procedure as described herein.

A mixture of 147 mg (0.546 mmol) of methyl 3-(azidomethyl)-5-(methylsulfonyl)benzoate and 18.5 mg of 10% Pd/C in 6 mL of MeOH was stirred at r.t. under $H_2$ balloon for 3 h. The mixture was filtered through Celite and concentrated. The crude (3-isopropyl-5-(methylsulfonyl)phenyl)methanamine (101 mg) was used in the next reaction without further purification.

Example 1.1.68

(5-isopropyl-2-methylpyridin-3-yl)methanamine

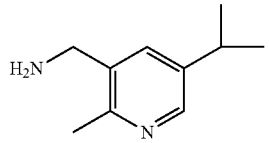

To a stirring solution of 1.1 g (9.47 mmol) of methyl acetoacetate in 20 mL of THF at 0° C. was added about 10 mL of $^tBuOK$ (1.0 M) in THF dropwise. The ice bath was removed and stirring was continued at r.t. After 1 h 0.5 mL of $^tBuOK$ was added, and after 10 min. 1.12 g (10 mmol) of DABCO (1,4-Diazabicyclo[2.2.2]octane) and 4.23 g (13.8 mmol) of the vinamidinium hexafluorophosphate salt (Davies, I. W., et al. *J. Org. Chem.* 2000, 65, 4571) were added. The mixture was heated at 45° C. and after 3 h, 1.35 g (17.5 mmol) of $NH_4OAc$ was added. The temperature was increased to 80° C., and after 1 hour, 130 mg of $NH_4OAc$ was added. After 4 h, the reaction was quenched with 45 mL of water. The aqueous layer was extracted with EtOAc (4×), and the combined extracts were washed with brine, dried over $Na_2SO_4$, filtered, and concentrated. Purification by flash silica gel chromatography (45% EtOAc/hexanes) provided 1.44 g of methyl 5-chloro-2-methylnicotinate as a yellow orange oil in about 80% yield.

To a stirring solution of 950 mg (5.12 mmol) of methyl 5-chloro-2-methylnicotinate in 20 mL of THF at 0° C. was added 500 mg (13.2 mmol) of $LiAlH_4$ in 2 portions. After stirring at 0° C. for about 1 h., the following were added in succession: 0.5 mL of $H_2O$, 0.5 mL of 15% NaOH (aqueous), and 1.5 mL of brine. The ice bath was removed and stirring was continued for 2 h. The mixture was filtered through Celite and concentrated. Purification by flash silica gel chromatography (2% MeOH/$CHCl_3$) provided 399 mg of (5-chloro-2-methylpyridin-3-yl)methanol as an orange-yellow oil in 50% yield.

To a stirring solution of 399 mg (2.55 mmol) of (5-chloro-2-methylpyridin-3-yl)methanol in 10 mL of toluene at r.t. was added 660 μL (3.06 mmol) of DPPA (diphenylphosphoryl azide). The solution was cooled to 0° C. and 450 μL of DBU (1,8-diazabicyclo[5.4.0]undec-7-ene) was added. The ice bath was removed and stirring was continued with warming to r.t. After 16 h, 1 N HCl was added to a pH=8. Water was added and the aqueous layer was extracted with EtOAc. The organic layer was washed with brine, dried over $Na_2SO_4$, filtered, and concentrated. Purification by flash silica gel chromatography (45% EtOAc/hexanes) provided 3-(azidomethyl)-5-chloro-2-methylpyridine as a yellow oil in quantitative yield.

(5-chloro-2-methylpyridin-3-yl)methanamine was synthesized from 3-(azidomethyl)-5-chloro-2-methylpyridine following the general procedure as described herein.

The Boc protected amine (tert-butyl (5-chloro-2-methylpyridin-3-yl)methylcarbamate) was synthesized from (5-chloro-2-methylpyridin-3-yl)methanamine following the general procedures as described herein.

To a solution of 262 mg (1.02 mmol) of tert-butyl (5-chloro-2-methylpyridin-3-yl)methylcarbamate, 163 mg (1.08 mmol) of potassium isopropenyltrifluoroborate, and 450 μL (4.28 mmol) of ᵗBuNH₂ in 7.2 mL of isopropanol and 2.8 mL of H₂O (degassed) was added 85.5 mg (0.105 mmol) of PdCl₂(dppf).CH₂Cl₂. After heating the solution for 15 h at 120° C., H₂O and EtOAc were added. The organic layer was washed with brine, dried over Na₂SO₄, filtered, and concentrated. Purification by flash silica gel chromatography (40% EtOAc/hexanes) provided 31.7 mg of 1-(2-methyl-5-(prop-1-en-2-yl)pyridin-3-yl)-N-((oxobornyl)methylene)methanamine as a yellow oil in 12% yield.

To a stirring solution of 96.6 mg (0.370 mmol) of 1-(2-methyl-5-(prop-1-en-2-yl)pyridin-3-yl)-N-((oxobornyl)methylene)methanamine and 88.5 mg (0.372 mmol) of CoCl₂.6H₂O in 4 mL of EtOH at 50° C. was added 160 mg of NaBH₄ in 2 portions. After heating the mixture at 50° C. under Ar for 5 h, the reaction mixture was cooled and 5 N HCl was added to a pH=1. The mixture was stirred at r.t. for 15 h and concentrated. Water was added, and NH₄OH was added to a pH=9. The aqueous layer was extracted with the extract of (40 mL of CHCl₃: 5 mL of MeOH: 5 mL H₂O) (2×). The combined extracts were dried over Na₂SO₄, filtered, and concentrated. (5-isopropyl-2-methylpyridin-3-yl)methanamine was used in the next reaction without further purification.

Example 1.1.69

(3-(benzyloxy)-5-(2-chloropropan-2-yl)phenyl)methanamine

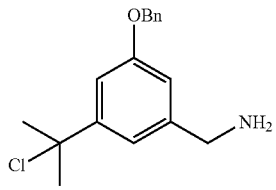

A mixture of 1.98 g (9.42 mmol) of dimethyl 5-hydroxyisophthalate 3.0 g (21.7 mmol) of K₂CO₃ and 1.8 mL (15.1 mmol) of BnBr in 30 mL of DMF was heated at 60° C. for 18 h. After the mixture was filtered through cotton, water and CHCl₃ were added. The organic layer was washed with water and brine, dried over Na₂SO₄, filtered, and concentrated. Purification by flash silica gel chromatography (15% EtOAc/hexanes) provided the 2.64 g of dimethyl 5-(benzyloxy)isophthalate as a colorless solid in 93% yield.

3-(benzyloxy)-5-(methoxycarbonyl)benzoic acid was synthesized from the dimethyl 5-(benzyloxy)isophthalate following the general procedures as described herein.

1-(azidomethyl)-3-(benzyloxy)-5-(2-chloropropan-2-yl)benzene was synthesized from 3-(benzyloxy)-5-(methoxycarbonyl)benzoic acid following the general procedures as described herein.

A mixture of 103 mg of 1-(azidomethyl)-3-(benzyloxy)-5-(2-chloropropan-2-yl)benzene and 10.4 mg of 10% Pd/C in 5 mL of MeOH was stirred at r.t. under H₂ balloon for 4.5 h. The mixture was filtered through Celite and concentrated. (3-(benzyloxy)-5-(2-chloropropan-2-yl)phenyl)methanamine was used in the next reaction without further purification.

Example 1.1.70

3-(aminomethyl)-5-isopropylphenyl methanesulfonate

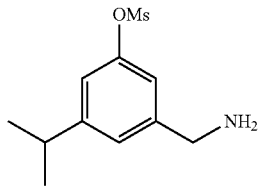

1-(azidomethyl)-3-(benzyloxy)-5-(prop-1-en-2-yl)benzene was synthesized from 3-(benzyloxy)-5-(methoxycarbonyl)benzoic acid following the general procedures as described herein.

A mixture of 573 mg (1.97 mmol) of 1-(azidomethyl)-3-(benzyloxy)-5-(prop-1-en-2-yl)benzene, 0.5 mL of BOC₂O, and 60.5 mg of 10% Pd/C in 10 mL of EtOAc was stirred at r.t. under H₂ balloon for 11.5 h. The mixture was filtered through Celite and concentrated. Purification by flash silica gel chromatography (10% EtOAc/hexanes) provided 336 mg of tert-butyl 3-(benzyloxy)-5-isopropylbenzylcarbamate in 62% yield.

tert-butyl 3-hydroxy-5-isopropylbenzylcarbamate was synthesized from tert-butyl 3-(benzyloxy)-5-isopropylbenzylcarbamate following the general procedures as described herein.

To a stirring solution of 91.8 mg of tert-butyl 3-hydroxy-5-isopropylbenzylcarbamate in 3 mL of CH₂Cl₂ and 300 μL of pyridine at 0° C. was added 30 μL (0.386 mmol) of MsCl. The ice bath was removed, and after stirring at r.t. for 75 min. 50 μL of Et₃N was added. After 30 min., the solution was concentrated and EtOAc and H₂O were added. The organic layer was washed with 15 mL of brine, and the aqueous layer was extracted with EtOAc. The combined extracts were dried over Na₂SO₄, filtered, and concentrated. Purification by flash silica gel chromatography (40% EtOAc/hexanes) provided 96.2 mg of 3-((tert-butoxycarbonylamino)methyl)-5-isopropylphenyl methanesulfonate as a pale yellow oil in about 80% yield.

3-(aminomethyl)-5-isopropylphenyl methanesulfonate was generated from 3-((tert-butoxycarbonylamino)methyl)-5-isopropylphenyl methanesulfonate by using a standard deprotection protocol of Boc group described herein.

Example 1.1.71

(3-(ethylsulfonyl)-5-isopropylphenyl)methanamine

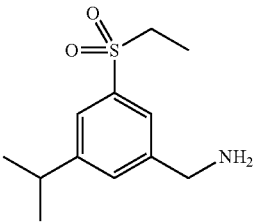

To a stirring solution of 4.1 g (73.1 mmol) of KOH in 70 mL of MeOH at r.t. was added 5 g (36.2 mmol) of 3,5-dimethylbenzenethiol. After 1.5 h, 5.4 mL of EtBr was added, and the solution was stirred at r.t. for about 40 min. and heated at 60° C. for 75 min. Water (300 mL) and CH₂Cl₂ (100 mL) were added, and the aqueous layer was extracted with CH₂Cl₂ (2×) (1×100 mL and 1×50 mL). The combined extracts were dried over Na₂SO₄, filtered, and concentrated. The crude yellow liquid of (3,5-dimethylphenyl)(ethyl)sulfane was used in the next reaction without further purification.

To stirring mixture of (3,5-dimethylphenyl)(ethyl)sulfane in 15 mL of pyridine and 50 mL of H₂O at 120° C. was added 36 g of KMnO₄ by 3 g portions. After the mixture was heated at 120° C. for 12.5 h, it was allowed to cool and was filtered through a Buchner funnel. The aqueous layer was extracted with CHCl₃ (2×), and concentrated HCl was added to the aqueous layer to a pH=1. A solid precipitated, and the mixture was filtered through a Buchner funnel to give 1.86 g (31% yield) of 5-(ethylsulfonyl)isophthalic acid as a colorless solid which was used without further purification.

(3-(ethylsulfonyl)-5-isopropylphenyl)methanamine was synthesized from 5-(ethylsulfonyl)isophthalic acid using a standard deprotection protocol of Boc group described herein.

Example 1.1.72

N-(3-(aminomethyl)-5-isopropylphenyl)acetamide

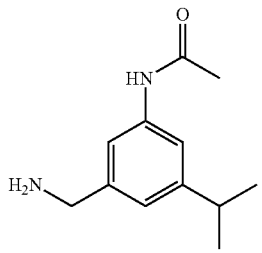

To a stirring mixture of 2.4 g (9.92 mmol) of 2-amino-3-bromo-5-nitrobenzonitrile in 56 mL of EtOH and 5.6 mL of $H_2SO_4$ at 90° C. was added 5.0 g of $NaNO_2$ in several portions. After 36.5 h, $H_2O$ was added, and the aqueous layer was extracted with $CHCl_3$. More $H_2O$ was added and the aqueous layer was extracted with $CHCl_3$. The combined extracts were dried over $Na_2SO_4$, filtered, and concentrated. Purification by flash silica gel chromatography (5% EtOAc/hexanes) resulted in 3-bromo-5-nitrobenzonitrile as a yellow solid.

To a stirring solution of 845 mg (3.72 mmol) of 3-bromo-5-nitrobenzonitrile in 5 mL of THF and 5 mL of EtOH was added 4.2 g (18.6 mmol) of $SnCl_2.2H_2O$ in several portions. The reaction became slightly exothermic and was stirred at r.t. for about 12.5 h. The mixture was concentrated and 30 mL of 2 N NaOH was added. After the mixture was stirred for 2 h, $H_2O$ and EtOAc were added, and the organic layer was washed with 50 mL of $H_2O$ and 40 mL of brine. The aqueous layer was extracted with EtOAc and washed with brine. The combined extracts were dried over $Na_2SO_4$, filtered, and concentrated. Purification by flash silica gel chromatography (35% EtOAc/hexanes) provided 461 mg of 3-amino-5-bromobenzonitrile as a yellow solid in 63% yield.

To a stirring solution of 103 mg (0.520 mmol) of 3-amino-5-bromobenzonitrile in 3 mL of pyridine was added 0.12 mL (1.27 mmol) of $Ac_2O$. The solution was stirred at r.t. for about 5.5 h and concentrated. Ethyl acetate was added, and the organic layer was washed with $H_2O$ and brine, dried over $Na_2SO_4$, filtered and concentrated. N-(3-bromo-5-cyanophenyl)acetamide was used for the next reaction without further purification.

N-(3-cyano-5-(prop-1-en-2-yl)phenyl)acetamide was synthesized from N-(3-bromo-5-cyanophenyl)acetamide following the general procedure as described herein.

To a stirring solution of 91.9 mg (0.459 mmol) of N-(3-cyano-5-(prop-1-en-2-yl)phenyl)acetamide and 110 mg (0.466 mmol) of $CoCl_2.6H_2O$ in 3 mL of EtOH at 50° C. was added 118 mg of $NaBH_4$ in 2 portions. After 3 h 45 min., 5 N HCl was added to a pH=1, and the mixture was concentrated. Ammonium hydroxide was added to a pH=9, and $H_2O$ was also added. The aqueous layer was extracted with the extract of (40 mL $CHCl_3$: 5 mL of MeOH: 5 mL of $H_2O$) (2×). The combined extracts were dried over $Na_2SO_4$, filtered, and concentrated to provide the crude N-(3-(aminomethyl)-5-isopropylphenyl)acetamide which was used without further purification.

Example 1.1.73

3-(aminomethyl)-5-isopropylphenyl dimethylcarbamate

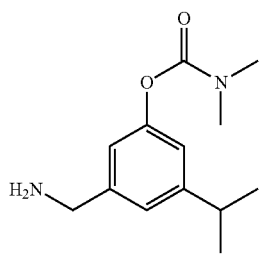

A solution of 57.4 mg (0.216 mmol) of tert-butyl 3-hydroxy-5-isopropylbenzylcarbamate (synthesis described herein) and 30 µL (0.327 mmol) of dimethylcarbamyl chloride in 3 mL of pyridine was heated at 120° C. for 16 h. The solution was concentrated, and $CHCl_3$ and $H_2O$ were added. The organic layer was washed with brine (10 mL), dried over $Na_2SO_4$, filtered and concentrated. Purification by flash silica gel chromatography (25% EtOAc/hexanes) provided 46 mg of Boc-protected 3-(aminomethyl)-5-isopropylphenyl dimethylcarbamate as a yellow oil in 63% yield.

A solution of 46 mg (0.137 mmol) of the Boc-protected 3-(aminomethyl)-5-isopropylphenyl dimethylcarbamate in 2.5 mL of 1.25 M HCl in MeOH was stirred at r.t. for 3.5 h. Trifluoroacetic acid (0.2 mL) was added and stirring was continued for 20 min., and the solution was concentrated. Saturated $NaHCO_3$ was added, and the aqueous layer was extracted with the extract of (40 mL $CHCl_3$: 5 mL of MeOH: 5 mL of $H_2O$) (3×). The combined extracts were dried over $Na_2SO_4$, filtered, and concentrated. Crude 3-(aminomethyl)-5-isopropylphenyl dimethylcarbamate was used in the next reaction without further purification.

Example 1.1.74 methyl 3-(aminomethyl)-5-isopropylphenylcarbamate

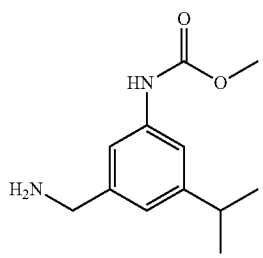

To a stirring solution of 97.3 mg (0.494 mmol) of 3-amino-5-bromobenzonitrile in 3 mL of pyridine at r.t. was added 0.1 mL of methyl chloroformate. After 15 h, 15 mL of $H_2O$ and EtOAc were added. The organic layer was washed with $H_2O$ and brine, dried over $Na_2SO_4$, filtered, and concentrated.

Crude methyl 3-bromo-5-cyanophenylcarbamate was used in the next reaction without further purification.

methyl 3-cyano-5-(prop-1-en-2-yl)phenylcarbamate was synthesized from methyl 3-bromo-5-cyanophenylcarbamate following the general procedures as described herein.

methyl 3-(aminomethyl)-5-(prop-1-en-2-yl)phenylcarbamate was synthesized from methyl 3-cyano-5-(prop-1-en-2-yl)phenylcarbamate following the general procedures as described herein.

A mixture of about 92 mg of crude methyl 3-(aminomethyl)-5-(prop-1-en-2-yl)phenylcarbamate and 17.6 mg of 10% Pd/C in 7 mL of MeOH and 2 mL of EtOAc was stirred at r.t. under $H_2$ balloon for 16 h. The mixture was filtered through Celite and concentrated to give the amine product which was used without further purification.

Example 1.1.75

3-(aminomethyl)-5-tert-butylphenol

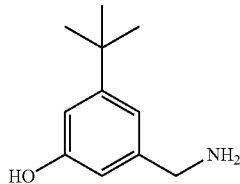

To a stirring solution of 5.0 g (33.5 mmol) of 4-tert-butylaniline in 250 mL of $CH_2Cl_2$ at 0° C. was added 6 mL of $Br_2$ in 30 mL of $CH_2Cl_2$ dropwise until a dark orange color persisted. The organic layer was washed with 100 mL of water, 100 mL of sat. $NaHCO_3$, and 100 mL of brine. It was dried over $Na_2SO_4$, filtered, and concentrated to form 2,6-dibromo-4-tert-butylaniline which was used in the next reaction without further purification.

To a stirring solution of 2,6-dibromo-4-tert-butylaniline in 115 mL of EtOH was added 11.5 mL of concentrated $H_2SO_4$. To the stirring solution at 90° C. was added 8.8 g of $NaNO_2$ in several portions. After 37 h, EtOAc and 120 mL of $H_2O$ were added, and the layers separated. The organic layer was washed with 40 mL of brine, dried over $Na_2SO_4$, filtered, and concentrated. Purification by flash silica gel chromatography (hexanes) provided 8.15 g of 1,3-dibromo-5-tert-butylbenzene as a yellow-brown oil with some impurity.

To a stirring solution of 34 mL of 1.6 M n-BuLi in hexanes in 20 mL of THF at −78° C. was added 8.15 g of 1,3-dibromo-5-tert-butylbenzene in 80 mL of THF dropwise over a period of 1 h. After 1 h at −78° C., 4.6 mL of $B(OMe)_3$ was added, and after 20 min. the cold bath was removed and stirring continued with warming to r.t. After 1 h, EtOAc and 70 mL of 1 N HCl were added, and the layers were separated. The organic layer was washed with brine, dried over $Na_2SO_4$, filtered, and concentrated. To a stirring mixture of the crude product in 105 mL of 1 N NaOH at 0° C. was added 22 mL of $H_2O_2$ (30 wt % in $H_2O$) dropwise. After 25 min. 5 N HCl was added to a pH=1. Ethyl acetate was added, and the organic layer was washed with 80 mL of brine, dried over $Na_2SO_4$, filtered, and concentrated. Purification by flash silica gel chromatography (hexanes to 10% EtOAc/hexanes) provided 6.54 g of 3-bromo-5-tert-butylphenol as an orange oil with some impurity.

A solution of 403 mg of 3-bromo-5-tert-butylphenol and 200 mg (1.28 mmol) of CuCN in 5 mL of DMF was stirred at 160° C. After 75 min. 365 mg of CuCN was added and stirring was continued at 160° C. After about 1 h, the temperature was increased to 170° C. and the mixture was refluxed for 19 h. Ethyl acetate and $H_2O$ were added, and the mixture was filtered through a Buchner funnel, and the layers were separated. The organic layer was washed with 10 mL of $H_2O$ and brine, dried over $Na_2SO_4$, filtered, and concentrated. Purification by flash silica gel chromatography (15% EtOAc/hexanes) provided 153 mg of 3-tert-butyl-5-hydroxybenzonitrile as an orange solid in 49% yield.

3-(aminomethyl)-5-tert-butylphenol was synthesized from 3-tert-butyl-5-hydroxybenzonitrile following the general procedures as described herein.

Example 1.1.76

(3-isopropyl-5-(methylsulfonylmethyl)phenyl)methanamine

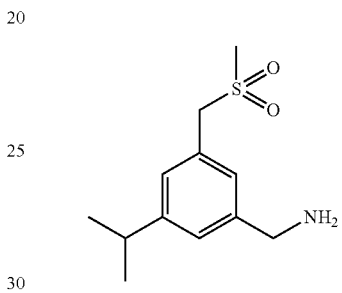

To stirring solution of 5.0 g (18.9 mmol) of 3,5-dibromobenzaldehyde in 30 mL of MeOH and 25 mL of THF at 0° C. was added 819 mg of $NaBH_4$ in 3 portions. The yellow solution was stirred at 0° C. for 30 min. and then concentrated. Water and EtOAc were added, and 1 N HCl was added to a pH=7. The organic layer was washed with 25 mL of brine, dried over $Na_2SO_4$, filtered, and concentrated. (3,5-dibromophenyl)methanol was used in the next reaction without further purification.

To a stirring cloudy solution of 2.41 g (9.04 mmol) of (3,5-dibromophenyl)methanol in 40 mL of $CH_2Cl_2$ at r.t. was added 1.4 mL of $Et_3N$ and 62.7 mg of DMAP. The solution was cooled to 0° C. and 1.0 mL of MsCl was added, and the solution was gradually allowed to warm to r.t. After 24.5 h, the organic layer was washed with water (20 mL) and brine (15 mL), dried over $Na_2SO_4$, filtered, and concentrated. Purification by flash silica gel chromatography (5% EtOAc/hexanes) provided 1.88 g of 1,3-dibromo-5-(chloromethyl)benzene as a yellow oil in 73% yield and 476 mg of the mesylate (35% EtOAc/hexanes) as a pale yellow solid.

A mixture of 1.88 g (6.61 mmol) of 1,3-dibromo-5-(chloromethyl)benzene and 456 mg (6.50 mmol) of NaSMe in 13 mL of EtOH was stirred at 95° C. After 4 h, 97.1 mg of NaSMe was added and after 30 min. EtOAc and $H_2O$ were added. The layers were separated, and the organic layer was washed with 30 mL of brine, dried over $Na_2SO_4$, filtered, and concentrated. (3,5-dibromobenzyl)(methyl)sulfane was used in the next reaction without further purification.

To a stirring solution of the crude (3,5-dibromobenzyl)(methyl)sulfane in 15 mL of MeOH at 0° C. was added 12.2 g of Oxone in 15-20 mL of $H_2O$. The slurry was stirred at 0° C. for 1.5 h and then $H_2O$ and EtOAc were added. The organic layer was washed with 20 mL of brine, dried over $Na_2SO_4$, filtered, and concentrated. 1,3-dibromo-5-(methylsulfonylmethyl)benzene was used in the next reaction without further purification.

A mixture of 1.37 g (4.17 mmol) of 1,3-dibromo-5-(methylsulfonylmethyl)benzene, 297 mg (2.53 mmol) of $Zn(CN)_2$, and 298 mg (0.258 mmol) of $Pd(PPh_3)_4$ in 10 mL of DMF (degassed) was heated at 80° C. After 2.5 h, a 10% $NH_4OH$ aqueous solution was added, and the aqueous layer was extracted with EtOAc. The organic layer was washed with $H_2O$ and brine, dried over $Na_2SO_4$, filtered, and concentrated. Purification by flash silica gel chromatography (50-60) % EtOAc/hexanes provided 228 mg of 3-bromo-5-(methylsulfonylmethyl)benzonitrile as a colorless solid in 20% yield.

3-(methylsulfonylmethyl)-5-(prop-1-en-2-yl)benzonitrile was synthesized from 3-bromo-5-(methylsulfonylmethyl)benzonitrile following the general procedures as described herein.

(3-isopropyl-5-(methylsulfonylmethyl)phenyl)methanamine was synthesized from 3-(methylsulfonylmethyl)-5-(prop-1-en-2-yl)benzonitrile following the general procedures as described herein.

Example 1.1.77

(3-isopropyl-5-(isopropylsulfonyl)phenyl)methanamine

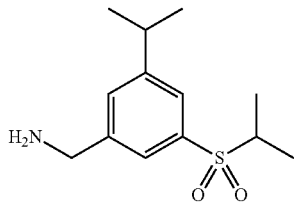

To a degassed mixture of 5.0 g (17.9 mmol) of 3,5-dibromophenylboronic acid in 50 mL of THF and 25 mL of 2 M $Na_2CO_3$ (aqueous) was added 1.13 g (0.975 mmol) of $Pd(PPh_3)_4$ and 2.3 mL of 2-bromopropene. The mixture was stirred at 40° C. for 5 h, and the mixture was extracted with EtOAc. The organic layer was washed with 25 mL of brine, dried over $Na_2SO_4$, filtered, and concentrated. Purification by flash silica gel chromatography (10% EtOAc/hexanes) provided 1,3-dibromo-5-(prop-1-en-2-yl)benzene with some impurity.

To a stirring mixture of 20 mL of $^tBuLi$ (1.7 M in pentane) in 15 mL of THF at −78° C. was added 3.1 g of 1,3-dibromo-5-(prop-1-en-2-yl)benzene in 50 mL of THF dropwise over a period of 20 min. After 55 min. 804 mg (25.1 mmol) of sulphur was added. The cooling bath was removed and stirring was continued with warming to r.t., and after 2.5 h, 1.6 mL of isopropyl iodide was added. After the stirring with the light off for 23.5 h, EtOAc and water were added. The organic layer was washed with brine, dried over $Na_2SO_4$, filtered, and concentrated. Purification by flash silica gel chromatography (hexanes) provided 382 mg of (3-bromo-5-(prop-1-en-2-yl)phenyl)(isopropyl)sulfane as a pale yellow liquid with some impurity.

1-bromo-3-(isopropylsulfonyl)-5-(prop-1-en-2-yl)benzene was synthesized from (3-bromo-5-(prop-1-en-2-yl)phenyl)(isopropyl)sulfane following the general procedures as described herein.

A mixture of 32 mg (0.106 mmol) of 1-bromo-3-(isopropylsulfonyl)-5-(prop-1-en-2-yl)benzene, 11.2 mmol (0.0954 mmol) of $Zn(CN)_2$ and 24.3 mg of (0.021 mmol) of $Pd(PPh_3)_4$ in 3 mL of DMF (degassed) was heated at 100° C. Over a period of 2.5 h, a total of 103 mg of $Pd(PPh_3)_4$ was added in 3 portions. Ethyl acetate and 10% $NH_4OH$ solution were added, and the organic layer was washed with $H_2O$ and brine. The aqueous layer was extracted with EtOAc (3×), and the combined extracts were dried over $Na_2SO_4$, filtered, and concentrated. Purification by flash silica gel chromatography (30% EtOAc/hexanes) provided 28.6 mg of 3-(isopropylsulfonyl)-5-(prop-1-en-2-yl)benzonitrile as a yellow solid.

(3-isopropyl-5-(isopropylsulfonyl)phenyl)methanamine was synthesized from 3-(isopropylsulfonyl)-5-(prop-1-en-2-yl)benzonitrile following the general procedure as described above for the isopropenyl acetamide.

Example 1.1.78

4-(aminomethyl)-6-isopropylpyrimidin-2-amine

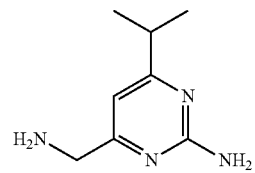

To a stirred slurry of NaH (1.02 g, 26 mmol, washed with anhydrous hexanes) in ether (10 mL) was added methyl methoxyacetate (2.3 mL, 23 mmol) followed by 3-methyl-2-butanone (2.4 mL, 23 mmol) in ether (5 mL). The resulting mixture was stirred for 15 h and became a clear yellow solution. The reaction was quenched with saturated aqueous $NH_4Cl$. The resulting mixture was extracted with EtOAc (2×20 mL). The combined organic layer was washed with $H_2O$, brine, dried with $Na_2SO_4$ and concentrated under reduced pressure to provide 1-methoxy-5-methylhexane-2,4-dione (2.90 g, 80%) as a mixture of keto and enol form.

To a stirred solution of 1-methoxy-5-methylhexane-2,4-dione (1.08 g, 6.8 mmol) in EtOH (15 mL) was added guanidine hydrochloride (1.3 g, 13.7 mmol). 5 min later, a solution of $Na_2CO_3$ (1.45 g, 13.7 mmol) in $H_2O$ was added and the resulting mixture was heated to reflux for 20 h. The reaction was cooled to room temperature and the solvent was removed. The residue was dissolved in EtOAc (20 mL) and $H_2O$ (20 mL). The layers were separated and the aqueous layer was extracted with EtOAc (2×20 mL). The combined organic layer was washed with brine, dried with $Na_2SO_4$ and concentrated under reduced pressure. The residue was purified by column chromatography (50% EtOAc in hexanes) to provide 4-isopropyl-6-(methoxymethyl)pyrimidin-2-amine (482 mg, 39%). $^1H$ NMR ($CDCl_3$): d 6.43 (s, 1H), 6.11 (s, 2H), 4.16 (s, 2H), 3.26 (s, 3H), 2.56-2.66 (m, 1H), 1.03 (d, J=6.9 Hz, 6H).

To a stirred solution of 4-isopropyl-6-(methoxymethyl)pyrimidin-2-amine (537 mg, 3.0 mmol) in $CH_2Cl_2$ (30 mL) at 0° C. was added $BBr_3$ (3 mL of 1.0 M solution, 3 mmol) dropwise. The reaction was quenched with saturated aqueous $NaHCO_3$ after 4 h. The resulting mixture was extracted with $CH_2Cl_2$ (2×20 mL). The combined organic layer was washed with brine, dried with $Na_2SO_4$ and concentrated under reduced pressure to provide (2-amino-6-isopropylpyrimidin-4-yl)methanol as a dark brown oil which was used for next step without further purification. $^1H$ NMR ($CDCl_3$): d 6.49 (s, 1H), 5.06 (br, 2H), 4.59 (s, 2H), 2.78-2.87 (m, 1H), 1.25 (m, 6H).

Following standard condition described herein for alcohol to azide transformation, (2-amino-6-isopropylpyrimidin-4- yl)methanol was converted to 4-(azidomethyl)-6-isopropylpyrimidin-2-amine in 66% yield. $^1$H NMR (CDCl$_3$): d 6.57 (s, 1H), 5.20 (br, 2H), 4.27 (s, 2H), 2.79-2.88 (m, 1H), 1.25-1.28 (m, 6H).

Following standard catalytic hydrogenation of azide to amine described herein, 4-(aminomethyl)-6-isopropylpyrimidin-2-amine was obtained from 4-(azidomethyl)-6-isopropylpyrimidin-2-amine in quantitative yield. $^1$H NMR (CDCl$_3$): d 6.44 (s, 1H), 5.63 (br, 2H), 3.70 (s, 2H), 2.71-2.76 (m, 1H), 1.19 (d, J=7.2 Hz, 6H).

Example 1.1.79

3-(aminomethyl)benzonitrile

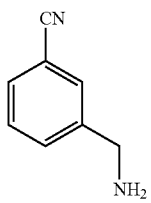

To (3-bromophenyl)methanamine hydrochloride (Aldrich, 4.0 g, 17.97 mmol) in MeOH (35 ml), triethylamine (5.45 g, 53.91 mmol) was added followed by (Boc)$_2$O (4.7 g, 21.6 mmol). Reaction mixture was stirred overnight at RT and the volatiles are removed on a rotavap under reduced pressure. Then the crude residue was column chromatographed (10% Ethyl acetate/Hexanes) to yield tert-butyl 3-bromobenzylcarbamate in 90% yield.

To the Boc compound tert-butyl 3-bromobenzylcarbamate (1.8 g, 6.3 mmol) in DMF (20 ml), Zn(CN)$_2$ (443 mg, 3.8 mmol) was added followed by the Pd(PPh$_3$)$_4$ and heated at 110° C. for 2.5 h. Then the reaction mixture was diluted with ether, washed with ammonium hydroxide solution, water and brine. Crude residue was column chromatographed (20% ethylacetate/Hexanes) to yield tert-butyl 3-cyanobenzylcarbamate in 70% yield.

To tert-butyl 3-cyanobenzylcarbamate in CH$_2$Cl$_2$ (10 ml), TFA (3 ml) was added. After 1 h, volatiles were removed on a rotavap under reduced pressure. Crude residue 3-(aminomethyl)benzonitrile was dissolved in water, basified with 2N NaOH and extracted with CHCl$_3$ (100 ml) and used without further purification.

Example 1.1.80

(5-bromopyridin-3-yl)methanamine

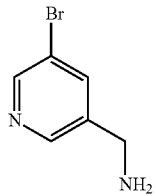

To the cobalt chloride hexahydrate (71 mg, 0.55 mmol) and 5-bromonicotinonitrile (Aldrich, 1 g, 5.5 mmol) in THF:water (19.5:9.25 ml) at 0° C., Sodium borohydride (416 mg, 11.0 mmol) was added in portions with intermittent cooling of the reaction mixture. Once all the sodium borohydride was added, the reaction mixture was stirred for RT for 2 h. Then the reaction mixture was acidified with 3N HCl and stirred at RT for 3.5 h. Then THF was removed under vacuum and the aqueous layer was extracted with ether and ethereal layer was discarded. Then aqueous layer was basified with aqueous NH$_4$OH solution and extracted repeatedly with CHCl$_3$ (3×100 ml). Organic layer was dried on anhydrous sodium sulfate and volatiles were removed under vacuum. Column chromatography (MeOH/CHCl$_3$: 3/97) of the crude residue resulted in (5-bromopyridin-3-yl)methanamine in 25% yield.

Example 1.1.81

2-(3-methoxyphenyl)propan-2-amine

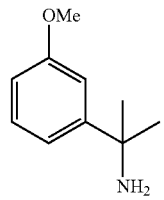

To methyl 2-(3-methoxyphenyl)acetate (Aldrich, 1 g, 5.55 mmol) in THF (10 ml) at 0° C., NaHMDS (5.55 ml, 5.55 mmol) was added. After stirring at 0° C. for 10 min, reaction mixture was stirred at RT for 0.5 h and then MeI (0.4 ml) was added. After 45 min, another 5.55 ml of NaHMDS was added at 0° C. Again after stirring at RT for 0.5 h, 0.5 ml of MeI was added and the reaction mixture was stirred at RT for 2 h. Then the reaction mixture was quenched with ammonium chloride and solvent removed. Then the reaction mixture was diluted with ethyl acetate, acidified with 2N HCl and washed with ether. Aqueous layer was then basified and extracted with CHCl$_3$. organic layer was dried and evaporated to yield methyl 2-(3-methoxyphenyl)-2-methylpropanoate.

To methyl 2-(3-methoxyphenyl)-2-methylpropanoate (800 mg, 4 mmol) in THF (10 ml) and MeOH (10 ml), aqueous LiOH (excess) was added and the reaction mixture was heated at 60° C. for 7 h. Then volatiles were removed in vacuum and the aqueous layer was extracted with ether. Ether layer was discarded. Then the aqueous layer was acidified and extracted with ethyl acetate. Organic layer was dried with sodium sulfate and volatiles removed under vacuum to yield 2-(3-methoxyphenyl)-2-methylpropanoic acid.

To 2-(3-methoxyphenyl)-2-methylpropanoic acid (330 mg, 1.70 mmol) and triethylamine (191 mg, 1.87 mmol) in t-BuOH (15 ml), DPPA (514 mg, 1.87 mmol) was added and the resultant solution was refluxed for 2 h. Then t-BuOH was removed under vacuum. Crude residue was dissolved in THF (10 ml) and 2N HCl (10 ml) was added and stirred overnight at RT. Then solvent was removed, crude residue dissolved in water and extracted with ether. Aqueous layer was basified with 5N NaOH and extracted with ethyl acetate. Organic layer was dried and evaporated to yield 2-(3-methoxyphenyl)propan-2-amine.

Example 1.1.82

5-(aminomethyl)nicotinonitrile

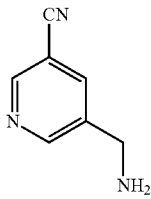

To (5-bromopyridin-3-yl)methanamine (880 mg, 4.70 mmol) in MeOH (20 ml), triethylamine (530 mg, 5.18 mmol) was added followed by (Boc)$_2$O (1.13 g, 5.18 mmol) at 0° C. Then reaction mixture was allowed to come to RT and stirred for 3 h. Then the volatiles were removed on a rotavap under reduced pressure. Crude residue was purified by column chromatography (ethyl acetate/Hexanes:40/60) to yield the Boc compound 17 in quantitative yield.

To tert-butyl (5-bromopyridin-3-yl)methylcarbamate (384 mg, 1.34 mmol) in DMF (10 ml), Zn(CN)$_2$ (94 mg, 0.80 mmol) and Pd(PPh$_3$)$_4$ were added and heated at 110° C. for 3 h. Then the reaction mixture was cooled to RT, diluted with ether, washed with ammonium hydroxide solution, water and brine. Crude residue was column chromatographed (40% ethylacetate/60% Hexanes) to yield tert-butyl (5-cyanopyridin-3-yl)methylcarbamate in 86% yield.

To tert-butyl (5-cyanopyridin-3-yl)methylcarbamate in CH$_2$Cl$_2$ (10 ml), TFA (3 ml) was added. After 1 h, volatiles were removed on a rotavap under reduced pressure. Crude residue was dissolved in water, basified with 2N NaOH and extracted with CHCl$_3$ (100 ml) to obtain 5-(aminomethyl)nicotinonitrile which was used without further purification.

Example 1.1.83

N-(3-(aminomethyl)-5-isopropylphenyl)-N-methylmethanesulfonamide

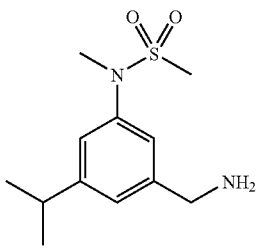

To a stirring solution of 234 mg of 3-(methoxycarbonyl)-5-(N-methylmethylsulfonamido)benzoic acid in 10 mL of THF at r.t. was added 1.2 mL of BH$_3$.THF (1.0 M in THF). After the solution was stirred at 75° C. for 3 h, 3 mL of acetic acid:H$_2$O (1:1) was added and stirring was continued until bubbling ceased. Saturated NaHCO$_3$ solution was added to a pH=7, and the solution was concentrated. Water was added, and the aqueous layer was extracted with EtOAc (2×). The combined extracts were washed with water and brine, dried over Na$_2$SO$_4$, filtered, and concentrated. Purification by flash silica gel chromatography (1.5% MeOH/CHCl$_3$) provided 191 mg of methyl 3-(hydroxymethyl)-5-(N-methylmethylsulfonamido)benzoate as a pale yellow oil in 86% yield.

To a stirring solution of 191 mg (0.699 mmol) of methyl 3-(hydroxymethyl)-5-(N-methylmethylsulfonamido)benzoate in 7 mL of THF at 0° C. was added 1.3-2.0 mL of MeMgBr (3.0 M in Et$_2$O). After the solution was stirred at 0° C. for about 90 min., the reaction was quenched with saturated NH$_4$Cl solution and H$_2$O. The aqueous layer was extracted with EtOAc, and the organic layer was washed with brine, dried over Na$_2$SO$_4$, filtered, and concentrated. N-(3-(hydroxymethyl)-5-(2-hydroxypropan-2-yl)phenyl)-N-methylmethanesulfonamide was used in the next reaction without further purification.

To a stirring solution of 189 mg of N-(3-(hydroxymethyl)-5-(2-hydroxypropan-2-yl)phenyl)-N-methylmethanesulfonamide in 7 mL of CH$_2$Cl$_2$ was added 600 μL of thionyl chloride (SOCl$_2$). The solution was stirred for 12 h at rt. and concentrated. The crude product was dissolved in CH$_2$Cl$_2$ and sat. NaHCO$_3$ solution was added. The organic layer was washed with brine, dried over Na$_2$SO$_4$, filtered, and concentrated. N-(3-(chloromethyl)-5-(prop-1-en-2-yl)phenyl)-N-methylmethanesulfonamide was used in the next reaction without further purification.

A mixture of crude N-(3-(chloromethyl)-5-(prop-1-en-2-yl)phenyl)-N-methylmethanesulfonamide and 91.2 mg (1.40 mmol) of NaN$_3$ in 4 mL of DMF was stirred at 70° C. for about 3 h. Water and EtOAc were added, and the organic layer was washed with water (2×) and then brine. The aqueous layer was extracted with EtOAc, and the combined extracts were dried over Na$_2$SO$_4$, filtered, and concentrated. Purification by flash silica gel chromatography provided 88.4 mg of N-(3-(azidomethyl)-5-(prop-1-en-2-yl)phenyl)-N-methylmethanesulfonamide as a mixture.

A solution of 88.4 mg of the impure N-(3-(azidomethyl)-5-(prop-1-en-2-yl)phenyl)-N-methylmethanesulfonamide and 90.3 mg (0.344 mmol) of PPh$_3$ in 6 mL of THF and 0.6 mL of H$_2$O was stirred at r.t. for 10 h, and then concentrated. Ethyl acetate was added, the solution was dried over Na$_2$SO$_4$, filtered, and concentrated. N-(3-(aminomethyl)-5-(prop-1-en-2-yl)phenyl)-N-methylmethanesulfonamide was used without further purification.

A solution of crude N-(3-(aminomethyl)-5-(prop-1-en-2-yl)phenyl)-N-methylmethanesulfonamide, 70 μL (0.502 mmol) of Et$_3$N and 110 μL (0.479 mmol) of BOC$_2$O in 7 mL of MeOH was stirred at r.t. for 30 min. and then concentrated. Ethyl acetate and water were added, and the organic layer was washed with water and brine, dried over Na$_2$SO$_4$, filtered, and concentrated. Purification by flash silica gel chromatography (40 to 70% EtOAc/hexanes) provided 55.7 mg of pure product and Boc protected N-(3-(aminomethyl)-5-(prop-1-en-2-yl)phenyl)-N-methylmethanesulfonamide which were combined and used in the next reaction.

A solution of Boc protected N-(3-(aminomethyl)-5-(prop-1-en-2-yl)phenyl)-N-methylmethanesulfonamide and 0.8 mL of trifluoroacetic acid (TFA) in 2 mL of CH$_2$Cl$_2$ was stirred at r.t. for 1 h. The solution was concentrated and sat. NaHCO$_3$ was added to a pH=8. The aqueous layer was extracted with the extract of (40 mL CHCl$_3$: 5 mL of MeOH: 5 mL of H$_2$O) (3×). The combined extracts were dried over Na$_2$SO$_4$, filtered, and concentrated. The crude N-(3-(aminomethyl)-5-(prop-1-en-2-yl)phenyl)-N-methylmethanesulfonamide was used in the next reaction without further purification.

To a stirring solution of crude N-(3-(aminomethyl)-5-(prop-1-en-2-yl)phenyl)-N-methylmethanesulfonamide and 68.3 mg (0.2871 mmol) of CoCl$_2$.6H$_2$O in 3 mL of EtOH and 1 mL of THF at 50° C. was added 0.169 g of NaBH$_4$ in 2 portions. After the mixture was stirred for about 3.5 h, 5 N HCl was added to a pH=1. The mixture was concentrated and (28-30) % NH$_4$OH solution was added to pH=8. The aqueous layer was extracted with the extract of (40 mL of CHCl$_3$: 5 mL of H$_2$O: 5 mL of MeOH) (3×). The combined extracts were dried over Na$_2$SO$_4$, filtered, and concentrated. N-(3-(aminomethyl)-5-isopropylphenyl)-N-methylmethanesulfonamide was used in the next reaction without further purification.

Example 1.1.84

N-(3-(aminomethyl)-5-isopropylbenzyl)methanesulfonamide

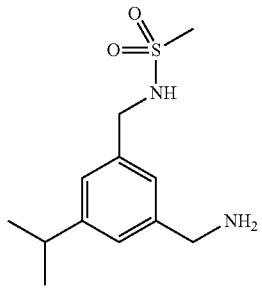

diethyl 5-(azidomethyl)isophthalate was synthesized from diethyl 5-(hydroxymethyl)isophthalate following the general procedures as described herein.

A mixture of 2.2 g (7.93 mmol) of diethyl 5-(azidomethyl) isophthalate and 224 mg of 10% Pd/C in 30 mL of EtOAc was stirred at r.t. under H$_2$ balloon overnight. The mixture was filtered through Celite and concentrated. The crude product was dissolved in 30 mL of MeOH, 478 mg of 20% Pd(OH)$_2$ was added, and the mixture was stirred at r.t. under H$_2$ balloon for about 5 h. The mixture was filtered through Celite and concentrated. The crude diethyl 5-(aminomethyl)isophthalate product was used in the next reaction without further purification.

To a stirring solution of crude diethyl 5-(aminomethyl) isophthalate in 30 mL of CH$_2$Cl$_2$ at 0° C. was added 1.2 mL of Et$_3$N and 0.7 mL of MsCl. The ice bath was removed, and after 2 h at r.t. the solution was concentrated, and EtOAc and H$_2$O were added. The organic layer was washed with brine, the aqueous layer was extracted with EtOAc, the combined extracts were dried over Na$_2$SO$_4$, filtered, and concentrated. Purification by flash silica gel chromatography (1% MeOH/ CHCl$_3$) provided 901 mg of diethyl 5-(methylsulfonamidomethyl)isophthalate as a pale yellow solid in 35% yield.

To a solution of 901 mg (2.73 mmol) of diethyl 5-(methylsulfonamidomethyl)isophthalate in 10 mL of THF and 10 mL of MeOH was added 115 mg of NaOH in 2.7 mL of H$_2$O. After the solution was stirred at r.t. for 50 h, the solution was concentrated, and H$_2$O and CHCl$_3$ were added. The aqueous layer was acidified to pH=1-2 with 1N HCl and extracted with the extract of (40 mL of CHCl$_3$: 5 mL of MeOH, and 5 mL of H$_2$O) several times. The combined extracts were dried over Na$_2$SO$_4$, filtered, and concentrated to give crude 3-(methoxycarbonyl)-5-(methylsulfonamidomethyl)benzoic acid which was used without further purification.

N-(3-(aminomethyl)-5-isopropylbenzyl)methanesulfonamide was synthesized from 3-(methoxycarbonyl)-5-(methylsulfonamidomethyl)benzoic acid following the general procedures as described herein.

tert-butyl 3-isopropyl-5-(methylsulfonamidomethyl)benzylcarbamate was synthesized and purified from N-(3-(aminomethyl)-5-isopropylbenzyl)methanesulfonamide following the general procedures as described herein.

N-(3-(aminomethyl)-5-isopropylbenzyl)methanesulfonamide was synthesized from the tert-butyl 3-isopropyl-5-(methylsulfonamidomethyl)benzylcarbamate following the general procedure as described above for the N-methyl methylsulfonamide.

Example 1.1.85

(5-methyl-1,3,4-oxadiazol-2-yl)methanamine

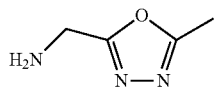

To a stirred solution of Boc-Glycine (1.75 g, 10.0 mmol) in CH$_2$Cl$_2$ at 0° C. was added carbonyl imidazole (1.7 g, 10.5 mmol) and the reaction was stirred for 30 min and then acetic hydrazide (740 mg, 10.0 mmol) was added. After 45 min, CBr$_4$ (6.63 g, 20.0 mmol) and PPh$_3$ (5.25 g, 20.0 mmol) were added and the reaction was stirred overnight at room temperature. The reaction mixture was concentrated partially and chromatographed (50% EtOAc in hexanes) to provide 2.3 g of tert-butyl (5-methyl-1,3,4-oxadiazol-2-yl)methylcarbamate with some triphenylphosphine oxide as impurity.

To a stirred solution of tert-butyl (5-methyl-1,3,4-oxadiazol-2-yl)methylcarbamate (2.3 g, 10.0 mmol) in CH$_2$Cl$_2$ (20 mL), was added TFA (8 mL) and stirred for 1 h. All the solvent was removed and residue is diluted with water and extracted with ether to remove triphenylphosphine oxide. Then the aq. layer was brought P$^H$~7 with satd. NaHCO$_3$, all the water was removed under reduced pressure and the residue was triturated with EtOAc and filtered and concentrated to obtain 900 mg of 20 which is about 90% pure.

Example 1.1.86

3-(aminomethyl)-5-isopropyl-N-methylbenzenesulfonamide

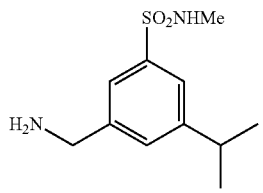

A mixture of 5 g (14.2 mmol) of sodium 4-amino-3,5-dibromobenzenesulfonate in 24 mL of POCl$_3$ was heated at 120° C. under a CaCl$_2$ drying tube for 15 min. and 125° C. for about 22 h. Initially ice and cold water were added to the crude product with ice bath cooling, and finally the crude product was poured into ice. Ethyl acetate was added, and the layers were separated. The organic layer was washed with 40 mL of brine, dried over Na$_2$SO$_4$, filtered, and concentrated. The 4-amino-3,5-dibromobenzenesulfonic hypochlorous anhydride product was used in the next reaction without further purification.

To a solution of crude 4-amino-3,5-dibromobenzene-sulfonic hypochlorous anhydride and 3.7 mL (21.3 mmol) of N,N-diisopropylethyl amine in 50 mL of $CH_2Cl_2$ at 0° C. was added 10.7 mL of $CH_3NH_2$ (2.0 M in THF). The mixture was stirred at 0° C. for 10 min. and the ice bath was removed. Stirring was continued with warming to r.t. for about 75 min. and then 3 mL of the $CH_3NH_2$ solution was added. After about 15 min., $H_2O$ and $CHCl_3$ were added, and the layers separated. The aqueous layer was extracted with $CHCl_3$ (2×). The combined extracts were washed with brine, dried over $Na_2SO_4$, filtered, and concentrated. Purification by flash silica gel chromatography (30-70) % EtOAc/hexanes provided 1.55 g of 2,6-dibromo-4-(methylaminooxysulfonyl) anilineas a pale yellow solid in 35% yield.

To a stirring mixture of 1.55 g (4.49 mmol) of 2,6-dibromo-4-(methylaminooxysulfonyl)aniline in 16 mL of EtOH was added 1.6 mL of $H_2SO_4$. To the stirring mixture at 90° C. was added 1.2 g (17.4 mmol) of $NaNO_2$ in 2 portions. The mixture was stirred at 90° C. for 15.75 h, and $H_2O$ and EtOAc were added. The organic layer was washed with brine, dried over $Na_2SO_4$, filtered, and concentrated. Purification by flash silica gel chromatography (20% EtOAc/hexanes) resulted in 771 mg of O-(3,5-dibromophenylsulfonyl)-N-methylhydroxylamine with impurity.

A mixture of 751 mg (2.29 mmol) of O-(3,5-dibromophenylsulfonyl)-N-methylhydroxylamine, 159 mg (1.35 mmol) of $Zn(CN)_2$ and 164 mg (0.142 mmol) of $Pd(PPh_3)_4$, 8 mL of DMF (degassed) was stirred at 80° C. After 70 min., 334 mg of $Pd((PPh_3)_4$, was added and after 35 min. 414 mg of $Pd(PPh_3)_4$ was added. After 1 h, EtOAc and 20 mL of 10% $NH_4OH$ (aq) was added, and the layers were separated. The organic layer was washed with 20 mL of 10% $NH_4OH$ (aq) and 20 mL of brine. The combined aqueous layer was extracted with EtOAc. The combined extracts were dried over $Na_2SO_4$, filtered, and concentrated. Purification by flash silica gel chromatography provided 194 mg of 3-bromo-5-(methylaminooxysulfonyl)benzonitrile as a yellow solid in 31% yield.

3-(methylaminooxysulfonyl)-5-(prop-1-en-2-yl)benzonitrile was synthesized from the 3-bromo-5-(methylaminooxysulfonyl)benzonitrile following the general procedure as described herein for the chloro substituted pyridine. 3-isopropyl-5-(methylaminooxysulfonyl)benzonitrile was synthesized from 3-(methylaminooxysulfonyl)-5-(prop-1-en-2-yl) benzonitrile following the general procedure as described herein for the isopropenyl acetamide.

Example 1.1.87

N-methyl-1-(4-((triisopropylsilyloxy)methyl)thiazol-2-yl)methanamine

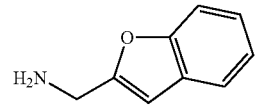

To a DCM solution of thiazol-4-ylmethanol (Combi-Blocks)(1 g, 8.69 mmol) stirred at 0° C., were added TIPSCl (2.2 mL, 10.43 mmol) and imidazole (1.48 g, 21.72 mmol). The resulting mixture was then warmed to room temperature and stirred for overnight. The reaction was quenched with saturated aqueous $NH_4Cl$ solution, extracted with ethyl acetate three times. The combined organic layers were washed with brine, dried with anhydrous $Na_2SO_4$, concentrated to a residue which was purified by flash column to give 4-((triisopropylsilyloxy)methyl)thiazole (2 g). $^1H$ NMR (300 MHz, $CDCl_3$), d: 8.794 (m, 1H), 7.338 (m, 1H), 5.065 (s, 2H), 1.209 (m, 3H), 1.133 (d, J=6 Hz, 18H).

To a solution of 4-((triisopropylsilyloxy)methyl)thiazole (2 g, 7.367 mmol) in diethyl ether solution (30 mL) at −78° C. was added butyl lithium (1.6 M in hexanes, 5.1 mL). The resulting solution was stirred at the same temperature for one hr, dimethylformate (1.14 mL, 14.734 mmol) was added to the light yellow reaction mixture. The reaction was warmed to room temperature and stirred for 3 hr, then quenched with water, extracted with ethyl acetate three times. The combined organic layers were washed with brine, dried with anhydrous $Na_2SO_4$, concentrated to a residue which was not purified and identified for the next step. Methylamine (2 M solution in methanol, 10 mL) in the flask at 0° C. was added titanium isopropoxide (2.55 mL, 8.692 mmol) and stirred for 20 minutes, then the above crude aldehyde was added to the reaction and stirred for 3 hr. The reaction mixture was added sodium borohydrate (354 mg, 9.36 mmol) portionwise. After overnight the reaction solvent was removed, diluted with DCM/water. The resulting precipitate was filtered through a celite. The clear liquid was extracted with chloroform three times, dried with anhydrous $Na_2SO_4$, concentrated to a residue which was purified by flash column to give N-methyl-1-(4-((triisopropylsilyloxy)methyl)thiazol-2-yl)methanamine (1.37 g). $^1H$ NMR (300 MHz, $CDCl_3$), d: 7.197 (s, 1H), 4.975 (s, 2H), 4.075 (s, 2H), 2.555 (s, 3H), 1.196 (m, 3H), 1.134 (d, J=5.7 Hz, 18H).

Example 1.1.88 benzofuran-2-ylmethanamine

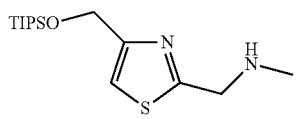

To a stirring solution of 1.02 g (6.96 mmol) of benzofuran-2-carbaldehyde (Aldrich) in 20 mL of MeOH at 0° C. was added 1.02 g (26.9 mmol) of $NaBH_4$. The ice bath was removed, and the mixture was allowed to cool to r.t. (Reaction was exothermic). After 45 min., the mixture was concentrated, and $H_2O$ was added and 1N HCl to pH=7. The aqueous layer was extracted with EtOAc (2×), and the combined extracts were washed with brine, dried over $Na_2SO_4$, filtered, and concentrated. Purification by flash silica gel chromatography provided 1 g of benzofuran-2-ylmethanol as a colorless oil in quantitative yield.

To a stirring solution of 1.00 g (6.77 mmol) of benzofuran-2-ylmethanol in 10 mL of toluene at r.t. was added 1.7 mL (7.89 mmol) of DPPA. The solution was cooled to 0° C. and 1.2 ml (8.02 mmol) of DBU was added. The ice bath was removed, and the mixture was stirred with warming to r.t. After 12.5 h, 1N HCl was added to a pH=4, and the aqueous layer was extracted with EtOAc. The pH of the aqueous layer was then adjusted to pH=6 with saturated $NaHCO_3$ solution, and the aqueous layer was extracted with EtOAc. The combined extracts were washed with brine, dried over $Na_2SO_4$, filtered, and concentrated. Purification by flash silica gel chromatography (5% EtOAc/hexanes) provided 2-(azidomethyl)benzofuran as a pale yellow oil in quantitative yield.

A mixture of 2-(azidomethyl)benzofuran and 267 mg of 20% $Pd(OH)_2$ in 10 mL of MeOH was stirred at r.t. under $H_2$ balloon for 2.5 h. The mixture was filtered through Celite and concentrated to give the crude benzofuran-2-ylmethanamine which was used without further purification.

To a stirring solution of crude benzofuran-2-ylmethanamine in 10 mL of MeOH was added 1.2 mL of Boc₂O and 800 μL of Et₃N. The solution was stirred at r.t. for 1 h and concentrated. Water and EtOAc were added, and the layers separated. The organic layer was washed with H₂O and brine, dried over Na₂SO₄, filtered, and concentrated. Purification by flash silica gel chromatography provided about 800 mg of the protected amine (tert-butyl benzofuran-2-ylmethylcarbamate) with some impurity.

To a stirring solution of tert-butyl benzofuran-2-ylmethylcarbamate in 10 mL was added 1.6 mL of TFA. After about 3.5 h, the solution was concentrated. Saturated NaHCO₃ solution was added to pH=7, and the aqueous layer was extracted with the extract of (40 mL of CHCl₃:5 mL of H₂O: 5 mL of MeOH) (3×). The combined extracts were dried over Na₂SO₄, filtered, and concentrated. Benzofuran-2-ylmethanamine was used in the next reaction without further purification.

Example 1.1.89

(3-isopropylisoxazol-5-yl)methanamine

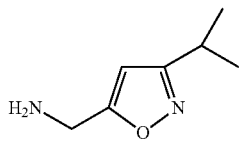

To a stirring solution of 1.0 g (11.5 mmol) of isobutyraldehyde oxime, 0.9 g (12.1 mmol) of propargyl chloride, and 0.7 mL (5.02 mmol) of Et₃N in 30 mL of CH₂Cl₂ at 0° C. was added 125 mL of sodium chlorite solution (>4% chlorine). The ice bath was removed and stirring was continued with warming to r.t. After 1.5 h, CH₂Cl₂ was added, and the organic layer was washed with 20 mL of brine, dried over Na₂SO₄, filtered, and concentrated. Purification by flash silica gel chromatography (10% EtOAc/hexanes) provided 1.14 g of 5-(chloromethyl)-3-isopropylisoxazole as a pale yellow liquid in about 62% yield. (60%)

A mixture of 5-(chloromethyl)-3-isopropylisoxazole and 952 mg of NaN₃ in 7 mL of DMF was stirred at 70° C. for 2 h. Water and EtOAc were added, and the layers separated. The organic layer was washed with water (2×) and brine, dried over Na₂SO₄, filtered, and concentrated. 5-(azidomethyl)-3-isopropylisoxazole was used in the next reaction without further purification.

(3-isopropylisoxazol-5-yl)methanamine was synthesized from 5-(azidomethyl)-3-isopropylisoxazole following the general procedure as described herein including the protection-deprotection steps to improve the purity of the amine.

Example 1.1.90

(5-methylisoxazol-3-yl)methanamine

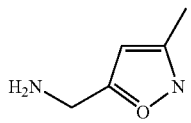

To a stirring solution of 618 mg (4.38 mmol) of methyl 5-methylisoxazole-3-carboxylate (Aldrich) in 20 mL of THF at 0° C. was added 401 mg (10.6 mmol) of LiAlH₄. After 45 min., the reaction was quenched by adding successively 400 μL of H₂O, 400 μL of 15% aqueous NaOH, and 1.2 mL of brine. The mixture was filtered through Celite, and the solution was concentrated to generate (5-methylisoxazol-3-yl) methanol. (5-methylisoxazol-3-yl)methanol (used without further purification) was converted to (5-methylisoxazol-3-yl)methanamine following the general procedure as described herein.

Example 1.2

Synthesis of Aldehyde Building Blocks

Example 1.2.1 methyl 3-formyl-5-methoxybenzoate

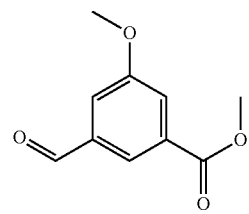

Dimethyl 5-methoxyisophthalate (4 g, 17.84 mmol) in MeOH/water (60 mL/16 mL) was added sodium hydroxide (0.642 g, 16.1 mmol) at 0° C. and the warmed to room temperature and stirred for overnight. After the organic solvent was removed in vacuo, water was added. The obtained suspension was washed with ether twice to remove the starting material. The resulting aqueous layer was acidified to pH ~4, extracted with EtOAc three times. The combined organic layers were dried in vacuo to produce a white solid. The monoacid (3-methoxy-5-(methoxycarbonyl)benzoic acid) was used directly for next reaction without further purification and identification.

To a stirred solution of 3-methoxy-5-(methoxycarbonyl) benzoic acid (2.6 g, 12.4 mmol) and triethylamine (2.6 mL, 18.6 mmol) in THF (200 mL), isopropyl chloroformate (1 M in toluene, 16 mL) was added at 0° C., and it was stirred at the same temperature for 30 min. After water was added, the mixture was extracted with ether. The combined organic layer was washed with aqueous NaHCO₃ solution, dried over NaSO₄, and concentrated in vacuo. The resulting residue was dissolved in THF (200 mL) and then NaBH₄ (1.4 g) in cold water (40 mL) was added to the solution with stirring at 0° C. After one hour, water was added and the mixture was extracted with EtOAc three times. The combined organic layer was washed with brine, dried over NaSO₄, and concentrated in vacuo, and purified by silica gel chromatography to afford the corresponding alcohol, methyl 3-(hydroxymethyl)-5-methoxybenzoate (2.4 g). ¹H NMR (300 MHz, CDCl₃+CD₃OD), d: 7.648 (s, 1H), 7.503 (s, 1H), 7.162 (s, 1H), 4.747 (s, 2H), 3.947 (s, 3H), 3.888 (s, 3H).

To a solution of methyl 3-(hydroxymethyl)-5-methoxybenzoate (2.18 g, 9.82 mmol) in DCM (100 mL), Dess-Martin periodinane (5 g, 11.79 mmol) was added at rt. After 30 min stirring, the mixture was poured into a mixture of aqueous 1 M Na₂S₂O₃ (30 mL) and aqueous saturated NaHCO₃ (30 mL), and it was extracted with DCM three times. The combined organic layers were concentrated in vacuo and methyl 3-formyl-5-methoxybenzoate residue white solid (~80% purity) was used directly for the next step reaction without further purification and identification.

Example 1.2.2

5-(2-fluoropropan-2-yl)nicotinaldehyde

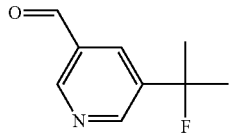

To a suspension of ethyl 5-bromonicotinate (10.0 g, 43.46 mmol) in anhydrous THF (20 mL) was added dropwise to a slurry of LiAlH₄ (1.91 g, 47.81 mmol) in anhydrous THF (200 mL) under argon at −78° C. and the mixture was stirred for 1.5 h at the same temperature, then warmed to r.t. The reaction mixture was added 15 ml of aqueous HCl (1 M) slowly at −78° C., the mixture was then warmed to rt and added anhydrous Na₂SO₄, stirred for overnight. The resulting mixture was filtered through celite and the solvent was removed under reduced pressure to give crude (5-bromopyridin-3-yl)methanol, which was used in the next step without purification. To a solution of (5-bromopyridin-3-yl)methanol (10.6 g, 56.40 mmol) in DMF (30 mL) was added, under argon, imidazole (9.98 g, 146.5 mmol) followed by triisopropylsilyl chloride (TIPS—Cl) (15.53 mL, 73.29 mmol). After stirring for 24 h at room temperature the reaction mixture was evaporated to dryness. Purification by flash chromatography (silica gel, hexanes/EtOAc, 9:1) gave 3-bromo-5-((triisopropylsilyloxy)methyl)pyridine as a colourless oil (11.8 g, 81% overall). ¹H NMR (CDCl₃): d: 1.00-1.237 (m, 21H), 4.837 (s, 2H), 7.849 (s, 1H), 8.480 (s, 1H), 8.556 (s, 1H).

Toluene (30 mL) in a 3-necked flask was cooled down to −78° C. n-BuLi (1.6 M in hexane, 8.35 mL, 0.13.35 mmol) was slowly added to the toluene. After 10 minutes a solution of the 3-bromo-5-((triisopropylsilyloxy)methyl)pyridine (4.0 g, 11.62 mmol) in toluene (30 mL) was added dropwise. A yellow solid precipitated. The resulting slurry was aged for 15-30 min, then THF (20 mL) was added slowly, keeping the internal temperature at <−50° C. The mixture was aged for 15 min, then acetone (1.7 mL, 23.24 mmol) was added over 2 min. The solids dissolved and a brown homogeneous solution was obtained. The reaction solution was warmed to rt and quenched with saturated aqueous NH₄Cl and diluted with EtOAc. The phases were separated and aqueous layer was extracted with EtOAc twice. The organic layers were combined and concentrated to dryness. Purification by flash chromatography (silica gel, hexanes/EtOAc) gave 2-(5-((triisopropylsilyloxy)methyl)pyridin-3-yl)propan-2-ol as a light yellow solid (3.56 g, 96%). ¹H NMR (CDCl₃): d: 1.250-1.055 (m, 21H), 1.606 (s, 6H), 4.865 (s, 2H), 7.830 (s, 1H), 8.458 (s, 1H), 8.621 (s, 1H).

To 2-(5-((triisopropylsilyloxy)methyl)pyridin-3-yl)propan-2-ol (1.1 g, 3.4 mmol) in DCM (30 mL) at −78° C. was added diethylaminosulfur trifluoride (DAST) (0.67 mL, 5.1 mmol) and stirred at the same temperature for 1 hr, then warmed to 0° C. for 3 hrs. The resulting mixture was quenched with MeOH and saturated aqueous NaHCO₃. The mixture was extracted with EtOAc three times and dried with anhydrous NaSO₄, filtered and concentrated to dryness. Careful purification by flash chromatography (silica gel, hexanes/EtOAc) gave the desired fluoride (3-(2-fluoropropan-2-yl)-5-((triisopropylsilyloxy)methyl)pyridine) as a light yellow solid (0.43 g). ¹H NMR (CDCl₃): d: 1.127 (d, J=6.3 Hz, 18H), 1.204 (m, 3H), 1.712 (s, 3H), 1.786 (s, 3H), 4.922 (s, 2H), 7.781 (s, 1H), 8.566 (s, 2H). 3-(2-fluoropropan-2-yl)-5-((triisopropylsilyloxy)methyl)pyridine was deprotected with excess aqueous HF in THF to provide (5-(2-fluoropropan-2-yl)pyridin-3-yl)methanol as a white solid. (5-(2-fluoropropan-2-yl)pyridin-3-yl)methanol was then oxidized to 5-(2-fluoropropan-2-yl)nicotinaldehyde using standard Swern Oxidation conditions.

Example 1.2.3

5-tert-butylnicotinaldehyde

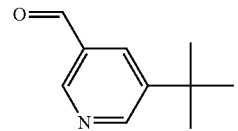

To a suspension of ethyl 5-bromonicotinate (Alfa Aesar, 10.0 g, 43.46 mmol) in anhydrous THF (20 mL) was added dropwise to a slurry of LiAlH₄ (1.91 g, 47.81 mmol) in anhydrous THF (200 mL) under argon at −78° C. and the mixture was stirred for 1.5 h at the same temperature, then warmed to r.t. The reaction mixture was added 15 ml of aqueous HCl (1 M) slowly at −78° C., the mixture was then warmed to rt and added anhydrous Na₂SO₄, stirred for overnight. The resulting mixture was filtered through celite and the solvent was removed under reduced pressure to give crude (5-bromopyridin-3-yl)methanol, which was used in the next step without purification.

To a solution of (5-bromopyridin-3-yl)methanol (10.6 g, 56.40 mmol) in DMF (30 mL) was added, under argon, imidazole (9.98 g, 146.5 mmol) followed by triisopropylsilyl chloride (TIPSCl, 15.53 mL, 73.29 mmol). After stirring for 24 h at room temperature the reaction mixture was evaporated to dryness. Purification by flash chromatography (silica gel, hexanes/EtOAc, 9:1) gave the TIPS ether, (3-bromo-5-((triisopropylsilyloxy)methyl)pyridine) as a colourless oil (11.8 g, 81% overall). ¹H NMR (CDCl₃): d: 1.00-1.237 (m, 21H), 4.837 (s, 2H), 7.849 (s, 1H), 8.480 (s, 1H), 8.556 (s, 1H).

A mixture of anhydrous CuCN (3.41 g, 38.03 mmol) in 150 mL of anhydrous THF, and ethereal tert-butylmagnesium bromide (38 mL, 76.1 mmol) was stirred under N₂ at −78° C. for 20 min. 3-bromo-5-((triisopropylsilyloxy)methyl)pyridine (3.274 g, 9.51 mmol) in THF was added, and the reaction mixture was stirred for 2-3 h at −78° C. and then overnight at room temperature. The reaction mixture was quenched by dropwise addition of saturated aqueous NH₄OH and the pH was adjusted to 10 by using 1 M aqueous NaOH, and the resulting solution was extracted with extracted with EtOAc (3×75 mL). The combined organic extracts were dried (Na₂SO₄,), and concentrated under vacuum to get a residue which was purified by flash column chromatography to give 3-tert-butyl-5-((triisopropylsilyloxy)methyl)pyridine (0.7 g). ¹H NMR shows the products contain the desired product and bromine-removed product. ¹H NMR (CDCl₃): d: 1.124 (m, 22H), 1.369 (s, 5H), 4.878 (s, 2H), 7.298 (m, 0.5H), 7.738 (m, 1H), 8.414 (s, 0.6H), 8.607 (m, 1.5H).

3-tert-butyl-5-((triisopropylsilyloxy)methyl)pyridine (0.7 g, 2.637 mmol) was dissolved in HCl in methanol (42 mL, 1.25M, 52.73 mmol) at room temperature and stirred for overnight. The solvent was removed under vacuum, dissolved in chloroform and washed with saturated aqueous $Na_2CO_3$. The resulting organic solvent was dried, concentrated to give a residue which was purified by flash column chromatography to give pure (5-tert-butylpyridin-3-yl)methanol (0.2 g). $^1$H NMR ($CDCl_3$): d: 1.280 (s, 9H), 4.663 (s, 2H), 7.730 (s, 1H), 8.225 (s, 1H), 8.368 (s, 1H).

Oxalyl chloride (158 µL, 1.819 mmol) in methylene chloride (10 mL) was placed in a two-necked flask at −78° C., followed by the addition of dimethyl sulfoxide (129 µL, 1.819 mmol). Stirring was continued for 20 min, followed by addition of (5-tert-butylpyridin-3-yl)methanol (0.2 g, 1.21 mmol) in methylene chloride (10 mL). After the mixture was stirred at −78° C. for additional 20 min, triethylamine (0.59 mL, 4.24 mmol) was added. The cooling bath was removed and the suspension was allowed to warm to room temperature. Water (50 mL) was added, the yellow organic layer was separated, and the aqueous layer was extracted with methylene chloride (3×30 mL). The combined organic solution was dried and concentrated to give 5-tert-butylnicotinaldehyde as an orange-yellow liquid which was used directly for next step without further purification.

Example 1.2.4

5-(1,1-difluoroethyl)nicotinaldehyde

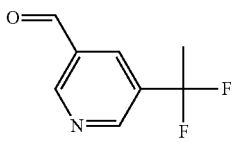

To 1-(5-bromopyridin-3-yl)ethanone (2.95 g, 14.75 mmol) in flask was added [Bis(2-methoxyethyl)amino]sulfur trifluoride (4.1 mL, 22.12 mmol) and heated to 80° C. The resulting mixture was stirred at this temperature for overnight. The reaction was cooled to room temperature and quenched with MeOH and saturated aqueous $NaHCO_3$. The mixture was extracted with methylene chloride three times and dried with anhydrous $NaSO_4$, filtered and concentrated to dryness. Careful purification by flash silica chromatography provided 3-bromo-5-(1,1-difluoroethyl)pyridine as a light yellow solid (1.5 g). $^1$H NMR ($CDCl_3$): d: 1.993 (t, J=18.3 Hz, 3H), 8.002 (s, 1H), 8.720 (s, 1H), 8.794 (s, 1H).

3-bromo-5-(1,1-difluoroethyl)pyridine was converted to 5-(1,1-difluoroethyl)nicotinaldehyde using BuLi in DMF under similar conditions as described herein and used for the next step without further purification.

Example 1.2.5

3-(1,1-difluoroethyl)benzaldehyde

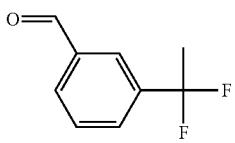

3-(1,1-difluoroethyl)benzonitrile was synthesized from 3-acetylbenzonitrile following the method described for 3-bromo-5-(1,1-difluoroethyl)pyridine. A solution of 3-(1,1-difluoroethyl)benzonitrile (1.6 g, 9.57 mmol) in $CH_2Cl_2$ (25 mL) was cooled to 0° C. and was treated dropwise with a 1 M solution of DIBAL in hexanes (11.5 mL, 11.2 mmol). The mixture was allowed to slowly warm to room temperature. The reaction was monitored by TLC. After 3 h, the reaction mixture was poured into a beaker containing crushed ice and 6 N HCl. The mixture was stirred for about 1 h. The layers were separated and the aqueous phase was extracted with $CH_2Cl_2$. The combined organic layer was washed with aqueous $NaHCO_3$ followed by water. The organic layer was dried ($Na_2SO_4$), concentrated, and silica chromatographed to afford 3-(1,1-difluoroethyl)benzaldehyde as a light yellow oil, which was used directly for next step without further purification and identification.

Example 1.2.6

3-hydroxy-5-isopropylbenzaldehyde

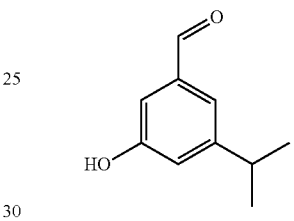

To a stirring solution of 5 g (18.9 mmol) of 3,5-dibromobenzaldehyde in 40 mL of MeOH and 15 mL of THF was added 3.2 mL (29.2 mmol) of HC(OMe)$_3$ followed by 278 mg (1.46 mmol) of p-TsOH.H$_2$O. The solution was stirred at r.t. for about 14 h and concentrated. Water was added to the crude product, and the aqueous layer was extracted with EtOAc. The organic layer was washed with brine, dried over $Na_2SO_4$, filtered, and concentrated. Purification by flash silica gel chromatography (5% EtOAc/hexanes) provided a mixture of the aldehyde and 1,3-dibromo-5-(dimethoxymethyl)benzene. Hexanes was added to separate the products by solubility, but the dimethyl acetal was still not pure and used without further purification.

To a stirring solution of 23 mL of n-BuLi (1.6 M in hexanes) in 20 mL of THF at −78° C. was added 5.31 g of 1,3-dibromo-5-(dimethoxymethyl)benzene in 80 mL of THF dropwise over a period of about 55 min. After 50 min., 3.2 mL (28.7 mmol) of B(OMe)$_3$ was added, and the solution was stirred at −78° C. for 20 min. The cold bath was removed and stirring continued with gradual warming to r.t. After 1 h, 1 N HCl (45 mL) was added, and the aqueous layer was extracted with EtOAc. The extract was washed with brine, dried over $Na_2SO_4$, filtered, and concentrated. To a stirring mixture of crude product in 70 mL of 1N NaOH at 0° C. was added 14.5 mL of H$_2$O$_2$ (30 wt % in H$_2$O) dropwise. After 25 min., 5 N HCl was added to a pH=1, and EtOAc and H$_2$O were added. The organic layer was washed with brine, dried over $Na_2SO_4$, filtered, and concentrated. Purification by flash silica gel chromatography (15% EtOAc/hexanes) provided 1.92 g of 3-bromo-5-(dimethoxymethyl)phenol as a pale yellow solid with some impurity.

3-(dimethoxymethyl)-5-(prop-1-en-2-yl)phenol was synthesized from 3-bromo-5-(dimethoxymethyl)phenol following the general procedures as described herein.

A mixture of 554 mg of 3-(dimethoxymethyl)-5-(prop-1-en-2-yl)phenol and 55.2 mg of 10% Pd/C in 10 mL of MeOH and 10 mL of EtOAc was stirred at r.t under H$_2$ balloon for 4 h. The mixture was filtered through Celite and concentrated. 3-(hydroxymethyl)-5-isopropylphenol was used in the next reaction without further purification.

To a stirring solution of 3-(hydroxymethyl)-5-isopropylphenol in 10 mL of CH$_2$Cl$_2$ was added 1.23 g (5.69 mmol) of PCC. The mixture was stirred for 4.5 h, Et$_2$O was added, and the mixture was stored in a refrigerator. The solvent was concentrated, and the crude product was purified by flash silica gel chromatography (15% EtOAc/hexanes) to provide 218 mg of 3-hydroxy-5-isopropylbenzaldehyde as a pale yellow solid.

Example 1.2.7

3-formyl-5-isopropylphenyl morpholine-4-carboxylate

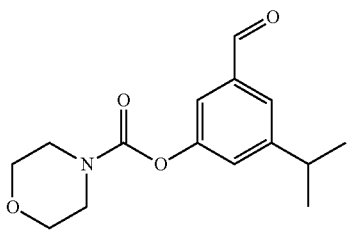

To a stirring solution of 91.9 mg (0.634 mmol) of 3-hydroxy-5-isopropylbenzaldehyde in 5 mL of CH$_2$Cl$_2$ at r.t. was added 220 µL (1.92 mmol) of 4-morpholinecarbonyl chloride and 0.5 mL (3.59 mmol) of Et$_3$N. After 3 h, sat. NaHCO$_3$ (15 mL) was added, and the aqueous layer was extracted with CHCl$_3$. The organic layer was washed with brine, dried over Na$_2$SO$_4$, filtered, and concentrated. Purification by flash silica gel chromatography (20% EtOAc/hexanes) provided 38.8 mg of 3-formyl-5-isopropylphenyl morpholine-4-carboxylate as a yellow oil in 24% yield.

Example 1.2.8

5-acetylnicotinaldehyde

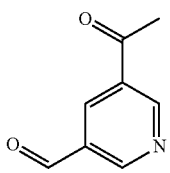

To a stirred solution of 3-(dimethoxymethyl)-5-(prop-1-en-2-yl)pyridine (7.1 mL) in CH$_2$Cl$_2$ (30 mL) at 0° C. was added CrO$_3$ (4.4 g, 44 mmol). The resulting mixture was stirred for 1 h and 10 (854 mg, 4.4 mmol) was added. The stirring was continued for 5 d and the mixture was filtered through a pad of Celite. The filtrate was concentrated and diluted with EtOAc. The organic layer was washed with NaHCO$_3$, NH$_4$Cl, brine and dried over Na$_2$SO$_4$. The solvent was removed and the residue was purified by column chromatography (60% EtOAc in hexanes) to provide 1-(5-(dimethoxymethyl)pyridin-3-yl)ethanone as a yellow oil.

To a stirred solution of 1-(5-(dimethoxymethyl)pyridin-3-yl)ethanone (214 mg, 1.1 mmol) in CH$_2$Cl$_2$ (5 mL) was added TFA (2 mL). The resulting mixture was stirred for 24 h and the solvent was removed. The residue was dissolved in CHCl$_3$ and saturated aqueous NaHCO$_3$. The layers were separated and the organic layer was washed with brine and dried over Na$_2$SO$_4$. The solvent was removed to provide 5-acetylnicotinaldehyde (112 mg) as a yellow solid.

Example 1.2.9

3-formyl-5-(prop-1-en-2-yl)pyridine 1-oxide

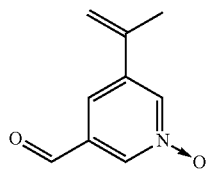

To a stirred solution of 3-(dimethoxymethyl)-5-(prop-1-en-2-yl)pyridine (178 mg, 0.92 mmol) in CH$_2$Cl$_2$ (10 mL) was added m-CPBA (227 mg, 1.0 mmol). The reaction mixture was stirred for 2 h and quenched with saturated aqueous NaHCO$_3$. The layers were separated and the organic layer was washed with brine and dried over Na$_2$SO$_4$. The solvent was removed to provide 3-(dimethoxymethyl)-5-(prop-1-en-2-yl)pyridine 1-oxide (209 mg), which was converted to 3-formyl-5-(prop-1-en-2-yl)pyridine 1-oxide as described herein.

Example 1.2.10

3-formyl-5-(prop-1-en-2-yl)benzonitrile

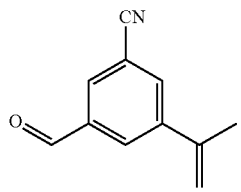

To the 3-formylbenzonitrile (1.3 gm, 10 mmol) in sulfuric acid (4.5 ml) at 60° C., N-bromosuccinimide (2.14 g, 12 mmol) was added in 3 portions. After 2 h, the reaction mixture was cooled, diluted with cold water and filtered. Filter cake was washed with hexane. Volatiles were removed under reduced pressure and the crude residue (3-bromo-5-formylbenzonitrile) was carried to the next step without further purification.

To 3-bromo-5-formylbenzonitrile (420 mg, 2 mmol), isopropenyl potassium trifluoroborate (296 mg, 2 mmol) and triethyl amine (0.42 ml) in 2-propanol and water (20 ml) in 2:1 ratio, PdCl$_2$(dppf) (65 mg, 0.08 mmol) was added and the reaction mixture was refluxed for 5 h. Then the reaction mixture was cooled, diluted with ether, washed with water, brine and dried. Crude residue was column chromatographed (60% ethylacetate: 40% hexane) to yield a white solid of 3-formyl-5-(prop-1-en-2-yl)benzonitrile.

Example 1.2.11

3-formyl-5-isopropylbenzonitrile

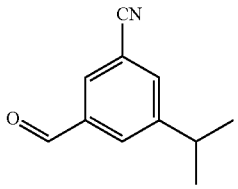

To 3-formyl-5-(prop-1-en-2-yl)benzonitrile (300 mg, 1.75 mg) in ethyl acetate (3 ml), ethanol (3 ml) mixture, 10% Pd/C (30 mg) was added and the reaction mixture was stirred under hydrogen atmosphere and under balloon pressure for 7 h. Then the reaction mixture was filtered and the solvent was evaporated to yield the aldehyde 3-formyl-5-isopropylbenzonitrile.

Example 1.2.12

4-(trifluoromethyl)picolinaldehyde

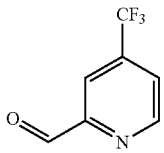

To 2-bromo-4-(trifluoromethyl)pyridine (700 mg, 3.1 mmol) in ether (30 ml) at −78° C., BuLi (1.6M in hexanes, 2.13 ml) was added. After 40 min, DMF (340 mg) was added and the reaction mixture was stirred at −78° C. for a further 45 minutes and the reaction mixture was allowed to come to rt over a period of 1 h. Then the reaction mixture was quenched with solid ammonium chloride and partitioned between water and ether. Organic layers were dried and evaporated to provide 4-(trifluoromethyl)picolinaldehyde as a crude residue which was carried to the next step without further purification.

Example 1.2.13

5-(isopropylamino)nicotinaldehyde

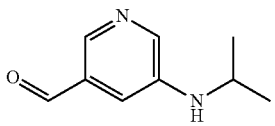

To 5-bromonicotinaldehyde (1.5 gm, 8.06 mmol) in DMF (5 ml), N,N-diethylsalicylidiamide (311 mg, 1.61 mmol), copper iodide (77 mg, 0.403 mmol), potassium phosphate (3.42 gm, 16.12 mmol) and isopropylamine (715 mg, 1.21 mmol) were added and the reaction mixture was heated overnight at 90° C. Then reaction mixture was diluted with ether and filtered. Ether layer was washed with water, brine and dried. Crude residue was column chromatographed (40% ethylacetate/60% Hexanes) to yield 5-(isopropylamino)nicotinaldehyde.

Example 1.2.14

3-bromo-5-(trifluoromethyl)benzaldehyde

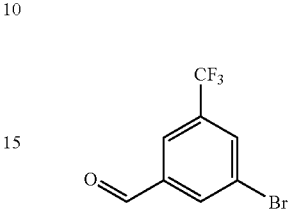

To 3-(trifluoromethyl)benzaldehyde (5 gm, 28.72 mmol) in sulfuric acid (13.5 ml) at 60° C., N-bromosuccinimide (6.13 g, 34.45 mmol) was added in 3 portions. After 2 h, the reaction mixture was cooled, diluted with cold water and filtered. Filter cake was washed with hexane. Volatiles were removed under reduced pressure and the crude residue of 3-bromo-5-(trifluoromethyl)benzaldehyde was carried to the next step without purification.

Example 1.2.15

3-formyl-5-(trifluoromethyl)benzonitrile

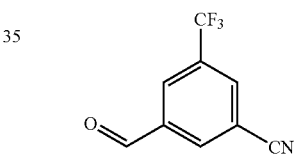

To 3-bromo-5-(trifluoromethyl)benzaldehyde (1.0 gm, 3.95 mmol) in DMF (10 ml), zinc cyanide (278 mg, 2.37 mmol) was added followed by Pd(PPh$_3$)$_4$ (365 mg, 0.32 mmol) was added and heated at 90° C. for 5 h. Then the reaction mixture was cooled, diluted with ether and quenched with aqueous ammonium hydroxide solution. Then the reaction mixture was partitioned between water and ether. Organic layer was dried, evaporated and column purified (10% ethylacetate/90% hexanes) to yield 400 mg of 3-formyl-5-(trifluoromethyl)benzonitrile.

Example 1.2.16

3-(pyridin-4-yl)-5-(trifluoromethyl)benzaldehyde

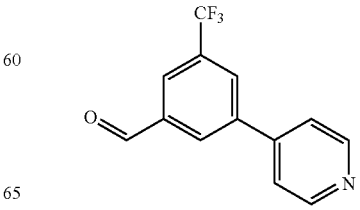

To 3-bromo-5-(trifluoromethyl)benzaldehyde (1.0 g, 3.95 mmol) in 1,4-dioxane (15 ml), pyridine-4-boronic acid) (583 mg, 4.74 mmol), sodium carbonate (2M aqueous solution) (1.67 gms in 7.9 ml water) and Pd(PPh$_3$)$_4$ 450 mg, 0.39 mmol) was added and heated at 90° C. for 5 h. Then reaction mixture was diluted with ether, washed with water, brine and dried. Volatiles were removed under vacuum and the crude residue was column chromatographed (50% ethylacetate/50% hexanes) to yield 250 mg of 3-(pyridin-4-yl)-5-(trifluoromethyl)benzaldehyde.

Example 1.2.17

N-(3-formyl-5-(trifluoromethyl)phenyl)acetamide

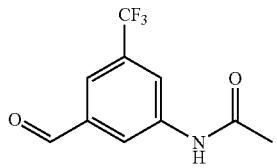

To the mixture of 3-(trifluoromethyl)benzaldehyde (10 g, 57.43 mmol) and sulfuric acid (20 ml) at 0° C., nitric acid (2.5 ml) was added and the reaction was stirred at 0° C. for 1 h, allowed to come to rt for 4 h and heated at 50° C. for 8 h. The reaction mixture was poured into ice water and extracted with ethyl acetate. Combined extracts were washed with water, bicarbonate and brine. Crude residue of 3-nitro-5-(trifluoromethyl)benzaldehyde was dried over sodium sulfate and volatiles removed in vacuum.

To the crude 3-nitro-5-(trifluoromethyl)benzaldehyde (2.4 g, 10.95 mmol) in MeOH (20 ml), P-TSA (1.1 g, 5.61 mmol) was added followed by trimethyl orthoformate (3.5 g, 33.02 mmol). After refluxing for 24 h, solvent was removed under vacuum. Then the resulting residue was diluted with ethyl acetate and basified with saturated aqueous sodium carbonate solution. Aqueous layer was extracted with ethyl acetate. Organic layer was dried and evaporated and the crude residue of 1-(dimethoxymethyl)-3-nitro-5-(trifluoromethyl)benzene was carried to the next step without any further purification.

To 1-(dimethoxymethyl)-3-nitro-5-(trifluoromethyl)benzene (1.9 gm, 7.6 mmol) in ethanol (20 ml), 10% Pd/C (200 m) was added, stirred under balloon pressure for 5 h. Then the reaction mixture was filtered and volatile were removed under vacuum to provide 3-(dimethoxymethyl)-5-(trifluoromethyl)aniline.

To 3-(dimethoxymethyl)-5-(trifluoromethyl)aniline in dichloromethane (5 ml) at 0° C., triethyl amine (0.2 ml) was added followed by acetyl chloride. Reaction mixture was stirred at rt for 2 h. Then dichloromethane was removed under reduced pressure. Reaction mixture was diluted with ether, washed with water, brine and dried. Crude residue was column chromatographed to yield 170 mg of the amide. Then solvent was removed and the crude residue was column purified (40% ethylacetate/60% hexanes) to yield 100 mg of N-(3-(dimethoxymethyl)-5-(trifluoromethyl)phenyl)acetamide.

To the acetal N-(3-(dimethoxymethyl)-5-(trifluoromethyl)phenyl)acetamide (170 mg, 0.65 mmol), TFA (5 ml) was added at 0° C., and the reaction mixture was stirred at rt for 16 h. Then volatiles were removed under vacuum and the reaction mixture was diluted with ether. Ether layer was washed with aqueous sodium bicarbonate solution, water, brine and dried. Organic layer was dried and evaporated to provide N-(3-formyl-5-(trifluoromethyl)phenyl)acetamide. The crude residue was carried to the next step without any further purification.

Example 1.2.18

3-(methylamino)-5-(trifluoromethyl)benzaldehyde

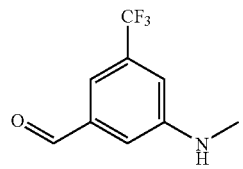

To 3-(dimethoxymethyl)-5-(trifluoromethyl)aniline (440 mg, 2.0 mmol) in methanol (5 ml) at 0° C., triethyl amine (0.2 ml) was added followed by (Boc)$_2$O (436 mg, 2.0 mmol). Then solvent was removed and the crude residue was column purified (40% ethylacetate/60% hexanes) to yield 100 mg of tert-butyl 3-(dimethoxymethyl)-5-(trifluoromethyl)phenylcarbamate.

To tert-butyl 3-(dimethoxymethyl)-5-(trifluoromethyl)phenylcarbamate (125 mg, 0.37 mmol) in DMF (5 ml) at 0° C., sodium hydride (22 mg, 0.56 mmol) was added. After stirring at rt for 0.5 h, methyl iodide (263 mg, 1.85 mmol) was added and stirred overnight at rt. Reaction mixture was then cooled, quenched with methanol, extracted with ether. Organic layer was dried and evaporated and the crude residue was column purified (10% ethylacetate/90% hexanes) to yield 110 mg of tert-butyl 3-(dimethoxymethyl)-5-(trifluoromethyl)phenyl(methyl)carbamate.

To tert-butyl 3-(dimethoxymethyl)-5-(trifluoromethyl)phenyl(methyl)carbamate (110 mg, 0.31 mmol), TFA (3 ml) was added at 0° C., and the reaction mixture was stirred at rt for 16 h. Then volatiles were removed under vacuum and the reaction mixture was diluted with ethyl acetate. Ethyl acetate layer was washed with aqueous sodium bicarbonate solution, water, brine and dried. Organic layer was dried and evaporated to yield the aldehyde 3-(methylamino)-5-(trifluoromethyl)benzaldehyde. The crude residue was carried to the next step without any further purification.

Example 1.2.19

5-(prop-1-en-2-yl)nicotinaldehyde

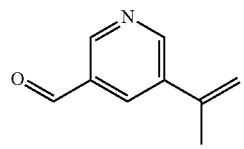

To 3-(dimethoxymethyl)-5-(prop-1-en-2-yl)pyridine (2.2 g, 11.3 mmol), TFA (5.2 ml, 67.8 mmol) was added at 0° C., and the reaction mixture was stirred at rt for 16 h. Then volatiles were removed under vacuum and the reaction mixture was diluted with ether. Ether layer was washed with aqueous sodium bicarbonate solution, water, brine and dried.

The organic layer was dried and evaporated to provide 5-(prop-1-en-2-yl)nicotinaldehyde.

Example 1.2.20

3-formyl-5-isopropylphenyl acetate

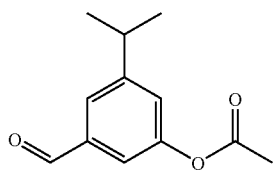

A solution of 33.2 mg (0.202 mmol) of 3-hydroxy-5-isopropylbenzaldehyde and 50 µL (0.53 mmol) of Ac$_2$O in 3 mL of pyridine was stirred at r.t. for 70 min. The solution was concentrated, water and EtOAc were added, and the layers were separated. The organic layer was washed with brine, dried over Na$_2$SO$_4$, filtered, concentrated, and purified by flash silica gel chromatography (20% EtOAc/hexanes) (neutral silica gel) to provide 47.4 mg of 3-formyl-5-isopropylphenyl acetate as a yellow oil with some impurity.

Example 1.2.21

5-(hydroxymethyl)-2-methylbenzaldehyde

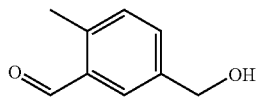

To a stirring mixture of 23.0 g (90.6 mmol) of I$_2$ and 5.4 mL (45.5 mmol) of tert-butylnitrile in 40 mL of CH$_3$CN at 35° C. was added 5.0 g (30.3 mmol) of methyl 3-amino-4-methylbenzoate in 4 portions. Stirring was continued with cooling to r.t. in the dark (light off only). After 2.5 h, 400 mL of Na$_2$SO$_3$ in H$_2$O was added gradually. The layers were separated, and the organic layer was washed with 80 mL of brine, dried over Na$_2$SO$_4$, filtered, and concentrated. Purification by flash silica gel chromatography (5% EtOAc/hexanes) provided 5.7 g of methyl 3-iodo-4-methylbenzoate as a red liquid with some impurity in approximately 68% yield.

To a solution of 5.7 g of methyl 3-iodo-4-methylbenzoate in 35 mL of DMF (degassed) was added 1.94 g (16.5 mmol) of Zn(CN)$_2$ and 1.58 g (1.37 mmol) of Pd(PPh$_3$)$_4$. The mixture was stirred at 80° C. in the dark (with the light off) for 6 h. To the mixture was added 50 mL of 10% NH$_4$OH (aq.) and EtOAc. The organic layer was washed with 50 mL of water and 30 mL of brine, and the combined aqueous layers were extracted with EtOAc. The combined extracts were dried over Na$_2$SO$_4$, filtered, and concentrated. Purification by flash silica gel chromatography (10% EtOAc/hexanes) provided about 3 g of methyl 3-cyano-4-methylbenzoate as a pale yellow solid.

To a stirring solution of 27 mL of DIBAL-H (1.5 M solution in toluene) in 10 mL of CH$_2$Cl$_2$ at −78° C. was added 1.32 g (7.54 mmol) of methyl 3-cyano-4-methylbenzoate in 35 mL of CH$_2$Cl$_2$ dropwise over a period of 30 min. After stirring for about 40 min. at −78° C., the solution was allowed to warm to r.t. After 75 min., the solution was cooled to −78° C. and 10 mL of H$_2$O and 16 mL of 1N HCl were added. The cold bath was removed, and the mixture was allowed to warm to r.t. Concentrated HCl (5-6 mL) was added and stirring was continued for 1.5 h. Chloroform was added, the layers were separated, and the organic layer was washed with 20 mL of brine. The combined aqueous layers were extracted with chloroform (4×). The combined extracts were dried over Na$_2$SO$_4$, filtered, and concentrated. Purification by flash silica gel chromatography (50% EtOAc/hexanes) provided the 800 mg of 5-(hydroxymethyl)-2-methylbenzaldehyde as a yellow oil with some impurity.

Example 1.2.22 methyl 5-formyl-2-methylbenzoate

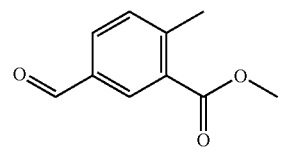

To a stirring solution of 800 mg of 5-(hydroxymethyl)-2-methylbenzaldehyde in 20 mL of MeOH was added 3.4 g (5.5 mmol) of Oxone. The mixture was stirred at r.t. for 3.75 h and 2 mL of MeOH was added. After 2.5 h, 15 mL of 1N HCl, 45 mL of H$_2$O, and EtOAc were added, and the layers separated. The aqueous layer was extracted, the combined extracts were washed with brine, dried over Na$_2$SO$_4$, filtered, and concentrated. Purification by flash silica gel chromatography (30% EtOAc/hexanes) provided 377 mg of methyl 5-(hydroxymethyl)-2-methylbenzoate as a yellow oil with some impurity.

A solution of 377 mg of methyl 5-(hydroxymethyl)-2-methylbenzoate and 0.8 mL (9.17 mmol) of oxalyl chloride in 20 mL of CH$_2$Cl$_2$ was cooled to −78° C. To this solution was added 1.1 mL (15.5 mmol) of DMSO dropwise, and after stirring for 10 min., 3.2 mL of Et$_3$N was added and stirring was continued at −78° C. for 10 min. The dry ice-acetone bath was removed, and the mixture was allowed to warm to r.t. and after 2 h, 30 mL of sat. NH$_4$Cl solution was added. The organic layer was washed with 25 mL of brine, dried over Na$_2$SO$_4$, filtered, and concentrated. Purification by flash silica gel chromatography (10% EtOAc/hexanes) provided 268 mg of methyl 5-formyl-2-methylbenzoate as a red liquid in 71% yield with some impurity.

Example 1.2.23

3-formyl-5-isopropylphenyl dimethyl phosphate

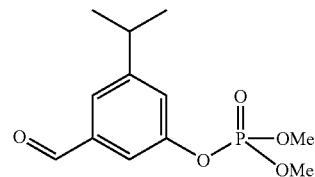

To a stirring solution of 172 mg (1.05 mmol) of 3-hydroxy-5-isopropylbenzaldehyde,
160 µL (1.98 mmol) of pyridine, and 1.6 mL of THF in 8 mL of CH$_2$Cl$_2$ was added 620 mg (2.44 mmol) of I$_2$ and 280 µL (2.37 mmol) of P(OMe)₃ in 5 mL of CH₂Cl₂. The mixture was stirred at r.t. in the dark (light off only) for 2.75 days. Chloroform and water were added, and the layers separated. The organic layer was washed with 20 mL of water and 20 mL of brine, dried over Na₂SO₄, filtered, and concentrated. Purification by flash silica gel chromatography (60% EtOAc/hexanes) (neutral silica gel) provided 40.1 mg of 3-formyl-5-isopropylphenyl dimethyl phosphate in 14% yield.

Example 1.2.24

5-(1-methoxyprop-1-en-2-yl)nicotinaldehyde

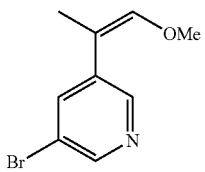

To a solution of methoxymethyltriphenylphosphonium chloride (20.57 g, 60 mmol) in THF at −78° C. was added slowly butyl lithium (1.6 M in hexanes, 37.5 mL). The resulting mixture was further stirred for 45 min to room temperature. After the reaction was cooled down to −78° C., 1-(5-bromopyridin-3-yl)ethanone (Aldrich) (8 g, 40 mmol) in THF was added to the reaction mixture. The resulting solution was stirred from −78° C. to room temperature for overnight, then quenched with saturated aqueous NH₄Cl solution, and extracted with diethyl ether three times. The combined organic layers were washed with brine, dried with anhydrous Na₂SO₄, and concentrated to a residue which was purified by flash column to give 3-bromo-5-(1-methoxyprop-1-en-2-yl) pyridine (E/Z mixture, 5 g). ¹H NMR (300 MHz, CDCl₃), d: 8.769 (m, 0.5H), 8.491 (m, 1.5H), 8.143 (m, 0.4H), 7.737 (m, 0.6H), 6.517 (m, 0.6H), 6.271 (m, 0.4H), 3.804, 3.773 (ss, 3H), 1.949 (m, 3H). The aldehyde was synthesized using the methods described herein.

Example 1.3

Synthesis of Cyclic Amine Building Blocks

Example 1.3.1

(R)-4-methyl-2-(pyrrolidin-2-yl)thiazole

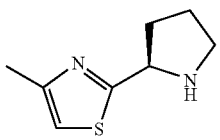

To a solution of the commercially available (R)-1-(benzyloxycarbonyl)pyrrolidine-2-carboxylic acid (Synthetech, 9.97 g, 40.0 mmoles) in 1,4-dioxane (60 mL) was added pyridine (2 mL), (Boc)₂O (11.35 mL, 52 mmoles) and NH₄HCO₃ (3.98 g, 50.4 mmoles) and stirred for 12 h. All solvent was evaporated, diluted with EtOAc and washed with water, 5% H₂SO₄ and brine. The organic layer was dried over anhydrous Na₂SO₄ and concentrated. (R)-benzyl 2-carbamoylpyrrolidine-1-carboxylate was generated in quantitative yield and used in the following step without further purification.

To a solution of (R)-benzyl 2-carbamoylpyrrolidine-1-carboxylate (9.97 g, 40.0 mmoles) in 1,2-DME (2000 mL) was added Lawesson's reagent (8.9 g, 0.55 mmoles) and stirred for 4 h. All solvent was evaporated, diluted with 100 mL of saturated NaHCO₃ and extracted with ether (2×200 mL). The combined organic layers was dried over anhydrous Na₂SO₄ and concentrated. Crude (R)-benzyl 2-carbamothioylpyrrolidine-1-carboxylate was carried on to the next step without further purification.

To a solution of (R)-benzyl 2-carbamothioylpyrrolidine-1-carboxylate (~40 mmoles) in EtOH (120 mL) was added chloroacetone (4.7 mL, 60 mmoles) and heated at 75° C. for 6 h. The reaction was cooled to room temperature and poured into 100 mL of saturated aq. NaHCO₃ solution. Ethanol was evaporated under reduced pressure and the aqueous layer was extracted with ethyl acetate (2×200 mL). The combined organic layers was dried over Na₂SO₄ and concentrated. The residue was chromatographed on silica gel (35% ethyl acetate/80% hexane) to generate (R)-benzyl 2-(4-methylthiazol-2-yl)pyrrolidine-1-carboxylate in 86% yield after three steps.

HBr in AcOH (60 mL) was added to (R)-benzyl 2-(4-methylthiazol-2-yl)pyrrolidine-1-carboxylate (neat) at room temperature. After 1 h, ether (150 mL) was added slowly with vigorous string. Stirring was continued for 10 min and allowed to settle for 5-10 min. The supernatant was decanted. This process was repeated 3-4 times until the supernatant was colourless. The semi-solid was dissolved in water (50 mL) and brought to P^H~8 with 1N LiOH and extracted with 5% MeoH/95% CHCl₃ (3×100 mL) to yield 4.0 g of (R)-4-methyl-2-(pyrrolidin-2-yl)thiazole.

Example 1.3.2

(S)-4-methyl-2-(pyrrolidin-2-yl)thiazole

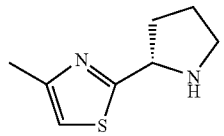

(S)-4-methyl-2-(pyrrolidin-2-yl)thiazole was prepared following the same procedure as in the preparation of (R)-4-methyl-2-(pyrrolidin-2-yl)thiazole starting from the commercially available Cbz-L-proline (Aldrich).

Example 1.3.3

(R)-4-methyl-2-(piperidin-2-yl)thiazole

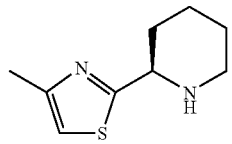

(R)-4-methyl-2-(piperidin-2-yl)thiazole was prepared following the same procedure as in the preparation of (R)-4-methyl-2-(pyrrolidin-2-yl)thiazole starting from the commercially available (R)-1-(tert-butoxycarbonyl)piperidine-2-carboxylic acid (Aldrich) to obtain (R)-tert-butyl 2-(4- methylthiazol-2-yl)piperidine-1-carboxylate which was deprotected using standard TFA conditions to obtain the desired product.

Example 1.3.4

(R)-4-methyl-2-(thiazolidin-4-yl)thiazole

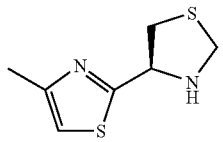

To a solution of commercially available (S)-2-amino-3-mercaptopropanoic acid hydrochloride (Aldrich, 3.0 g, 24.8 mmoles) in $H_2O$ (8 mL) at room temperature, was added 37% solution of formaldehyde (817 mg, 27.3 mmoles) and stirred for 24 h. Then $NH_2OH.HCl$ (172 mg, 2.48 mmoles), NaOH (50 mL, 2N, 100 mmoles), acetone (50 mL), $(Boc)_2O$ (6.27 mL, 27.28 mmol) were added and stirred for 12 h. The reaction mixture was extracted with ether. The aqueous layer was acidified to pH ~3.5 with 1N HCl and then extracted with 5% MeOH/95% CHCl3 (3×100 mL). The combined organic extracts is dried over anhydrous sodium sulfate and concentrated to yield 2.49 g of crude (S)-tert-butyl 4-carbamoylthiazolidine-3-carboxylate.

(R)-4-methyl-2-(thiazolidin-4-yl)thiazole was made from (S)-tert-butyl 4-carbamoylthiazolidine-3-carboxylate following similar procedure described for the synthesis of (R)-4-methyl-2-(piperidin-2-yl)thiazole.

Example 1.3.5

(R)-4-(4-methylthiazol-2-yl)oxazolidine

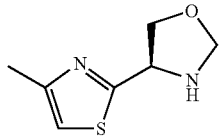

Methyl thiazole-D-oxaproline (R)-4-(4-methylthiazol-2-yl)oxazolidine was made from (R)-2-amino-3-hydroxypropanoic acid (Aldrich), following similar procedure described for the synthesis of (R)-4-methyl-2-(thiazolidin-4-yl)thiazole. The intermediate (R)-tert-butyl 4-(4-methylthiazol-2-yl)oxazolidine-3-carboxylate was deprotected using 4N HCl in 1,4-dioxane (20 min) and the desired product was used for the next step without further purification.

Example 1.3.6

(R)-4-methyl-2-(pyrrolidin-2-yl)oxazole

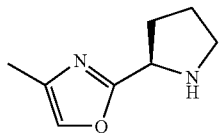

To a solution of L-Serine methyl ester hydrochloride (Aldrich, 5.0 g, 32.0 mmoles), in $CH_2Cl_2$ (150 mL) at 0° C., were added $Et_3N$ (4.88 mL, 35.2 mmoles), Cbz-D-Proline (8.01 g, 32.0 mmoles) and DCC (7.26 g, 35.2 mmoles) sequentially. The reaction was allowed to warm to room temperature and stirred overnight. All the solvent was evaporated and the residue was triturated with ethyl acetate and the precipitate was filtered off. The filtrate was concentrated under low pressure and chromatographed on silica gel (70% ethyl acetate/30% chloroform) to yield 8.5 g of (R)-benzyl 2-((S)-3-hydroxy-1-methoxy-1-oxopropan-2-ylcarbamoyl)pyrrolidine-1-carboxylate.

Deoxo-flour (4.5 mL, 24.16 mmoles) was added drop-wise to a solution of (R)-benzyl 2-((S)-3-hydroxy-1-methoxy-1-oxopropan-2-ylcarbamoyl)pyrrolidine-1-carboxylate (8.5 g, 22.0 mmoles) in $CH_2Cl_2$ (150 mL) at −20° C. The solution was stirred for 30 min and $BrCCl_3$ (7.8 mL, 79.0 mmoles) was added drop-wise followed by DBU (11.8 mL, 79 mmoles). The reaction was stirred at 2-3° C., for 10 h., quenched with Satd. Aq. $NaHCO_3$ solution and extracted with ethyl actetate. The organic layer was concentrated and chromatographed on silica gel (10% ethyl acetate/90% chloroform) to yield 6.95 of (R)-methyl 2-(1-(benzyloxycarbonyl)pyrrolidin-2-yl)oxazole-4-carboxylate.

To a solution of (R)-methyl 2-(1-(benzyloxycarbonyl)pyrrolidin-2-yl)oxazole-4-carboxylate (6.95 g, 21.1 mmoles) in THF (50 mL) at 0° C., was added $LiBH_4$ (32 mL, 2.0M in THF, 63.2 mmoles). The reaction was allowed to warm to room temperature and stirred for 3 h. Ethyl acetate (25 mL) was added drop-wise and stirred for 30 min. The reaction was cooled to 0° C. and 50 mL of 1N HCl was added drop-wise and diluted with 100 mL of water. It was then extracted with ethyl acetate, dried on $Na_2SO_4$, concentrated, and chromatographed on silica gel (3% MeOH/97% chloroform) to yield 4.1 g of (R)-benzyl 2-(4-(hydroxymethyl)oxazol-2-yl)pyrrolidine-1-carboxylate.

To a solution of (R)-benzyl 2-(4-(hydroxymethyl)oxazol-2-yl)pyrrolidine-1-carboxylate (1.1 g, 3.64 mmoles) in HMPA (18 mL), was added methyltriphenoxyphosphonium iodide (3.29 g, 7.28 mmoles) and stirred for 30 min. Then $NaCNBH_3$ was added and the reaction was heated at 50° C. for 3 h and poured into 100 mL of ice-cold water and extracted with ether (2×100 mL). The organic layer was dried on $Na_2SO_4$, concentrated, and chromatographed on silica gel (50% ethyl acetate/50% hexanes) to yield 180 mg of (R)-benzyl 2-(4-methyloxazol-2-yl)pyrrolidine-1-carboxylate.

HBr in AcOH (60 mL) was added to (R)-benzyl 2-(4-methyloxazol-2-yl)pyrrolidine-1-carboxylate (neat) at room temperature. After 1 h, ether (20 mL) was added slowly with vigorous string. Stirring was continued for 10 min and allowed to settle for 5-10 min. The supernatant was decanted. This process was repeated 3-4 times until the supernatant was colourless. The semi-solid was dissolved in water (50 mL) and brought to pH ~8 with 1N LiOH and extracted with 5% MeoH/95% $CHCl_3$ (3×100 mL) to yield 55 mg of (R)-4-methyl-2-(pyrrolidin-2-yl)oxazole.

Example 1.3.7

2-((2R,4R)-4-methoxypyrrolidin-2-yl)-4-methylthiazole

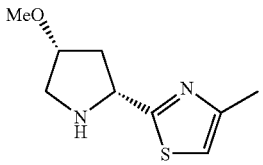

To (2R,4R)-4-hydroxypyrrolidine-2-carboxylic acid (Aldrich, 2 g, 15.3 mmol) in THF/$H_2O$ (3:1) mixture, $K_2CO_3$ (15 g, 107.1 mmol) was added followed by benzyloxycarbonyl chloride (5.22 g, 30.6 mmol). After stirring at 0° C. for 3 h, THF was removed. Then the reaction mixture was acidified with concentrated HCl and extracted with a mixture of ethylacetate/methanol. Organic layer was dried, evaporated and the crude residue was carried to the next step.

To the sodiumhydride (2.08 g, 52.02 mmol) in THF (30 ml) at −10° C. was added Cbz-protected (2R,4R)-4-hydroxypyrrolidine-2-carboxylic acid (2.3 g, 8.67 mmol). After 30 min, dimethylsulfate was added and stirred at RT for 16 h. Then the reaction mixture was quenched with ammonium chloride and THF was removed on a rotavap under reduced pressure. Reaction mixture was basified and aqueous layer was extracted with ether. Then aqueous layer was acidified and extracted with 10% methanol/90% chloroform. Organic layer was dried and evaporated to obtain Cbz-protected (2R,4R)-4-methoxypyrrolidine-2-carboxylic acid in 90% yield.

To a solution of Cbz-protected (2R,4R)-4-methoxypyrrolidine-2-carboxylic acid (2.2 g, 7.88 mmoles) in 1,4-dioxane (15 mL) were added pyridine (0.4 mL), (Boc)$_2$O (2.32 ml, 10 mmol) and NH$_4$HCO$_3$ (785 mg, 9 mmol) and stirred for 12 h. All solvent was evaporated, diluted with EtOAc and washed with water, 5% H$_2$SO$_4$ and brine. The organic layer is dried over anhydrous Na$_2$SO$_4$ and concentrated. The crude yield of Cbz-protected (2R,4R)-4-methoxypyrrolidine-2-carboxamide is quantitative and carried onto the next step without purification.

To a solution of Cbz-protected (2R,4R)-4-methoxypyrrolidine-2-carboxamide (2.0 g, 7.17 mmoles) in 1,2-DME (40 mL) was added Lawesson's reagent (1.6 g, 3.94 mmoles) and stirred for 4 h. All solvent was evaporated, and diluted with 100 mL of saturated NaHCO$_3$ and extracted with ether (2×200 mL). The combined organic layers is dried over anhydrous Na$_2$SO$_4$ and concentrated. The crude Cbz-protected (2R,4R)-4-methoxypyrrolidine-2-carbothioamide is carried on to the next step.

To a solution of Cbz-protected (2R,4R)-4-methoxypyrrolidine-2-carbothioamide (~6.79 mmoles) in EtOH (20 mL), calcium carbonate (2.04 g, 20.4 mmol) was added chloroacetone (0.8 mL, 10.2 mmoles) and heated at 60° C. for 4 h. The reaction was cooled to room temperature and poured into 100 mL of saturated aq. NaHCO$_3$ solution. Ethanol was evaporated under reduced pressure and the aqueous layer was extracted with ethyl acetate (2×200 mL). The combined organic layers was dried over Na$_2$SO$_4$ and concentrated. The residue was chromatographed on silica gel (35% ethyl acetate/80% hexane) to yield 86% of Cbz-protected 2-((2R,4R)-4-methoxypyrrolidin-2-yl)-4-methylthiazole after three steps.

HBr in AcOH (5 mL) was added to Cbz-protected 2-((2R,4R)-4-methoxypyrrolidin-2-yl)-4-methylthiazole (470 mg, 1.5 mmol, neat) at room temperature. After 1 h, ether (20 mL) was added slowly with vigorous string. Stirring was continued for 10 min and allowed to settle for 5-10 min. The supernatant was decanted. This process was repeated 3-4 times until the supernatant was colorless. The semi-solid was dissolved in water (50 mL) and brought to P$^H$~8 with 1N LiOH and extracted with 5% MeOH/95% CHCl$_3$ (3×100 mL) to obtain 250 mg of 2-((2R,4R)-4-methoxypyrrolidin-2-yl)-4-methylthiazole.

Example 1.3.8

(R)-2-(methoxymethyl)pyrrolidine

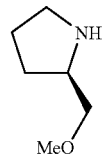

To (R)-pyrrolidin-2-ylmethanol (500 mg, 4.95 mmol) in MeOH (15 mL) was added triethyl amine (1.38 mL, 9.9 mmol), followed by (BoC)$_2$O (1.3 gm, 5.94 mmol) at 0° C. The reaction mixture was stirred at rt for 0.5 h and the volatiles were removed under vacuum. Crude residue containing (R)-tert-butyl 2-(hydroxymethyl)pyrrolidine-1-carboxylate was carried to the next step without any further purification.

To the sodium hydride (48 mg, 2 mmol) in THF (5 ml) at −78° C., (R)-tert-butyl 2-(hydroxymethyl)pyrrolidine-1-carboxylate was slowly added. After 15 min, methyl iodide (0.124 ml, 2 mmol) was added and the reaction mixture was slowly allowed to come to rt overnight. Then the reaction mixture was quenched with MeOH and diluted with water (15 ml). Aqueous layer was extracted with EtOAc and the combined organic layers were washed with brine, dried over sodium sulfate and then filtered. The solvent was removed under vacuum, and the crude product was purified by silica gel chromatography (eluting with 15% EtOAc/hexanes) to afford (R)-tert-butyl 2-(methoxymethyl)pyrrolidine-1-carboxylate in 80% yield. (R)-2-(methoxymethyl)pyrrolidine was generated by removal of the Boc protecting group by treatment with trifluoroacetic acid.

Example 1.3.9

(R)—N',N'-dimethylpyrrolidine-2-carbohydrazide

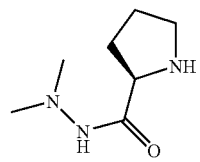

Et$_3$N (0.74 ml, 0.53 g, 5.31 mmol, 4 eq) was added to a stirred solution of (R)-methyl pyrrolidine-2-carboxylate hydrochloride (0.22 g, 1.33 mmol, 1 eq) in 4 ml anhydrous MeOH at 0° C. under Ar. After 5 min (Boc)$_2$ (0.46 ml, 0.43 g, 1.99 mmol, 1.5 eq) was added. The reaction was stirred at 0° C. to room temperature overnight. The solvent was removed in vacuo and residue was dissolved in Et$_2$O. The organic layer was washed with water (×3), brine (×1), and dried over Na$_2$SO$_4$. The inorganics were filtered off, and the solvent removed in vacuo, followed by purification via flash chromatography to yield (R)-1-tert-butyl 2-methylpyrrolidine-1,2-dicarboxylate.

1N NaOH (1.2 ml, 1.2 mmol, 1.2 eq) was added to a stirred solution of (R)-1-tert-butyl 2-methylpyrrolidine-1,2-dicarboxylate (0.267 g, 1.0 mmol, 1 eq) in 4 ml of 3:1 THF/MeOH. After stirring overnight the solvent was removed in vacuo. The residue was dissolved in saturated aqueous NaHCO$_3$ and extracted with Et$_2$O (×2). The aqueous layer was adjusted to pH 4 with 1N HCl and extracted with EtOAc (×4). The combined EtOAc fractions were dried over Na$_2$SO$_4$. The inorganics were filtered off, and the solvent removed in vacuo yielding 0.1615 g (0.64 mmol, 64% yield) of (R)-1-(tert-butoxycarbonyl)pyrrolidine-2-carboxylic acid.

HOBT.H$_2$O (0.0953 g, 0.71 mmol, 1.1 eq) was added to a stirred solution of (R)-1-(tert-butoxycarbonyl)pyrrolidine-2-carboxylic acid (0.1615 g, 0.64 mmol, 1 eq) in 5 ml anhydrous CH$_2$Cl$_2$ at 0° C. under Ar. After 30 min EDCI.HCl (0.135 g, 0.71 mmol, 1.1 eq) was added. After 1 h 1,1-Dimethylhydrazine (0.058 ml, 0.046 g, 0.77 mmol, 1.2 eq) and DIPEA (0.33 ml, 0.25 g, 1.92 mmol, 3 eq) were added sequentially. The reaction was stirred at 0° C. to room temperature overnight. The solvent was removed in vacuo and the residue partitioned between EtOAc/water. The layers were separated. The aqueous layer was saturated with NaCl and extracted with EtOAc (×2). The combined EtOAc fractions were dried over Na$_2$SO$_4$. The inorganics were filtered off, and the solvent removed in vacuo. Purification via flash chromatography yielded 0.1489 g, 0.51 mmol, 79% yield) of (R)-tert-butyl 2-(2,2-dimethylhydrazinecarbonyl)pyrrolidine-1-carboxylate with some impurity. TFA (0.5 ml, 0.74 g, 6.49 mmol) was added to a stirred solution of (R)-tert-butyl 2-(2,2-dimethylhydrazinecarbonyl)pyrrolidine-1-carboxylate (0.045 g, 0.155 mmol, 1 eq) in anhydrous CH$_2$Cl$_2$ under Ar. After 1 h the solvent was removed in vacuo to generate (R)—N',N'-dimethylpyrrolidine-2-carbohydrazide.

Example 1.4

Synthesis of Isophthalate Building Blocks

Example 1.4.1

3-(methoxycarbonyl)-5-(N-methylmethylsulfonamido)benzoic acid

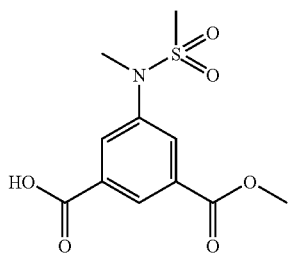

To a stirred solution of dimethyl 5-aminoisophthalate (2.09 g, 10 mmol) in dichloromethane (30 mL), pyridine (2.43 mL, 30 mmol) was added at room temperature. At 0° C., methanesulfonyl chloride (0.86 mL, 11 mmol) was added and the resulting mixture was stirred overnight at room temperature. The reaction mixture was then concentrated under reduced pressure and ethyl acetate (50 mL) was added. The resulting white precipitate was filtered and washed with hexanes to give dimethyl 5-(methylsulfonamido)isophthalate in 95% (2.715 g) yield as a white solid.

To a stirred suspension of NaH (0.24 g, 10 mmol, 60% in oil dispersion) in 10 mL of DMF was added dimethyl 5-(methylsulfonamido)isophthalate (1.435 g, 5 mmol) followed by iodomethane (0.62 mL, 10 mmol) at room temperature. After 5 h, the reaction was quenched by H$_2$O (25 mL). Then the reaction mixture was extracted with EtOAc, further washed with H$_2$O to remove excess of DMF, dried over anhydrous Na$_2$SO$_4$ and concentrated. The crude product thus obtained was washed with hexanes to give dimethyl 5-(N-methylmethylsulfonamido)isophthalate as a white solid in 91% (1.37 g) yield.

Dimethyl 5-(N-methylmethylsulfonamido)isophthalate (0.842 g, 2.8 mmol) was dissolved in THF:MeOH (1:1) (8 mL) and H$_2$O (3 mL). Solid NaOH (0.112 g, 2.8 mmol) was added and stirred at room temperature for 18 h. The reaction mixture was concentrated under reduced pressure. Saturated NaHCO$_3$ (10 mL) was added to the reaction mixture and extracted with toluene (to remove <10% unreacted starting material). The aqueous solution was acidified with dilute HCl (10%), extracted with EtOAc, and dried over anhydrous Na$_2$SO$_4$. The solvent was evaporated and dried under reduced pressure to give 3-(methoxycarbonyl)-5-(N-methylmethylsulfonamido)benzoic acid as a white solid (75%, 0.598 g), which was used without further purification.

Example 1.4.2 dimethyl 5-(methylsulfonyloxy)isophthalate

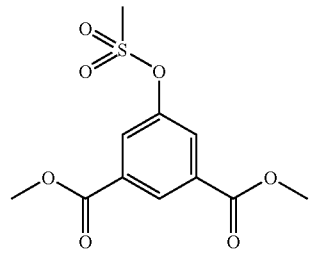

MsCl (0.16 mL, 0.234 g, 2.06 mmol, 1.1 eq) was added to a stirred solution of dimethyl 5-hydroxyisophthalate (0.40 g, 1.86 mmol, 1 eq) and Et$_3$N (0.78 mL, 0.56 g, 5.6 mmol, 3 eq) in 5 mL anhydrous CH$_2$Cl$_2$ at 0° C. under Ar. The reaction was stirred at 0° C. to room temperature over the weekend. The reaction was quenched with water, and the layers were separated. The organic layer was washed with water (×2), brine (×1), and dried over Na$_2$SO$_4$. The inorganics were filtered off, and the solvent was removed in vacuo yielding 0.54 g (1.87 mmol, 100% yield) of dimethyl 5-(methylsulfonyloxy)isophthalate.

Example 1.4.3

5-fluoroisophthalic acid

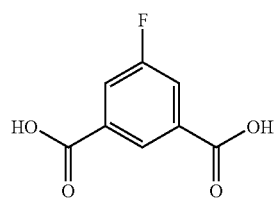

To a gently refluxing solution of 1.9 g (15.3 mmol) of 5-fluoro-m-xylene in about 13.5 mL of pyridine and about 9.5 mL of water was added 13.8 g (87.3 mmol) of KMnO$_4$ in several portions. The mixture was refluxed for about 7 h, followed by the addition of sodium sulfite to quench the excess KMnO$_4$. The warm mixture was filtered, and 1N HCl was added to a pH=3. The filtrate was washed with EtOAc, saturated with NaCl, and extracted with the extract of a mixture of (80 mL CHCl$_3$: 10 mL MeOH: 10 mL H$_2$O) 3-4 times. The combined extracts were dried over sodium sulfate, filtered, and concentrated to give about 400 mg (14% yield) of 5-fluoroisophthalic acid as a pale yellow solid.

Example 1.4.4

4-fluoro-isophthalic acid

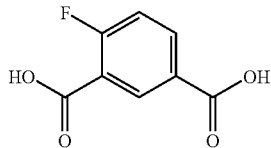

4-fluoro-isophthalic acid was synthesized from 2-fluoro-5-methylbenzoic acid following the procedure described for 5-fluoro-isophthalic acid.

Example 1.4.5 dimethyl 5-iodoisophthalate

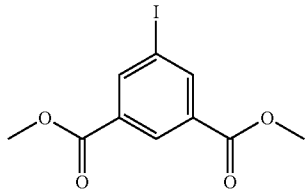

To a stirred solution of dimethyl 5-aminoisophthalate (2.0 g, 9.6 mmol) in 2 N HCl (60 mL) at 0° C. was added NaNO$_2$ (662 mg, 9.6 mmol) in H$_2$O (5 mL). The mixture was transferred to a solution of KI (3.2 g, 19.2 mmol) in H$_2$O (10 mL) at 0° C. The resulting mixture was stirred for 35 min and diluted with EtOAc and H$_2$O. The layers were separated and the organic layer was washed with 5% Na$_2$S$_2$O$_3$, brine, dried with Na$_2$SO$_4$ and concentrated under reduced pressure. The residue was purified by column chromatography (15% EtOAc in hexanes) to provide dimethyl 5-iodoisophthalate (1.53 g, 50%).

Example 1.4.6

3-(methoxycarbonyl)-5-methylbenzoic acid

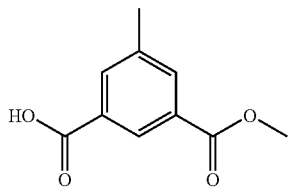

To 5-methylisophthalic acid (Aldrich, 5 g, 27.7) in MeOH (37.5 ml)/THF (112.5 ml), conc. H$_2$SO$_4$ (1.25 ml) was added and stirred at 65° C. for 8 h. Reaction mixture was cooled to room temperature and solvent removed. Then reaction mixture was diluted with water and extracted with ethylacetate. Crude residue was column chromatographed to yield 2.5 g of 3-(methoxycarbonyl)-5-methylbenzoic acid as a white solid.

Example 1.4.7

4-methylisophthalic acid

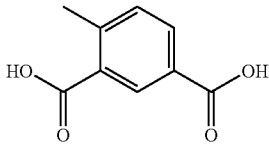

4-methylisophthalic acid was synthesized from 2,5-dimethylbenzoic acid following a similar procedure to that described for 5-fluoroisophthalic acid.

Example 1.4.8 dimethyl 5-vinylisophthalate

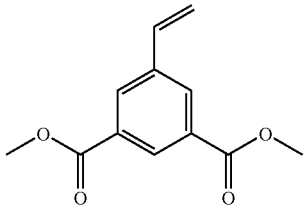

A stirred solution of dimethyl 5-bromoisophthalate (273 mg, 1.0 mmol), potassium vinyltrifluoroborate (134 mg, 1.0 mmol) PdCl$_2$(dppf).CH$_2$Cl$_2$ (16.3 mg, 0.02 mmol) and Et$_3$N (0.42 mL, 3.0 mmol) in i-PrOH (6 mL) and H$_2$O (3 mL) was heated to reflux for 3 h. The solution was cooled to room temperature and diluted with EtOAc and H$_2$O. The layers were separated and the aqueous layer was extracted with EtOAc (2×10 mL). The combined organic layer was washed with brine, dried with Na$_2$SO$_4$ and concentrated under reduced pressure. The residue was purified by column chromatography (8% EtOAc in hexanes) to provide dimethyl 5-vinylisophthalate (153.6 mg, 70%).

Example 1.4.9 diethyl 5-acetylisophthalate

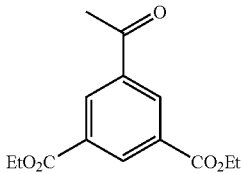

To a stirred solution of diethyl 5-formylisophthalate (2.83 g, 11.3 mmol) in ether (20 mL) was added MeMgBr (3.8 ml of 3.0 M solution, 11.3 mmol) dropwise. The resulting yellow suspension was stirred for 5 h and quenched with saturated aqueous NH$_4$Cl. The resulting mixture was extracted with EtOAc (2×20 mL). The combined organic layer was washed with brine, dried with Na₂SO₄ and concentrated under reduced pressure. The residue was purified by column chromatography (20% EtOAc in hexanes) to provide diethyl 5-(1-hydroxyethyl)isophthalate (1.15 g, 40%) as a white solid. $^1$H NMR (CDCl₃): d 8.60-8.61 (m, 1H), 8.26-8.27 (m, 2H), 5.02-5.09 (m, 1H), 4.45 (q, J=7.2 Hz, 2H), 1.56 (d, J=6.3 Hz, 3H), 1.45 (t, J=7.2, 3H).

A stirred solution of diethyl 5-(1-hydroxyethyl)isophthalate (587 mg, 2.2 mmol) and MnO₂ (960 mg, 11 mmol) was heated to reflux. After 5 h, the reaction was cooled to room temperature and additional MnO₂ (0.6 g) was added and heated to reflux for another 16 h. The reaction mixture was cooled to room temperature and filtered through Celite. The filtrate was concentrated to provide diethyl 5-acetylisophthalate (521 mg, 90%) as a white solid. $^1$H NMR (CDCl₃): d 8.62 (s, 1H), 8.56 (s, 2H), 4.32 (q, J=7.2 Hz, 2H), 2.58 (s, 3H), 1.32 (t, J=7.2 Hz, 3H).

Example 1.4.10 dimethyl 5-(methylamino)isophthalate

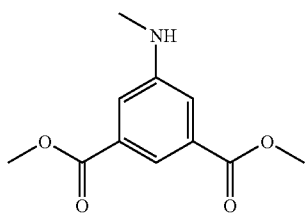

A solution of dimethyl 5-aminoisophthalate (0.250 g, 1.17 mmol, 1 eq) dissolved in 3 mL anhydrous DMF was added dropwise to a stirred suspension of NaH (60% dispersion in mineral oil, 0.14 g, 3.5 mmol, 3 eq) in 2 mL anhydrous DMF at 0° C. under Ar. MeI (0.23 mL, 0.53 g, 3.7 mmol, 3.2 eq) was added dropwise to the resulting mixture. The reaction was stirred at 0° C. to room temperature overnight. The reaction was poured into ice water to quench. The aqueous mixture was extracted with EtOAc (×2), and the combined organic extracts were washed with water (×3), brine (×1), and dried over Na₂SO₄. The inorganics were filtered off, and the solvent was removed in vacuo. Purification via flash chromatography on silica gel yielded 0.14 g (0.63 mmol, 54% yield) of dimethyl 5-(methylamino)isophthalate.

Example 1.4.11 dimethyl 5-(dimethylamino)isophthalate

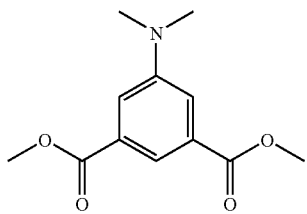

TiCl₄ (1.0 M in CH₂Cl₂, 2.0 mL, 2.0 mmol, 2.1 eq) was add dropwise to a stirred suspension of dimethyl 5-aminoisophthalate (0.2 g, 0.94 mmol, 1 eq) and (HCHO)$_n$ (0.059 g, 1.87 mmol, 2.0 eq) in 5 mL anhydrous THF at 0° C. under Ar. After 20 min the ice bath was removed and the mixture was stirred at room temperature for 2 h. The reaction was cooled to 0° C. and NaBH₄ (0.0756 g, 2.0 mmol, 2.1 eq) was added in two approximately equal batches. The reaction was stirred at 0° C. to room temperature over the weekend. The reaction was quenched with water, and the mixture was concentrated in vacuo. The residue was diluted with EtOAc, washed with water (×2), brine (×1), and dried over Na₂SO₄. The inorganics were filtered off. A small amount of silica gel was added, and the solvent was removed in vacuo. The resulting silica gel/crude mixture was loaded onto a column and purified via flash chromatography on silica gel yielded 0.105 g (0.44 mmol, 47% yield) of dimethyl 5-(dimethylamino)isophthalate.

Alternatively, CH₂O (aq, 37%) (3.2 ml, 3.49 g, 43.0 mmol, 6 eq) was added to a stirred solution of the diester (1.5 g, 7.17 mmol, 1 eq) in CH₃CN (50 ml) at 0° C. After 15 min NaBH₃CN (1.09 g, 16.49 mmol, 2.3 eq) was added. The reaction was adjusted to pH 7 with HOAc. Stir at 0° C. to RT overnight. The solvent was removed in vacuo, and the residue was partitioned between EtOAc and saturated aqueous NaHCO₃. The layers were separated. The organic layer was washed with water (×3), brine (×1), and dried over Na₂SO₄. The inorganics were filtered off, and the solvent was removed in vacuo. Purification via flash chromatography yielded 1.62 g (6.83 mmol, 95% yield) of dimethyl 5-(dimethylamino)isophthalate.

Example 1.4.12 dimethyl 5-(diethylamino)isophthalate

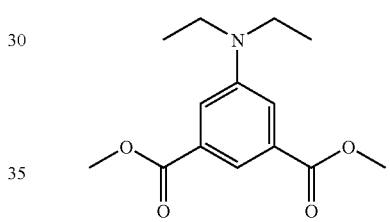

Acetaldehyde (1.07 ml, 0.8 g, 19.12 mmol, 8 eq) was added to a stirred solution of dimethyl 5-aminoisophthalate (0.500 g, 2.39 mmol, 1 eq) in CH₃CN (15 ml) and water (0.5 ml) at 0° C. After 10 min NaBH₃CN (0.395 g, 5.98 mmol, 2.5 eq) was added. The reaction was adjusted to pH 7 with HOAc. After 1.5 h the reaction was adjusted to pH 7 with HOAc a second time. The reaction was stirred at 0° C. to room temperature overnight. The solvent was removed in vacuo, and the residue was dissolved in EtOAc. The organic layer was washed with saturated aqueous NaHCO₃ (×2), water (×3), brine (×1), and dried over Na₂SO₄. The inorganics were filtered off, and the solvent was removed in vacuo. Purification via flash chromatography yielded 0.575 g (2.17 mmol, 91% yield) of the product.

Example 1.4.13 diethyl 5-carbamoylisophthalate

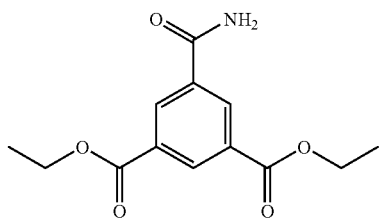

NH$_4$HCO$_3$ (0.15 g, 1.89 mmol, 1.26 eq) was added to a stirred solution of 3,5-bis(ethoxycarbonyl)benzoic acid (0.42 g, 1.5 mmol, 1 eq), pyridine (0.24 mL, 0.237 g, 3.0 mmol, 2 eq), and (Boc)$_2$O (0.45 mL, 0.43 g, 1.95 mmol, 1.3 eq) in 2 mL anh. dioxane under Ar. The reaction was stirred over the weekend to form a white solid. EtOAc was added, but the solid did not dissolve. The mixture was washed with 0.1 N HCl (×2) and water (×4). The solid stayed suspended in the organic layer, but did dissolve. The solvent was removed in vacuo yielding 0.369 g (1.39 mmol, 93% yield) of diethyl 5-carbamoylisophthalate as an insoluble white solid.

Example 1.4.14 diethyl 5-(methylcarbamoyl)isophthalate

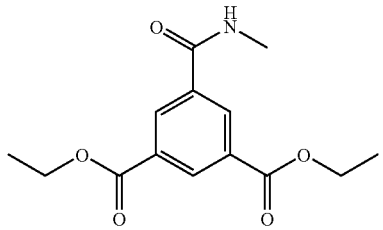

1 drop of Et$_3$N (catalytic) was added to a stirred solution of 3,5-bis(ethoxycarbonyl)benzoic acid (0.42 g, 1.5 mmol, 1 eq) in SOCl$_2$ (4 mL, 6.54 g, 55 mmol, 37 eq) under Ar. The solution was heated to reflux at 95° C. After 2 h the reaction was cooled to room temperature, and the solvent was removed in vacuo. The resulting yellow oil was placed under Ar and dissolved in 5 mL anh. CH$_2$Cl$_2$. The solution was cooled to 0° C., and MeNH$_2$ (2.0 M in THF, 2.7 mL, 5.4 mmol, 3.6 eq) was added with stirring. After stirring for 1 h, Et$_3$N (0.2 mL, 0.15 g, 1.5 mmol, 1 eq) was added. The reaction was stirred at 0° C. to room temperature overnight. The solvent was removed in vacuo. The residue was diluted with saturated NaHCO$_3$/water and extracted with EtOAc (×3). The combined organics were washed with water (×2), brine (×1), and dried over Na$_2$SO$_4$. The inorganics were filtered off, and the solvent was removed in vacuo yielding 0.2914 g (1.0 mmol, 70% yield) of diethyl 5-(methylcarbamoyl)isophthalate.

Example 1.4.15 diethyl biphenyl-3,5-dicarboxylate

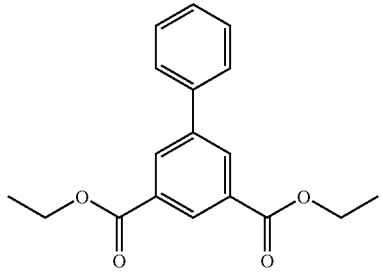

A mixture of Na$_2$CO$_3$ (776 mg, 7.32 mmol), Pd(OAc)$_2$ (4.5 mg, 0.02 mmol), diethyl 5-bromoisophthalate (1 g, 3.66 mmol), phenyl boronic acid (670 mg, 5.49 mmol), distilled water (14 mL) and acetone (12 mL) was stirred at 35° C. for 0.5 h. The reaction solution was then extracted four times with diethyl ether (4×20 mL). The combined organic phase washed with brine, dried over sodium sulfate and then filtered. The solvent was removed under vacuum, and the crude diethyl biphenyl-3,5-dicarboxylate was taken to the next step without any further purification.

Example 1.4.16 dimethyl 5-(oxazol-2-yl)isophthalate

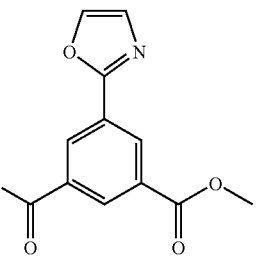

To a stirred solution of oxazole ((0.28 mL, 4.2 mmol) in THF (10 mL) at −78° C. was added nBuLi (2.8 mL 1.6 N solution in hexane, 4.4 mmol). ZnCl$_2$ (20 mL 0.5M soln, 10 mmol) was added after 30 min and the reaction mixture was warmed up to 0° C. for 1 h. To the resulting mixture was added dimethyl 5-iodoisophthalate (1.28 g, 4.0 mmol) and Pd(PPh$_3$)$_4$ and was heated at reflux for 5 h. The reaction mixture was cooled to room temperature and diluted with EtOAc and H$_2$O. The layers were separated and the organic layer was washed with, brine, dried with Na$_2$SO$_4$ and concentrated under reduced pressure. The residue was purified by column chromatography (20% EtOAc in hexanes) to provide dimethyl 5-(oxazol-2-yl)isophthalate (568 mg, 54%).

Example 1.4.17

3-(methoxycarbonyl)-5-(oxazol-5-yl)benzoic acid

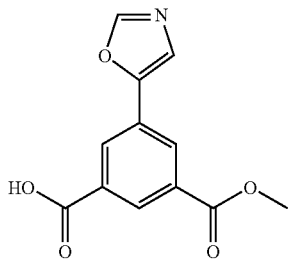

To a stirred solution of diethyl 5-hydroxyisophthalate (4.0 g, 15.9 mmol) in HOAc (40 mL) was added a solution of CAN (19 g, 34.9 mmol) in H$_2$O (40 mL) dropwise. The reaction mixture was heated at 70° C. for 6 h during which time the color of the solution turned from red to colorless. The reaction mixture was cooled to room temperature and dilute with H$_2$O and was extracted with EtOAc. The combined organic layer was washed with saturated aqueous NaHCO$_3$, brine, dried with Na$_2$SO$_4$ and concentrated under reduced pressure to provide diethyl 5-formylisophthalate (3.93 g, 99%) as a white solid. $^1$H NMR (CDCl$_3$): d 10.17 (s, 1H), 8.95-8.96 (m, 1H), 8.74-8.75 (m, 2H), 4.50 (q, J=7.2 Hz, 4H), 1.47 (t, J=7.2 Hz, 6H).

To a stirred solution of diethyl 5-formylisophthalate (529 mg, 2.1 mmol) and p-toluenesulfonylmethyl isocyanide (483 mg, 2.5 mmol) in DME (15 mL) and MeOH (15 mL) was added K$_2$CO$_3$. The resulting mixture was heated to reflux for 4 h and cooled to room temperature. The solvent was removed and the residue was dissolved in EtOAc and H$_2$O. The layers were separated and the aqueous layer was extracted with EtOAc (2×20 mL). The combined organic layer was washed with brine, dried with Na$_2$SO$_4$ and concentrated under reduced pressure to provide 9 (103 mg, 19%). $^1$H NMR (CDCl$_3$): d 8.63 (s, 1H), 8.49 (s, 2H), 8.00 (s, 1H), 7.54 (s, 1H), 4.00 (s, 6H).

Example 1.4.18 dimethyl 5-(pyrrolidin-1-yl)isophthalate

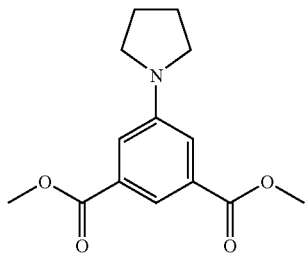

Anhydrous DMF (3 ml) was added to a flask charged with dimethyl 5-aminoisophthalate (0.250 g, 1.2 mmol, 1 eq) and 4-dimethylaminopyridine (0.308 g, 2.52 mmol, 2.1 eq) under Ar. 1,4-diiodobutane (0.16 ml, 0.37 g, 1.20 mmol, 1 eq) was added with stirring and the solution was heated to 90° C. After heating overnight the reaction was not complete. More diiodide (0.25 ml, 1.9 mmol, 1.6 eq) was added and the reaction was heated to 100° C. After heating overnight the reaction was cooled to room temperature and poured in water. The mixture was extracted with EtOAc (×2). The combined organic extracts were washed with water (×3), brine (×1), and dried over Na$_2$SO$_4$. The inorganics were filtered off, and the solvent was removed in vacuo. The residue was stirred in CH$_2$Cl$_2$ and filtered through cotton to remove any insoluble material. The solvent was removed in vacuo. Purification via flash chromatography yielded the crude product. The crude was triturated with hexanes and the solid was collected via filtration. 0.167 g (0.63 mmol, 53% yield) of the product was collected.

Example 1.4.19 dimethyl 5-(piperidin-1-yl)isophthalate

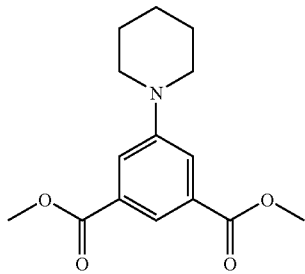

1,5-diiodopentane (0.85 ml, 1.8 g, 5.74 mmol, 3 eq) was added to a stirred solution of dimethyl 5-aminoisophthalate (0.40 g, 1.91 mmol, 1 eq) and DMAP (0.467 g, 3.82 mmol, 2.1 eq) at 100° C. under Ar. After heating overnight the reaction was cooled to room temperature and poured in water. The mixture was extracted with EtOAc (×2). The combined organic extracts were washed with water (×4), brine (×1), and dried over Na$_2$SO$_4$. The inorganics were filtered off, and the solvent was removed in vacuo. Purification via flash chromatography yielded 0.1736 g, 0.626 mmol, 33% yield) of the product.

Example 1.4.20 dimethyl 5-(4-chlorobutanamido)isophthalate

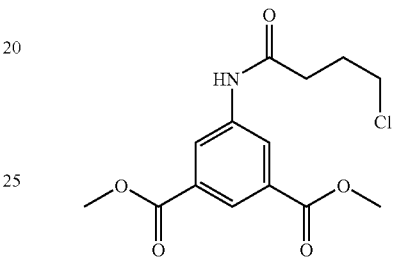

1 drop of Et$_3$N (catalytic) was added to a stirred solution of 4-chlorobutanoic acid (0.029 ml, 0.35 g, 2.87 mmol 1.2 eq) in SOCl$_2$ (2 ml, 3.27 g, 27.5 mmol, 11.5 eq) and the mixture was heated to 80° C. After 1.5 h the reaction was cooled to room temperature, and the solvent was removed in vacuo. The flask was evacuated and back-filled with Ar (×3). The residue was dissolved in 2 ml anhydrous CH$_2$Cl$_2$. The resulting solution was added dropwise to a stirred suspension of dimethyl 5-aminoisophthalate in 8 ml anhydrous CH$_2$Cl$_2$. After 1 h Et$_3$N (1 ml, 0.73 g, 7.17 mmol, 3 eq) was added. After 2 h the solvent was removed in vacuo, and the resulting residue was dissolved EtOAc. The organic layer was washed with saturated aqueous NaHCO$_3$ (×2), water (×3), brine (×1), and dried over Na$_2$SO$_4$. The inorganics were filtered off, and the solvent was removed in vacuo. Purification via flash chromatography yielded 0.6353 g (2.0 mmol, 85% yield) of the product.

Example 1.4.21 dimethyl 5-(2-oxopyrrolidin-1-yl)isophthalate

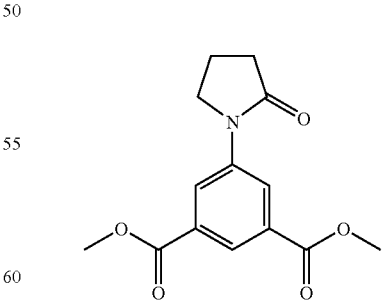

A solution of dimethyl 5-(4-chlorobutanamido)isophthalate (0.635 g, 2.02 mmol, 1 eq) dissolved in 5 ml anhydrous DMF was added dropwise to a stirred suspension of NaH (60% dispersion in oil, 0.101 g, 2.53 mmol, 1.25 eq) in 2 ml anhydrous DMF at 0° C. under Ar. The reaction was stirred at 0° C. to room temperature overnight. After stirring overnight the reaction was heated to 100° C. for 19 h. After cooling to room temperature the reaction was poured into ice-water to quench. The mixture was extracted with EtOAc (×1). The organic layer was washed with water (×4), brine (×1), and dried over Na₂SO₄. The inorganics were filtered off, and the solvent was removed in vacuo. Purification via flash chromatography yielded 0.3487 g (1.26 mmol, 62% yield) of the product.

Example 1.4.22 dimethyl 5-(1H-pyrrol-1-yl)isophthalate

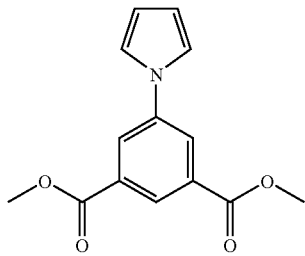

2,5-dimethoxytetrahydrofuran (0.74 ml, 0.76 g, 5.74 mmol, 1.2 eq) was added to a stirred suspension of dimethyl 5-aminoisophthalate (1.0 g, 4.78 mmol, 1 eq) in 7 ml acetic acid under Ar. The mixture was heated to reflux at 135° C. After 45 min the reaction was cooled to RT, and the solvent was removed in vacuo. The residue was stirred in saturated aqueous NaHCO₃/EtOAc overnight. The layers were separated. The organic layer was washed with saturated aqueous NaHCO₃ (×1), water (×2), brine (×1), and dried over Na₂SO₄. The inorganics were filtered off, and the solvent was removed in vacuo. Purification via flash chromatography yielded 0.288 g (1.11 mmol, 23% yield) of the product. A significant amount of crude product was also collected.

Example 1.4.23 dimethyl 5-(pyridin-2-yl)isophthalate

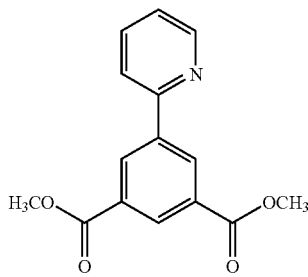

To dimethyl 5-iodoisophthalate (Matrix Scientific, 800 mg, 2.5 mmol) in THF (20 ml), 2-pyridine boronic acid N-phenyldiethanol amine ester (Aldrich, 1.8 g, 6.6 mmol), K₂CO₃ (912 mg, 6.6 mmol), triphenyl phosphine (173 mg, 0.66 mmol) were added followed by Pd(OAc)₂ and cuprous iodide (251 mg, 1.32 mmol). After refluxing for 24 h, reaction mixture was filtered through a pad of celite. Residual solvent was evaporated on a rotavap under reduced pressure and the crude was dissolved in ethyl acetate. Insoluble material was filtered off and the remaining residue was evaporated to dryness and column purified (60% ethylacetate/40% hexanes) to yield 400 mg of dimethyl 5-(pyridin-2-yl)isophthalate as yellow solid.

Example 1.4.24 dimethyl 5-(pyridin-3-yl)isophthalate

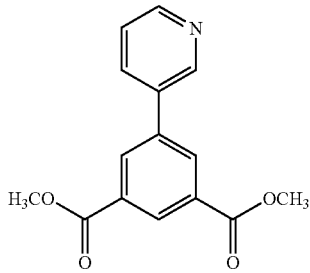

To dimethyl 5-iodoisophthalate (Matrix scientific) in 1,4-dioxane (10 ml), pyridine 3-boronoic acid, sodium carbonate (2M aqueous solution) and Pd(PPh₃)₄ was added and heated at 90° C. for 4 h. Then reaction mixture was diluted with ether, washed with water, brine and dried. Volatiles were removed under vacuum and the crude residue was column chromatographed (60% ethylacetate/40% hexanes) to yield 450 mg of dimethyl 5-(pyridin-3-yl)isophthalate as pale yellow solid.

Example 1.4.25 dimethyl 2'-methoxybiphenyl-3,5-dicarboxylate

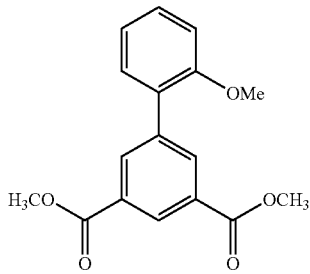

To dimethyl 5-bromoisophthalate (1.5 g, 5.5 mmol, Aldrich) in i-PrOH (33.3 ml) and water (16.7 ml), 2-methoxy phenyl boronic acid (Aldrich), triethyl amine (841 mg, 8.25 mmol) and PdCl₂(dppf) (180 mg, 0.22 mmol) were added and the reaction mixture was refluxed for 4 h. Then reaction mixture was diluted with ether, washed with water, brine and dried. Volatiles were removed under vacuum and the crude residue was column chromatographed (30% ethylacetate/70% hexanes) to yield 650 mg of dimethyl 2'-methoxybiphenyl-3,5-dicarboxylate as white solid.

Example 1.4.26 dimethyl 5-(pyrazin-2-yl)isophthalate

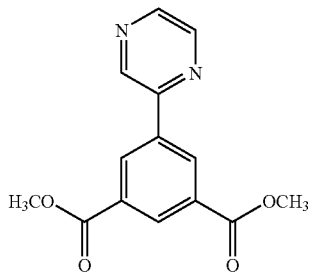

To dimethyl 5-bromoisophthalate (617 mg, 2.26 mmol) in toluene (10 ml), 2-tributylstannyl pyrazine (1 g, 2.71 mmol) was added followed by Pd(PPh₃)₄ (102 mg, 0.09 mmol). Then reaction mixture was refluxed for 22 h. Then the reaction mixture was filtered through celite and volatiles were removed under vacuum. Crude residue was column chromatographed (50% ethylacetate/50% Hexanes) to obtain 455 mg of dimethyl 5-(pyrazin-2-yl)isophthalate as a pale yellow solid.

Example 1.4.27

5-(1H-pyrazol-4-yl)isophthalic acid

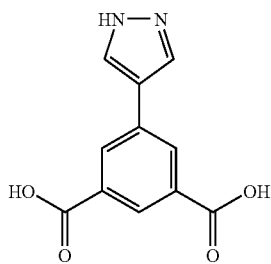

Following standard cross coupling procedure described herein, dimethy 5-bromoisophthalate (623 mg, 2.3 mmol) and 4-pyrazoleboronic acid pinacol ester (443 mg, 2.3 mmol) were reacted. The resulting aqueous layer was acidified to pH 5 and extracted with EtOAc to provide 5-(1H-pyrazol-4-yl) isophthalic acid as a yellow solid.

Example 1.4.28 dimethyl 5-(3-hydroxypyrrolidin-1-yl)isophthalate

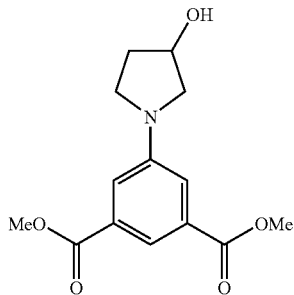

1,4-dibromo-2-butanol (85%, 0.48 ml, 1.1 g, 4.78 mmol, 1 eq) was added to a stirred suspension of K₂CO₃ (1.982 g, 14.34 mmol, 3 eq) in 5 ml triethyl phosphate under Ar. Dimethyl 5-aminoisophthalate (1.00 g, 4.78 mmol, 1 eq) was added and the mixture was heated to reflux at 150° C. After refluxing for 9 h the reaction was cooled to room temperature. The mixture was diluted with Et₂O/H₂O and the layers were separated. The organic layer was washed with water (×3), brine (×1), and dried over Na₂SO₄. The inorganics were filtered off, and the solvent was removed in vacuo. Purification via flash chromatography yielded the crude product. After concentrating in vacuo the residue was cooled to 0° C. Dropwise addition of ice-water to the rapidly stirred solution resulted in the formation of a yellow solid. 0.45 g (1.61 mmol, 34% yield) of dimethyl 5-(3-hydroxypyrrolidin-1-yl)isophthalate was collected via filtration.

Example 1.4.29 dimethyl 5-(3-oxopyrrolidin-1-yl)isophthalate

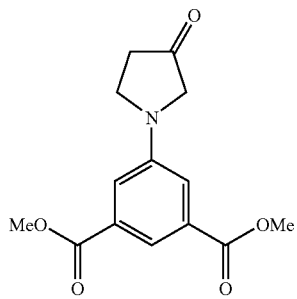

Trifluoroacetic acid (0.061 ml, 0.091 g, 0.794 mmol, 0.5 eq) was added dropwise to a stirred solution of dimethyl 5-(3-hydroxypyrrolidin-1-yl)isophthalate (0.4434 g, 1.59 mmol, 1 eq), anhydrous pyridine (0.135 ml, 0.13 g, 1.67 mmol, 1.05 eq), anhydrous DMSO (0.124 ml, 0.13 g, 1.67 mmol, 1.05 eq), and 1,3-dicyclohexylcarbodiimide (0.655 g, 3.18 mmol, 2 eq) in 5 ml anhydrous benzene at ° C. under Ar. After stirring at 0° C. to room temperature overnight the reaction was diluted with Et₂O/H₂O and stirred for 20 h. The mixture was filtered through cotton and the layers were separated. The organic layer was washed with water (×3), brine (×1), and dried over Na₂SO₄. The inorganics were filtered off and the solvent was removed in vacuo. Purification via flash chromatography yielded only crude product. Purification via a second column yielded 0.201 g (0.73 mmol, 46% yield) of dimethyl 5-(3-oxopyrrolidin-1-yl)isophthalate.

Example 1.4.30 dimethyl 5-(3,3-dihydroxypyrrolidin-1-yl)isophthalate

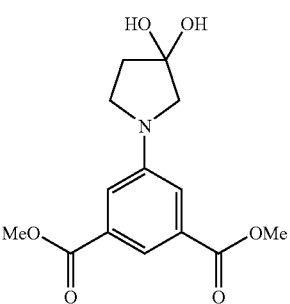

Dimethyl 5-(3-oxopyrrolidin-1-yl)isophthalate (0.1114 g, 0.401 mmol, 1 eq) and NH₄Cl (0.086 g, 1.61 mmol, 4 eq) in 5 ml anhydrous MeOH were heated to reflux at 80° C. for 22 h. After cooling to room temperature the solvent was removed in vacuo. The residue was stirred in EtOH and filtered through cotton to remove any insoluble material. Purification via flash chromatography yielded 0.082 g, (0.25 mmol, 63% yield) of dimethyl 5-(3,3-dihydroxypyrrolidin-1-yl)isophthalate.

Example 1.4.31 dimethyl 5-(1H-imidazol-1-yl)isophthalate

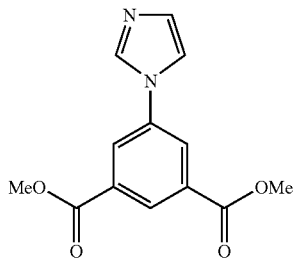

Dimethyl 5-aminoisophthalate (1.00 g, 4.78 mmol, 1 eq) and glyoxal trimer 2H$_2$O (1.004 g, 4.78 mmol, 1 eq) were stirred in 6 ml EtOH overnight. NH$_4$Cl (0.5114 g, 9.56 mmol, 2 eq) was added. After 15 min aqueous formaldehyde (37%, 0.71 ml, 0.78 g, 9.56 mmol, 2 eq) was added and the mixture was heated to reflux at 90° C. After 1 h the reaction was cooled to room temperature. After the dropwise addition of H$_3$PO$_4$ (85%, 0.65 ml, 1.1 g, 9.56 mmol, 2 eq) the reaction was heated to reflux at 95° C. After 6 h the reaction was cooled to room temperature and the solvent was removed in vacuo. The residue was stirred in CHCl$_3$ and the mixture was filtered through cotton to remove any insoluble material. Purification via flash chromatography yielded 0.7329 g (2.82 mmol, 59% yield) of dimethyl 5-(1H-imidazol-1-yl)isophthalate.

Example 1.4.32 diethyl 5-(1H-imidazol-2-yl)isophthalate

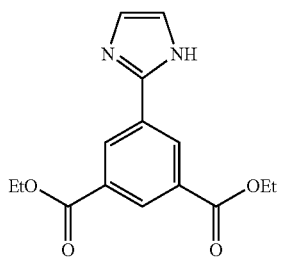

NH$_3$ (2.0 M in MeOH, 4.8 ml, 9.6 mmol, 8 eq) was added to a flask charged with diethyl 5-formylisophthalate (0.300 g, 1.2 mmol, 1 eq) and glyoxal trimer 2H$_2$O (0.252 g, 1.2 mmol, 1 eq) at 0° C. under Ar. The reaction was stirred at 0° C. to room temperature overnight. The solvent was removed in vacuo. The residue was stirred in EtOAc and filtered through cotton to remove any insoluble material. Purification via flash chromatography yielded 0.1293 g (0.45 mmol, 37% yield) of diethyl 5-(1H-imidazol-2-yl)isophthalate.

Example 1.4.33 diethyl 5-(1-methyl-1H-imidazol-2-yl)isophthalate

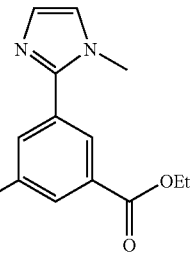

A solution of diethyl 5-(1H-imidazol-2-yl)isophthalate (0.0689 g, 0.239 mmol, 1 eq) in anhydrous THF (2 ml) was added dropwise to a stirred suspension of NaH (60% dispersion in oil, 0.0105 g, 0.263 mmol, 1.1 eq) in anhydrous THF (3 ml) at 0° C. under Ar. After 1 h the reaction was warmed to room temperature. After 1 h the reaction was cooled to 0° C. and MeI (0.016 ml, 0.037 g, 0.263 mmol, 1.1 eq) was added dropwise. The reaction was stirred at 0° C. to room temperature overnight. The reaction was quenched with water and diluted with EtOAc. The organic layer was washed with water (×3), brine (×1), and dried over Na$_2$SO$_4$. The inorganics were filtered off and the solvent was removed in vacuo. Purification via flash chromatography yielded 0.305 g (0.1.1 mmol, 42% yield) of diethyl 5-(1-methyl-1H-imidazol-2-yl)isophthalate.

Example 1.4.34 dimethyl 2-methoxyisophthalate

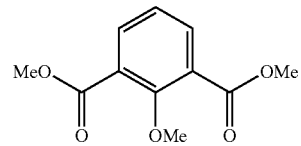

KMNO$_4$ (19.15 g, 121.2 mmol, 6.6 eq) followed by 2-methoxy-1,3-dimethylbenzene (2.6 ml, 2.5 g, 18.36 mmol, 1 eq) were added to a stirred solution of KOH (3.30 g, 58.74 mmol, 3.2 eq) in 98 ml of water. The reaction was heated to 80° C. After 3 h the reaction was cooled to room temperature. The mixture was filtered through Celite. The solution was adjusted to pH 7 with concentrated HCl and again the mixture was filtered through Celite. The solution was adjusted to pH=2-3 with concentrated HCl and extracted with EtOAc (×2). The combined organics were washed with brine (×1) and dried over Na$_2$SO$_4$. The inorganics were filtered off and the solvent was removed in vacuo yielding 1.552 g (7.91 mmol, 43% yield) of 2-methoxyisophthalic acid.

SOCl$_2$ (1.85 ml, 3.03 g, 25.5 mmol, 10 eq) was added dropwise with stirring to a solution of 2-methoxyisophthalic acid (0.500 g, 2.55 mmol, 1 eq) in 10 ml anhydrous MeOH at 0° C. under Ar. The reaction was stirred at 0° C. to room temperature overnight. The solvent was removed in vacuo and the residue dissolved in EtOAc. The solution was washed with saturated aqueous NaHCO$_3$ (×2), water (×3), brine (×1), and dried over Na$_2$SO$_4$. The inorganics were filtered off and the solvent was removed in vacuo yielding 0.6785 g (3.01 mmol, 118% yield) of dimethyl 2-methoxyisophthalate with some impurities.

Example 1.4.35 dimethyl 2-(benzyloxy)isophthalate

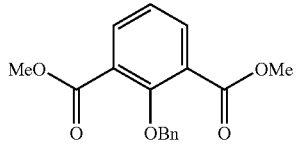

BBr$_3$ (1.0M in CH$_2$Cl$_2$, 7.53 ml, 7.53 mmol, 2.5 eq) was added dropwise to a stirred solution of dimethyl 2-methoxyisophthalate (0.6785 g, 3.01 mmol, 1 eq) in anhydrous CH$_2$Cl$_2$ (4 ml) at 0° C. under Ar. After 30 min the reaction was warmed to room temperature. After 2 h the reaction was quenched anhydrous MeOH (1 ml) and stirred overnight. The solvent was removed in vacuo and the residue dissolved in EtOAc. The organic layer was washed with saturated aqueous NaHCO$_3$ (×2), water (×3), brine (×1), and dried over Na$_2$SO$_4$. The inorganics were filtered off and the solvent was removed in vacuo. Purification via flash chromatography yielded 0.4045 g (1.92 mmol, 64% yield) of dimethyl 2-hydroxyisophthalate.

Benzyl bromide (0.34 ml, 0.49 g, 2.89 mmol, 1.5 eq) was added to a stirred suspension of dimethyl 2-hydroxyisophthalate (0.4045 g, 1.92 mmol, 1 eq) and K$_2$CO$_3$ (0.5317 g, 3.85 mmol, 2 eq) in anhydrous DMF (2 ml) under Ar. After 48 h the reaction was diluted with Et$_2$O. The mixture was washed with water (×4), brine (×1), and dried over Na$_2$SO$_4$. The inorganics were filtered off and the solvent was removed in vacuo. Purification via flash chromatography yielded 0.5207 g (1.73 mmol, 90% yield) of dimethyl 2-(benzyloxy)isophthalate.

Example 1.4.36 dimethyl 4'-(dimethylamino)biphenyl-3,5-dicarboxylate

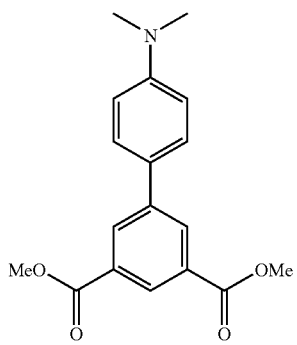

To dimethyl 5-bromoisophthalate (1.38 gm, 5.05 mmol) (Matrix scientific) in 1,4-dioxane (20 ml), 4-(N,N-dimethyl amino phenyl boronic acid) (1.0 g, 6.06 mmol), sodium carbonate (2M aqueous solution) (2.12 g in 10 ml water) and Pd(PPh$_3$)$_4$ (589 mg, 0.51 mmol) was added and heated at 90° C. for 4 h. Then reaction mixture was diluted with ether, washed with water, brine and dried. Volatiles were removed under vacuum and the crude residue was column chromatographed (60% ethylacetate/40% hexanes) to yield 420 mg of dimethyl 4'-(dimethylamino)biphenyl-3,5-dicarboxylate.

Example 1.4.37 dimethyl 3'-chlorobiphenyl-3,5-dicarboxylate

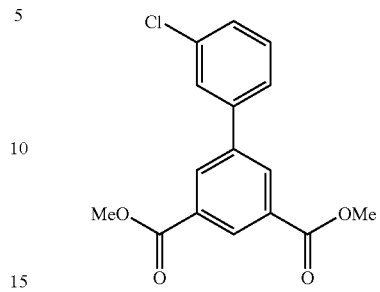

To dimethyl 5-bromoisophthalate (880 mg, 3.22 mmol) (commercial source: Matrix scientific) in 1,4-dioxane (15 ml), 3-chlorophenyl boronic acid) (756 mg, 4.83 mmol), sodium carbonate (2M aqueous solution) (1.38 gms in 6.5 ml water) and Pd(PPh$_3$)$_4$ (370 mg, 0.32 mmol) was added and heated at 90° C. for 5 h. Then reaction mixture was diluted with ether, washed with water, brine and dried. Volatiles were removed under vacuum and the crude residue was column chromatographed (10% ethylacetate/90% hexanes) to yield 700 mg of dimethyl 3'-chlorobiphenyl-3,5-dicarboxylate.

Example 1.4.38

3-(methoxycarbonyl)-4-methylbenzoic acid

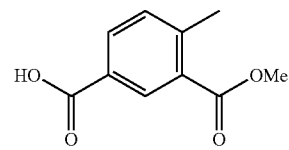

A mixture of 268 mg of the methyl 5-formyl-2-methylbenzoate and 1.08 g (1.76 mmol) of Oxone in 6 mL of DMF was stirred at r.t. for 16.75 h. Water, 1N HCl, and EtOAc were added, and the aqueous layer was extracted with EtOAc. The combined extracts were dried over Na$_2$SO$_4$, filtered, and concentrated, and 3-(methoxycarbonyl)-4-methylbenzoic acid, which was used for the next reaction without further purification.

Example 1.4.39

5-(methoxycarbonyl)-2-methylbenzoic acid

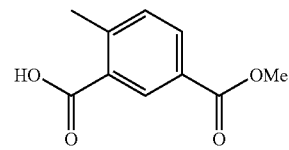

A solution of 305 mg (1.74 mmol) of methyl 3-cyano-4-methylbenzoate and excess Et$_3$O$^+$BF$_4^-$ in 7 mL of CH$_2$Cl$_2$ was stirred at 45° C. After 13 h and about 24 h more Et$_3$O$^+$BF$_4^-$ was added and after a further 20 min. the temperature was increased to 50° C. After 37 h, the temperature was increased to 55° C. and heating was continued for 1.5 h. After this time, the crude solution was added with 3 mL of CH$_2$Cl$_2$ to 0.16 mL of Et$_3$SiH in 5 mL of CH$_2$Cl$_2$. After the solution was stirred at 55° C. for 2 h, 10 mL of H$_2$O was added, and the mixture was stirred at 120° C. for 15 min. and the temperature was decreased to 115° C. for 1 h, stopped for 2 h, and then resumed for 17 h. EtOAc was added, and the layers were separated. The organic layer was washed with brine, dried over Na$_2$SO$_4$, filtered, and concentrated. Purification by flash silica gel chromatography (7.5% EtOAc/hexanes) provided 25 mg of methyl 3-formyl-4-methylbenzoate as colorless oil with some impurity. 5-(methoxycarbonyl)-2-methylbenzoic acid was synthesized from the aldehyde following the general procedure as described above for the methyl substituted benzoic acid.

Example 1.4.40

5-(methoxycarbonyl)nicotinic acid

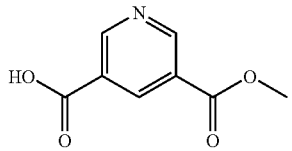

1 drop of Et$_3$N (catalytic) was added to a stirred solution of pyridine-3,5-dicarboxylic acid (Aldrich, 6.0 g, 35.9 mmol, 1 eq) in SOCl$_2$ (20 ml, 32.7 g, 274 mmol, 7.7 eq) under Argon. The solution was heated to reflux at 95° C. After 4 h the reaction was cooled to room temperature, and the solvent was removed in vacuo. The resulting yellow oil was placed under Argon and dissolved in 20 ml anhydrous CH$_2$Cl$_2$. The solution was cooled to 0° C., and MeOH (40 ml) was added with stirring. After stirring for 2 h, Et$_3$N (10 ml, 7.26 g, 71.7 mmol, 2 eq) was added. The reaction was stirred at 0° C. to room temperature overnight. The solvent was removed in vacuo. The residue was dissolved in EtOAc. Washed with saturated aqueous NaHCO$_3$ (×2), water (×3), brine (×1), and dried over Na$_2$SO$_4$. The inorganics were filtered off, and the solvent was removed in vacuo yielding 6.3 g (32.3 mmol, 90% yield) of dimethylpyridine-3,5-dicarboxylate.

NaOH (0.68 g, 16.46 mmol, 0.85 eq) was added to a stirred solution of dimethyl pyridine-3,5-dicarboxylate (3.78 g, 19.36 mmol, 1 eq) in 2:3:3 H$_2$O/MeOH/THF (67 ml). The mixture was stirred overnight. The solvent was removed in vacuo, and the residue dissolved in saturated aqueous NaHCO$_3$. The mixture was extracted with EtOAc (×1). The pH of the aqueous layer was adjusted to 3 with concentrated HCl, and the mixture extracted with EtOAc (×5). The organics were combined washed with water (×1), brine (×1), and dried over Na$_2$SO$_4$. The inorganics were filtered, and solvent removed in vacuo. 2.195 g (12.1 mmol, 62% yield) of the product 5-(methoxycarbonyl)nicotinic acid with some diacid impurity was collected. 1.0 g (5.1 mmol) of the starting material was recovered from the initial EtOAc extraction.

Example 1.4.41

2-(methoxycarbonyl)-6-methylisonicotinic acid

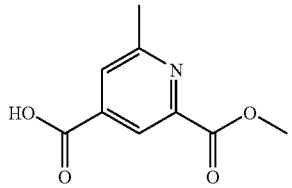

To a solution of 2.03 g (11 mmol) of methyl 2-chloro-6-methylisonicotinate (Aldrich) in 20 mL of DMF (degassed) was added 1.14 g (9.73 mmol) of Zn(CN)$_2$ and 1.18 g (1.02 mmol) of Pd(PPh$_3$)$_4$. The mixture was stirred at 80° C. for 12.5 h, and EtOAc and 20 mL of 10% NH$_4$OH aqueous solution were added. The organic layer was washed with 20 mL of 10% NH$_4$OH and 20 mL of brine. The combined aqueous layers were reextracted with EtOAc and washed with brine. The combined extracts were dried over Na$_2$SO$_4$, filtered, and concentrated. Purification by flash silica gel chromatography (30% EtOAc/hexanes) provided 1.3 g of methyl 2-cyano-6-methylisonicotinate in 68% yield.

To a stirring solution of 1.3 g (7.33 mmol) of methyl 2-cyano-6-methylisonicotinate in 25 mL of MeOH and 5 mL of THF at 0° C. was added 823 mg (21.7 mmol) of NaBH$_4$. After 2 h the ice bath was removed and stirring was continued with warming to r.t. and after a further 15 min. 1.06 g of NaBH$_4$ was added. After another 15 min., the solution was concentrated, and EtOAc was added. The pH was adjusted to 7 with 1N HCl, and the layers were separated. The aqueous layer was extracted with EtOAc (2×), and the combined extracts were washed with brine (50 mL), dried over Na$_2$SO$_4$, filtered, and concentrated. Purification by flash silica gel chromatography (2-3) % MeOH/CHCl$_3$ provided 440 mg of 4-(hydroxymethyl)-6-methylpicolinonitrile in 40% yield as a colorless solid.

A mixture of 440 mg of the 4-(hydroxymethyl)-6-methylpicolinonitrile in 3 mL of concentrated H$_2$SO$_4$ and 1.8 mL of H$_2$O was stirred at 135° C. for 12 h. The temperature was decreased to 95° C., 6 mL of MeOH was added, and the solution was stirred at 95° C. for 1 h. The solution was added to ice with H$_2$O and EtOAc. Solid NaHCO$_3$ and sat. NaHCO$_3$ solution were added to a pH=8. The aqueous layer was extracted with EtOAc (2×). The combined extracts washed with brine (40 mL), dried over Na$_2$SO$_4$, filtered and concentrated to give 393 mg of methyl 4-(hydroxymethyl)-6-methylpicolinate which was used without further purification.

A mixture of 393 mg of methyl 4-(hydroxymethyl)-6-methylpicolinate and 1.89 g (21.8 mmol) of MnO$_2$ in 10 mL of CH$_2$Cl$_2$ was stirred at 50° C. After 70 min., 1.20 g of MnO$_2$ was added; after 30 min., 1.29 g of MnO$_2$, was added, and after another 20 min. the mixture was filtered through Celite and concentrated to give 216 mg of methyl 4-formyl-6-methylpicolinatee which was used in the next reaction without further purification.

To a stirring solution of 216 mg (1.20 mmol) of methyl 4-formyl-6-methylpicolinate in 4 mL of DMF was added 790 mg (1.29 mmol) of Oxone. After about 2 h, 5 mL of 1N HCl and 5 mL of H$_2$O were added, and the aqueous layer was extracted with EtOAc (3×). The combined extracts were dried over Na$_2$SO$_4$, filtered, and concentrated. The desired product (2-(methoxycarbonyl)-6-methylisonicotinic acid) was used in the next reaction without further purification.

Example 1.4.42

4-(methoxycarbonyl)-6-methylpicolinic acid

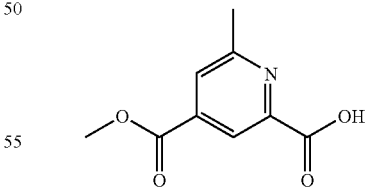

A solution of 2.23 g (18.1 mmol) of 2,6-dimethylpyridine 1-oxide (Alfa Aesar) in 7 mL of H$_2$SO$_4$ and 2.7 mL of HNO$_3$ was stirred at 130° C. for 23.5 h. The solution was added to ice with CHCl$_3$ and H$_2$O, and the aqueous layer was extracted with CHCl$_3$ (2×). The combined extracts were washed with 75 mL of saturated NaHCO$_3$ solution, and the aqueous layer was extracted with CHCl$_3$. The combined extracts were washed with brine, dried over Na$_2$SO$_4$, filtered, and concentrated to give 2.3 g of 2,6-dimethyl-4-nitropyridine 1-oxide in 76% yield which was used without further purification.

A mixture of 2.4 g of 2,6-dimethyl-4-nitropyridine 1-oxide and 16.5 mL of acetyl bromide was stirred at 75° C. under a CaCl$_2$ drying tube for 4 h. The mixture was added to ice with H$_2$O, CHCl$_3$, and EtOAc and solid NaHCO$_3$ was added to pH=7-8. The aqueous layer was extracted with CHCl$_3$ (3×), and the combined extracts were dried over Na$_2$SO$_4$, filtered, and concentrated. Purification by flash silica gel chromatography (1 to 5) % MeOH/CHCl$_3$ provided 1.39 g of 4-bromo-2,6-dimethylpyridine 1-oxide as a pale brown solid in 48% yield.

To a stirring solution of 2.14 g 4-bromo-2,6-dimethylpyridine 1-oxide in 10 mL of CH$_2$Cl$_2$ was added 7.4 mL of trifluoroacetic anhydride. After 20 h, the solution was concentrated, and the crude product was purified by flash silica gel chromatography (5% MeOH/CHCl$_3$) to give 1.93 g of (4-bromo-6-methylpyridin-2-yl)methyl 2,2,2-trifluoroacetate with some impurity.

To a solution of 1.93 g of (4-bromo-6-methylpyridin-2-yl) methyl 2,2,2-trifluoroacetate in 10 mL of DMF (degassed) was added 667 mg (5.68 mmol) of Zn(CN)$_2$ and 689 mg (0.600 mmol) of Pd(PPh$_3$)$_4$. The mixture was stirred at 80° C. for about 4 h, and 233 mg of Pd(PPh$_3$)$_4$ was added. After 2.5 h, 50 mL of 10% NH$_4$OH solution, and EtOAc were added. The aqueous layer was extracted with EtOAc, and the combined extracts were washed with brine, dried over Na$_2$SO$_4$, filtered, and concentrated. Purification by flash silica gel chromatography (1 to 5) % MeOH/CHCl$_3$ provided 1.20 g of (4-cyano-6-methylpyridin-2-yl)methyl 2,2,2-trifluoroacetate as a yellow solid with some impurity.

To a stirring solution of 1.20 g of (4-cyano-6-methylpyridin-2-yl)methyl 2,2,2-trifluoroacetate in 7 mL of THF was added 7% NaHCO$_3$ (aqueous) solution to pH=8. The mixture was stirred at r.t. for 18 h, and EtOAc was added. The aqueous layer was extracted with EtOAc, and the combined extracts were washed with brine, dried over Na$_2$SO$_4$, filtered, and concentrated. Purification by flash silica gel chromatography (1 to 6) % MeOH/CHCl$_3$ provided 535 mg of 2-(hydroxymethyl)-6-methylisonicotinonitrile in 73% yield.

methyl 2-(hydroxymethyl)-6-methylisonicotinate was synthesized from 2-(hydroxymethyl)-6-methylisonicotinonitrile following the general procedure as described herein.

To a stirring mixture of 51.6 mg (0.283 mmol) of methyl 2-(hydroxymethyl)-6-methylisonicotinate in 1.6 mL of CCl$_4$, 1.6 mL of CH$_3$CN, and 2.4 mL of H$_2$O was added 348 mg (1.63 mmol) of NaIO$_4$, and 8.8 mg (0.0424 mmol) of RuCl$_3$.(H$_2$O)$_n$. After 2 h, 6 mg of RuCl$_3$.(H$_2$O)$_n$ was added, and after 2.5 h the mixture was filtered through Celite twice with EtOAc and MeOH. The solution was concentrated and then reconcentrated with MeOH (2×) to remove H$_2$O. Crude 4-(methoxycarbonyl)-6-methylpicolinic acid was used in the next reaction without further purification.

Example 1.4.43

6-(furan-2-yl)-4-(methoxycarbonyl)picolinic acid

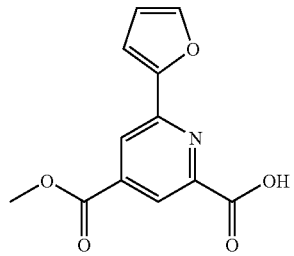

A solution of 6.05 g (32.6 mmol) of methyl 2-chloro-6-methylisonicotinate (Aldrich) in 30 mL of AcOH and 30 mL of H$_2$O$_2$ (30 wt. % in H$_2$O) was stirred at 135° C. for 45 min. and 9 mL of H$_2$O$_2$ (30 wt. % in water) was added. Heating was continued for 3 h, and saturated NaHCO$_3$ solution was added to pH=8. The aqueous layer was extracted with EtOAc (4×), and the combined extracts were washed with 100 mL of brine, dried over Na$_2$SO$_4$, filtered, and concentrated. Purification by flash silica gel chromatography (80% EtOAc/hexanes) provided 4.1 g of the 2-chloro-4-(methoxycarbonyl)-6-methylpyridine 1-oxide as an off-white solid in 63% yield.

To a stirring solution of 7.61 g (37.8 mmol) of 2-chloro-4-(methoxycarbonyl)-6-methylpyridine 1-oxide in 60 mL of CH$_2$Cl$_2$ was added 24 mL of trifluoroacetic anhydride slowly. The solution was stirred at r.t. for 15.5 h. The temperature was increased to 50° C., and the solution was stirred at 50° C. for 5.5 h and then concentrated. The crude residue was dissolved in 50 mL of THF, and 7% NaHCO$_3$ solution (aqueous) was added to a pH=8. The solution was stirred at r.t. for about 40 h, and EtOAc was added. The aqueous layer was extracted with EtOAc (3×), and the combined extracts were washed with brine (100 mL), dried over Na$_2$SO$_4$, filtered, and concentrated. Purification by flash silica gel chromatography (50% EtOAc/hexanes) provided 4.99 g of methyl 2-chloro-6-(hydroxymethyl)isonicotinate as a pale yellow solid in 66% yield.

To a stirring mixture of 3.6 g (17.9 mmol) of methyl 2-chloro-6-(hydroxymethyl)isonicotinate, 8.9 g of 4A powdered molecular sieves, 3.1 g (26.5 mmol) of NMO in 55 mL of CH$_2$Cl$_2$ was added (after about 10 min.) 659 mg (1.87 mmol) of TPAP. The mixture began to gently reflux, and the mixture was stirred for 75 min., filtered through Celite, and concentrated. Purification by flash silica gel chromatography (10% EtOAc/hexanes) provided 1.53 g of methyl 2-chloro-6-formylisonicotinate in 43% yield as an off-white solid.

To a degassed mixture of 205 mg (1.027 mmol) of methyl 2-chloro-6-formylisonicotinate, 183 mg (1.64 mmol) of 2-furanboronic acid, and 316 mg (2.98 mmol) of Na$_2$CO$_3$ in 2 mL of H$_2$O and 4 mL of THF was added 263 mg (0.227 mmol) of Pd(PPh$_3$)$_4$. The mixture was stirred at 55° C. for 14 h, and EtOAc and H$_2$O were added. The aqueous layer was extracted with EtOAc, and the combined extracts were washed with brine, dried over Na$_2$SO$_4$, filtered, and concentrated. Purification by flash silica gel chromatography (10% EtOAc/hexanes) provided methyl 2-formyl-6-(furan-2-yl) isonicotinate as a yellow solid (101 mg) in 43% yield. The desired 6-(furan-2-yl)-4-(methoxycarbonyl)picolinic acid was synthesized from the aldehyde (methyl 2-formyl-6-(furan-2-yl)isonicotinate) following the general procedures as described herein.

Example 1.4.44

2-(dimethylamino)-6-(methoxycarbonyl)isonicotinic acid

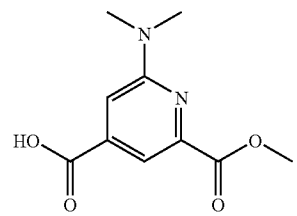

A mixture of 5.0 g (32.2 mmol) of citrazinic acid (Aldrich), 3.9 g (35.6 mmol) of Me$_4$NCl, and 9 mL of POCl$_3$ was stirred with gradual heating to 130° C. under a CaCl$_2$ drying tube for about 16 h. MeOH (100 mL) was added with ice bath cooling; after 1 h, solid NaHCO$_3$ was added to pH=8. Water was added, and the aqueous layer was extracted with EtOAc (2×). The combined extracts were washed with brine (100 mL), dried over Na₂SO₄, filtered, and concentrated. Purification by flash silica gel chromatography (10% EtOAc/hexanes) provided 4.27 g of methyl 2,6-dichloroisonicotinate as a pink solid in 64% yield.

(2,6-dichloropyridin-4-yl)methanol was synthesized from methyl 2,6-dichloroisonicotinate following the general procedure as described herein.

A mixture of crude (2,6-dichloropyridin-4-yl)methanol in 7 mL of (CH₃)₂NH (40 wt % solution in H₂O) was stirred at r.t. for 45 min. The temperature was increased to 50° C., and the solution was stirred at 50° C. for about 24 h. Ethyl acetate and H₂O (15 mL) were added, and the aqueous layer was extracted with EtOAc. The combined extracts were washed with brine, and the aqueous layer was extracted with EtOAc. The combined extracts were dried over Na₂SO₄, filtered, and concentrated. Purification by flash silica gel chromatography (40% EtOAc/hexanes) provided 1.01 g of (2-chloro-6-(dimethylamino)pyridin-4-yl)methanol with some impurity (unreacted starting material).

To a stirring solution of (2-chloro-6-(dimethylamino)pyridin-4-yl)methanol in 7 mL of pyridine was added 1.2 mL of Ac₂O. After the solution was stirred for 12 h, the solution was concentrated, and saturated NaHCO₃ solution was added to pH=7. The aqueous layer was extracted with EtOAc, and the organic layer was washed with H₂O (15 mL) and brine (15 mL), dried over Na₂SO₄, filtered, and concentrated. Purification by flash silica gel chromatography (15% EtOAc/hexanes) provided (2-chloro-6-(dimethylamino)pyridin-4-yl)methyl acetate as a yellow oil with some impurity.

To a solution of 1.17 g (5.10 mmol) of (2-chloro-6-(dimethylamino)pyridin-4-yl)methyl acetate in 10 mL of DMF (degassed) was added 488 mg (4.16 mmol) of Zn(CN)₂ and 519 mg (0.449 mmol) of Pd(PPh₃)₄. The mixture was stirred at 80° C. and more Pd(PPh₃)₄ was added in the following quantities at various intervals in a period of 10 h: 486 mg (50 min.), 708 mg (3 h), 657 mg (6 h). The temperature was increased to 100° C. and stirring was continued for about 11 h. Ethyl acetate and 50 mL of 10% NH₄OH solution were added. The aqueous layer was extracted with EtOAc, and the combined extracts were washed with brine. The aqueous layer (brine) was extracted with EtOAc, and the combined extracts were dried over Na₂SO₄, filtered, and concentrated. Purification by flash silica gel chromatography (30% EtOAc/hexanes) provided 284 mg of (2-cyano-6-(dimethylamino)pyridin-4-yl)methyl acetate as a pale yellow solid.

To a stirring solution of 364 mg (1.66 mmol) of (2-cyano-6-(dimethylamino)pyridin-4-yl)methyl acetate in 7 mL of MeOH was added 365 mg (2.64 mmol) of K₂CO₃. After 1 h, the mixture was filtered through Celite with MeOH and EtOAc. More EtOAc and H₂O (30 mL) were added; the aqueous layer was extracted with EtOAc (4×). The combined extracts were washed with brine (50 mL), dried over Na₂SO₄, filtered, and concentrated. Purification by flash silica gel chromatography (50% EtOAc/hexanes) provided 253 mg of 6-(dimethylamino)-4-(hydroxymethyl)picolinonitrile as a pale yellow solid in 86% yield.

methyl 6-(dimethylamino)-4-(hydroxymethyl)picolinate was synthesized from 6-(dimethylamino)-4-(hydroxymethyl)picolinonitrile following the general procedure as described herein.

A mixture of 250 mg (1.19 mmol) of methyl 6-(dimethylamino)-4-(hydroxymethyl)picolinate and 1.12 g (12.8 mmol) of MnO₂ in 10 mL of CH₂Cl₂ was stirred at 50° C. To the mixture was added more MnO₂ in the following quantities at various (15 min.), 788 mg (15 min.), 924 mg (10 min.), 675 mg (15 min.), 690 mg (15 min.). The mixture was filtered through Celite with EtOAc and MeOH and concentrated. 2-(dimethylamino)-6-(methoxycarbonyl)isonicotinic acid was used in the next reaction without further purification.

Example 1.4.45

6'-fluoro-4-(methoxycarbonyl)-2,3'-bipyridine-6-carboxylic acid

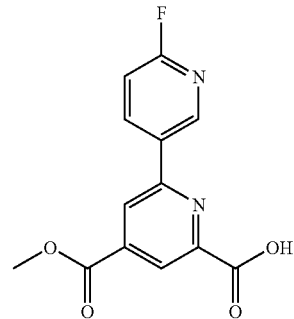

methyl 6'-fluoro-6-formyl-2,3'-bipyridine-4-carboxylate was synthesized from methyl 2-chloro-6-formylisonicotinate and converted to 6'-fluoro-4-(methoxycarbonyl)-2,3'-bipyridine-6-carboxylic acid following the general procedures as described herein.

Example 1.4.46

6-(3-chlorophenyl)-4-(methoxycarbonyl)picolinic acid

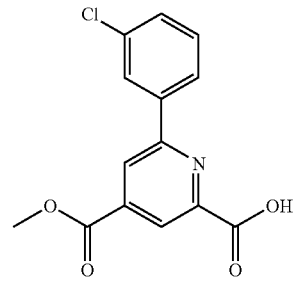

methyl 2-(3-chlorophenyl)-6-formylisonicotinate was synthesized from methyl 2-chloro-6-formylisonicotinate and converted to 6-(3-chlorophenyl)-4-(methoxycarbonyl)picolinic acid following the general procedure as described herein.

Example 1.4.47

6-(dimethylamino)-4-(methoxycarbonyl)picolinic acid

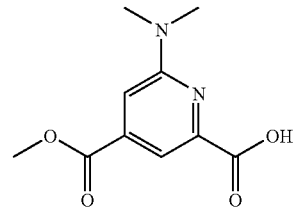

A solution of 314 mg methyl 2-chloro-6-(hydroxymethyl) isonicotinate in 8 mL of $(CH_3)_2NH$ (40 wt % in water) was stirred at 50° C. After 74 h, $H_2O$ and EtOAc were added, and the layers were separated. The aqueous layer was extracted with EtOAc (9×). The combined extracts were washed with 70 mL of brine, dried over $Na_2SO_4$, filtered, and concentrated. Purification by flash silica gel chromatography (100% EtOAc) provided 167 mg of 2-(dimethylamino)-6-(hydroxymethyl)-N,N-dimethylisonicotinamide as a yellow oil in 48% yield.

A mixture of 167 mg of 2-(dimethylamino)-6-(hydroxymethyl)-N,N-dimethylisonicotinamide in 2 mL of $H_2SO_4$ and 1.2 mL of $H_2O$ was stirred at 135° C. for 12.5 h. The temperature was decreased to 95° C., methanol (5 mL) was added, and the solution was heated for 1 h. The solution was added to ice with $H_2O$ and EtOAc, and solid $NaHCO_3$ and sat. $NaHCO_3$ solution were added to pH=8. The aqueous layer was extracted with EtOAc (4×), and the combined extracts were washed with brine (50 mL), dried over $Na_2SO_4$, filtered, and concentrated. Purification by flash silica gel chromatography (30% EtOAc/hexanes) provided 102 mg of methyl 2-(dimethylamino)-6-(hydroxymethyl)isonicotinate as a yellow solid in 65% yield.

A mixture of 102 mg of methyl 2-(dimethylamino)-6-(hydroxymethyl)isonicotinate and 475 mg of $MnO_2$ in 10 mL of $CH_2Cl_2$ was stirred at 50° C. for 20 min and within a period of 70 min., 1.3 g of $MnO_2$ was added in 4, 300-400 mg portions every 25 min. After 30 min., the mixture was filtered through Celite with EtOAc and MeOH. The solution was concentrated to give the product 6-(dimethylamino)-4-(methoxycarbonyl) picolinic acid which was used in the next reaction without further purification.

Example 1.4.48 dimethyl 2-(dimethylamino)pyrimidine-4,6-dicarboxylate

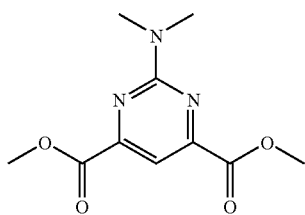

MeI (0.46 ml, 1.04 g, 7.32 mmol, 2.4 eq) was added to a stirred solution of 4,6-dichloropyrimidin-2-amine (Aldrich, 0.5 g, 3.05 mmol, 1 eq) in 10 ml anhydrous DMF under Ar. After cooling to 0° C., NaH (0.27 g, 6.71 mmol, 2.2 eq) was added. The reaction was stirred at 0° C. to room temperature overnight. The reaction was quenched with water and extracted with $Et_2O$ (×1). The organic layer was washed with water (×3), brine (×1), and dried over $Na_2SO_4$. The inorganics were filtered off, and the solvent was removed in vacuo. Purification via flash chromatography yielded 0.4947 g (2.58 mmol, 84% yield) of 4,6-dichloro-N,N-dimethylpyrimidin-2-amine.

A mixture of 4,6-dichloro-N,N-dimethylpyrimidin-2-amine (0.4 g, 2.08 mmol, 1 eq) and $Zn(CN)_2$ (0.2689 g, 2.29 mol, 1.1 eq) in 5 ml anhydrous DMF under Ar was purged with Ar for 5 minutes. $Pd(PPh_3)_4$ (0.48 g, 0.42 mmol, 20 mol %) was added, and the mixture was heated to 90° C. with stirring overnight. After cooling to room temperature the mixture was diluted with aqueous $NH_3/Et_2O$. After stirring for 1 h the layers were separated. The organic layer was washed with water (×3), brine (×1), and dried over $Na_2SO_4$. The inorganics were filtered off, and the solvent was removed in vacuo. Purification via flash chromatography yielded 0.1595 g (0.92 mmol, 44% yield) of 2-(dimethylamino)pyrimidine-4,6-dicarbonitrile.

$H_2SO_4$ (2.45 ml, 4.5 g, 46 mmol, 50 eq) and 1.5 ml of water were added to a flask charged with 2-(dimethylamino)pyrimidine-4,6-dicarbonitrile (0.1595 g, 0.92 mmol, 1 eq). The resulting solution was heated to 135° C. with stirring overnight. After cooling to 95° C. 5 ml MeOH were added the reaction was refluxed with stirring for 2.5 h. After diluting with water a yellow precipitate formed and was collected via filtration. The precipitate was washed with saturated aqueous NaHCO3 and water. 0.0958 g (0.4 mmol, 44% yield) of dimethyl 2-(dimethylamino)pyrimidine-4,6-dicarboxylate was collected after drying.

Example 1.5

Cyclic Amide Coupling

Example 1.5.1

(R)-3-(2-(4-methylthiazol-2-yl)pyrrolidine-1-carbonyl)benzoic acid

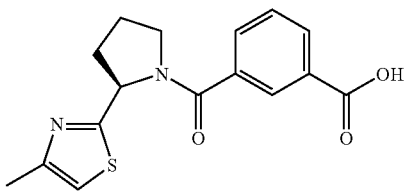

To mono-methyl isopthalate (Aldrich, 124 mg, 0.7 mmol) in $CH_2Cl_2$ (4 mL) at room temperature, thionyl chloride (5 ml) was added and reaction mixture was refluxed for 2 h. Then the volatiles were removed on a rotavap under reduced pressure. To that mixture, (R)-4-methyl-2-(pyrrolidin-2-yl) thiazole was added followed by triethylamine (1 drop). The reaction mixture was stirred at rt for 3 h, then diluted with ethyl acetate, washed with water, brine, and dried. Crude residue was purified by column chromatography to yield 155 mg of (R)-methyl 3-(2-(4-methylthiazol-2-yl)pyrrolidine-1-carbonyl)benzoate.

To the solution of (R)-methyl 3-(2-(4-methylthiazol-2-yl) pyrrolidine-1-carbonyl)benzoate (155 mg, 0.49 mmol) in THF (5 mL) was added 1N LiOH (2 mL) and the reaction mixture was stirred at rt for 1 h. Then the volatiles were removed on a rotavap under reduced pressure. Then reaction mixture was diluted with water, acidified with 1N HCl to pH ~3 and extracted with ethyl acetate. Organic layer was dried and evaporated to yield 132 mg of the acid (R)-3-(2-(4-methylthiazol-2-yl)pyrrolidine-1-carbonyl)benzoic acid.

Example 1.5.2

(R)-methyl 3-(hydroxymethyl)-5-(2-(4-methylthiazol-2-yl)pyrrolidine-1-carbonyl)benzoate

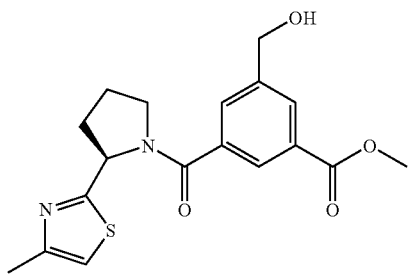

A solution of (R)-4-methyl-2-(pyrrolidin-2-yl)thiazole (511 mg, 3.037 mmol) and 3-(hydroxymethyl)-5-(methoxycarbonyl)benzoic acid (702.5 mg, 3.34 mmol) in DCM (50 mL) were added diisopropylthylamine (3 mL, excess), HOBt (410 mg, 3.34 mmol) and EDCI (754.1 mg, 3.948 mmol). The resulting solution was stirred at room temperature for overnight. The reaction mixture was diluted with chloroform, washed with sodium bicarbonate saturated aqueous solution and separated. The aqueous layer was extracted one more time with chloroform. The combined organic layers were concentrated to give a residue, which was purified with flash chromatography to produce the desired compound (840 mg). $^1$H NMR (300 MHz, CDCl$_3$), d: 8.011 (m, 1.5H), 7.876 (br, 0.5H), 7.683 (m, 1H), 6.749 (m, 1H), 5.579 (m, 0.7H), 5.061 (br, 0.3H), 4.641 (br, 1.2H), 4.525 (br, 0.8H), 3.875 (m, 3H), 3.692 (m, 1H), 3.457 (m, 1H), 2.345 (m, 5H), 2.034 (m, 2H).

Example 1.6

Coupled Cyclic Amide Modifications

Example 1.6.1

(R)-methyl 3-(fluoromethyl)-5-(2-(4-methylthiazol-2-yl)pyrrolidine-1-carbonyl)benzoate

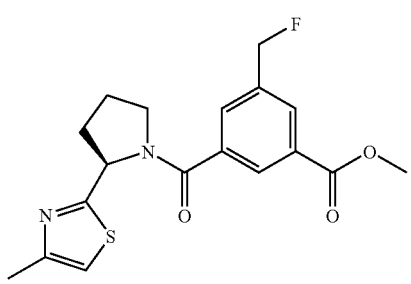

(R)-methyl 3-(hydroxymethyl)-5-(2-(4-methylthiazol-2-yl)pyrrolidine-1-carbonyl)benzoate (280 mg, 0.777 mmol) in dry DCM (40 mL) at −78° C. was added [Bis(2-methoxyethyl)amino]sulfur trifluoride (0.17 mL, 0.932 mmol) slowly and stirred at the same temperature for 2 hrs, then warmed to room temperature for overnight. The reaction was carefully quenched with aqueous saturated NaHCO$_3$, extracted with chloroform three times. The combined organic solvent was dried with anhydrous Na$_2$SO$_4$, removed in vacuum and the residue was purified by silica gel chromatography to afford monofluoride (177 mg). $^1$H NMR (CDCl$_3$): d: 8.211-7.784 (m, 2.7H), 7.420 (s, 0.3H), 6.778 (s, 1H), 5.645-5.076 (m, 3H), 3.929-3.741 (m, 4H), 3.519 (m, 1H), 2.428-2.325 (m, 5H), 2.088-1.930 (m, 2H).

Example 1.6.2

(R)-methyl 3-formyl-5-(2-(4-methylthiazol-2-yl)pyrrolidine-1-carbonyl)benzoate

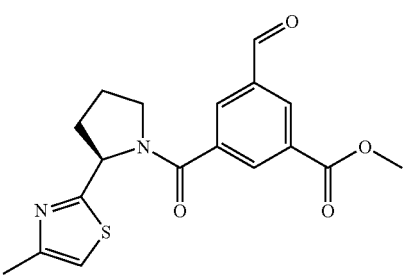

To a solution of (R)-methyl 3-(hydroxymethyl)-5-(2-(4-methylthiazol-2-yl)pyrrolidine-1-carbonyl)benzoate (560 mg, 1.554 mmol) in DCM (60 mL), Dess-Martin periodinane (790.8 mg, 1.864 mmol) was added at rt. After stirring for 2 hrs, the mixture was poured into a mixture of aqueous 1 M Na$_2$S$_2$O$_3$ (30 mL) and aqueous saturated NaHCO$_3$ (30 mL), and it was extracted with DCM three times. The combined organic layers were concentrated in vacuum and the residue was purified by flash silica chromatography to give the product (530 mg). $^1$H NMR (CDCl$_3$): d: 10.094, 9.933 (s, s, 1H), 8.592-7.908 (m, 3H), 6.796 (s, 1H), 5.661 (m, 0.65H), 5.083 (m, 0.35H), 3.969-3.743 (m, 4H), 3.515 (m, 1H), 2.429-2.308 (m, 5H), 2.145-1.939 (m, 2H).

Example 1.6.3

(R)-methyl 3-(difluoromethyl)-5-(2-(4-methylthiazol-2-yl)pyrrolidine-1-carbonyl)benzoate

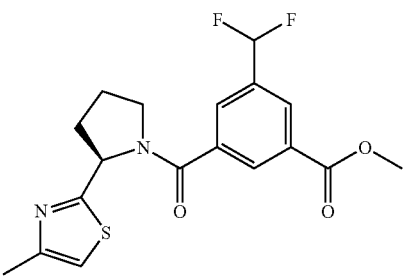

To a solution of (R)-methyl 3-formyl-5-(2-(4-methylthiazol-2-yl)pyrrolidine-1-carbonyl)benzoate (530 mg, 1.47 mmol) in CH$_2$Cl$_2$ (50 mL) at −78° C. was added [Bis(2-methoxyethyl)amino]sulfur trifluoride (0.46 mL, 2.49 mmol) slowly, then a couple drops of ethanol was added, and the mixture was stirred at same temperature for 2 hr. The resulting mixture was warmed to room temperature and stirred overnight. The solution was slowly poured into saturated NaHCO$_3$, extracted with methylene chloride three times, dried (Na$_2$SO$_4$), filtered, and evaporated in vacuo. Flash chromatography on silica gel afforded the pure product (442 mg). $^1$H NMR (CDCl$_3$): d: 8.330-7.919 (m, 2.7H), 7.528 (s, 0.3H), 6.902-6.368 (m, 3H), 5.638 (m, 0.7H), 5.048 (m, 0.3H), 3.946-3.746 (m, 4H), 3.488 (m, 1H), 2.412-2.312 (m, 5H), 2.112-1.950 (m, 2H).

Example 1.7

Hydroxylamine Synthesis by Epoxide Ring Opening

Example 1.7.1

(2R,3S)-3-amino-4-phenyl-1-(3-(trifluoromethyl)benzylamino)butan-2-ol

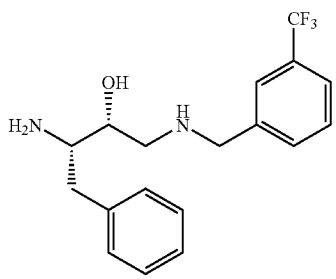

To tert-butyl (S)-1-((S)-oxiran-2-yl)-2-phenylethylcarbamate (Aldrich, 3.0 g, 11.4 mmol) in i-PrOH (50 ml), 3-trifluoromethyl benzyl amine (5 g, 28.5 mmol) was added and the reaction mixture was refluxed for 5 h. Then reaction mixture was cooled to RT and volatiles were removed on a rotavap under reduced pressure. Crude residue was purified by column chromatography to yield 40% of the Boc-amine. Then Boc-amine was dissolved in MeOH (25 ml) and excess 4N HCl in dioxane was added and the reaction mixture was stirred for 16 h at RT. Then volatiles were removed on a rotavap under reduced pressure to yield (2R,3S)-3-amino-4-phenyl-1-(3-(trifluoromethyl)benzylamino)butan-2-ol as the HCl salt in quantitative yield.

Example 1.7.2 tert-butyl (2S,3R)-3-hydroxy-4-(3-methoxybenzylamino)-1-phenylbutan-2-ylcarbamate

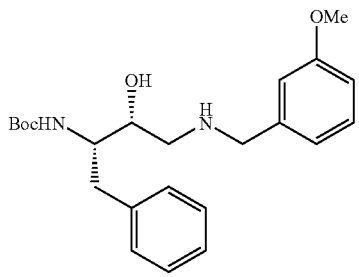

To a stirred solution of tert-Butyl (1-oxiranyl-2-phenylethyl)carbamate (0.5 g, 1.9 mmol) in iPrOH was added 3-methoxybenzyl amine (0.28 mL, 2.1 mmol). The mixture was heated to reflux overnight followed by cooling and removal of the volatiles under reduced pressure. Flash chromatography of the residue resulted in the corresponding aminoalcohol as a solid. $^1$H NMR (300 MHz, CDCl$_3$): d 7.35-7.17 (m, 6H), 6.93-6.78 (m, 3H), 4.65 (d, 1H), 3.90-3.7 (m, 5H), 3.51 (m, 1H), 3.15-2.65 (m, 6H), 1.34 (s, 9H).

Example 1.7.3 tert-butyl 4-41H-benzo[d]imidazol-2-yl)methylamino)-3-hydroxy-1-phenylbutan-2-ylcarbamate

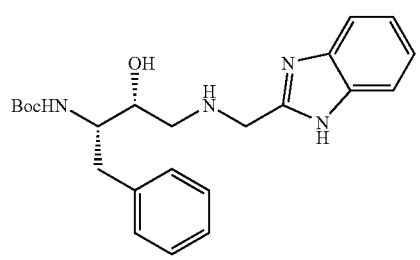

A solution of tert-butyl 1-(oxiran-2-yl)-2-phenylethylcarbamate (185 mg, 0.7 mmol), (1H-benzo[d]imidazol-2-yl)methanamine dihydrochloride salt (232 mg, 1.01 mmol) and Hunig's base (0.49 mL, 2.8 mmol) in iPrOH (6 mL) was refluxed for 12 h. The reaction was cooled to room temperature, solvent evaporated under reduced pressure and chromatographed (5% MeOH/95% CHCl$_3$) to obtain 175 mg (61%) of the desired product.

Example 1.7.4 tert-butyl (2S,3R)-3-hydroxy-1-phenyl-4-(6-(trifluoromethyl)pyridin-3-yl)methylamino)butan-2-ylcarbamate

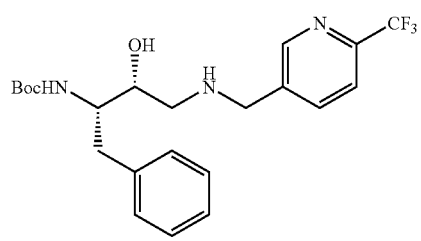

Crude (6-(trifluoromethyl)pyridin-3-yl)methanamine was directly used for opening tert-butyl 1-(oxiran-2-yl)-2-phenylethylcarbamate using the general procedure without further purification. tert-butyl 1-(oxiran-2-yl)-2-phenylethylcarbamate (300 mg, 1.14 mmol) and (6-(trifluoromethyl)pyridin-3-yl)methanamine (300 mg, 1.71 mmol) in isopropanol was heated at 80° C. for 16 h. The solvent was evaporated and purified by silica gel chromatography to afford tert-butyl (2S,3R)-3-hydroxy-1-phenyl-4-(6-(trifluoromethyl)pyridin-3-yl)methylamino)butan-2-ylcarbamate (100 mg) of a light yellow solid: $^1$H NMR (300 MHz, CDCl$_3$+CD$_3$OD), d: 8.679 (s, 1H), 7.896 (d, J=8.1 Hz, 1H), 7.672 (d, J=7.8 Hz, 1H), 7.344-7.211 (m, 5H), 3.914-3.811 (m, 3H), 3.559 (m, 1H), 3.048-2.986 (m, 1H), 2.901-2.679 (m, 3H), 1.266 (s, 9H).

Example 1.7.5

(2R,3S)-3-amino-1-(3-tert-butylbenzylamino)-4-phenylbutan-2-ol

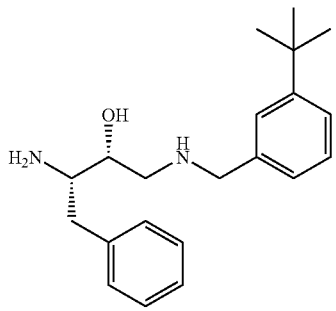

To tert-butyl (S)-1-((S)-oxiran-2-yl)-2-phenylethylcarbamate (Aldrich, 263 mg, 1.0 mmol) in i-PrOH (5 ml), 3-tert-butyl benzyl amine (170 mg, 1.0 mmol) was added and the reaction mixture was refluxed for 5 h. Then reaction mixture was cooled to rt and volatiles were removed on a rotavap under reduced pressure. Crude residue was purified by column chromatography to yield 40% of the Boc-amine. Then Boc-amine was dissolved in MeOH (25 ml) and excess 4N HCl in dioxane was added and the reaction mixture was stirred for 16 h at RT. Then volatiles were removed on a rotavap under reduced pressure to yield (2R,3S)-3-amino-1-(3-tert-butylbenzylamino)-4-phenylbutan-2-ol as HCl salt in quantitative yield.

Example 1.7.6 tert-butyl (2S,3R)-4-(3-(diethylamino)benzylamino)-3-hydroxy-1-phenylbutan-2-ylcarbamate

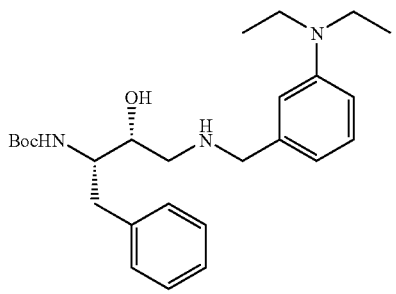

Al(OTf)$_3$ (0.0168 g, 0.036 mmol, 5 mol %) was added to a flask charged with 3-(aminomethyl)-N,N-diethylaniline (0.19 g, 1.07 mmol, 1.5 eq) under Ar. After stirring for 10 min tert-butyl (S)-1-((S)-oxiran-2-yl)-2-phenylethylcarbamate (0.187 g, 0.71 mmol, 1 eq) was added and the mixture was heated to 70° C. for 1 h. After cooling to room temperature the residue was dissolved in EtOAc with a few drops of water. After 20 min of vigorous stirring the mixture was filtered through cotton and dried over Na$_2$SO$_4$. The inorganics were filtered off, and the solvent was removed in vacuo. Purification via flash chromatography yielded 0.0682 g (0.154 mmol, 22% yield) of the product.

Example 1.7.7 tert-butyl (2S,3R)-4-(3-(benzylamino)benzylamino)-3-hydroxy-1-phenylbutan-2-ylcarbamate

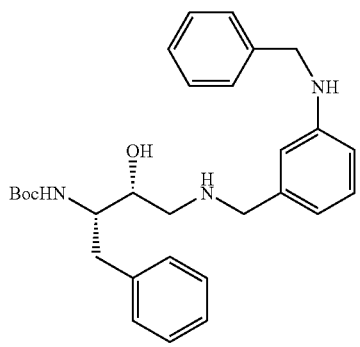

1 ml anhydrous $^i$PrOH was added to a flask charged with 3-(aminomethyl)-N-benzylaniline (0.057 g, 0.269 mmol, 1.3 eq) and tert-butyl (S)-1-((S)-oxiran-2-yl)-2-phenylethylcarbamate (0.054 g, 0.207 mmol, 1 eq) under Ar. The mixture was heated to reflux at 90° C. overnight. After cooling to room temperature the solvent was removed in vacuo. The residue was dissolved in EtOAc, washed with water (×3), brine (×1), and dried over Na$_2$SO$_4$. The inorganics were filtered off, and the solvent was removed in vacuo. Purification via flash chromatography yielded 0.0526 g (0.11 mmol, 53% yield) of the product.

Example 1.7.8 tert-butyl (2S,3R)-4-(3-(dimethylamino)-5-methoxybenzylamino)-3-hydroxy-1-phenylbutan-2-ylcarbamate

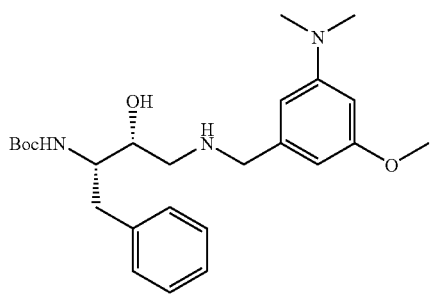

(3-(aminomethyl)-5-(dimethylamino)phenoxy)methylium (0.0361 g, 0.2 mmol, 1.2 eq) was dissolved in the minimum amount of anhydrous CH$_2$Cl$_2$ under Ar. tert-butyl (S)-1-((S)-oxiran-2-yl)-2-phenylethylcarbamate (0.0439 g, 0.167 mmol, 1 eq) was added with stirring. Anhydrous CH$_2$Cl$_2$ was added dropwise until all of the epoxide had dissolved. The reaction was heated to 50° C. After heating overnight all of the solvent was gone leaving a solid in the flask. Purification via flash chromatography yielded 0.0405 g, (0.091 mmol, 54% yield) of the product.

Example 1.7.9 tert-butyl (2S,3R)-4-(3-(dimethylamino)-5-methoxy-benzylamino)-3-hydroxy-1-phenylbutan-2-ylcarbamate

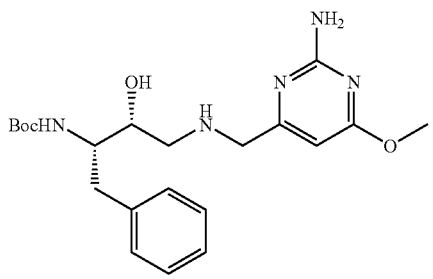

(2-amino-6-(aminomethyl)pyrimidin-4-yloxy)methylium (0.100 g, 0.65 mmol, 1.3 eq) and tert-butyl (S)-1-((S)-oxiran-2-yl)-2-phenylethylcarbamate (0.13 g, 0.5 mmol, 1 eq) were dissolved in anhydrous $CH_2Cl_2$ (1.2 ml) and anhydrous iPrOH (0.4 ml) under Ar. The reaction was heated to 55° C. After heating overnight all of the solvent was gone leaving a solid in the flask. The residue was dissolved in EtOAc, washed with water (×2), brine (×1), and dried over $Na_2SO_4$. The inorganics were filtered off, and the solvent was removed in vacuo. Purification via flash chromatography yielded 0.105 g, (0.25 mmol, 50% yield) of the product.

Example 1.7.10 tert-butyl (2S,3R)-4-(3-cyanobenzylamino)-3-hydroxy-1-phenylbutan-2-ylcarbamate

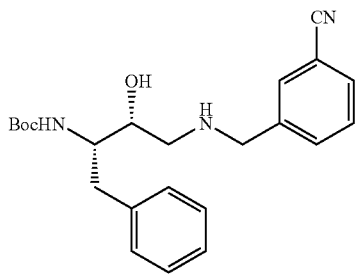

To 3-(aminomethyl)benzonitrile (270 mg, 2.04 mmol), $Al(OTf)_3$ (47 mg, 0.1 mmol) was added. After 10 min, tert-butyl (S)-1-((S)-oxiran-2-yl)-2-phenylethylcarbamate (268 mg, 1.02 mmol) was added and the reaction mixture was heated to 70° C. for 1.5 h. then the crude residue was loaded onto a column and eluted with Chloroform/MeOH mixture (97:3) to obtain the epoxide opened product in 70% yield.

Example 1.7.11 tert-butyl (2S,3R)-4-(3-(dimethylamino)benzylamino)-3-hydroxy-1-phenylbutan-2-ylcarbamate

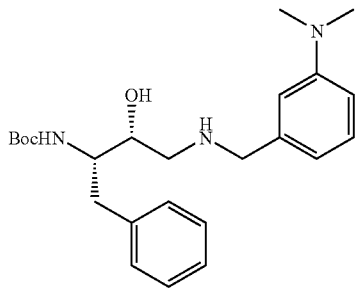

3-(aminomethyl)-N,N-dimethylaniline (1.2 eq) was dissolved in the minimum amount of anhydrous $CH_2Cl_2$ under Ar, followed by the addition of tert-butyl (S)-1-((S)-oxiran-2-yl)-2-phenylethylcarbamate (1 eq) with stirring. Anhydrous $CH_2Cl_2$ was added dropwise until all of the epoxide had dissolved. The reaction was heated to 50° C. After heating overnight all of the solvent was gone leaving a solid in the flask. Purification via flash chromatography yielded tert-butyl (2S,3R)-4-(3-(dimethylamino)benzylamino)-3-hydroxy-1-phenylbutan-2-ylcarbamate.

Example 1.8

Alternative Hydroxylamine Synthesis

Example 1.8.1 tert-butyl (2S,3R)-4-((5-(2-fluoropropan-2-yl)pyridin-3-yl)methylamino)-3-hydroxy-1-phenylbutan-2-ylcarbamate

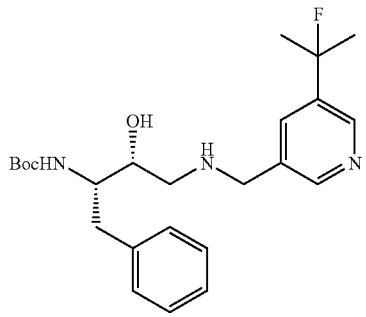

A solution of tert-butyl (S)-1-((S)-oxiran-2-yl)-2-phenylethylcarbamate (1.5 g, 5.7 mmol) in EtOH (35 mL) was added, with stirring, over 1 h to $NH_4OH$ (35 mL) at 0° C. $NH_3$ gas was bubbled through the reaction mixture during the addition and for 1 h afterward. The reaction mixture was allowed to warm to room temperature and stirred overnight. The resulting slurry was diluted with EtOAc (80 mL), and the organic layer was washed with brine and dried ($MgSO_4$). Concentration in vacuo, followed by trituration with 10% i-PrOH-EtOAc (overnight stirring), afforded tert-butyl (2S,3R)-4-amino-3-hydroxy-1-phenylbutan-2-ylcarbamate (0.44 g) as a white solid. The mother liquors were concentrated in vacuo and triturated again as above to give an additional quantity of tert-butyl (2S,3R)-4-amino-3-hydroxy-1-phenylbutan-2-ylcarbamate (0.57 g; 64% total yield): $^1H$ NMR ($CD_3OD$) d: 1.29 (s, 9H), 2.55 (m, 1H), 2.63 (m, 1H), 2.76 (m, 1H), 3.11 (m, 1H), 3.40 (m, 1H), 3.65 (m, 1H), 7.10-7.30 (m, 5H).

A solution of tert-butyl (2S,3R)-4-amino-3-hydroxy-1-phenylbutan-2-ylcarbamate (297 mg, 1.06 mmol) in THF was added 5-(2-fluoropropan-2-yl)nicotinaldehyde (180 mg, 1.06 mmol) and stirred for 30 min at room temperature, $NaB(OAc)_3H$ (460 mg, 2.12 mmol) was then added portionwise in 30 min., finally 5 drops of acetic acid was added and the resulting mixture was stirred at the same temperature overnight. The reaction mixture was diluted with EtOAc, and washed with saturated aqueous $NaHCO_3$. The organic layer was separated and dried ($MgSO_4$). Concentration in vacuo, followed purification with flash chromatography to give tert-butyl (2S,3R)-4-((5-(2-fluoropropan-2-yl)pyridin-3-yl)methylamino)-3-hydroxy-1-phenylbutan-2-ylcarbamate as a white solid (230 mg, 70% yield). $^1H$ NMR ($CDCl_3$): d: 8.776 (d, J=11.5 Hz, 2H), 7.952 (s, 1H), 7.330-7.205 (m, 5H), 4.823 (d, J=7.7 Hz, 1H), 3.900 (s, 2H), 3.842 (m, 1H), 3.586 (m, 1H), 2.995 (m, 1H), 2.856 (m, 1H), 2.762 (m, 2H), 1.363 (s, 9H).

Example 1.8.2 methyl 3-(((2R,3S)-3-(tert-butoxycarbonylamino)-2-hydroxy-4-phenylbutylamino)methyl)-5-methoxybenzoate

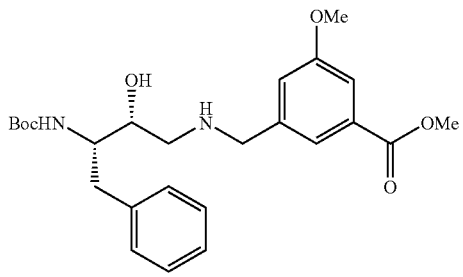

A solution of tert-butyl (2S,3R)-4-amino-3-hydroxy-1-phenylbutan-2-ylcarbamate (300 mg, 1.07 mmol) in THF was added methyl 3-formyl-5-methoxybenzoate (294 mg, ~80% purity, 1.07 mmol) and stirred for 30 min at room temperature, NaB(OAc)$_3$H (453.7 mg, 2.14 mmol) was then added portionwise in 30 min, finally 5 drops of acetic acid was added and the resulting mixture was stirred at the same temperature overnight. The reaction mixture was diluted with EtOAc, and washed with saturated aqueous NaHCO$_3$. The organic layer was separated and dried (MgSO$_4$). Concentration in vacuo, followed purification with flash chromatography to give the desired product methyl 3-(((2R,3S)-3-(tert-butoxycarbonylamino)-2-hydroxy-4-phenylbutylamino)methyl)-5-methoxybenzoate as a white solid (390 mg, % yield). $^1$H NMR (CDCl$_3$): d: 8.583 (s, 1H), 7.447 (s, 1H), 7.298-7.166 (m, 5H), 7.092 (s, 1H), 3.899 (s, 3H), 3.832 (s, 4H), 3.779 (s, 2H), 3.572 (m, 1H), 2.2.946 (m, 1H), 2.777 (m, 1H), 2.711 (m, 2H), 1.330 (s, 9H).

Example 1.8.3 methyl 3-(((2R,3S)-3-(tert-butoxycarbonylamino)-2-hydroxy-4-phenylbutylamino)methyl)benzoate

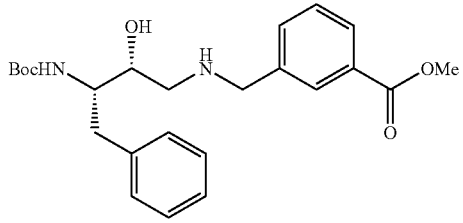

A solution of tert-butyl (2S,3R)-4-amino-3-hydroxy-1-phenylbutan-2-ylcarbamate (200 mg, 0.713 mmol) in THF was added methyl 3-formylbenzoate (117.1 mg, 0.713 mmol) and stirred for 30 min at room temperature. NaB(OAc)$_3$H (302.5 mg, 1.43 mmol) was then added portionwise in 30 min, finally 5 drops of acetic acid was added and the resulting mixture was stirred at the same temperature overnight. The reaction mixture was diluted with EtOAc, and washed with saturated aqueous NaHCO$_3$. The organic layer was separated and dried (MgSO$_4$). Concentration in vacuo was followed by purification with flash chromatography to give the desired product as a white solid (300 mg, % yield). $^1$H NMR (CDCl$_3$): d: 7.999 (m, 2H), 7.589 (m, 1H), 7.451 (m, 1H), 7.254 (m, 5H), 3.956 (s, 3H), 3.892 (m, 3H), 3.549 (m, 1H), 3.040-2.850 (m, 2H), 2.793 (m, 2H), 1.374 (s, 9H).

Example 1.8.4 tert-butyl (2S,3R)-4-((5-tert-butylpyridin-3-yl)methylamino)-3-hydroxy-1-phenylbutan-2-ylcarbamate

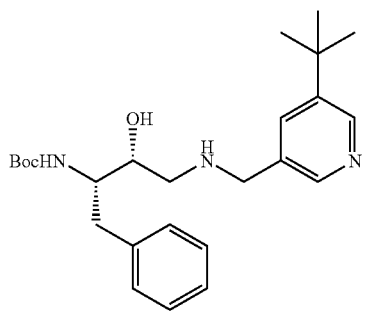

5-tert-butylnicotinaldehyde was coupled with tert-butyl (S)-1-((S)-oxiran-2-yl)-2-phenylethylcarbamate using the typical reductive amination procedure described herein. $^1$H NMR (CDCl$_3$): d: 8.580 (d, J=2.1 Hz, 1H), 8.384 (d, J=1.8 Hz, 1H), 7.667 (t, J=2.1 Hz, 1H), 7.233 (m, 5H), 4.843 (br, 1H), 3.806 (s, 3H), 3.585 (m, 1H), 3.008-2.828 (m, 2H), 2.778 (d, J=5.1 Hz, 2H), 1.372 (s, 9H).

Example 1.8.5 tert-butyl (2S,3R)-1-(3,5-difluorophenyl)-3-hydroxy-4-((5-isopropylpyridin-3-yl)methylamino)butan-2-ylcarbamate

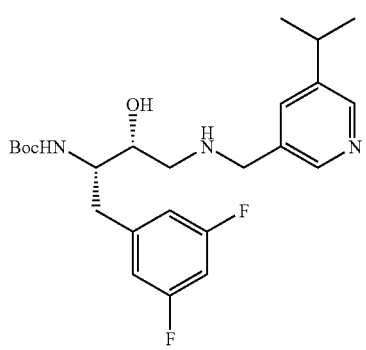

tert-butyl (2S,3R)-1-(3,5-difluorophenyl)-3-hydroxy-4-((5-isopropylpyridin-3-yl)methylamino)butan-2-ylcarbamate was generated using the general procedure described herein starting from tert-butyl (S)-2-(3,5-difluorophenyl)-1-((S)-oxiran-2-yl)ethylcarbamate (Peptech Corp.) in 35% chemical yield. $^1$H NMR (CDCl$_3$): d: 8.393 (m, 2H), 7.525 (m, 1H), 6.768 (m, 2H), 6.664 (m, 1H), 3.804 (s, 3H), 3.574 (m, 1H), 2.977 (m, 2H), 2.778 (m, 3H), 1.375 (s, 9H), 1.302 (d, J=6.9 Hz, 6H).

Example 1.8.6 tert-butyl (2S,3R)-4-((5-(1,1-difluoroethyl)pyridin-3-yl)methylamino)-3-hydroxy-1-phenylbutan-2-ylcarbamate

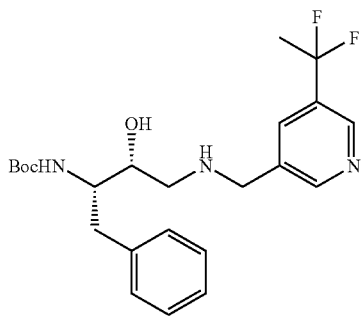

5-(1,1-difluoroethyl)nicotinaldehyde was coupled to tert-butyl (S)-1-((S)-oxiran-2-yl)-2-phenylethylcarbamate using standard reductive amination procedures described herein to generate the desired tert-butyl (2S,3R)-4-((5-(1,1-difluoroethyl)pyridin-3-yl)methylamino)-3-hydroxy-1-phenylbutan-2-ylcarbamate. $^1$H NMR (CDCl$_3$): d: 8.514 (m, 2H), 7.717 (s, 1H), 7.321-7.203 (m, 5H), 3.831 (s, 3H), 3.580 (m, 1H), 2.978 (m, 1H), 2.890-2.755 (m, 3H), 1.724 (d, J=11.1 Hz, 6H), 1.364 (s, 9H).

Example 1.8.7 tert-butyl (2S,3R)-4-(3-(1,1-difluoroethyl)benzylamino)-3-hydroxy-1-phenylbutan-2-ylcarbamate

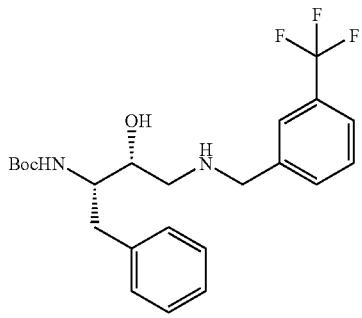

3-(1,1-difluoroethyl)benzaldehyde was coupled to tert-butyl (S)-1-((S)-oxiran-2-yl)-2-phenylethylcarbamate using standard reductive amination procedures described herein to generate the desired tert-butyl (2S,3R)-4-(3-(1,1-difluoroethyl)benzylamino)-3-hydroxy-1-phenylbutan-2-ylcarbamate.

Example 1.8.8

(2R,3S)-3-amino-1-((5-chloropyridin-3-yl)methylamino)-4-phenylbutan-2-ol

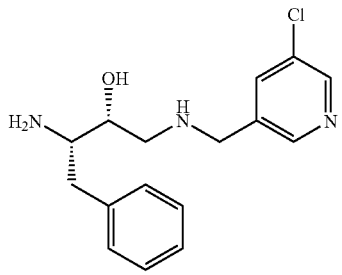

To tert-butyl (2S,3R)-4-amino-3-hydroxy-1-phenylbutan-2-ylcarbamate (672 mg, 2.4 mmol) in THF (15 ml) at RT, 5-chloronicotinaldehyde (Frontier Scientific, 300 mg, 2.4 mmol) was added followed by acetic acid (165 µL). After stirring for 3 h at RT, Na(OAc)$_3$BH (1.02 g, 4.8 mmol) was added. After stirring for 2 h another 500 mg of Na(OAc)$_3$BH was added and the reaction mixture was stirred at RT for 48 h. Then AcOH (0.1 ml) was added and stirred for 0.5 h, then saturated aqueous sodium bicarbonate solution was added and stirred for 1 h. Then reaction mixture was extracted with ethyl acetate. Organic layer was dried over sodium sulfate, and volatiles removed under vacuum. Crude residue was column chromatographed to yield the Boc protected amine in 65% yield. The so obtained Boc-protected amine was stirred with 4N HCl in dioxane (4 ml) overnight. Removal of the volatiles yielded (2R,3S)-3-amino-1-((5-chloropyridin-3-yl)methylamino)-4-phenylbutan-2-ol as HCl salt.

Example 1.8.9

(2R,3S)-3-amino-1-((5-fluoropyridin-3-yl)methylamino)-4-phenylbutan-2-ol

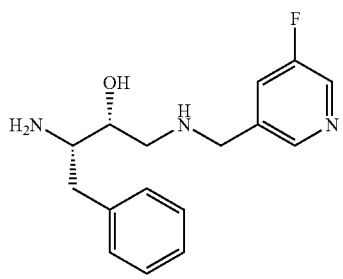

5-fluoronicotinaldehyde (Frontier Scientific) was coupled to tert-butyl (S)-1-((S)-oxiran-2-yl)-2-phenylethylcarbamate using standard reductive amination procedures described herein to generate the desired (2R,3S)-3-amino-1-((5-fluoropyridin-3-yl)methylamino)-4-phenylbutan-2-ol.

Example 1.8.10

(2R,3S)-3-amino-1-(3,5-dichlorobenzylamino)-4-phenylbutan-2-ol

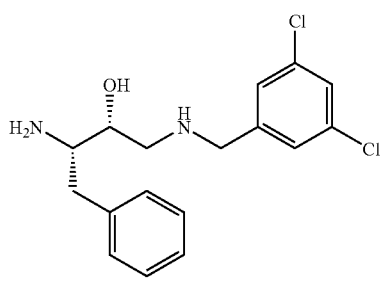

3,5-dichlorobenzaldehyde (Aldrich) was coupled to tert-butyl (S)-1-((S)-oxiran-2-yl)-2-phenylethylcarbamate using standard reductive amination procedures described herein to generate the desired (2R,3S)-3-amino-1-(3,5-dichlorobenzylamino)-4-phenylbutan-2-ol.

Example 1.8.11 tert-butyl (2S,3R)-3-hydroxy-4-(3-(2-hydroxypropan-2-yl)benzylamino)-1-phenylbutan-2-ylcarbamate

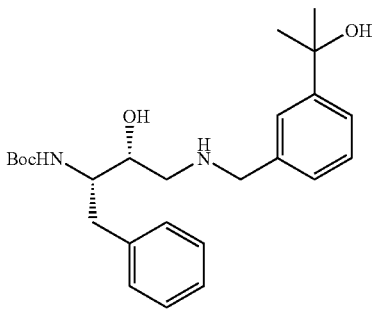

A solution of tert-butyl (2S,3R)-4-amino-3-hydroxy-1-phenylbutan-2-ylcarbamate (230 mg, 0.82 mmol) in THF was added 3-(2-hydroxypropan-2-yl)benzaldehyde (180 mg, 01.06 mmol) and stirred for 30 min at room temperature, NaB(OAc)$_3$H (302.5 mg, 1.43 mmol) was then added portionwise in 30 min, and the resulting mixture was stirred at the same temperature overnight. The reaction mixture was diluted with EtOAc, and washed with saturated aqueous NaHCO$_3$. The organic layer was separated and dried (Na$_2$SO$_4$). Concentration in vacuo, followed purification with flash chromatography to give the desired product as a white solid (230 mg, 65% yield). $^1$H NMR (CDCl$_3$): d: 8.514 (m, 2H), 7.717 (s, 1H), 7.321-7.203 (m, 5H), 3.831 (s, 3H), 3.580 (m, 1H), 2.978 (m, 1H), 2.890-2.755 (m, 3H), 1.724 (d, J=11.1 Hz, 6H), 1.364 (s, 9H).

Example 1.8.12

N-((2R,3S)-3-amino-2-hydroxy-4-phenylbutyl)-5-(prop-1-en-2-yl)nicotinamide

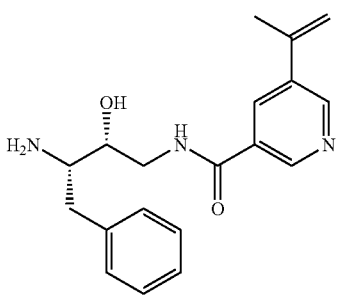

To the 5-(prop-1-en-2-yl)nicotinaldehyde (500 mg, 3.40 mmol) in t-BuOH:water (10:1) (10 ml) at 0° C., 2-methyl-2-butene (9 ml), NaH$_2$ PO$_4$ (1.57 g, 13.09 mmol) were added, followed by sodium chlorite (1.53 g, 17.0 mmol) in water. After 1 h, reaction mixture was quenched by the addition of concentrated HCl. Then reaction mixture was stirred for 1 h. Then reaction mixture was basified and extracted with ethyl acetate. Aqueous layer was then acidified and extracted with a 10% MeOH in ethyl acetate and the organic layer was dried and evaporated. Crude residue contained 5-(prop-1-en-2-yl) nicotinic acid which was carried to the next step without any further purification.

To 5-(prop-1-en-2-yl)nicotinic acid (200 mg, 1.23 mmol) in dichlormethane (10 ml) at rt, EDCI (330 mg, 1.72 mmol) and HOBT (200 mg, 1.48 mmol) were added. After stirring at rt for 10 minutes, tert-butyl (2S,3R)-4-amino-3-hydroxy-1-phenylbutan-2-ylcarbamate (344 mg, 1.23 mmol) was added followed by DIPEA (0.2 ml). After stirring overnight at rt, reaction mixture was worked up as usual and residue was column purified (90% ethylacetate/10% hexanes) to yield 280 mg of tert-butyl (2S,3R)-3-hydroxy-1-phenyl-4-(5-(prop-1-en-2-yl)nicotinamido)butan-2-ylcarbamate, which on stirring with 4N HCl in dioxane for 4 h yields the HCl salt of N-((2R,3S)-3-amino-2-hydroxy-4-phenylbutyl)-5-(prop-1-en-2-yl)nicotinamide.

Example 1.9

Hydroxylamine Modifications

Example 1.9.1

3-(((2R,3S)-3-amino-2-hydroxy-4-phenylbutylamino)methyl)-5-isopropylphenol

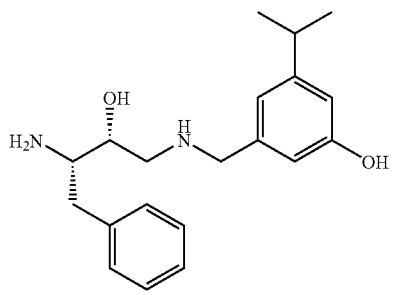

A mixture of 21.2 mg (0.04 mmol) of tert-butyl (2S,3R)-4-(3-(benzyloxy)-5-isopropylbenzylamino)-3-hydroxy-1-phenylbutan-2-ylcarbamate and 7.7 mg of 10% Pd/C in 4 mL of 1.25M HCl in MeOH was stirred at r.t. under H$_2$ balloon for 20.5 h. The mixture was filtered through Celite, concentrated, and reconcentrated with toluene 3 times. The amine HCl salt was used for the next reaction without further purification.

Example 1.9.2

3-(((2R,3S)-3-amino-2-hydroxy-4-phenylbutylamino)methyl)-5-(prop-1-en-2-yl)phenol

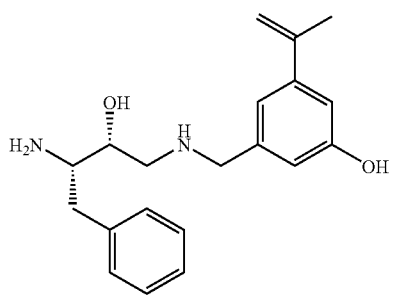

A mixture of 81.8 mg (0.148 mmol) of tert-butyl (2S,3R)-4-(3-(benzyloxy)-5-(2-chloropropan-2-yl)benzylamino)-3- hydroxy-1-phenylbutan-2-ylcarbamate and 16.1 mg of 20% Pd(OH)$_2$ in 5 mL of MeOH was stirred at r.t. under H$_2$ balloon for 21 h. The mixture was filtered through Celite and concentrated. The tert-butyl (2S,3R)-4-(3-(2-chloropropan-2-yl)-5-hydroxybenzylamino)-3-hydroxy-1-phenylbutan-2-ylcarbamate product was used in the next reaction without further purification.

A solution of 27.5 mg of tert-butyl (2S,3R)-4-(3-(2-chloropropan-2-yl)-5-hydroxybenzylamino)-3-hydroxy-1-phenylbutan-2-ylcarbamate and 0.8 mL of trifluoroacetic acid in 2 mL of CH$_2$Cl$_2$ was stirred at r.t. for 1 h and then concentrated. The 3-(((2R,3S)-3-amino-2-hydroxy-4-phenylbutylamino)methyl)-5-(prop-1-en-2-yl)phenol amine salt was used in the next reaction without further purification.

Example 1.9.3

Boc-protected tert-butyl (2R,3S)-3-amino-2-hydroxy-4-phenylbutyl(3-isopropyl-5-(N-methylmethylsulfonamido)benzyl)carbamate

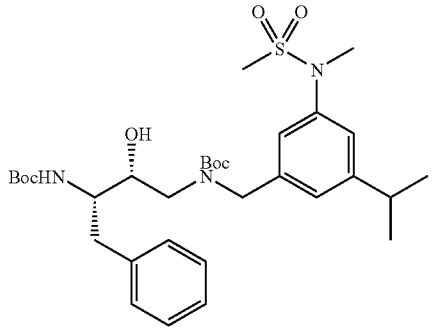

A mixture of 16.4 mg of Boc-protected tert-butyl (2R,3S)-3-amino-2-hydroxy-4-phenylbutyl(3-(N-methylmethylsulfonamido)-5-(prop-1-en-2-yl)benzyl)carbamate and 2.5 mg of 10% Pd/C in 3 mL of MeOH and 1 mL of EtOAc was stirred at r.t. under H$_2$ balloon for 12.5 h. The mixture was filtered through Celite and concentrated. Purification by flash silica gel chromatography (60% EtOAc/hexanes) provided 13.5 mg of Boc-protected tert-butyl (2R,3S)-3-amino-2-hydroxy-4-phenylbutyl(3-isopropyl-5-(N-methylmethylsulfonamido)benzyl)carbamate in 82% yield.

Example 1.9.4

Boc-protected tert-butyl (2R,3S)-3-amino-2-hydroxy-4-phenylbutyl(3-isopropyl-5-(methylsulfonyl)benzyl)carbamate

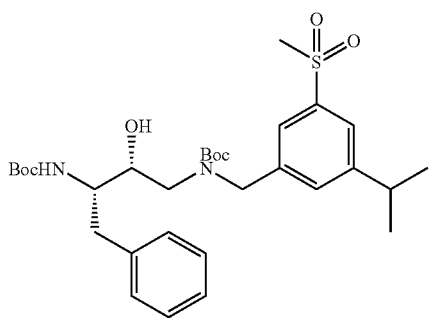

Boc-protected tert-butyl (2R,3S)-3-amino-2-hydroxy-4-phenylbutyl(3-isopropyl-5-(methylsulfonyl)benzyl)carbamate was synthesized in a similar manner to Boc-protected tert-butyl (2R,3S)-3-amino-2-hydroxy-4-phenylbutyl(3-isopropyl-5-(N-methylmethylsulfonamido)benzyl)carbamate by reducing Boc-protected tert-butyl (2R,3S)-3-amino-2-hydroxy-4-phenylbutyl(3-(methylsulfonyl)-5-(prop-1-en-2-yl)benzyl)carbamate.

Example 1.9.5 tert-butyl (2S,3R)-4-(3-acetamido-5-isopropylbenzylamino)-3-hydroxy-1-phenylbutan-2-ylcarbamate

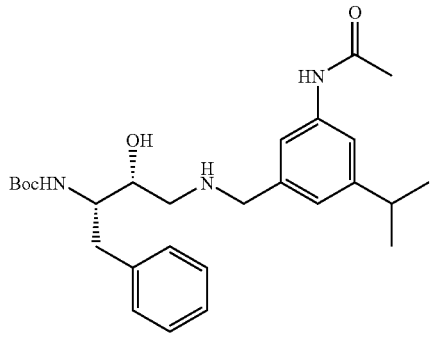

tert-butyl (2S,3R)-4-(3-acetamido-5-isopropylbenzylamino)-3-hydroxy-1-phenylbutan-2-ylcarbamate was synthesized in a similar manner to Boc-protected tert-butyl (2R,3S)-3-amino-2-hydroxy-4-phenylbutyl(3-isopropyl-5-(N-methylmethylsulfonamido)benzyl)carbamate by reducing tert-butyl (2S,3R)-4-(3-acetamido-5-(prop-1-en-2-yl)benzylamino)-3-hydroxy-1-phenylbutan-2-ylcarbamate.

Example 1.9.6

3-(((2R,3S)-3-amino-2-hydroxy-4-phenylbutylamino)methyl)-5-(prop-1-en-2-yl)phenyl dimethylcarbamate

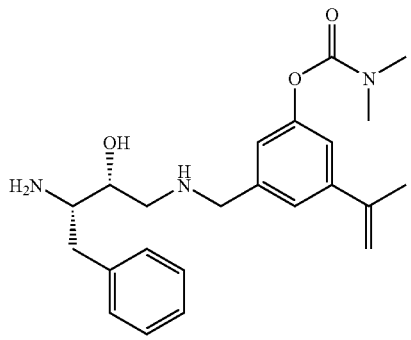

A solution of Boc protected 3-(((2R,3S)-3-amino-2-hydroxy-4-phenylbutylamino)methyl)-5-(prop-1-en-2-yl)phenyl dimethylcarbamate in 3 mL of 1.25 M HCl in MeOH was stirred at r.t. for about 13.5 h. The solution was concentrated, and the crude 3-(((2R,3S)-3-amino-2-hydroxy-4-phenylbutylamino)methyl)-5-(prop-1-en-2-yl)phenyl dimethylcarbamate product was used in the next reaction without further purification.

Example 1.10

Hydroxylamine/Isophthalate Coupling

Example 1.10.1

N-((2S,3R)-3-hydroxy-1-phenyl-4-(3-(trifluoromethyl)benzylamino)butan-2-yl)-3-methyl-5-((R)-2-(4-methylthiazol-2-yl)pyrrolidine-1-carbonyl)benzamide

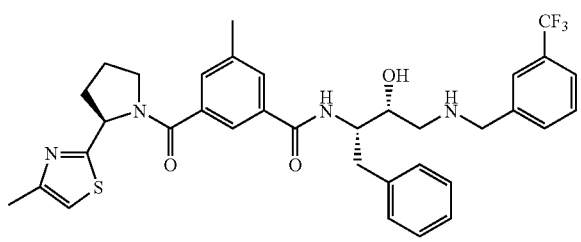

To (R)-3-methyl-5-(2-(4-methylthiazol-2-yl)pyrrolidine-1-carbonyl)benzoic acid (330 mg, 1 mmol) in $CH_2Cl_2$ at rt, EDCI (269 mg, 1.4 mmol) and HOBT (162 mg, 1.20 mmol) were added and stirred at rt for 20 min. In a separate flask (2R,3S)-3-amino-4-phenyl-1-(3-(trifluoromethyl)benzylamino)butan-2-ol was taken in $CH_2Cl_2$ and treated with DIPEA (2 ml). After 20 min, flask containing acid was cooled to 0° C. and the amine was added to it. Reaction mixture was stirred at rt for 16 h. Then reaction mixture was diluted with ethyl acetate, washed with sodium bicarbonate, water, brine and dried. Crude residue was purified by column chromatography to yield 60% of desired product.

Example 1.11

Alternative Synthesis: Hydroxylamine Coupling to Isophthalate Followed by Cyclic Amide Addition

Example 1.11.1

(R)-1-(3-((2S,3R)-3-hydroxy-4-((5-isopropylpyridin-3-yl)methylamino)-1-phenylbutan-2-ylcarbamoyl)benzoyl)pyrrolidine-2-carboxylic acid

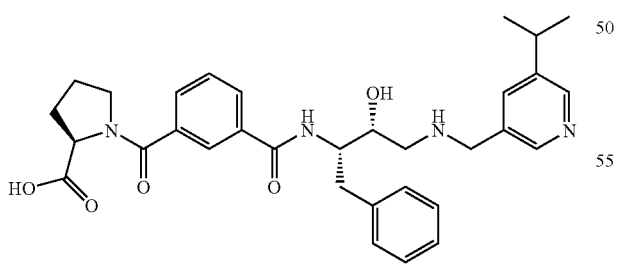

EDCI.HCl (0.175 g, 0.915 mmol, 1.1 eq) and HOBT.$H_2O$ (0.124 g, 0.915 mmol, 1.1 eq) were added to a stirred solution of 3-(methoxycarbonyl)benzoic acid in 5 ml anhydrous $CH_2Cl_2$ at 0° C. under Ar. In a separate flask (2R,3S)-3-amino-1-((5-isopropylpyridin-3-yl)methylamino)-4-phenylbutan-2-ol (0.3118 g, 0.832 mmol, 1.1 eq) in 3 ml anhydrous $CH_2Cl_2$ under Ar was treated with DIPEA (1.2 ml, 0.86 g, 6.66 mmol, 8 eq). After both solutions had stirred for 1 h, the active ester was treated with the free-base amine. The reaction was stirred at 0° C. to room temperature overnight. The solvent was removed in vacuo. The residue was partitioned between EtOAc/$H_2O$ and the layers were separated. The organic layer was washed with water (×3), brine (×1), and dried over $Na_2SO_4$. The inorganics were filtered off, and the solvent removed in vacuo. Purification via flash chromatography yielded 0.274 g (0.58 mmol, 69% yield) of methyl 3-((2S,3R)-3-hydroxy-4-((5-isopropylpyridin-3-yl)methylamino)-1-phenylbutan-2-ylcarbamoyl)benzoate.

methyl 3-((2S,3R)-3-hydroxy-4-((5-isopropylpyridin-3-yl)methylamino)-1-phenylbutan-2-ylcarbamoyl)benzoate (0.060 g, 0.126 mmol, 1 eq) was dissolved in 2 ml of 1:1 MeOH/THF. 1N NaOH (0.158 ml, 0.158 mmol, 1.25 eq) was added and the reaction was stirred over the weekend. The solvent was removed in vacuo. 1N HCl was added to pH 3-4. The mixture was diluted with 10% MeOH in $CHCl_3$ and dried over $Na_2SO_4$. The inorganics were filtered off, and the solvent removed in vacuo yielding 0.055 g (0.119 mmol, 95% yield) of 3-((2S,3R)-3-hydroxy-4-((5-isopropylpyridin-3-yl)methylamino)-1-phenylbutan-2-ylcarbamoyl)benzoic acid.

HOBT.$H_2O$ (0.0177 g, 0.131 mmol, 1.1 eq) was added to a stirred solution of 3-((2S,3R)-3-hydroxy-4-((5-isopropylpyridin-3-yl)methylamino)-1-phenylbutan-2-ylcarbamoyl)benzoic acid (0.055 g, 0.119 mmol, 1 eq) in 2 ml anhydrous $CH_2Cl_2$ at 0° C. under Ar. After 30 min EDCI.HCl (0.0197 g, 0.119 mmol, 1.1 eq) was added. After 30 min 1 ml anhydrous DMF was added. In a separate flask (R)-methylpyrrolidine-2-carboxylate hydrochloride (Bachem, 0.0197 g, 0.119 mmol, 1 eq) in 2 ml anhydrous $CH_2Cl_2$ under Ar was treated with DIPEA (0.083 ml, 0.062 g, 0.476 mmol, 4 eq). After both solutions had stirred for 1 h, the active ester was treated with the free-base amine. The reaction was stirred at 0° C. to room temperature overnight. The solvent was removed in vacuo. The residue was partitioned between EtOAc/$H_2O$ and the layers were separated. The organic layer was washed with water (×3), brine (×1), and dried over $Na_2SO_4$. The inorganics were filtered off, and the solvent removed in vacuo. Purification via flash chromatography yielded 0.0208 g (0.036 mmol, 31% yield) of (R)-methyl 1-(3-((2S,3R)-3-hydroxy-4-((5-isopropylpyridin-3-yl)methylamino)-1-phenylbutan-2-ylcarbamoyl)benzoyl)pyrrolidine-2-carboxylate, which was treated under hydrolysis conditions as described herein to generate (R)-1-(3-((2S,3R)-3-hydroxy-4-((5-isopropylpyridin-3-yl)methylamino)-1-phenylbutan-2-ylcarbamoyl)benzoyl)pyrrolidine-2-carboxylic acid.

Example 1.11.2

3-((R)-2-(2,2-dimethylhydrazinecarbonyl)pyrrolidine-1-carbonyl)-N-((2S,3R)-3-hydroxy-4-((5-isopropylpyridin-3-yl)methylamino)-1-phenylbutan-2-yl)benzamide

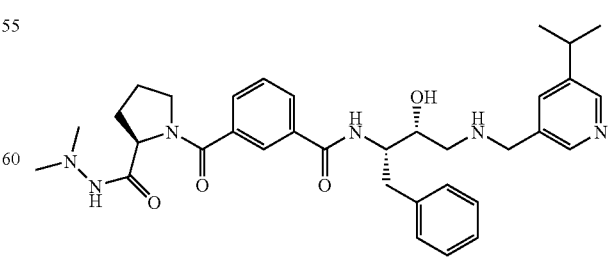

A flask containing (R)—N',N'-dimethylpyrrolidine-2-carbohydrazide was evacuated and back-filling with Ar (×3), followed by the sequential addition of 1 mL anhydrous CH$_2$Cl$_2$ and DIPEA (0.22 ml, 0.16 g, 1.24 mmol, 8 eq). In a separate flask HOBT.H$_2$O (0.023 g, 0.17 mmol, 1.1 eq) was added to a stirred solution of 3-((2S,3R)-3-hydroxy-4-((5-isopropylpyridin-3-yl)methylamino)-1-phenylbutan-2-yl-carbamoyl)benzoic acid (0.0714 g, 0.155 mmol, 1 eq) in 4 ml anhydrous CH$_2$Cl$_2$ at and 1 ml anhydrous DMF at 0° C. under Ar. After 30 min EDCI.HCl (0.032 g, 0.17 mmol, 1.1 eq) was added. After both solutions had stirred for at least 1 h the active ester was treated with the free-base amine. The reaction was stirred at 0° C. to room temperature overnight. The solvent was removed in vacuo and the residue partitioned between EtOAc/water. The layers were separated. The aqueous layer was saturated with NaCl and extracted with 10% MeOH in CHCl$_3$ (×4). The combined organic fractions were dried over Na$_2$SO$_4$. The inorganics were filtered off, and the solvent removed in vacuo. Purification via flash chromatography yielded only crude product. The crude was stirred with water and filtered through Celite. The water was removed in vacuo. The resulting solid was dissolved in saturated aqueous NaHCO$_3$ and filtered through Celite. The solution was extracted with 10% MeOH in CHCl$_3$ (×2). The combined organics were dried over Na$_2$SO$_4$. The inorganics were filtered off, and the solvent removed in vacuo. The residue was stirred with water and filtered through cotton. The solvent was removed in vacuo yielding 0.0046 g (0.0077 mmol, 4.9% yield) of 3-((R)-2-(2,2-dimethylhydrazinecarbonyl)pyrrolidine-1-carbonyl)-N-((2S,3R)-3-hydroxy-4-((5-isopropylpyridin-3-yl)methylamino)-1-phenylbutan-2-yl)benzamide.

Example 1.12

Post-Coupling Modifications

Example 1.12.1

N-((2S,3R)-3-hydroxy-4-(3-methoxybenzylamino)-1-phenylbutan-2-yl)-3-((R)-4-(4-methylthiazol-2-yl)thiazolidine-5-dioxide-3-carbonyl)benzamide

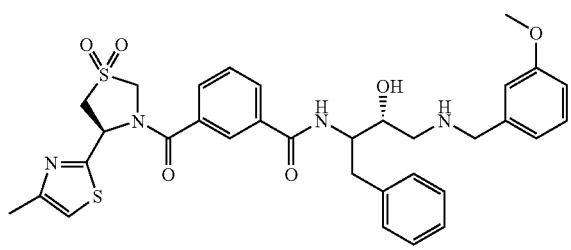

To a stirred solution of N-((2S,3R)-3-hydroxy-1-phenyl-4-(3-(trifluoromethyl)benzylamino)butan-2-yl)-3-methyl-5-((R)-2-(4-methylthiazol-2-yl)pyrrolidine-1-carbonyl)benzamide (35 mg, 0.06 mmol) in anhydrous MeOH (3 mL), was added (Boc)$_2$O (0.015 mL, 0.07 mmoles), Et$_3$N (0.023 mL, 0.17 mmoles) and stirred at RT from 12 hrs. The reaction mixture was concentrated and chromatographed (40% EtOAc/60% CHCl$_3$) to obtain 36 mg of tert-butyl (2R)-2-hydroxy-3-(3-((R)-4-(4-methylthiazol-2-yl)thiazolidine-3-carbonyl)benzamido)-4-phenylbutyl(3-methoxybenzyl)carbamate.

To a stirred solution of tert-butyl (2R)-2-hydroxy-3-(3-((R)-4-(4-methylthiazol-2-yl)thiazolidine-3-carbonyl)benzamido)-4-phenylbutyl(3-methoxybenzyl)carbamate (36 mg, 0.05 mmoles) in CH$_2$Cl$_2$ (3 mL), was added mCPBA (35 mg, 77% suspension in water, 0.11 mmoles) at 0° C., allowed to warm to RT and stirred for 6 h. The reaction was quenched with NaHCO$_3$ and extracted with EtOAc. The organic layer was dried on Na$_2$SO$_4$, concentrated, and chromatographed (50% ethyl acetate/50% CHCl$_3$) to yield 15 mg of tert-butyl (2R)-2-hydroxy-3-(3-((R)-4-(4-methylthiazol-2-yl)thiazolidine-S-dioxide-3-carbonyl)benzamido)-4-phenylbutyl(3-methoxybenzyl)carbamate.

To a stirred solution of tert-butyl (2R)-2-hydroxy-3-(3-((R)-4-(4-methylthiazol-2-yl)thiazolidine-5-dioxide-3-carbonyl)benzamido)-4-phenylbutyl(3-methoxybenzyl)carbamate (15 mg, 0.02 mmoles) in CH$_2$Cl$_2$ (3 mL), was added TFA (1 mL) at RT and stirred for 20 min. All volatiles were removed and the crude was diluted with NaHCO$_3$ and extracted with EtOAc. The organic layer was dried on Na$_2$SO$_4$, concentrated to yield 12 mg of N-((2S,3R)-3-hydroxy-4-(3-methoxybenzylamino)-1-phenylbutan-2-yl)-3-((R)-4-(4-methylthiazol-2-yl)thiazolidine-5-dioxide-3-carbonyl)benzamide.

Example 2

Inhibition of Memapsin 2 Beta-Secretase Activity

Potency of compounds were determined by measurement of their inhibition of memapsin 2 activity toward a fluorescent substrate. Kinetic inhibition experiments were performed using the procedure as described in Ermolieff, et al. (*Biochemistry* 39:12450-12456 (2000), the teachings of which are incorporated hereby in their entirety). Briefly, assays were performed at pH 4, 37° C., by pre-incubation of memapsin 2 enzyme with compound for 20 minutes. Activity measurements were initiated by addition of a fluorogenic substrate FS-2 (Bachem Americas, Torrance, Calif.) MCA-SEVNLDAEFK-DNP (SEQ ID NO.: 2). The substrate was derived from 10 amino acids of the human amyloid precursor protein (APP), with the Swedish variant amino acids at the beta-secretase cleavage site. The terminal amino acid was modified from arginine to lysine to facilitate derivatization with a functional group for detection by autofluorescence. The amino acid sequence of the "core" peptide of the substrate is SEVNLDAEFK (SEQ ID NO.: 3). The amino terminus was derivatized with (7-methoxycoumarin-4-yl)acetyl (MCA), and the epsilon amine of the lysine side chain of the terminal residue (K in sequence SEVNLDAEFK (SEQ ID NO.: 4)) was derivatized with 2,4-dinitrophenyl (DNP).

TABLE 1

Compound inhibition data.

| Ref # | Structure | M2Ki nM | CDKi nM | M1Ki nM | IC50 nM |
|---|---|---|---|---|---|
| 1 | N-((2S,3R)-3-hydroxy-4-(3-methoxybenzylamino)-1-phenylbutan-2-yl)-3-((R)-2-(4-methylthiazol-2-yl)pyrrolidine-1-carbonyl)benzamide | +++ | ++ | +++ | +++ |

TABLE 1-continued

Compound inhibition data.

| Ref # | Structure | M2Ki nM | CDKi nM | M1Ki nM | IC50 nM |
|---|---|---|---|---|---|
| 2 | N-((2S,3R)-3-hydroxy-4-((5-isopropylpyridin-3-yl)methylamino)-1-phenylbutan-2-yl)-3-((R)-2-(4-methylthiazol-2-yl)pyrrolidine-1-carbonyl)benzamide | +++ | ++ | +++ | +++ |
| 3 | N-((2S,3R)-3-hydroxy-4-(3-methoxybenzylamino)-1-phenylbutan-2-yl)-3-((R)-2-(methoxymethyl)pyrrolidine-1-carbonyl)-5-methylbenzamide | +++ | | | +++ |
| 4 | N-((2S,3R)-3-hydroxy-4-(3-methoxybenzylamino)-1-phenylbutan-2-yl)-3-((S)-2-(4-methylthiazol-2-yl)pyrrolidine-1-carbonyl)benzamide | + | | | |
| 5 | N-((2S,3R)-3-hydroxy-4-(3-methoxybenzylamino)-1-phenylbutan-2-yl)-3-((R)-2-(4-methylthiazol-2-yl)piperidine-1-carbonyl)benzamide | +++ | | | + |
| 6 | N-((2S,3R)-3-hydroxy-4-(3-methoxybenzylamino)-1-phenylbutan-2-yl)-3-methyl-5-((R)-2-(4-methylthiazol-2-yl)pyrrolidine-1-carbonyl)benzamide | +++ | ++ | + | +++ |
| 7 | N-((2S,3R)-3-hydroxy-4-(3-methoxybenzylamino)-1-phenylbutan-2-yl)-3-((2R,4R)-4-methoxy-2-(4-methylthiazol-2-yl)pyrrolidine-1-carbonyl)benzamide | + | | | |
| 8 | N-((2S,3R)-3-hydroxy-4-(3-methoxybenzylamino)-1-phenylbutan-2-yl)-3-((R)-4-(4-methylthiazol-2-yl)thiazolidine-3-carbonyl)benzamide | +++ | | | +++ |
| 9 | N-((2S,3R)-3-hydroxy-1-phenyl-4-(3-(trifluoromethyl)benzylamino)butan-2-yl)-3-((R)-2-(4-methylthiazol-2-yl)pyrrolidine-1-carbonyl)benzamide | +++ | + | ++ | +++ |
| 10 | N-((2S,3R)-4-(3-tert-butylbenzylamino)-3-hydroxy-1-phenylbutan-2-yl)-3-((R)-2-(4-methylthiazol-2-yl)pyrrolidine-1-carbonyl)benzamide | +++ | + | ++ | +++ |
| 11 | N-((2S,3R)-3-hydroxy-4-(3-methoxybenzylamino)-1-phenylbutan-2-yl)-3-methoxy-5-((R)-2-(4-methylthiazol-2-yl)pyrrolidine-1-carbonyl)benzamide | +++ | | | +++ |
| 12 | N-((2S,3R)-3-hydroxy-1-phenyl-4-(3-(trifluoromethyl)benzylamino)butan-2-yl)-3-methyl-5-((R)-2-(4-methylthiazol-2-yl)pyrrolidine-1-carbonyl)benzamide | +++ | + | +++ | +++ |
| 13 | N-((2S,3R)-3-hydroxy-4-(3-methoxybenzylamino)-1-phenylbutan-2-yl)-3-((R)-4-(4-methylthiazol-2-yl)thiazolidine-S-dioxide-3-carbonyl)benzamide | + | | | |
| 14 | N-((2S,3R)-4-(3-tert-butylbenzylamino)-3-hydroxy-1-phenylbutan-2-yl)-3-methyl-5-((R)-2-(4-methylthiazol-2-yl)pyrrolidine-1-carbonyl)benzamide | +++ | +++ | +++ | +++ |
| 15 | N-((2S,3R)-3-hydroxy-4-(3-methoxybenzylamino)-1-phenylbutan-2-yl)-3-((R)-4-(4-methylthiazol-2-yl)oxazolidine-3-carbonyl)benzamide | +++ | +++ | ++ | +++ |
| 16 | N-((2S,3R)-4-(3-tert-butylbenzylamino)-3-hydroxy-1-phenylbutan-2-yl)-3-methoxy-5-((R)-2-(4-methylthiazol-2-yl)pyrrolidine-1-carbonyl)benzamide | +++ | | | +++ |
| 17 | N-((2S,3R)-4-(3-chlorobenzylamino)-3-hydroxy-1-phenylbutan-2-yl)-3-((R)-2-(4-methylthiazol-2-yl)pyrrolidine-1-carbonyl)benzamide | +++ | | | +++ |
| 18 | N-((2S,3R)-4-(3-chlorobenzylamino)-3-hydroxy-1-phenylbutan-2-yl)-3-methoxy-5-((R)-2-(4-methylthiazol-2-yl)pyrrolidine-1-carbonyl)benzamide | +++ | | | +++ |
| 19 | N-((2S,3R)-4-(cyclopropylamino)-3-hydroxy-1-phenylbutan-2-yl)-3-((R)-2-(4-methylthiazol-2-yl)pyrrolidine-1-carbonyl)benzamide | + | | | |
| 20 | N-((2S,3R)-3-hydroxy-4-((S)-1-(3-methoxyphenyl)ethylamino)-1-phenylbutan-2-yl)-3-methoxy-5-((R)-2-(4-methylthiazol-2-yl)pyrrolidine-1-carbonyl)benzamide | +++ | | | +++ |

TABLE 1-continued

Compound inhibition data.

| Ref # | Structure | M2Ki nM | CDKi nM | M1Ki nM | IC50 nM |
|---|---|---|---|---|---|
| 21 | N-((2S,3R)-3-hydroxy-4-(3-methoxybenzylamino)-1-phenylbutan-2-yl)-3-(pyrrolidine-1-carbonyl)benzamide | + | | | + |
| 22 | N-((2S,3R)-3-hydroxy-4-((S)-1-(3-methoxyphenyl)ethylamino)-1-phenylbutan-2-yl)-3-((R)-2-(4-methylthiazol-2-yl)pyrrolidine-1-carbonyl)benzamide | +++ | | | +++ |
| 23 | N-((2S,3R)-3-hydroxy-4-((5-isopropylpyridin-3-yl)methylamino)-1-phenylbutan-2-yl)-3-((R)-2-(methoxymethyl)pyrrolidine-1-carbonyl)-5-methylbenzamide | +++ | | | +++ |
| 24 | N-((2S,3R)-3-hydroxy-4-(3-hydroxy-5-isopropylbenzylamino)-1-phenylbutan-2-yl)-3-((R)-2-(4-methylthiazol-2-yl)pyrrolidine-1-carbonyl)benzamide | +++ | | | +++ |
| 25 | N-((2S,3R)-3-hydroxy-4-((5-isopropylpyridin-3-yl)methylamino)-1-phenylbutan-2-yl)-3-((R)-2-(4-methylthiazol-2-yl)pyrrolidine-1-carbonyl)-5-(oxazol-2-yl)benzamide | +++ | | | +++ |
| 26 | N-((2S,3R)-3-hydroxy-1-phenyl-4-(3-(trifluoromethyl)benzylamino)butan-2-yl)-3-((R)-4-(4-methylthiazol-2-yl)oxazolidine-3-carbonyl)benzamide | +++ | | | +++ |
| 27 | N-((2S,3R)-3-hydroxy-4-((5-isopropylpyridin-3-yl)methylamino)-1-phenylbutan-2-yl)-5-((R)-2-(4-methylthiazol-2-yl)pyrrolidine-1-carbonyl)nicotinamide | +++ | | | +++ |
| 28 | N-((2S,3R)-3-hydroxy-1-phenyl-4-(3-(trifluoromethyl)benzylamino)butan-2-yl)-3-((R)-2-(4-methylthiazol-2-yl)pyrrolidine-1-carbonyl)-5-(oxazol-2-yl)benzamide | +++ | | | +++ |
| 29 | 3-(dimethylamino)-N-((2S,3R)-3-hydroxy-4-((5-isopropylpyridin-3-yl)methylamino)-1-phenylbutan-2-yl)-5-((R)-2-(4-methylthiazol-2-yl)pyrrolidine-1-carbonyl)benzamide | +++ | | | +++ |
| 30 | 3-(dimethylamino)-N-((2S,3R)-3-hydroxy-1-phenyl-4-(3-(trifluoromethyl)benzylamino)butan-2-yl)-5-((R)-2-(4-methylthiazol-2-yl)pyrrolidine-1-carbonyl)benzamide | +++ | | | +++ |
| 31 | N-((2S,3R)-3-hydroxy-1-phenyl-4-(3-(trifluoromethyl)benzylamino)butan-2-yl)-5-((R)-2-(4-methylthiazol-2-yl)pyrrolidine-1-carbonyl)nicotinamide | +++ | | | +++ |
| 32 | N-((2S,3R)-4-(3-tert-butylbenzylamino)-3-hydroxy-1-phenylbutan-2-yl)-5-((R)-2-(4-methylthiazol-2-yl)pyrrolidine-1-carbonyl)nicotinamide | ++ | | | +++ |
| 33 | N-((2S,3R)-3-hydroxy-4-((5-isopropylpyridin-3-yl)methylamino)-1-phenylbutan-2-yl)-3-((R)-2-(4-methylthiazol-2-yl)pyrrolidine-1-carbonyl)-5-(oxazol-5-yl)benzamide | +++ | | | +++ |
| 34 | N-((2S,3R)-3-hydroxy-4-((5-isopropylpyridin-3-yl)methylamino)-1-phenylbutan-2-yl)-3-((R)-2-(4-methyloxazol-2-yl)pyrrolidine-1-carbonyl)benzamide | +++ | | | +++ |
| 35 | N-((2S,3R)-3-hydroxy-1-phenyl-4-(3-(trifluoromethyl)benzylamino)butan-2-yl)-3-((R)-2-(4-methyloxazol-2-yl)pyrrolidine-1-carbonyl)benzamide | +++ | | | +++ |
| 36 | 3-(dimethylamino)-N-((2S,3R)-4-((5-(2-fluoropropan-2-yl)pyridin-3-yl)methylamino)-3-hydroxy-1-phenylbutan-2-yl)-5-((R)-2-(4-methylthiazol-2-yl)pyrrolidine-1-carbonyl)benzamide | +++ | | | |
| 37 | N-((2S,3R)-4-(3-tert-butylbenzylamino)-3-hydroxy-1-phenylbutan-2-yl)-3-((R)-2-(4-methylthiazol-2-yl)pyrrolidine-1-carbonyl)-5-(oxazol-2-yl)benzamide | | | | |
| 38 | N-((2S,3R)-4-((5-(2-fluoropropan-2-yl)pyridin-3-yl)methylamino)-3-hydroxy-1-phenylbutan-2-yl)-3-((R)-2-(4-methylthiazol-2-yl)pyrrolidine-1-carbonyl)-5-(oxazol-2-yl)benzamide | +++ | | | +++ |

TABLE 1-continued

Compound inhibition data.

| Ref # | Structure | M2Ki nM | CDKi nM | M1Ki nM | IC50 nM |
|---|---|---|---|---|---|
| 39 | N-((2S,3R)-4-((5-(2-fluoropropan-2-yl)pyridin-3-yl)methylamino)-3-hydroxy-1-phenylbutan-2-yl)-3-((R)-2-(4-methyloxazol-2-yl)pyrrolidine-1-carbonyl)benzamide | +++ | | | +++ |
| 40 | N-((2S,3R)-4-((5-(1,1-difluoroethyl)pyridin-3-yl)methylamino)-3-hydroxy-1-phenylbutan-2-yl)-3-(dimethylamino)-5-((R)-2-(4-methylthiazol-2-yl)pyrrolidine-1-carbonyl)benzamide | +++ | | | +++ |
| 41 | N-((2S,3R)-4-(3-tert-butylbenzylamino)-3-hydroxy-1-phenylbutan-2-yl)-3-(dimethylamino)-5-((R)-2-(4-methylthiazol-2-yl)pyrrolidine-1-carbonyl)benzamide | +++ | | | +++ |
| 42 | N-((2S,3R)-4-((5-(2-fluoropropan-2-yl)pyridin-3-yl)methylamino)-3-hydroxy-1-phenylbutan-2-yl)-3-methyl-5-((R)-2-(4-methylthiazol-2-yl)pyrrolidine-1-carbonyl)benzamide | +++ | | | +++ |
| 43 | N-((2S,3R)-3-hydroxy-4-((5-isopropylpyridin-3-yl)methylamino)-1-phenylbutan-2-yl)-3-((R)-2-(4-methylthiazol-2-yl)pyrrolidine-1-carbonyl)-5-(pyrazin-2-yl)benzamide | +++ | | | +++ |
| 44 | N-((2S,3R)-4-((5-(2-fluoropropan-2-yl)pyridin-3-yl)methylamino)-3-hydroxy-1-phenylbutan-2-yl)-5-((R)-2-(4-methylthiazol-2-yl)pyrrolidine-1-carbonyl)nicotinamide | +++ | | | +++ |
| 45 | N-((2S,3R)-4-((5-(2-fluoropropan-2-yl)pyridin-3-yl)methylamino)-3-hydroxy-1-phenylbutan-2-yl)-3-((R)-2-(4-methylthiazol-2-yl)pyrrolidine-1-carbonyl)benzamide | +++ | | | +++ |
| 46 | N-((2S,3R)-3-hydroxy-4-((R)-1-(5-isopropylpyridin-3-yl)ethylamino)-1-phenylbutan-2-yl)-3-((R)-2-(4-methylthiazol-2-yl)pyrrolidine-1-carbonyl)benzamide | +++ | | | +++ |
| 47 | N-((2S,3R)-4-(3-chlorobenzylamino)-3-hydroxy-1-phenylbutan-2-yl)-3-(dimethylamino)-5-((R)-2-(4-methylthiazol-2-yl)pyrrolidine-1-carbonyl)benzamide | +++ | | | +++ |
| 48 | N-((2S,3R)-4-(3,5-dichlorobenzylamino)-3-hydroxy-1-phenylbutan-2-yl)-3-(dimethylamino)-5-((R)-2-(4-methylthiazol-2-yl)pyrrolidine-1-carbonyl)benzamide | +++ | | | +++ |
| 49 | N-((2S,3R)-3-hydroxy-1-phenyl-4-(3-(trifluoromethyl)benzylamino)butan-2-yl)-3-((R)-2-(4-methylthiazol-2-yl)pyrrolidine-1-carbonyl)-5-(pyrazin-2-yl)benzamide | +++ | | | +++ |
| 50 | 3-(fluoromethyl)-N-((2S,3R)-4-((5-(2-fluoropropan-2-yl)pyridin-3-yl)methylamino)-3-hydroxy-1-phenylbutan-2-yl)-5-((R)-2-(4-methylthiazol-2-yl)pyrrolidine-1-carbonyl)benzamide | +++ | | | +++ |
| 51 | 3-(fluoromethyl)-N-((2S,3R)-3-hydroxy-1-phenyl-4-((5-(trifluoromethyl)pyridin-3-yl)methylamino)butan-2-yl)-5-((R)-2-(4-methylthiazol-2-yl)pyrrolidine-1-carbonyl)benzamide | +++ | | | +++ |
| 52 | N-((2S,3R)-3-hydroxy-4-((5-isopropylpyridin-3-yl)methylamino)-1-phenylbutan-2-yl)-3-methyl-5-((R)-2-(4-methylthiazol-2-yl)pyrrolidine-1-carbonyl)benzamide111117 | +++ | | | +++ |
| 53 | 3-(dimethylamino)-N-((2S,3R)-3-hydroxy-4-((S)-1-(3-methoxyphenyl)ethylamino)-1-phenylbutan-2-yl)-5-((R)-2-(4-methylthiazol-2-yl)pyrrolidine-1-carbonyl)benzamide | ++ | | | |
| 54 | N-((2S,3R)-4-(3,5-dichlorobenzylamino)-3-hydroxy-1-phenylbutan-2-yl)-3-methoxy-5-((R)-2-(4-methylthiazol-2-yl)pyrrolidine-1-carbonyl)benzamide | +++ | | | |
| 55 | N-((2S,3R)-3-hydroxy-1-phenyl-4-(3-(trifluoromethyl)benzylamino)butan-2-yl)-3-methyl-5-((R)-2-(4-methyloxazol-2-yl)pyrrolidine-1-carbonyl)benzamide | +++ | | | +++ |
| 56 | N-((2S,3R)-3-hydroxy-4-((5-isopropylpyridin-3-yl)methylamino)-1-phenylbutan-2-yl)-3-methyl-5-((R)-2-(4-methyloxazol-2-yl)pyrrolidine-1-carbonyl)benzamide | +++ | | | +++ |

TABLE 1-continued

Compound inhibition data.

| Ref # | Structure | M2Ki nM | CDKi nM | M1Ki nM | IC50 nM |
|---|---|---|---|---|---|
| 57 | 3-(difluoromethyl)-N-((2S,3R)-3-hydroxy-1-phenyl-4-(3-(trifluoromethyl)benzylamino)butan-2-yl)-5-((R)-2-(4-methylthiazol-2-yl)pyrrolidine-1-carbonyl)benzamide | +++ | | | +++ |
| 58 | 3-(difluoromethyl)-N-((2S,3R)-4-((5-(2-fluoropropan-2-yl)pyridin-3-yl)methylamino)-3-hydroxy-1-phenylbutan-2-yl)-5-((R)-2-(4-methylthiazol-2-yl)pyrrolidine-1-carbonyl)benzamide | +++ | | | |
| 59 | N-((2S,3R)-4-((5-(2-fluoropropan-2-yl)pyridin-3-yl)methylamino)-3-hydroxy-1-phenylbutan-2-yl)-3-methyl-5-((R)-2-(4-methyloxazol-2-yl)pyrrolidine-1-carbonyl)benzamide | +++ | | | +++ |
| 60 | N-((2S,3R)-4-(3,5-dichlorobenzylamino)-3-hydroxy-1-phenylbutan-2-yl)-5-((R)-2-(4-methylthiazol-2-yl)pyrrolidine-1-carbonyl)nicotinamide | +++ | | | +++ |
| 61 | N-((2S,3R)-4-(3-cyano-5-isopropylbenzylamino)-3-hydroxy-1-phenylbutan-2-yl)-5-((R)-2-(4-methylthiazol-2-yl)pyrrolidine-1-carbonyl)nicotinamide | +++ | | | |
| 62 | 3-(difluoromethyl)-N-((2S,3R)-3-hydroxy-4-((5-isopropylpyridin-3-yl)methylamino)-1-phenylbutan-2-yl)-5-((R)-2-(4-methylthiazol-2-yl)pyrrolidine-1-carbonyl)benzamide | +++ | | | |
| 63 | 3-(difluoromethyl)-N-((2S,3R)-3-hydroxy-4-((S)-1-(3-methoxyphenyl)ethylamino)-1-phenylbutan-2-yl)-5-((R)-2-(4-methylthiazol-2-yl)pyrrolidine-1-carbonyl)benzamide | +++ | | | |
| 64 | N-((2S,3R)-3-hydroxy-1-phenyl-4-(3-(trifluoromethyl)benzylamino)butan-2-yl)-2-((R)-2-(4-methylthiazol-2-yl)pyrrolidine-1-carbonyl)isonicotinamide | +++ | | | +++ |
| 65 | N-((2S,3R)-3-hydroxy-4-((3-methylisoxazol-5-yl)methylamino)-1-phenylbutan-2-yl)-3-((R)-2-(4-methylthiazol-2-yl)pyrrolidine-1-carbonyl)benzamide | + | | | ++ |
| 66 | N-((2S,3R)-3-hydroxy-4-((5-methylisoxazol-3-yl)methylamino)-1-phenylbutan-2-yl)-3-((R)-2-(4-methylthiazol-2-yl)pyrrolidine-1-carbonyl)benzamide | +++ | | | +++ |
| 67 | N-((2S,3R)-3-hydroxy-4-((4-methylthiazol-2-yl)methylamino)-1-phenylbutan-2-yl)-3-((R)-2-(4-methylthiazol-2-yl)pyrrolidine-1-carbonyl)benzamide | + | | | |
| 68 | N-((2S,3R)-3-hydroxy-1-phenyl-4-(3-(trifluoromethyl)benzylamino)butan-2-yl)-6-methyl-4-((R)-2-(4-methylthiazol-2-yl)pyrrolidine-1-carbonyl)picolinamide | +++ | | | +++ |
| 69 | N-((2S,3R)-4-(3-(dimethylamino)benzylamino)-3-hydroxy-1-phenylbutan-2-yl)-3-((R)-2-(4-methylthiazol-2-yl)pyrrolidine-1-carbonyl)benzamide | +++ | | | +++ |
| 70 | N-((2S,3R)-4-(3-tert-butylbenzylamino)-3-hydroxy-1-phenylbutan-2-yl)-3-((R)-2-(4-methyloxazol-2-yl)pyrrolidine-1-carbonyl)benzamide | +++ | | | +++ |
| 71 | N-((2S,3R)-3-hydroxy-4-((5-isopropylpyridin-3-yl)methylamino)-1-phenylbutan-2-yl)-5-((R)-2-(4-methyloxazol-2-yl)pyrrolidine-1-carbonyl)nicotinamide | +++ | | | +++ |
| 72 | N-((2S,3R)-3-hydroxy-1-phenyl-4-(3-(trifluoromethyl)benzylamino)butan-2-yl)-5-((R)-2-(4-methyloxazol-2-yl)pyrrolidine-1-carbonyl)nicotinamide | +++ | | | |
| 73 | N-((2S,3R)-4-((5-(2-fluoropropan-2-yl)pyridin-3-yl)methylamino)-3-hydroxy-1-phenylbutan-2-yl)-5-((R)-2-(4-methyloxazol-2-yl)pyrrolidine-1-carbonyl)nicotinamide | +++ | | | +++ |
| 74 | N-((2S,3R)-3-hydroxy-4-((5-isopropylpyridin-3-yl)methylamino)-1-phenylbutan-2-yl)-3-((R)-2-(4-methylthiazol-2-yl)pyrrolidine-1-carbonyl)-5-(1H-pyrrol-1-yl)benzamide | +++ | | | +++ |

TABLE 1-continued

Compound inhibition data.

| Ref # | Structure | M2Ki nM | CDKi nM | M1Ki nM | IC50 nM |
|---|---|---|---|---|---|
| 75 | 2-(furan-2-yl)-N-((2S,3R)-3-hydroxy-1-phenyl-4-(3-(trifluoromethyl)benzylamino)butan-2-yl)-6-((R)-2-(4-methylthiazol-2-yl)pyrrolidine-1-carbonyl)isonicotinamide | +++ | | | +++ |
| 76 | N-((2S,3R)-4-(3-tert-butylbenzylamino)-3-hydroxy-1-phenylbutan-2-yl)-5-((R)-2-(4-methyloxazol-2-yl)pyrrolidine-1-carbonyl)nicotinamide | +++ | | | +++ |
| 77 | 3-(fluoromethyl)-N-((2S,3R)-3-hydroxy-4-((5-isopropylpyridin-3-yl)methylamino)-1-phenylbutan-2-yl)-5-((R)-2-(4-methyloxazol-2-yl)pyrrolidine-1-carbonyl)benzamide | +++ | | | +++ |
| 78 | 3-(fluoromethyl)-N-((2S,3R)-4-((5-(2-fluoropropan-2-yl)pyridin-3-yl)methylamino)-3-hydroxy-1-phenylbutan-2-yl)-5-((R)-2-(4-methyloxazol-2-yl)pyrrolidine-1-carbonyl)benzamide | +++ | | | +++ |
| 79 | N-((2S,3R)-3-hydroxy-1-phenyl-4-(3-(trifluoromethyl)benzylamino)butan-2-yl)-2-methyl-6-((R)-2-(4-methylthiazol-2-yl)pyrrolidine-1-carbonyl)isonicotinamide | +++ | | | +++ |
| 80 | N-((2S,3R)-3-hydroxy-1-phenyl-4-(3-(trifluoromethyl)benzylamino)butan-2-yl)-3-((R)-2-(4-methylthiazol-2-yl)pyrrolidine-1-carbonyl)-5-(1H-pyrrol-1-yl)benzamide | +++ | | | +++ |
| 81 | 6-(dimethylamino)-N-((2S,3R)-3-hydroxy-1-phenyl-4-(3-(trifluoromethyl)benzylamino)butan-2-yl)-4-((R)-2-(4-methylthiazol-2-yl)pyrrolidine-1-carbonyl)picolinamide | +++ | | | +++ |
| 82 | 3-(fluoromethyl)-N-((2S,3R)-3-hydroxy-1-phenyl-4-(3-(trifluoromethyl)benzylamino)butan-2-yl)-5-((R)-2-(4-methyloxazol-2-yl)pyrrolidine-1-carbonyl)benzamide | +++ | | | +++ |
| 83 | N-((2S,3R)-3-hydroxy-4-((5-isopropylpyridin-3-yl)methylamino)-1-phenylbutan-2-yl)-3-methoxy-5-((R)-2-(4-methylthiazol-2-yl)pyrrolidine-1-carbonyl)benzamide | +++ | | | +++ |
| 84 | N-((2S,3R)-3-hydroxy-1-phenyl-4-(3-(trifluoromethyl)benzylamino)butan-2-yl)-2-methyl-6-((R)-2-(4-methyloxazol-2-yl)pyrrolidine-1-carbonyl)isonicotinamide | +++ | | | +++ |
| 85 | N-((2S,3R)-3-hydroxy-4-(3-(methylamino)-5-(trifluoromethyl)benzylamino)-1-phenylbutan-2-yl)-3-((R)-2-(4-methylthiazol-2-yl)pyrrolidine-1-carbonyl)benzamide | +++ | | | +++ |
| 86 | N-((2S,3R)-3-hydroxy-4-((5-isopropylpyridin-3-yl)methylamino)-1-phenylbutan-2-yl)-3-((R)-2-(4-methyloxazol-2-yl)pyrrolidine-1-carbonyl)-5-(oxazol-2-yl)benzamide | +++ | | | +++ |
| 87 | N-((2S,3R)-3-hydroxy-1-phenyl-4-(3-(trifluoromethyl)benzylamino)butan-2-yl)-3-((R)-2-(4-methyloxazol-2-yl)pyrrolidine-1-carbonyl)-5-(oxazol-2-yl)benzamide | +++ | | | +++ |
| 88 | 6'-fluoro-N-((2S,3R)-3-hydroxy-1-phenyl-4-(3-(trifluoromethyl)benzylamino)butan-2-yl)-6-((R)-2-(4-methylthiazol-2-yl)pyrrolidine-1-carbonyl)-2,3'-bipyridine-4-carboxamide | ++ | | | +++ |
| 89 | N-((2S,3R)-3-hydroxy-4-((5-isopropylpyridin-3-yl)methylamino)-1-phenylbutan-2-yl)-3-methoxy-5-((R)-2-(4-methyloxazol-2-yl)pyrrolidine-1-carbonyl)benzamide | +++ | | | +++ |
| 90 | N-((2S,3R)-4-((5-(2-fluoropropan-2-yl)pyridin-3-yl)methylamino)-3-hydroxy-1-phenylbutan-2-yl)-3-((R)-2-(4-methyloxazol-2-yl)pyrrolidine-1-carbonyl)-5-(oxazol-2-yl)benzamide | +++ | | | +++ |
| 91 | 2-(3-chlorophenyl)-N-((2S,3R)-3-hydroxy-1-phenyl-4-(3-(trifluoromethyl)benzylamino)butan-2-yl)-6-((R)-2-(4-methylthiazol-2-yl)pyrrolidine-1-carbonyl)isonicotinamide | +++ | | | ++ |
| 92 | 3-(dimethylamino)-N-((2S,3R)-3-hydroxy-4-((5-isopropylpyridin-3-yl)methylamino)-1-phenylbutan-2-yl)-5-((R)-2-(4-methyloxazol-2-yl)pyrrolidine-1-carbonyl)benzamide | +++ | | | +++ |

TABLE 1-continued

Compound inhibition data.

| Ref # | Structure | M2Ki nM | CDKi nM | M1Ki nM | IC50 nM |
|---|---|---|---|---|---|
| 93 | N-((2S,3R)-3-hydroxy-1-phenyl-4-(3-(trifluoromethyl)benzylamino)butan-2-yl)-3-methoxy-5-((R)-2-(4-methyloxazol-2-yl)pyrrolidine-1-carbonyl)benzamide | +++ | | | +++ |
| 94 | N-((2S,3R)-3-hydroxy-1-phenyl-4-(3-(trifluoromethyl)benzylamino)butan-2-yl)-2-((R)-2-(4-methyloxazol-2-yl)pyrrolidine-1-carbonyl)isonicotinamide | +++ | | | +++ |
| 95 | N-((2S,3R)-4-(3-tert-butylbenzylamino)-3-hydroxy-1-phenylbutan-2-yl)-3-(fluoromethyl)-5-((R)-2-(4-methyloxazol-2-yl)pyrrolidine-1-carbonyl)benzamide | +++ | | | +++ |
| 96 | N-((2S,3R)-3-hydroxy-1-phenyl-4-(3-(trifluoromethyl)benzylamino)butan-2-yl)-6-methyl-4-((R)-2-(4-methyloxazol-2-yl)pyrrolidine-1-carbonyl)picolinamide | +++ | | | |
| 97 | N-((2S,3R)-4-(benzofuran-2-ylmethylamino)-3-hydroxy-1-phenylbutan-2-yl)-3-methyl-5-((R)-2-(4-methylthiazol-2-yl)pyrrolidine-1-carbonyl)benzamide | + | | | |
| 98 | 2-(dimethylamino)-N-((2S,3R)-3-hydroxy-1-phenyl-4-(3-(trifluoromethyl)benzylamino)butan-2-yl)-6-((R)-2-(4-methylthiazol-2-yl)pyrrolidine-1-carbonyl)isonicotinamide | +++ | | | |
| 99 | N-((2S,3R)-3-hydroxy-4-((3-isopropylisoxazol-5-yl)methylamino)-1-phenylbutan-2-yl)-3-((R)-2-(4-methylthiazol-2-yl)pyrrolidine-1-carbonyl)benzamide | +++ | | | |
| 100 | 2-(dimethylamino)-N-((2S,3R)-3-hydroxy-1-phenyl-4-(3-(trifluoromethyl)benzylamino)butan-2-yl)-6-((R)-2-(4-methylthiazol-2-yl)pyrrolidine-1-carbonyl)pyrimidine-4-carboxamide | +++ | | | |
| 101 | N-((2S,3R)-4-(3-(1,1-difluoroethyl)benzylamino)-3-hydroxy-1-phenylbutan-2-yl)-3-((R)-2-(4-methyloxazol-2-yl)pyrrolidine-1-carbonyl)benzamide | +++ | | | +++ |
| 102 | N-((2S,3R)-4-((5-(1,1-difluoroethyl)pyridin-3-yl)methylamino)-3-hydroxy-1-phenylbutan-2-yl)-3-((R)-2-(4-methyloxazol-2-yl)pyrrolidine-1-carbonyl)benzamide | +++ | | | +++ |
| 103 | N-((2S,3R)-3-hydroxy-1-phenyl-4-((5-(trifluoromethyl)pyridin-3-yl)methylamino)butan-2-yl)-3-((R)-2-(4-methyloxazol-2-yl)pyrrolidine-1-carbonyl)benzamide | +++ | | | +++ |
| 104 | N-((2S,3R)-4-(3-(1,1-difluoroethyl)benzylamino)-3-hydroxy-1-phenylbutan-2-yl)-3-methyl-5-((R)-2-(4-methyloxazol-2-yl)pyrrolidine-1-carbonyl)benzamide | +++ | | | +++ |
| 105 | N-((2S,3R)-3-hydroxy-1-phenyl-4-(3-(prop-1-en-2-yl)benzylamino)butan-2-yl)-3-((R)-2-(4-methyloxazol-2-yl)pyrrolidine-1-carbonyl)benzamide | +++ | | | +++ |
| 106 | N-((2S,3R)-3-hydroxy-4-((5-isopropylisoxazol-3-yl)methylamino)-1-phenylbutan-2-yl)-3-((R)-2-(4-methylthiazol-2-yl)pyrrolidine-1-carbonyl)benzamide | +++ | | | |
| 107 | N-((2S,3R)-4-(cyclohexylamino)-3-hydroxy-1-phenylbutan-2-yl)-3-((R)-2-(4-methyloxazol-2-yl)pyrrolidine-1-carbonyl)benzamide | + | | | |
| 108 | N-((2S,3R)-3-hydroxy-1-phenyl-4-(3-(prop-1-en-2-yl)benzylamino)butan-2-yl)-3-methyl-5-((R)-2-(4-methyloxazol-2-yl)pyrrolidine-1-carbonyl)benzamide | +++ | | | |
| 109 | N-((2S,3R)-4-((1-ethyl-1H-pyrazol-4-yl)methylamino)-3-hydroxy-1-phenylbutan-2-yl)-3-((R)-2-(4-methyloxazol-2-yl)pyrrolidine-1-carbonyl)benzamide | ++ | | | |
| 110 | N-((2S,3R)-4-((1-ethyl-1H-pyrazol-4-yl)methylamino)-3-hydroxy-1-phenylbutan-2-yl)-3-methyl-5-((R)-2-(4-methyloxazol-2-yl)pyrrolidine-1-carbonyl)benzamide | +++ | | | |
| 111 | N-((2S,3R)-4-((5-tert-butylpyridin-3-yl)methylamino)-3-hydroxy-1-phenylbutan-2-yl)-3-((R)-2-(4-methyloxazol-2-yl)pyrrolidine-1-carbonyl)benzamide | +++ | | | |

TABLE 1-continued

Compound inhibition data.

| Ref # | Structure | M2Ki nM | CDKi nM | M1Ki nM | IC50 nM |
|---|---|---|---|---|---|
| 112 | N-((2S,3R)-4-((5-tert-butylpyridin-3-yl)methylamino)-3-hydroxy-1-phenylbutan-2-yl)-3-methyl-5-((R)-2-(4-methyloxazol-2-yl)pyrrolidine-1-carbonyl)benzamide | +++ | | | |
| 113 | N-((2S,3R)-4-((5-(1,1-difluoroethyl)pyridin-3-yl)methylamino)-3-hydroxy-1-phenylbutan-2-yl)-3-methyl-5-((R)-2-(4-methyloxazol-2-yl)pyrrolidine-1-carbonyl)benzamide | +++ | | | |
| 114 | N-((2S,3R)-3-hydroxy-1-phenyl-4-(3-(trifluoromethoxy)benzylamino)butan-2-yl)-3-((R)-2-(4-methyloxazol-2-yl)pyrrolidine-1-carbonyl)benzamide | +++ | | | |
| 115 | N-((2S,3R)-3-hydroxy-1-phenyl-4-(3-(trifluoromethoxy)benzylamino)butan-2-yl)-3-methyl-5-((R)-2-(4-methyloxazol-2-yl)pyrrolidine-1-carbonyl)benzamide | +++ | | | |
| 116 | N-((2S,3R)-4-((5-(1,1-difluoroethyl)pyridin-3-yl)methylamino)-3-hydroxy-1-phenylbutan-2-yl)-3-methyl-5-((R)-2-(4-methylthiazol-2-yl)pyrrolidine-1-carbonyl)benzamide | +++ | | | |

In Table 1, for the M2 Ki data, a "+" represents a Ki of greater than >201 nM, a "++" represents a Ki from 200 nm to 101 nm, and a "+++" represents a Ki of less than 100 nm. For the CD Ki and M1 Ki data, a "+" represents a Ki of greater than >501 nM, a "++" represents a Ki from 500 nm to 301 nm, and a "+++" represents a Ki of less than 300 nm. For the IC50 data, a "+" represents an IC50 of greater than >501 nM, a "++" represents an IC50 from 500 nm to 301 nm, and a "+++" represents an IC50 of less than 300 nm. For example, N-((2S,3R)-3-hydroxy-1-phenyl-4-(3-(trifluoromethyl)benzylamino)butan-2-yl)-3-((R)-2-(4-methylthiazol-2-yl)pyrrolidine-1-carbonyl)benzamide has values for M2 Ki=7.09 nM, CathD Ki=1079.9 nM, M1 Ki=825.73 nM, and IC50=23 nM, represented in Table 1 as +++, +, ++, and +++ for M2 Ki, CD Ki, M1 Ki, and IC50, respectively.

Example 3

Physical Characterization Data for Inhibitors

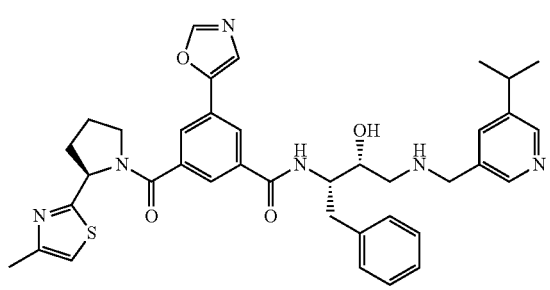

N-((2S,3R)-3-hydroxy-4-((5-isopropylpyridin-3-yl)methylamino)-1-phenylbutan-2-yl)-3-((R)-2-(4-methylthiazol-2-yl)pyrrolidine-1-carbonyl)-5-(oxazol-5-yl)benzamide: $^1$H NMR: δ 8.40-8.44 (m, 2H), 7.86-7.96 (m, 2H), 7.76 (s, 1H), 7.60 (s, 1H), 7.44 (s, 1H), 7.23-7.31 (m, 6h), 6.84 (S, 1H), 5.68 (m, 1H), 4.43 (m, 1H), 3.86-3.93 (m, 2H), 3.69 (m, 1H), 3.50 (m, 1H), 2.85-3.07 (m, 5H), 2.48 (s, 3H), 1.98-2.41 (m, 4H), 1.26 (m, 6H).

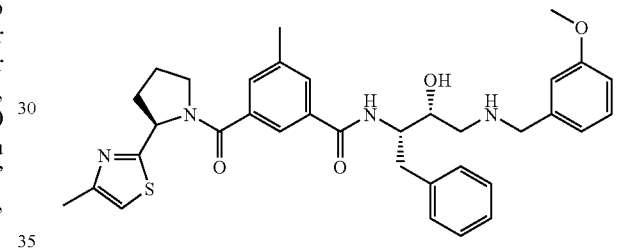

N-((2S,3R)-3-hydroxy-4-(3-methoxybenzylamino)-1-phenylbutan-2-yl)-3-methyl-5-((R)-2-(4-methylthiazol-2-yl)pyrrolidine-1-carbonyl)benzamide: $^1$H NMR (300 MHz, CDCl$_3$): δ 1.91-1.98 (m, 1H), 2.05-2.13 (m, 1H), 2.33-2.46 (m, 8H), 2.74-2.82 (m, 2H), 2.94-3.09 (m, 2H), 3.39-3.47 (m, 1H), 3.62-3.89 (m, 7H), 4.24-4.44 (m, 1H), 5.60-5.70 9m, 1H), 6.64 (s, 1H), 6.80-6.84 (m, 2H), 6.90-6.93 (m, 2H), 7.23-7.30 (m, 5H), 7.44 (br s, 1H), 7.48 (br s, 1H), 7.58 (br s, 1H).

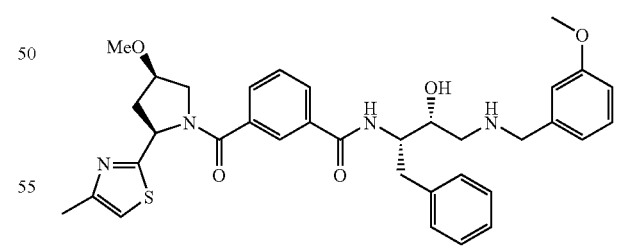

N-((2S,3R)-3-hydroxy-4-(3-methoxybenzylamino)-1-phenylbutan-2-yl)-3-((2R,4R)-4-methoxy-2-(4-methylthiazol-2-yl)pyrrolidine-1-carbonyl)benzamide: $^1$H NMR (300 MHz, CDCl$_3$): δ 2.46-2.63 (m, 5H), 2.84 (br s, 2H), 3.02 (d, 2H, J=6.3 Hz), 3.25 (s, 3H), 3.70-3.88 (m, 8H), 3.95-4.04 (m, 1H), 4.36-4.44 (m, 1H), 5.63-5.76 (m, 1H), 6.82-6.85 (m, 2H), 6.92-6.94 (m, 2H), 7.25-7.31 (m, 6H), 7.42-7.48 (m, 1H), 7.68-7.71 (m, 2H), 7.87 (br s, 1H).

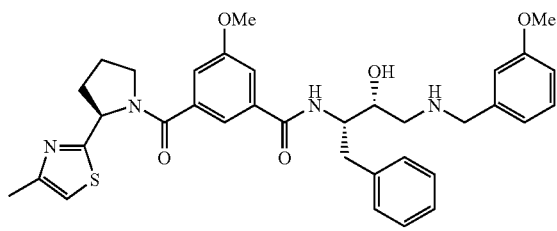

N-((2S,3R)-3-hydroxy-4-(3-methoxybenzylamino)-1-phenylbutan-2-yl)-3-methoxy-5-((R)-2-(4-methylthiazol-2-yl)pyrrolidine-1-carbonyl)benzamide: $^1$H NMR (300 MHz, CDCl$_3$): δ 1.84-2.02 (m, 1H), 2.12-2.24 (m, 1H), 2.43-2.52 (m, 5H), 2.72-2.82 (m, 2H), 2.93-3.02 (m, 2H), 3.42-3.50 (m, 1H), 3.53-3.83 (m, 10H), 4.34-4.44 (m, 1H), 5.61-5.71 (m, 1H), 6.66 (s, 1H), 6.78-6.94 (m, 4H), 7.04-7.12 (m, 1H), 7.18-7.34 (m, 7H).

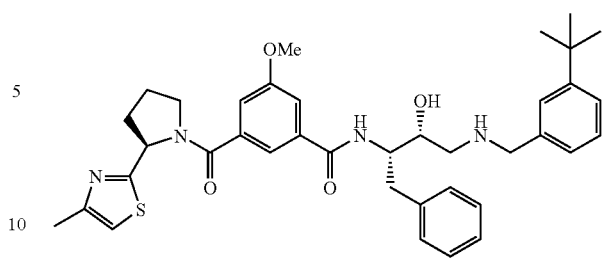

N-((2S,3R)-4-(3-tert-butylbenzylamino)-3-hydroxy-1-phenylbutan-2-yl)-3-methoxy-5-((R)-2-(4-methylthiazol-2-yl)pyrrolidine-1-carbonyl)benzamide: $^1$H NMR (300 MHz, CDCl$_3$): δ 1.22 (s, 9H), 1.80-1.89 (m, 1H), 1.97-2.03 (m, 1H), 2.25-2.38 (m, 5H), 2.71-2.77 (m, 2H), 2.92-2.94 9m, 2H), 3.36-3.42 (m, 1H), 3.55-3.82 (m, 7H), 4.24-4.46 (m, 1H), 5.55-5.59 (m, 1H), 6.71 (m, 1H), 7.05-7.28 (m, 12H).

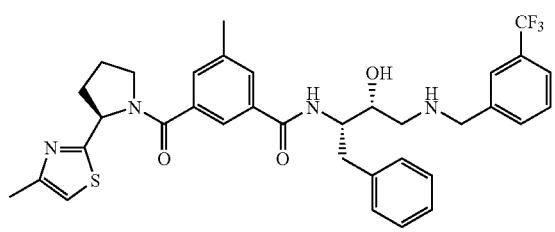

N-((2S,3R)-3-hydroxy-1-phenyl-4-(3-(trifluoromethyl)benzylamino)butan-2-yl)-3-methyl-5-((R)-2-(4-methylthiazol-2-yl)pyrrolidine-1-carbonyl)benzamide: $^1$H NMR (300 MHz, CDCl$_3$): δ 1.90-1.99 (m, 1H), 2.07-2.16 (m, 1H), 2.26-2.47 (m, 8H), 2.75-2.82 (m, 2H), 2.98-3.14 (m, 2H), 3.42-3.48 (m, 1H), 3.64-3.72 (m, 1H), 3.85-3.95 (m, 3H), 4.36-4.42 (m, 1H), 5.65-5.69 (m, 1H), 6.82 (s, 1H), 7.26-7.32 (m, 9H), 7.49 (s, 1H), 7.54 (s, 1H), 7.57 (s, 1H), 7.62 (s, 1H).

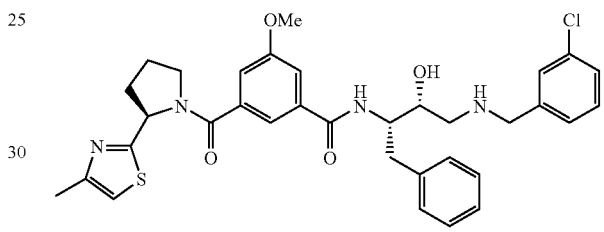

N-((2S,3R)-4-(3-chlorobenzylamino)-3-hydroxy-1-phenylbutan-2-yl)-3-methoxy-5-((R)-2-(4-methylthiazol-2-yl)pyrrolidine-1-carbonyl)benzamide: $^1$H NMR (300 MHz, CDCl$_3$): δ 1.82-1.89 (m, 1H), 1.97-2.06 (m, 1H), 2.25-2.37 (m, 5H), 2.65-2.76 (m, 2H), 2.86-3.01 (m, 2H), 3.34-3.40 (m, 1H), 3.57-3.80 (m, 7H), 4.26-4.32 (m, 1H), 5.54-5.58 (m, 1H), 6.71 (s, 1H), 6.98-7.25 (m, 12H).

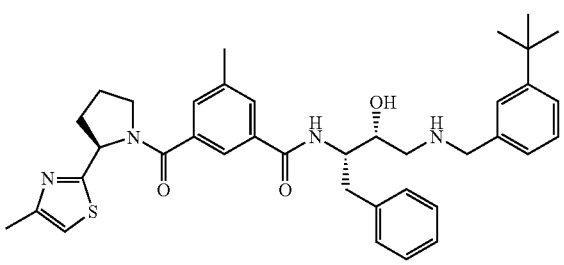

N-((2S,3R)-4-(3-tert-butylbenzylamino)-3-hydroxy-1-phenylbutan-2-yl)-3-methyl-5-((R)-2-(4-methylthiazol-2-yl)pyrrolidine-1-carbonyl)benzamide: δ $^1$H NMR (300 MHz, CDCl$_3$): δ 1.28 (s, 9H), 1.82-1.91 (m, 1H), 1.97-2.04 (m, 1H), 2.16-2.39 (m, 8H), 2.72-2.79 (m, 2H), 2.92-2.97 (m, 2H), 3.33-3.42 (m, 1H), 3.56-3.64 (m, 1H), 3.71-3.83 (m, 3H), 4.26-4.38 (m, 1H), 5.57-5.61 (m, 1H), 6.72 (m, 1H), 7.08-7.28 (m, 9H), 7.39-7.43 (m, 2H), 7.53 (s, 1H).

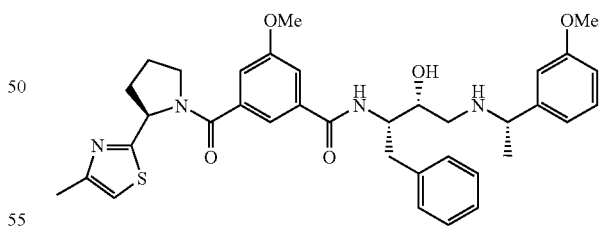

N-((2S,3R)-3-hydroxy-4-((S)-1-(3-methoxyphenyl)ethylamino)-1-phenylbutan-2-yl)-3-methoxy-5-((R)-2-(4-methylthiazol-2-yl)pyrrolidine-1-carbonyl)benzamide: $^1$H NMR (300 MHz, CDCl$_3$): δ 1.42 (d, 3H, J=6.9 Hz), 1.84-2.16 (m, 2H), 2.38-2.42 (m, 5H), 2.62-2.85 (m, 2H), 2.96-3.02 (m, 2H), 3.42-3.58 (m, 1H), 3.61-3.84 (m, 9H), 4.22-4.38 (m, 1H), 5.62 (m, 1H), 6.74-6.79 (m, 4H), 7.12-7.47 (m, 9H).

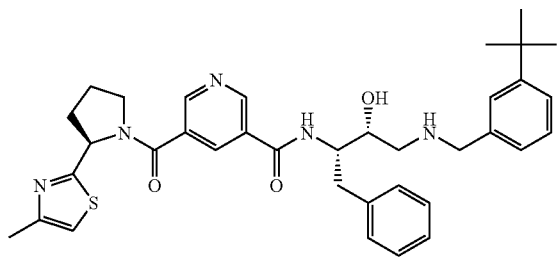

N-((2S,3R)-4-(3-tert-butylbenzylamino)-3-hydroxy-1-phenylbutan-2-yl)-5-((R)-2-(4-methylthiazol-2-yl)pyrrolidine-1-carbonyl)nicotinamide: $^1$H NMR (300 MHz, CDCl$_3$): δ 1.33 (s, 9H), 1.95-2.23 (m, 2H), 2.25-2.47 (m, 5H), 2.82-3.06 (m, 4H), 3.47-3.55 (m, 1H), 3.68-3.93 (m, 4H), 4.42-4.49 (m, 1H), 5.66-5.70 (m, 1H), 6.82 (s, 1H), 7.16-7.36 (m, 9H), 8.20 (m, 1H), 8.90 (s, 2H).

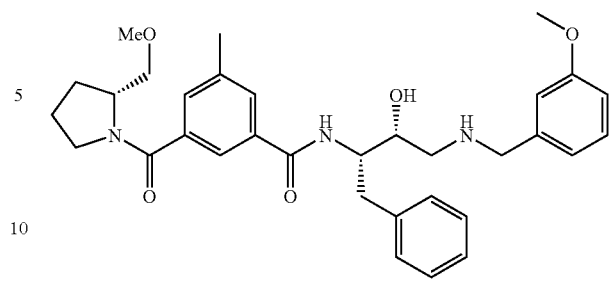

N-((2S,3R)-3-hydroxy-4-(3-methoxybenzylamino)-1-phenylbutan-2-yl)-3-((R)-2-(methoxymethyl)pyrrolidine-1-carbonyl)-5-methylbenzamide: $^1$H NMR (300 MHz, CDCl$_3$): δ 1.71-1.82 (m, 1H), 1.96-2.09 (m, 3H), 2.37 (s, 3H), 2.81-2.83 (m, 2H), 2.94-3.11 (m, 3H), 3.30-3.43 (m, 4H), 3.66-3.88 (m, 8H), 4.39-4.46 (m, 2H), 6.81-6.94 (m, 4H), 7.22-7.31 (m, 6H), 7.42-7.51 (m, 2H).

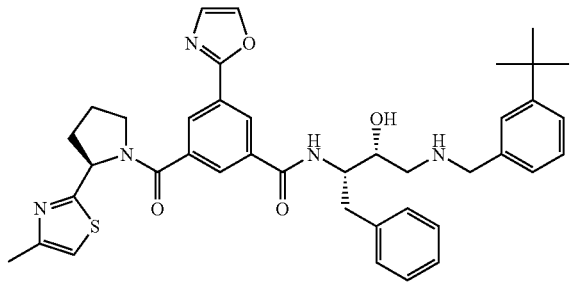

N-((2S,3R)-4-(3-tert-butylbenzylamino)-3-hydroxy-1-phenylbutan-2-yl)-3-((R)-2-(4-methylthiazol-2-yl)pyrrolidine-1-carbonyl)-5-(oxazol-2-yl)benzamide: $^1$H NMR (300 MHz, CDCl$_3$): δ 1.31 (s, 9H), 1.93-2.04 (m, 1H), 2.08-2.17 (m, 1H), 2.25-2.47 (m, 5H), 2.84-3.02 (m, 4H), 3.46-3.52 (m, 1H), 3.70-3.96 (m, 4H), 4.41-4.49 (m, 1H), 5.67-5.71 (m, 1H), 6.81 (s, 1H), 7.17-7.33 (m, 9H), 7.38 (s, 1H), 7.75 (s, 1H), 7.95 (s, 1H), 8.31 (s, 1H), 8.38 (s, 1H).

N-((2S,3R)-3-hydroxy-4-(3-methoxybenzylamino)-1-phenylbutan-2-yl)-3-((R)-2-(4-methylthiazol-2-yl)pyrrolidine-1-carbonyl)benzamide: $^1$H NMR (300 MHz, CDCl$_3$): δ 1.91-1.98 (m, 1H), 2.05-2.13 (m, 1H), 2.20-2.46 (m, 2H), 2.44 (s, 3H), 2.78-3.18 (m, 4H), 3.39-3.52 (m, 1H), 3.62-3.92 (m, 4H), 3.79 (s, 3H), 4.24-4.42 (m, 1H), 5.58-5.64 (m, 1H), 6.78-6.84 (m, 3H), 6.90-6.93 (m, 2H), 7.23-7.30 (m, 5H), 7.40-7.48 (m, 1H), 7.63-7.80 (m, 2H), 7.82 (br s, 1H).

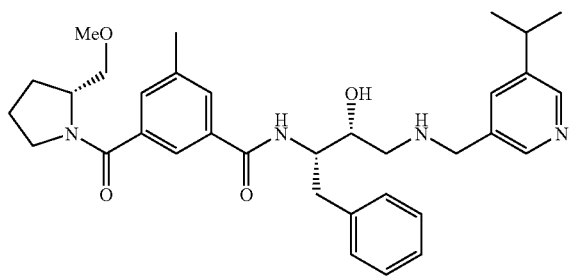

N-((2S,3R)-3-hydroxy-4-((5-isopropylpyridin-3-yl)methylamino)-1-phenylbutan-2-yl)-3-((R)-2-(methoxymethyl)pyrrolidine-1-carbonyl)-5-methylbenzamide: $^1$H NMR (300 MHz, CDCl$_3$): δ 1.28 (d, 6H, J=6.6 Hz), 1.71-1.82 (m, 1H), 1.96-2.09 (m, 3H), 2.37 (s, 3H), 2.81-2.83 (m, 2H), 2.95-3.12 (m, 6H), 3.33-3.43 (m, 5H), 3.65-3.84 (m, 5H), 4.38-4.45 (m, 2H), 6.74-6.77 (d, 1H, 7.2 Hz), 7.23-7.55 (m, 8H), 8.39-8.41 (m, 2H).

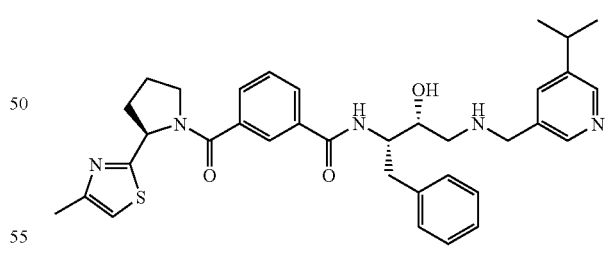

N-((2S,3R)-3-hydroxy-4-((5-isopropylpyridin-3-yl)methylamino)-1-phenylbutan-2-yl)-3-((R)-2-(4-methylthiazol-2-yl)pyrrolidine-1-carbonyl)benzamide: $^1$H NMR (300 MHz, CDCl$_3$): δ 1.20-1.26 (m, 6H), 1.90-1.98 (m, 1H), 2.05-2.15 (m, 1H), 2.22-2.52 (m, 2H), 2.44 (s, 3H), 2.74-3.22 (m, 5H), 3.39-3.52 (m, 1H), 3.62-3.92 (m, 4H), 4.28-4.42 (m, 1H), 5.56-5.66 (m, 1H), 6.81 (s, 1H), 7.12-7.30 (m, 5H), 7.40-7.47 (m, 1H), 7.52-7.58 (m, 1H), 7.65-7.75 (m, 2H), 7.83 (br s, 1H), 8.33-8.35 (m, 2H).

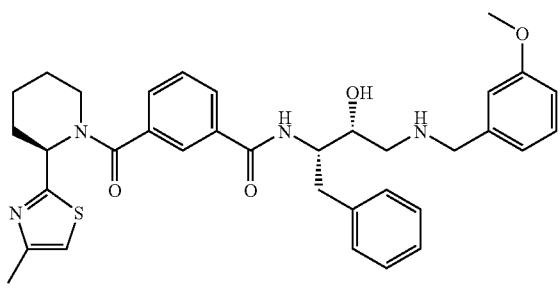

N-((2S,3R)-3-hydroxy-4-(3-methoxybenzylamino)-1-phenylbutan-2-yl)-3-((R)-2-(4-methylthiazol-2-yl)piperidine-1-carbonyl)benzamide: $^1$H NMR (300 MHz, CDCl$_3$): δ 1.40-2.13 (m, 7H), 2.46 (s, 3H), 2.54-3.34 (m, 5H), 3.49-3.88 (m, 3H), 3.81 (s, 3H), 4.30-4.50 (m, 1H), 6.10-6.30 (m, 1H), 6.78-6.94 (m, 3H), 7.23-7.30 (m, 5H), 7.30-7.50 (m, 1H), 7.52-7.60 (m, 1H), 7.62-7.70 (m, 1H), 7.78 (br s, 1H).

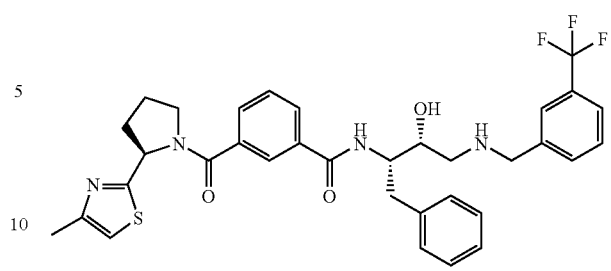

N-((2S,3R)-3-hydroxy-1-phenyl-4-(3-(trifluoromethyl)benzylamino)butan-2-yl)-3-((R)-2-(4-methylthiazol-2-yl)pyrrolidine-1-carbonyl)benzamide: $^1$H NMR (300 MHz, CDCl$_3$): δ 1.88-2.02 (m, 1H), 2.02-2.18 (m, 1H), 2.35-2.50 (m, 2H), 2.46 (s, 3H), 2.70-2.90 (m, 2H), 2.90-3.12 (m, 2H), 3.39-3.52 (m, 1H), 3.62-3.76 (m, 2H), 3.80-3.96 (m, 2H), 4.28-4.48 (m, 1H), 5.62-5.72 (m, 1H), 6.80 (s, 1H), 7.16-7.36 (m, 5H), 7.36-7.68 (m, 7H), 7.82 (s, 1H).

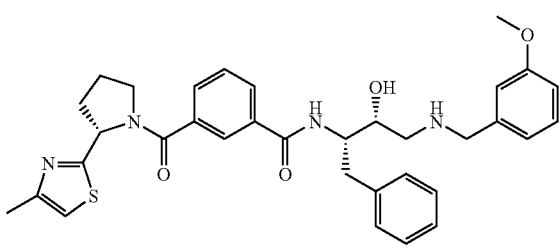

N-((2S,3R)-3-hydroxy-4-(3-methoxybenzylamino)-1-phenylbutan-2-yl)-3-((S)-2-(4-methylthiazol-2-yl)pyrrolidine-1-carbonyl)benzamide: $^1$H NMR (300 MHz, CDCl$_3$): δ 1.94-2.00 (m, 1H), 2.00-2.20 (m, 1H), 2.20-2.46 (m, 2H), 2.45 (s, 3H), 2.78-2.84 (m, 2H), 2.96-3.08 (m, 2H), 3.39-3.60 (m, 1H), 3.62-3.96 (m, 4H), 3.81 (s, 3H), 4.32-4.50 (m, 1H), 5.60-5.74 (m, 1H), 6.78-6.98 (m, 5H), 7.23-7.30 (m, 5H), 7.38-7.48 (m, 1H), 7.63-7.72 (m, 2H), 7.90 (br s, 1H).

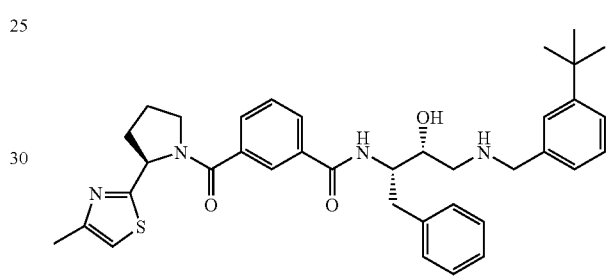

N-((2S,3R)-4-(3-tert-butylbenzylamino)-3-hydroxy-1-phenylbutan-2-yl)-3-((R)-2-(4-methylthiazol-2-yl)pyrrolidine-1-carbonyl)benzamide: $^1$H NMR (300 MHz, CDCl$_3$): δ 1.33 (s, 9H) 1.88-2.02 (m, 1H), 2.02-2.18 (m, 1H), 2.30-2.52 (m, 2H), 2.47 (s, 3H), 2.68-2.86 (m, 2H), 2.86-3.12 (m, 2H), 3.42-3.58 (m, 1H), 3.62-3.96 (m, 4H), 4.32-4.54 (m, 1H), 5.62-5.76 (m, 1H), 6.80 (s, 1H), 7.16-7.50 (m, 10H), 7.64-7.76 (m, 2H), 7.86 (s, 1H).

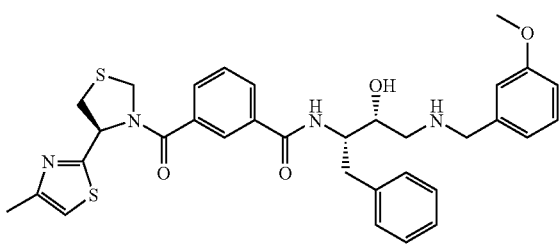

N-((2S,3R)-3-hydroxy-4-(3-methoxybenzylamino)-1-phenylbutan-2-yl)-3-((R)-4-(4-methylthiazol-2-yl)thiazolidine-3-carbonyl)benzamide: $^1$H NMR (300 MHz, CDCl$_3$): δ 2.46 (s, 3H), 2.82-2.85 (m, 2H), 2.92-3.08 (m, 2H), 3.48-3.64 (m, 2H), 3.64-3.90 (m, 4H), 3.82 (s, 3H), 4.40-4.50 (m, 1H), 4.60-4.70 (m, 1H), 6.10-6.30 (m, 1H), 6.80-6.94 (m, 5H), 7.20-7.32 (m, 5H), 7.38-7.48 (m, 1H), 7.63-7.72 (m, 2H), 7.72-7.90 (m, 1H).

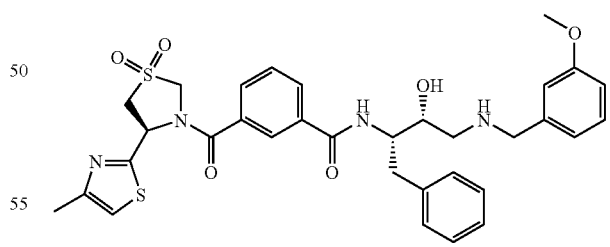

N-((2S,3R)-3-hydroxy-4-(3-methoxybenzylamino)-1-phenylbutan-2-yl)-3-((R)-4-(4-methylthiazol-2-yl)thiazolidine-5-dioxide-3-carbonyl)benzamide: $^1$H NMR (300 MHz, CDCl$_3$): δ 2.45 (s, 3H), 2.86-3.22 (m, 4H), 3.68-3.84 (m, 4H), 3.78 (s, 3H), 4.08-4.20 (m, 1H), 4.32-4.40 (m, 1H), 4.46-4.90 (m, 2H), 6.38-6.58 (m, 1H), 6.88-6.96 (m, 5H), 7.16-7.32 (m, 5H), 7.40-7.46 (m, 1H), 7.60-7.72 (m, 1H), 7.68-7.82 (m, 2H).

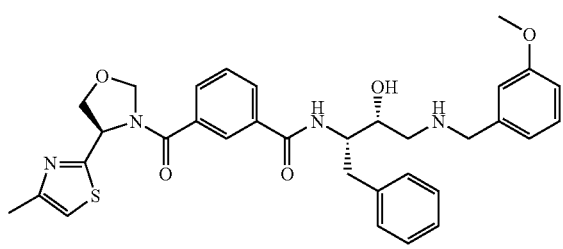

N-((2S,3R)-3-hydroxy-4-(3-methoxybenzylamino)-1-phenylbutan-2-yl)-3-((R)-4-(4-methylthiazol-2-yl)oxazolidine-3-carbonyl)benzamide: $^1$H NMR (300 MHz, CDCl$_3$): δ 2.46 (s, 3H), 2.78-2.90 (m, 2H), 2.90-3.04 (m, 2H), 3.52-3.84 (m, 3H), 3.81 (s, 3H), 4.26-4.38 (m, 1H), 4.38-4.60 (m, 2H), 4.90-5.24 (m, 2H) 5.60-5.80 (m, 1H), 6.78-6.94 (m, 5H), 7.18-7.34 (m, 5H), 7.38-7.48 (m, 1H), 7.60-7.78 (m, 2H), 7.80-7.90 (br s, 1H).

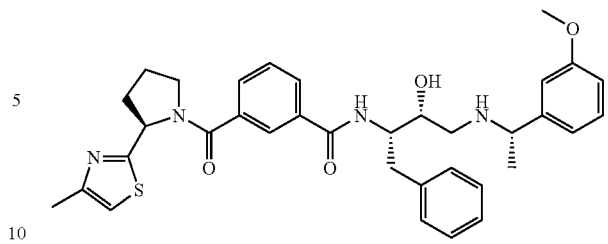

N-((2S,3R)-3-hydroxy-4-((S)-1-(3-methoxyphenyl)ethylamino)-1-phenylbutan-2-yl)-3-((R)-2-(4-methylthiazol-2-yl)pyrrolidine-1-carbonyl)benzamide: $^1$H NMR (300 MHz, CDCl$_3$): δ 1.43 (d, J=6.6 Hz, 3H), 1.88-2.00 (m, 1H), 2.00-2.18 (m, 1H), 2.26-2.50 (m, 2H), 2.47 (s, 3H), 2.60-2.80 (m, 2H), 2.98-3.06 (m, 2H), 3.39-3.96 (m, 4H), 3.82 (s, 3H), 4.32-4.44 (m, 1H), 5.60-5.72 (m, 1H), 6.78-6.84 (m, 5H), 7.16-7.26 (m, 5H), 7.40-7.42 (m, 1H), 7.60-7.72 (m, 2H), 7.82 (br s, 1H).

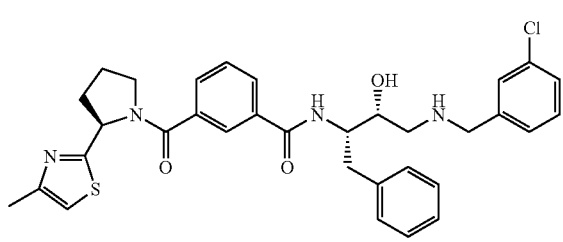

N-((2S,3R)-4-(3-chlorobenzylamino)-3-hydroxy-1-phenylbutan-2-yl)-3-(R)-2-(4-methylthiazol-2-yl)pyrrolidine-1-carbonyl)benzamide: $^1$H NMR (300 MHz, CDCl$_3$): δ 1.88-2.02 (m, 1H), 2.02-2.18 (m, 1H), 2.28-2.50 (m, 2H), 2.47 (s, 3H), 2.70-2.90 (m, 2H), 2.94-3.12 (m, 2H), 3.39-3.52 (m, 1H), 3.60-3.86 (m, 4H), 4.30-4.48 (m, 1H), 5.62-5.72 (m, 1H), 6.80 (s, 1H), 7.16-7.36 (m, 9H), 7.36-7.46 (m, 1H), 7.60-7.70 (m, 2H), 7.82 (s, 1H).

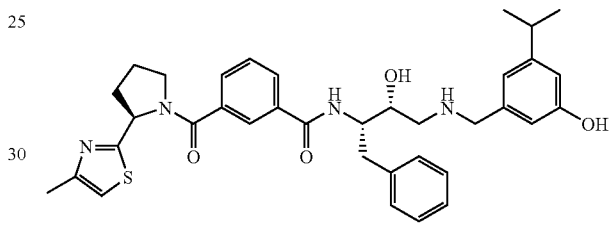

N-((2S,3R)-3-hydroxy-4-(3-hydroxy-5-isopropylbenzylamino)-1-phenylbutan-2-yl)-3-((R)-2-(4-methylthiazol-2-yl)pyrrolidine-1-carbonyl)benzamide: $^1$H NMR (300 MHz, CDCl$_3$): δ 1.20-1.26 (m, 6H), 1.88-2.20 (m, 2H), 2.22-2.60 (m, 2H), 2.44 (s, 3H), 2.74-3.22 (m, 5H), 3.42-3.52 (m, 1H), 3.62-3.98 (m, 4H), 4.32-4.42 (m, 1H), 5.58-5.64 (m, 1H), 6.60-6.80 (m, 3H), 6.82 (s, 1H), 7.16-7.30 (m, 5H), 7.38-7.42 (m, 1H), 7.56-7.78 (m, 2H), 7.83 (br s, 1H).

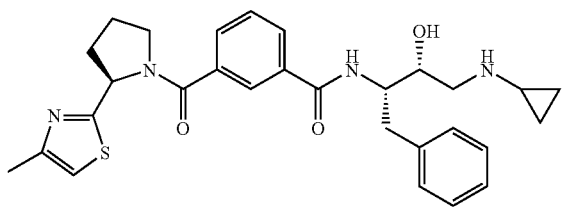

N-((2S,3R)-4-(cyclopropylamino)-3-hydroxy-1-phenylbutan-2-yl)-3-((R)-2-(4-methylthiazol-2-yl)pyrrolidine-1-carbonyl)benzamide: $^1$H NMR (300 MHz, CDCl$_3$): δ 0.36-0.40 (m, 2H), 0.42-0.52 (m, 2H), 1.82-2.00 (m, 1H), 2.00-2.18 (m, 2H), 2.14-2.30 (m, 2H), 2.44 (s, 3H), 2.78-3.14 (m, 4H), 3.40-3.52 (m, 1H), 3.62-3.78 (m, 2H), 4.24-4.40 (m, 1H), 5.58-5.64 (m, 1H), 6.80 (s, 1H), 7.22-7.38 (m, 5H), 7.40-7.48 (m, 1H), 7.60-7.78 (m, 2H), 7.82 (s, 1H).

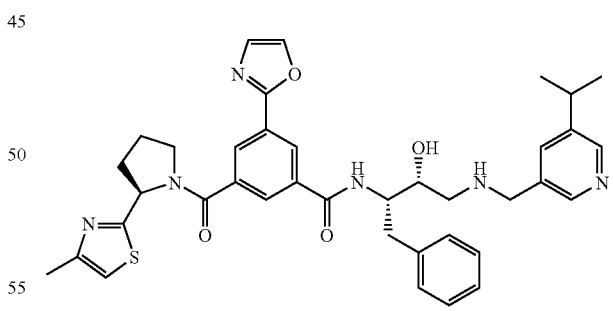

N-((2S,3R)-3-hydroxy-4-((5-isopropylpyridin-3-yl)methylamino)-1-phenylbutan-2-yl)-3-((R)-2-(4-methylthiazol-2-yl)pyrrolidine-1-carbonyl)-5-(oxazol-2-yl)benzamide: $^1$H NMR (300 MHz, CDCl$_3$): δ 1.25 (d, J=6.6 Hz, 6H), 1.90-2.02 (m, 1H), 2.05-2.20 (m, 1H), 2.22-2.52 (m, 2H), 2.48 (s, 3H), 2.78-3.08 (m, 5H), 3.40-3.58 (m, 1H), 3.68-3.98 (m, 4H), 4.30-4.52 (m, 1H), 5.64-5.74 (m, 1H), 6.81 (s, 1H), 7.18-7.38 (m, 5H), 7.58 (br s, 1H), 7.78 (br s, 1H), 7.92 (br s, 2H), 8.30-8.42 (m, 4H).

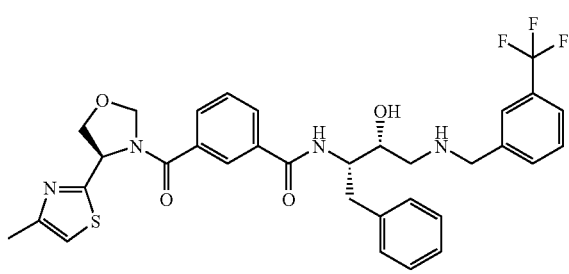

N-((2S,3R)-3-hydroxy-1-phenyl-4-(3-(trifluoromethyl)benzylamino)butan-2-yl)-3-((R)-4-(4-methylthiazol-2-yl)oxazolidine-3-carbonyl)benzamide: ¹H NMR (300 MHz, CDCl₃): δ 2.45 (s, 3H), 2.82 (d, J=4.5 Hz, 2H), 3.01 (d, J=7.2 Hz, 2H), 3.70-3.80 (m, 1H), 3.80-3.98 (m, 2H), 4.30-4.60 (m, 3H), 4.90-5.22 (m, 2H), 5.60-5.80 (m, 1H), 6.82 (s, 1H), 7.20-7.36 (m, 5H), 7.36-7.92 (m, 8H).

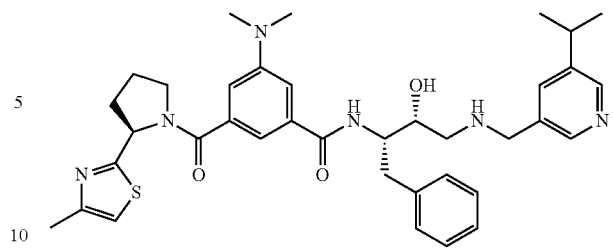

3-(dimethylamino)-N-((2S,3R)-3-hydroxy-4-((5-isopropylpyridin-3-yl)methylamino)-1-phenylbutan-2-yl)-5-((R)-2-(4-methylthiazol-2-yl)pyrrolidine-1-carbonyl)benzamide: ¹H NMR (300 MHz, CDCl₃): δ 1.25 (d, J=6.6 Hz, 6H), 1.84-1.98 (m, 1H), 1.98-2.16 (m, 1H), 2.20-2.52 (m, 2H), 2.44 (s, 3H), 2.72-3.20 (m, 5H), 2.97 (s, 6H), 3.39-3.52 (m, 1H), 3.62-3.76 (m, 1H), 3.76-3.84 (m, 3H), 4.24-4.42 (m, 1H), 5.54-5.62 (m, 1H), 6.80 (s, 1H), 6.84-7.04 (m, 3H), 7.04-7.38 (m, 5H), 7.62 (br s, 1H), 8.35 (br s, 2H).

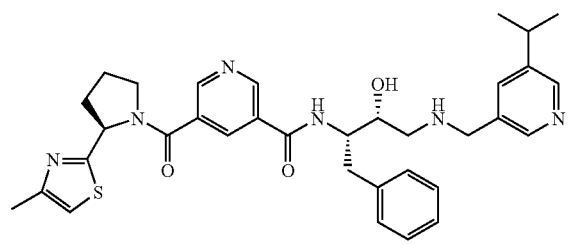

N-((2S,3R)-3-hydroxy-4-((5-isopropylpyridin-3-yl)methylamino)-1-phenylbutan-2-yl)-5-((R)-2-(4-methylthiazol-2-yl)pyrrolidine-1-carbonyl)nicotinamide: ¹H NMR (300 MHz, CDCl₃): δ 1.26 (d, J=7.2 Hz, 6H), 1.92-2.54 (m, 4H), 2.45 (s, 3H), 2.78-3.10 (m, 5H), 3.40-3.58 (m, 1H), 3.70-3.98 (m, 4H), 4.32-4.44 (m, 1H), 5.60-5.66 (m, 1H), 6.82 (s, 1H), 7.18-7.32 (m, 5H), 7.56-7.58 (m, 1H), 8.18-8.20 (m, 1H), 8.38-8.40 (m, 2H), 8.84-8.88 (m, 2H).

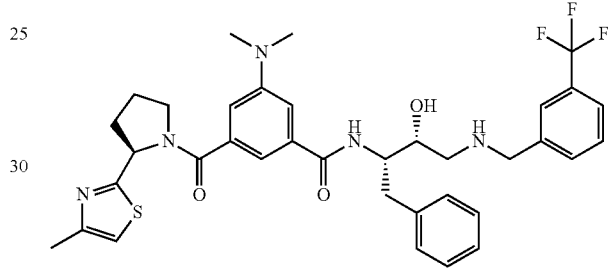

3-(dimethylamino)-N-((2S,3R)-3-hydroxy-1-phenyl-4-(3-(trifluoromethyl)benzylamino)butan-2-yl)-5-((R)-2-(4-methylthiazol-2-yl)pyrrolidine-1-carbonyl)benzamide: ¹H NMR (300 MHz, CDCl₃): δ 1.88-2.00 (m, 1H), 2.00-2.24 (m, 1H), 2.24-2.40 (m, 2H), 2.45 (s, 3H), 2.70-2.90 (m, 2H), 2.90-3.14 (m, 2H), 2.98 (s, 6H), 3.39-3.52 (m, 1H), 3.62-3.80 (m, 2H), 3.80-3.96 (m, 2H), 4.28-4.42 (m, 1H), 5.56-5.62 (m, 1H), 6.80 (s, 1H), 6.90-7.08 (m, 3H), 7.10-7.60 (m, 5H), 7.40-7.58 (m, 3H), 7.60 (br s, 1H).

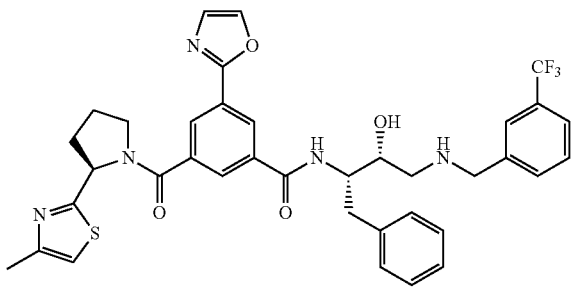

N-((2S,3R)-3-hydroxy-1-phenyl-4-(3-(trifluoromethyl)benzylamino)butan-2-yl)-3-((R)-2-(4-methylthiazol-2-yl)pyrrolidine-1-carbonyl)-5-(oxazol-2-yl)benzamide: ¹H NMR (300 MHz, CDCl₃): δ 1.90-2.02 (m, 1H), 2.02-2.20 (m, 1H), 2.20-2.54 (m, 2H), 2.47 (s, 3H), 2.78-2.92 (m, 2H), 2.98-3.10 (m, 2H), 3.40-3.52 (m, 1H), 3.68-3.80 (m, 2H), 3.80-4.00 (m, 2H), 4.34-4.5 (m, 1H), 5.64-5.72 (m, 1H), 6.81 (s, 1H), 7.10-7.38 (m, 5H), 7.40-7.60 (m, 4H), 7.62 (br s, 1H), 7.76 (br s, 1H), 7.86 (br s, 1H), 8.28 (br s, 2H).

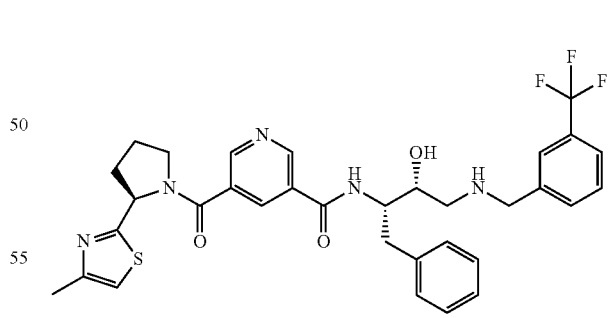

N-((2S,3R)-3-hydroxy-1-phenyl-4-(3-(trifluoromethyl)benzylamino)butan-2-yl)-5-((R)-2-(4-methylthiazol-2-yl)pyrrolidine-1-carbonyl)nicotinamide: ¹H NMR (300 MHz, CDCl₃): δ 1.84-2.02 (m, 1H), 2.02-2.20 (m, 1H), 2.20-2.56 (m, 2H), 2.42 (s, 3H), 2.72-3.14 (m, 4H), 3.42-3.56 (m, 1H), 3.72-3.80 (m, 2H), 3.80-3.94 (m, 2H), 4.28-4.42 (m, 1H), 5.56-5.62 (m, 1H), 6.82 (s, 1H), 7.10-7.30 (m, 5H), 7.40-7.60 (m, 4H), 8.18 (m, 1H), 8.83-8.86 (m, 2H).

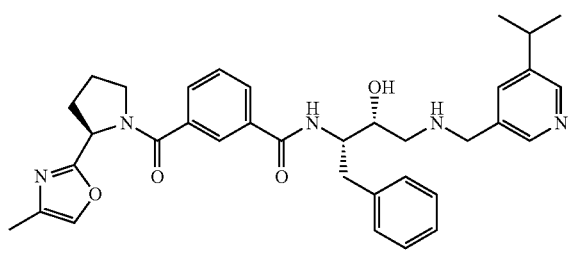

N-((2S,3R)-3-hydroxy-4-((5-isopropylpyridin-3-yl)methylamino)-1-phenylbutan-2-yl)-3-((R)-2-(4-methyloxazol-2-yl)pyrrolidine-1-carbonyl)benzamide: $^1$H NMR (300 MHz, CDCl$_3$): δ 1.27 (d, J=7.2 Hz, 6H), 1.90-2.42 (m, 4H), 2.17 (s, 3H), 2.78-3.16 (m, 5H), 3.42-3.56 (m, 1H), 3.64-3.92 (m, 4H), 4.32-4.50 (m, 1H), 5.36-5.44 (m, 1H), 7.20-7.38 (m, 6H), 7.38-7.44 (m, 1H), 7.52-7.57 (m, 2H), 7.64-7.76 (m, 1H), 7.84 (br s, 1H), 8.40 (br s, 2H).

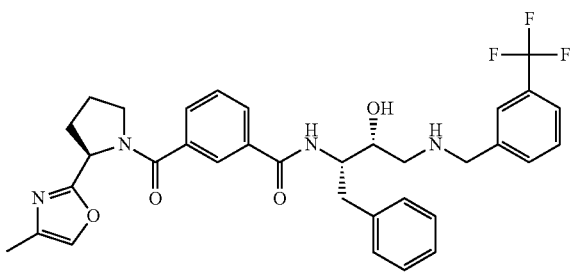

N-((2S,3R)-3-hydroxy-1-phenyl-4-(3-(trifluoromethyl)benzylamino)butan-2-yl)-3-((R)-2-(4-methyloxazol-2-yl)pyrrolidine-1-carbonyl)benzamide: $^1$H NMR (300 MHz, CDCl$_3$): δ 1.80-2.44 (m, 4H), 2.18 (s, 3H), 2.76-2.86 (m, 2H), 2.94-3.16 (m, 2H), 3.44-3.58 (m, 1H), 3.64-3.80 (m, 2H), 3.80-3.96 (m, 2H), 4.34-4.50 (m, 1H), 5.36-5.44 (m, 1H), 7.20-7.38 (m, 7H), 7.38-7.76 (m, 6H), 7.84 (br s, 1H).

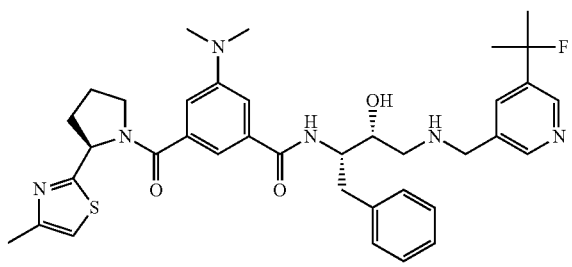

3-(dimethylamino)-N-((2S,3R)-4-((5-(2-fluoropropan-2-yl)pyridin-3-yl)methylamino)-3-hydroxy-1-phenylbutan-2-yl)-5-((R)-2-(4-methylthiazol-2-yl)pyrrolidine-1-carbonyl)benzamide: $^1$H NMR (300 MHz, CDCl$_3$+CD$_3$OD), δ: 8.557 (s, 2H), 7.892 (s, 2H), 7.510 (br, 1H), 7.235 (m, 5H), 6.989 (s, 2H), 6.897 (s, 1H), 6.761 (m, 1.5H), 6.593 (m, 0.5H), 5.618 (br, 1H), 4.336 (br, 1H), 4.060-3.751 (m, 3H), 3.684-3.401 (m, 2H), 3.155 (m, 1H), 2.951 (m, 7H), 2.761 (s, 2H), 2.439 (s, 3H), 2.335 (m, 2H), 2.039 (m, 2H), 1.693 (d, J=21.9 Hz, 6H).

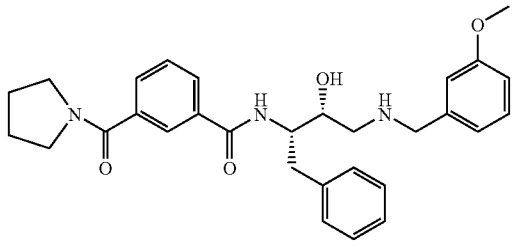

N-((2S,3R)-3-hydroxy-4-(3-methoxybenzylamino)-1-phenylbutan-2-yl)-3-(pyrrolidine-1-carbonyl)benzamide: $^1$H NMR (300 MHz, CDCl$_3$+CD$_3$OD), d: 7.759-7.557 (m, 3H), 7.408-7.147 (m, 7H), 6.902-6.787 (m, 3H), 4.361 (m, 1H), 3.826-3.702 (m, 3H), 3.780 (s, 3H), 3.617 (m, 2H), 3.362 (m, 2H), 3.053-2.839 (m, 3H), 2.798 (m, 3H), 2.014-1.831 (m, 4H).

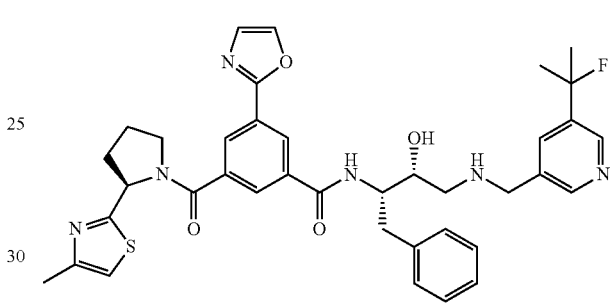

N-((2S,3R)-4-((5-(2-fluoropropan-2-yl)pyridin-3-yl)methylamino)-3-hydroxy-1-phenylbutan-2-yl)-3-((R)-2-(4-methylthiazol-2-yl)pyrrolidine-1-carbonyl)-5-(oxazol-2-yl)benzamide: $^1$H NMR (300 MHz, CDCl$_3$): δ 1.67 (d, 3H, J=2.4 Hz), 1.67 (d, 3H, J=2.4 Hz), 1.90-2.02 (m, 1H), 2.02-2.20 (m, 3H), 2.20-2.32 (m, 1H), 2.34-2.45 (m, 1H), 2.48 (s, 3H), 2.78-2.92 (m, 2H), 2.98-3.12 (m, 2H), 3.42-3.58 (m, 1H), 3.64-3.82 (m, 2H), 3.82-4.00 (m, 2H), 4.34-4.5 (m, 1H), 5.64-5.72 (m, 1H), 6.81 (s, 1H), 7.15-7.38 (m, 5H), 7.73-7.80 (m, 2H), 7.92 (br s, 1H), 8.28-8.38 (m, 2H), 8.50-8.58 (m, 2H).

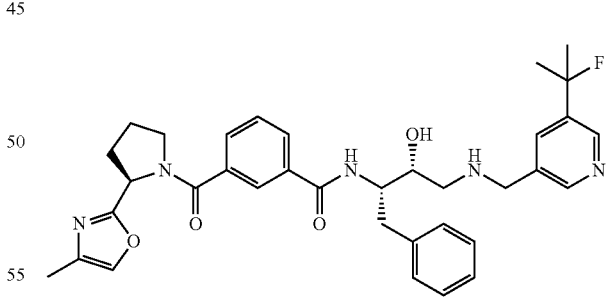

N-((2S,3R)-4-((5-(2-fluoropropan-2-yl)pyridin-3-yl)methylamino)-3-hydroxy-1-phenylbutan-2-yl)-3-((R)-2-(4-methyloxazol-2-yl)pyrrolidine-1-carbonyl)benzamide: $^1$H NMR (300 MHz, CDCl$_3$): δ 1.63 (s, 3H), 1.70 (s, 3H), 1.86-2.00 (m, 1H), 2.01-2.18 (m, 1H), 2.13 (s, 3H), 2.30-2.45 (m, 1H), 2.70-2.78 (m, 2H), 2.81-2.93 (m, 1H), 2.96-3.12 (m, 1H), 3.32-3.50 (m, 1H), 3.62-3.86 (m, 4H), 4.22-4.38 (m, 1H), 5.24-5.32 (m, 1H), 7.19-7.28 (m, 5H), 7.29-7.34 (m, 1H), 7.39-7.45 (m, 1H), 7.62-7.68 (m, 1H), 7.70-7.76 (m, 2H), 7.83 (br s, 1H), 8.40-8.42 (m, 1H), 8.44-8.48 (m, 1H).

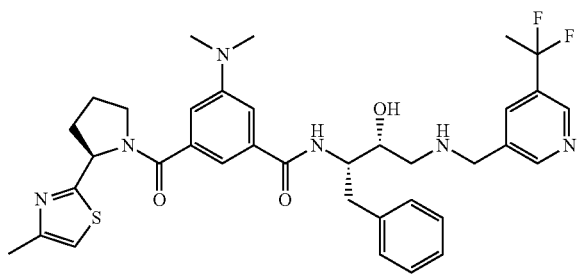

N-((2S,3R)-4-((5-(1,1-difluoroethyl)pyridin-3-yl)methylamino)-3-hydroxy-1-phenylbutan-2-yl)-3-(dimethylamino)-5-((R)-2-(4-methylthiazol-2-yl)pyrrolidine-1-carbonyl)benzamide: $^1$H NMR (300 MHz, CDCl$_3$+CD$_3$OD), d: 8.628 (d, J=6.9 Hz, 2H), 7.873 (s, 1H), 7.245 (m, 5H), 7.013-6.593 (m, 4H), 5.582 (m, 0.7H), 5.087 (m, 0.3H), 4.327 (m, 1H), 3.819 (s, 2H), 3.783 (m, 1H), 3.639 (m, 1H), 3.442 (m, 1H), 3.081 (m, 1H), 2.953 (s, 6H), 2.893 (m, 1H), 2.791 (m, 2H), 2.434 (s, 3H), 2.334 (m, 2H), 2.043 (m, 2H), 1.938 (t, J=18.3, Hz, 3H).

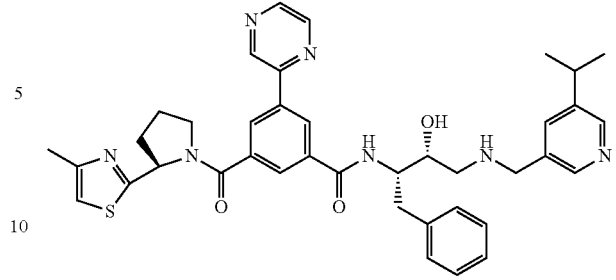

N-((2S,3R)-3-hydroxy-4-((5-isopropylpyridin-3-yl)methylamino)-1-phenylbutan-2-yl)-3-((R)-2-(4-methylthiazol-2-yl)pyrrolidine-1-carbonyl)-5-(pyrazin-2-yl)benzamide: $^1$H NMR (300 MHz, CDCl$_3$): δ 1.23 (d, 6H, J=6.9 Hz), 1.91-1.98 (m, 1H), 2.06-2.14 (m, 1H), 2.34-2.44 (m, 5H), 2.82-3.04 (m, 5H), 3.44-3.50 (m, 1H), 3.66-3.90 (m, 3H), 4.40-4.45 (m, 1H), 5.64-5.68 (m, 1H), 6.80 (s, 1H), 7.17-7.30 (m, 6H), 7.55 (s, 1H), 7.90 (br s, 2H), 8.23 (s, 1H), 8.34-8.39 (m, 2H), 8.52-8.57 (m, 2H), 8.96 (s, 1H).

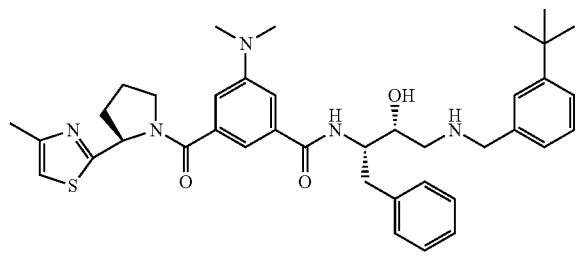

N-((2S,3R)-4-(3-tert-butylbenzylamino)-3-hydroxy-1-phenylbutan-2-yl)-3-(dimethylamino)-5-((R)-2-(4-methylthiazol-2-yl)pyrrolidine-1-carbonyl)benzamide: $^1$H NMR (300 MHz, CDCl$_3$): δ 1.31 (s, 9H), 1.89-1.96 (m, 1H), 2.02-2.10 (m, 1H), 2.35-2.46 (m, 5H), 2.78-3.09 (m, 10H), 3.43-3.49 (m, 1H), 3.60-3.96 (m, 4H), 4.34-4.48 (m, 1H), 5.62-5.66 (m, 1H), 7.05 (s, 1H), 7.19-7.35 (m, 11H), 7.42 (s, 1H).

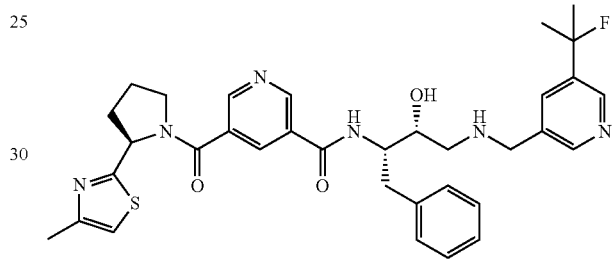

N-((2S,3R)-4-((5-(2-fluoropropan-2-yl)pyridin-3-yl)methylamino)-3-hydroxy-1-phenylbutan-2-yl)-5-((R)-2-(4-methylthiazol-2-yl)pyrrolidine-1-carbonyl)nicotinamide: $^1$H NMR (300 MHz, CDCl$_3$): δ 1.65 (s, 3H), 1.72 (s, 3H), 1.90-2.02 (m, 1H), 2.02-2.20 (m, 1H), 2.22-2.52 (m, 2H), 2.42 (s, 3H), 2.78-2.97 (m, 3H), 2.98-3.18 (m, 2H), 3.41-3.54 (m, 1H), 3.70-3.98 (m, 4H), 4.24-4.42 (m, 1H), 5.54-5.62 (m, 1H), 6.82 (s, 1H), 7.10-7.28 (m, 5H), 7.73-7.78 (m, 1H), 8.13-8.18 (m, 1H), 8.40-8.50 (m, 2H), 8.80-8.88 (m, 1H).

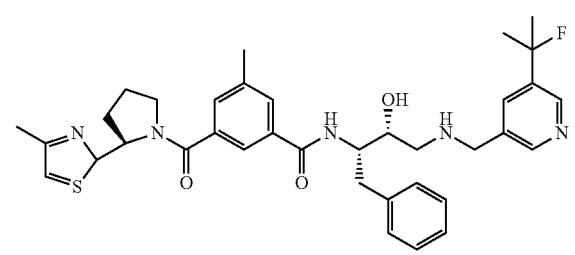

N-((2S,3R)-4-((5-(2-fluoropropan-2-yl)pyridin-3-yl)methylamino)-3-hydroxy-1-phenylbutan-2-yl)-3-methyl-5-((R)-2-(4-methylthiazol-2-yl)pyrrolidine-1-carbonyl)benzamide: $^1$H NMR (300 MHz, CDCl$_3$): δ 1.70 (d, 6H, J=24 Hz), 1.90-2.02 (m, 1H), 205-2.17 (m, 1H), 2.23-2.46 (m, 8H), 2.76-2.83 (m, 2H), 2.95-3.12 (m, 2H), 3.43-3.47 (m, 1H), 3.63-3.86 (m, 4H), 4.26-4.41 (m, 1H), 5.63-5.67 (m, 1H), 6.81 (s, 1H), 7.21-7.30 (m, 5H), 7.43 (s, 1H), 7.47 (s, 1H), 7.57 (s, 1H), 7.74 (t, 1H, J=2.1 Hz), 8.51-8.55 (m, 2H).

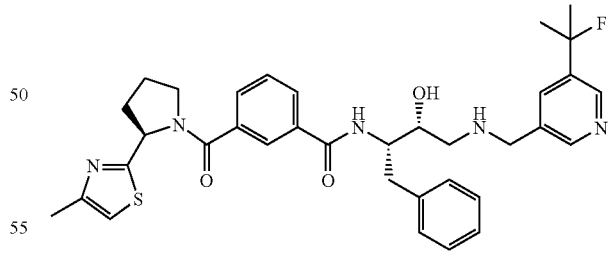

N-((2S,3R)-4-((5-(2-fluoropropan-2-yl)pyridin-3-yl)methylamino)-3-hydroxy-1-phenylbutan-2-yl)-3-((R)-2-(4-methylthiazol-2-yl)pyrrolidine-1-carbonyl)benzamide: $^1$H NMR (300 MHz, CDCl$_3$): δ 1.65 (d, 3H, J=2.1 Hz), 1.72 (d, 3H, J=2.1 Hz), 1.82-2.16 (m, 2H), 2.20-2.60 (m, 2H), 2.44 (s, 3H), 2.70-2.78 (m, 1H), 2.74-2.82 (m, 2H), 2.86-3.12 (m, 2H), 3.40-3.54 (m, 1H), 3.60-3.94 (m, 4H), 4.24-4.42 (m, 1H), 5.54-5.64 (m, 1H), 6.8 (s, 1H), 7.12-7.32 (m, 5H), 7.40-7.48 (m, 1H), 7.62-7.78 (m, 2H), 7.82 (br s, 1H), 8.44-8.53 (m, 2H).

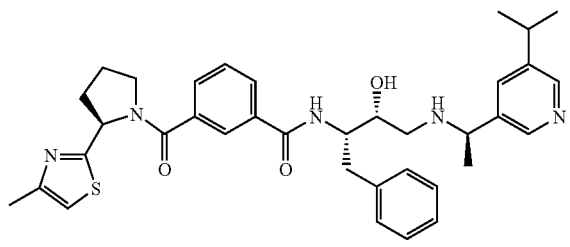

N-((2S,3R)-3-hydroxy-4-((R)-1-(5-isopropylpyridin-3-yl)ethylamino)-1-phenylbutan-2-yl)-3-((R)-2-(4-methylthiazol-2-yl)pyrrolidine-1-carbonyl)benzamide: $^1$H NMR (300 MHz, CDCl$_3$): δ 1.19 (d, J=6.9 Hz, 6H), 1.40 (d, J=6.6 Hz, 3H), 1.84-2.16 (m, 2H), 2.22-2.98 (m, 7H), 2.43 (s, 3H), 3.40-3.52 (m, 1H), 3.62-3.80 (m, 3H), 4.28-4.40 (m, 1H), 5.57-5.64 (m, 1H), 6.79 (br s, 1H), 7.12-7.32 (m, 5H), 7.40-8.00 (m, 5H), 8.30-8.33 (m, 2H).

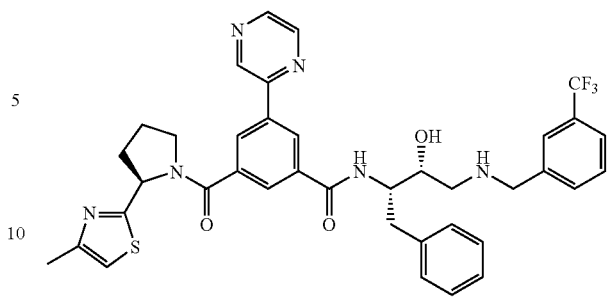

N-((2S,3R)-3-hydroxy-1-phenyl-4-(3-(trifluoromethyl)benzylamino)butan-2-yl)-3-((R)-2-(4-methylthiazol-2-yl)pyrrolidine-1-carbonyl)-5-(pyrazin-2-yl)benzamide: $^1$H NMR (300 MHz, CDCl$_3$): δ 1.94-2.11 (m, 2H), 2.39-2.46 (m, 5H), 2.81-3.08 (m, 4H), 3.41-3.45 (m, 1H), 3.59-3.88 (m, 4H), 4.32-4.39 (m, 1H), 5.62-5.66 (m, 1H), 6.80 (s, 1H), 7.14-7.79 (m, 9H), 7.84 (s, 1H), 8.21 (br s, 2H), 8.48-8.61 (m, 2H), 9.01 (s, 1H).

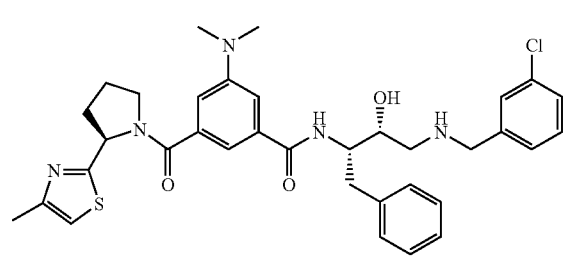

N-((2S,3R)-4-(3-chlorobenzylamino)-3-hydroxy-1-phenylbutan-2-yl)-3-(dimethylamino)-5-((R)-2-(4-methylthiazol-2-yl)pyrrolidine-1-carbonyl)benzamide: $^1$H NMR (300 MHz, CDCl$_3$): δ 1.90-2.10 (m, 2H), 2.35-2.46 (m, 5H), 2.74-3.10 (m, 10H), 3.41-3.47 (m, 1H), 3.62-3.88 (m, 4H), 4.31-4.47 (m, 1H), 5.62-5.66 (m, 1H), 6.79 (s, 1H), 6.91-7.02 (m, 3H), 7.21-7.35 (m, 9H).

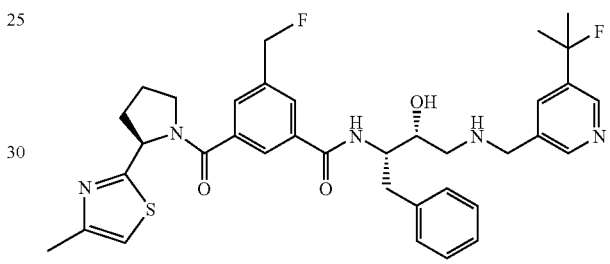

3-(fluoromethyl)-N-((2S,3R)-4-((5-(2-fluoropropan-2-yl)pyridin-3-yl)methylamino)-3-hydroxy-1-phenylbutan-2-yl)-5-((R)-2-(4-methylthiazol-2-yl)pyrrolidine-1-carbonyl)benzamide: $^1$H NMR (300 MHz, CDCl$_3$+CD$_3$OD), d: 8.488 (m, 2H), 7.726 (m, 4H), 7.226 (m, 5H), 6.804 (br, 1H), 5.605 (m, 0.7H), 5.344 (d, J=47.4 Hz, 2H), 5.037 (m, 0.3H), 4.377 (m, 1H), 3.891-3.649 (m, 4H), 3.433 (m, 1H), 3.085-2.888 (m, 2H), 2.795 (m, 2H), 2.502-2.289 (m, 5H), 2.161-1.888 (m, 2H), 1.690 (dd, J=21.9, 2.1 Hz, 6H).

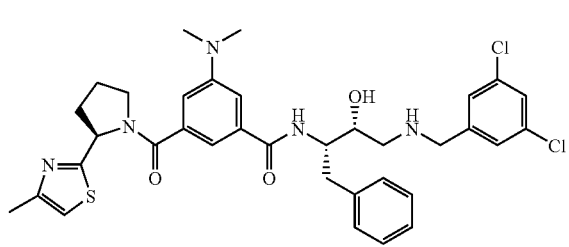

N-((2S,3R)-4-(3,5-dichlorobenzylamino)-3-hydroxy-1-phenylbutan-2-yl)-3-(dimethylamino)-5-((R)-2-(4-methylthiazol-2-yl)pyrrolidine-1-carbonyl)benzamide: $^1$H NMR (300 MHz, CDCl$_3$): δ 1.92-1.95 (m, 1H), 2.04-2.10 (m, 1H), 2.35-2.46 (m, 5H), 2.68-3.14 (m, 10H), 3.42-3.46 (m, 1H), 3.59-3.87 (m, 4H), 4.30-4.37 (m, 1H), 5.62-5.66 (m, 1H), 6.80-7.01 (m, 4H), 7.24-7.30 (m, 8H).

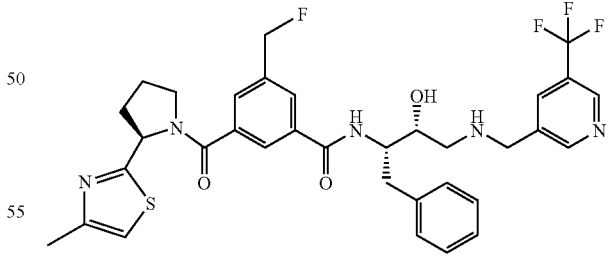

3-(fluoromethyl)-N-((2S,3R)-3-hydroxy-1-phenyl-4-((5-(trifluoromethyl)pyridin-3-yl)methylamino)butan-2-yl)-5-((R)-2-(4-methylthiazol-2-yl)pyrrolidine-1-carbonyl)benzamide: $^1$H NMR (300 MHz, CDCl$_3$+CD$_3$OD), d: 7.776-7.407 (m, 6H), 7.218 (m, 5H), 6.797 (br, 1H), 5.595 (m, 0.7H), 5.318 (d, J=47.1 Hz, 2H), 5.025 (m, 0.3H), 4.356 (m, 1H), 3.907-3.640 (m, 4H), 3.418 (m, 1H), 3.082-2.838 (m, 2H), 2.795 (m, 2H), 2.433 (s, 3H), 2.281 (m, 1H), 2.085 (m, 2H), 1.920 (m, 1H).

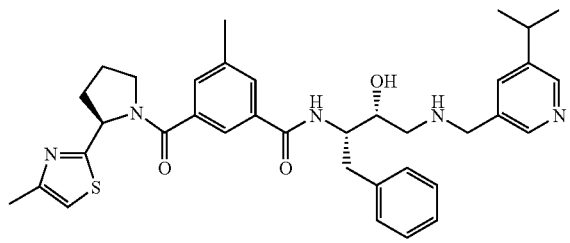
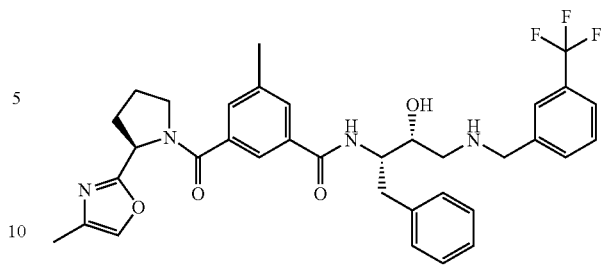

N-((2S,3R)-3-hydroxy-4-((5-isopropylpyridin-3-yl)methylamino)-1-phenylbutan-2-yl)-3-methyl-5-((R)-2-(4-methylthiazol-2-yl)pyrrolidine-1-carbonyl)benzamide: $^1$H NMR (300 MHz, CDCl$_3$): δ 1.26 (d, J=8.4 Hz, 6H), 1.88-1.98 (m, 1H), 2.05-2.18 (m, 1H), 2.18-2.52 (m, 2H), 2.33 (s, 3H), 2.45 (s, 3H), 2.74-3.22 (m, 5H), 3.39-3.50 (m, 1H), 3.62-3.92 (m, 4H), 4.28-4.44 (m, 1H), 5.60-5.68 (m, 1H), 6.80 (s, 1H), 7.14-7.30 (m, 5H), 7.40-7.48 (m, 1H), 7.52-7.55 (m, 2H), 7.58 (br s, 1H), 8.38 (br s, 2H).

N-((2S,3R)-3-hydroxy-1-phenyl-4-(3-(trifluoromethyl)benzylamino)butan-2-yl)-3-methyl-5-((R)-2-(4-methyloxazol-2-yl)pyrrolidine-1-carbonyl)benzamide: $^1$H NMR (300 MHz, CDCl$_3$): δ 1.65-2.44 (m, 4H), 2.18 (s, 3H), 2.38 (s, 3H), 2.72-2.86 (m, 2H), 2.90-3.20 (m, 2H), 3.40-3.50 (m, 1H), 3.64-3.80 (m, 2H), 3.80-3.94 (m, 2H), 4.30-4.44 (m, 1H), 5.30-5.40 (m, 1H), 7.10-7.36 (m, 7H), 7.36-7.66 (m, 6H).

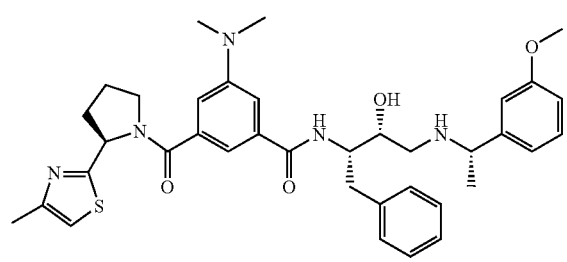
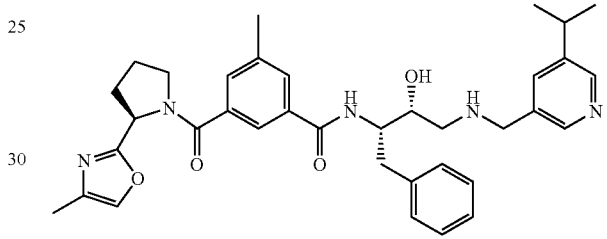

3-(dimethylamino)-N-((2S,3R)-3-hydroxy-4-((S)-1-(3-methoxyphenyl)ethylamino)-1-phenylbutan-2-yl)-5-((R)-2-(4-methylthiazol-2-yl)pyrrolidine-1-carbonyl)benzamide: $^1$H NMR (300 MHz, CDCl$_3$+CD$_3$OD), d: 7.207 (m, 6H), 6.995-6.723 (m, 7H), 5.573 (m, 0.7H), 5.073 (m, 0.3H), 4.289 (m, 1H), 3.780 (s, 3H), 3.851-3.601 (m, 3H), 3.423 (m, 1H), 3.085-2.860 (m, 6H), 2.746-2.623 (m, 4H), 2.430 (s, 3H), 2.320 (m, 2H), 2.118-1.874 (m, 2H), 1.425 (d, J=6.6 Hz, 3H).

N-((2S,3R)-3-hydroxy-4-((5-isopropylpyridin-3-yl)methylamino)-1-phenylbutan-2-yl)-3-methyl-5-((R)-2-(4-methyloxazol-2-yl)pyrrolidine-1-carbonyl)benzamide: $^1$H NMR (300 MHz, CDCl$_3$): δ 1.26 (d, J=6.9 Hz, 6H), 1.88-2.42 (m, 4H), 2.17 (s, 3H), 2.37 (s, 3H), 2.76-2.84 (m, 2H), 2.84-3.00 (m, 2H), 3.00-3.16 (m, 1H), 3.40-3.52 (m, 1H), 3.62-3.94 (m, 4H), 4.28-4.44 (m, 1H), 5.30-5.40 (m, 1H), 7.16-7.40 (m, 6H), 7.40-7.64 (m, 4H), 8.38 (br s, 2H)

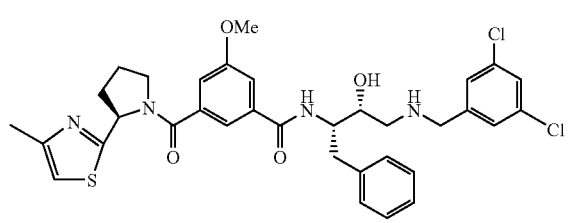
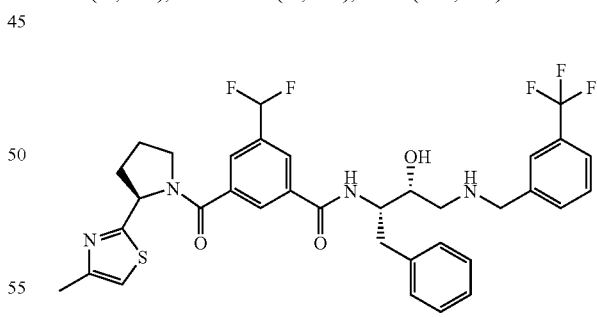

N-((2S,3R)-4-(3,5-dichlorobenzylamino)-3-hydroxy-1-phenylbutan-2-yl)-3-methoxy-5-((R)-2-(4-methylthiazol-2-yl)pyrrolidine-1-carbonyl)benzamide: $^1$H NMR (300 MHz, CDCl$_3$): δ 1.91-1.97 (m, 1H), 2.05-2.14 (m, 1H), 2.33-2.46 (m, 5H), 2.70-2.81 (m, 2H), 2.93-3.12 (m, 2H), 3.42-3.48 (m, 1H), 3.61-3.79 (m, 7H), 4.32-4.38 (m, 1H), 5.62-5.66 (m, 1H), 6.80 (s, 1H), 7.05-7.32 (m, 11H).

3-(difluoromethyl)-N-((2S,3R)-3-hydroxy-1-phenyl-4-(3-(trifluoromethyl)benzylamino)butan-2-yl)-5-((R)-2-(4-methylthiazol-2-yl)pyrrolidine-1-carbonyl)benzamide: $^1$H NMR (300 MHz, CDCl$_3$+CD$_3$OD), d: 7.948-7.408 (m, 7H), 7.217 (m, 5H), 6.811 (s, 1H), 6.617 (t, J=57.2, 114.3 Hz, 1H), 5.579 (m, 0.7H), 4.988 (m, 0.3H), 4.356 (m, 1H), 3.909-3.656 (m, 4H), 3.409 (m, 1H), 3.096-2.856 (m, 2H), 2.782 (m, 2H), 2.431 (s, 3H), 2.305 (m, 2H), 2.162-1.890 (m, 2H).

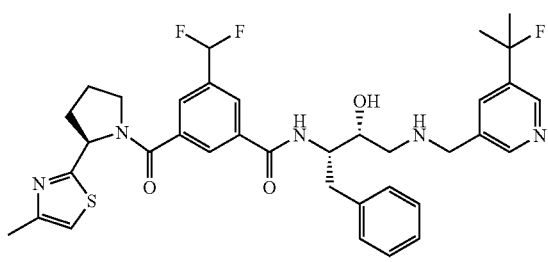

3-(difluoromethyl)-N-((2S,3R)-4-((5-(2-fluoropropan-2-yl)pyridin-3-yl)methylamino)-3-hydroxy-1-phenylbutan-2-yl)-5-((R)-2-(4-methylthiazol-2-yl)pyrrolidine-1-carbonyl)benzamide: $^1$H NMR (300 MHz, CDCl$_3$+CD$_3$OD), d 8.452 (m, 2H), 7.902-7.593 (m, 4H), 7.218 (m, 5H), 6.812 (s, 1H), 6.618 (t, J=57.0, 114.0 Hz, 1H), 5.588 (m, 0.7H), 4.966 (m, 0.3H), 4.360 (m, 1H), 3.888-3.651 (m, 4H), 3.441 (m, 1H), 3.094-2.868 (m, 2H), 2.794 (m, 2H), 2.434 (s, 3H), 2.334 (m, 2H), 2.126-1.894 (m, 2H), 1.752 (d, J=21.9 Hz, 6H).

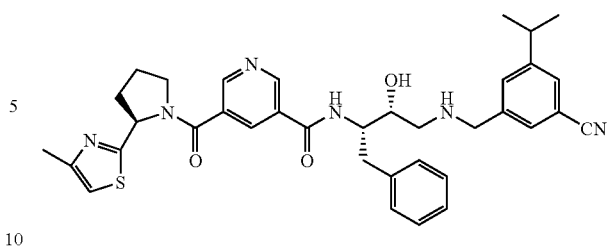

N-((2S,3R)-4-(3-cyano-5-isopropylbenzylamino)-3-hydroxy-1-phenylbutan-2-yl)-5-((R)-2-(4-methylthiazol-2-yl)pyrrolidine-1-carbonyl)nicotinamide: $^1$H NMR (300 MHz, CDCl$_3$): δ 1.16 (d, 6H, J=6.9 Hz), 1.92-1.98 (m, 1H), 2.08-2.13 (m, 1H), 2.27-2.43 (m, 5H), 2.85-3.03 (m, 5H), 3.42-3.48 (m, 1H), 3.67-3.72 (m, 1H), 3.84-3.98 (m, 3H), 4.38-4.45 (m, 1H), 5.61-5.65 (m, 1H), 6.80 (s, 1H), 7.21-7.30 (m, 6H), 7.62 (s, 1H), 7.77 (s, 1H), 8.18 (s, 1H), 8.79 (s, 1H), 8.87 (s, 1H).

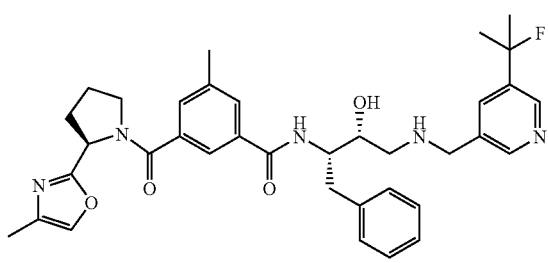

N-((2S,3R)-4-((5-(2-fluoropropan-2-yl)pyridin-3-yl)methylamino)-3-hydroxy-1-phenylbutan-2-yl)-3-methyl-5-((R)-2-(4-methyloxazol-2-yl)pyrrolidine-1-carbonyl)benzamide: $^1$H NMR (300 MHz, CDCl$_3$): δ 1.66 (d, 3H, J=2.1 Hz), 1.74 (d, 3H, J=2.1 Hz), 1.80-2.06 (m, 2H), 2.06-2.43 (m, 2H), 2.18 (s, 3H), 2.38 (s, 3H), 2.70-2.84 (m, 2H), 2.84-3.20 (m, 2H), 3.40-3.54 (m, 1H), 3.62-3.94 (m, 4H), 4.26-4.42 (m, 1H), 5.32-5.40 (m, 1H), 7.16-7.40 (m, 6H), 7.40-7.80 (m, 4H), 8.46-8.48 (m, 2H).

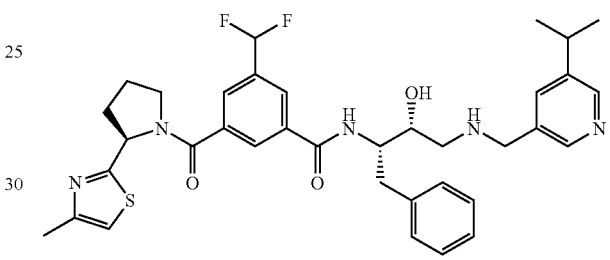

3-(difluoromethyl)-N-((2S,3R)-3-hydroxy-4-((5-isopropylpyridin-3-yl)methylamino)-1-phenylbutan-2-yl)-5-((R)-2-(4-methylthiazol-2-yl)pyrrolidine-1-carbonyl)benzamide: $^1$H NMR (300 MHz, CDCl$_3$+CD$_3$OD), d: 8.327 (s, 2H), 7.982-7.539 (m, 4H), 7.215 (m, 5H), 6.809 (s, 1H), 6.623 (t, J=55.8, 111.6 Hz, 1H), 5.592 (m, 0.7H), 4.991 (m, 0.3H), 4.363 (m, 1H), 3.790 (m, 4H), 3.421 (m, 1H), 3.083-2.866 (m, 3H), 2.798 (m, 2H), 2.430 (s, 3H), 2.309 (m, 2H), 2.141-1.891 (m, 2H), 1.234 (d, J=6.6 Hz, 3H).

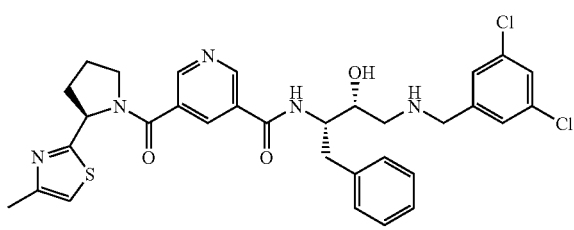

N-((2S,3R)-4-(3,5-dichlorobenzylamino)-3-hydroxy-1-phenylbutan-2-yl)-5-((R)-2-(4-methylthiazol-2-yl)pyrrolidine-1-carbonyl)nicotinamide: $^1$H NMR (300 MHz, CDCl$_3$): δ 1.95-2.01 (m, 1H), 2.07-2.18 (m, 1H), 2.29-2.45 (m, 5H), 2.78-3.09 (m, 4H), 3.45-3.49 (m, 1H), 3.69-3.85 (m, 4H), 4.36-4.42 (m, 1H), 5.62-5.66 (m, 1H), 6.81 (s, 1H), 7.18-7.30 (m, 8H), 8.12 (s, 1H), 8.78-8.81 (m, 2H).

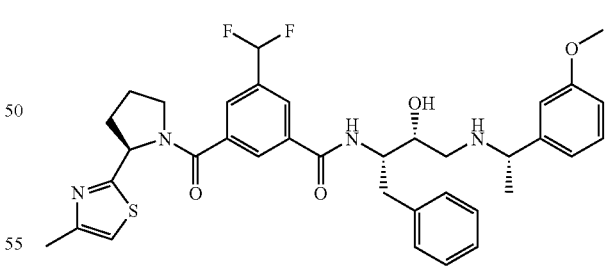

3-(difluoromethyl)-N-((2S,3R)-3-hydroxy-4-((S)-1-(3-methoxyphenyl)ethylamino)-1-phenylbutan-2-yl)-5-((R)-2-(4-methylthiazol-2-yl)pyrrolidine-1-carbonyl)benzamide: $^1$H NMR (300 MHz, CDCl$_3$+CD$_3$OD), d: 7.919-7.630 (m, 3H), 7.230 (m, 5H), 6.913-6.459 (m, 5H), 5.612 (m, 0.7H), 5.005 (m, 0.3H), 4.352 (m, 1H), 3.801 (s, 3H), 3.897-3.658 (m, 3H), 3.425 (m, 1H), 3.082-2.893 (m, 2H), 2.696 (m, 2H), 2.452 (s, 3H), 2.346 (m, 2H), 2.158-1.902 (m, 2H), 1.234 (d, J=6.6 Hz, 3H).

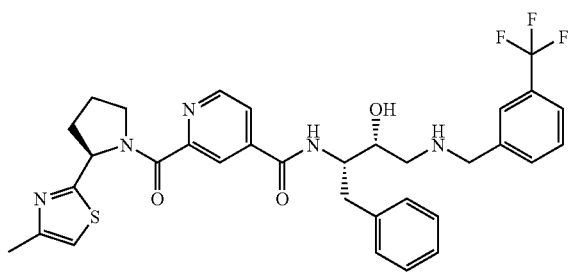

N-((2S,3R)-3-hydroxy-1-phenyl-4-(3-(trifluoromethyl) benzylamino)butan-2-yl)-2-((R)-2-(4-methylthiazol-2-yl) pyrrolidine-1-carbonyl)isonicotinamide: $^1$H NMR (300 MHz, CDCl$_3$) δ 8.63-8.65 (m, 1H), 8.26 (s, 1H), 8.10-8.14 (m, 1H), 7.44-7.63 (m, 4H), 7.19-7.35 (m, 5H), 6.827-6.83 (m, 1H), 5.66-5.70 (m, 1H), 4.27-4.44 (m, 1H), 3.90 (s, 3H), 3.84-4.02 (m, 1H), 3.62-3.84 (m, 2H), 3.44-3.52 (m, 1H), 3.14-3.20 (m, 1H), 2.97-3.11 (m, 1H), 2.73-2.88 (m, 2H), 2.33-2.51 (m, 4H), 2.07-2.33 (m, 2H), 1.95-2.07 (m, 1H).

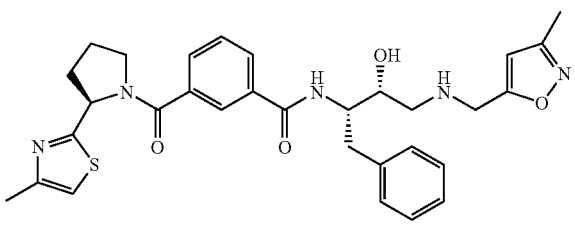

N-((2S,3R)-3-hydroxy-4-((3-methylisoxazol-5-yl)methylamino)-1-phenylbutan-2-yl)-3-((R)-2-(4-methylthiazol-2-yl)pyrrolidine-1-carbonyl)benzamide: $^1$H NMR (300 MHz, CDCl$_3$) δ 7.34 (s, 1H), 7.72-7.64 (m, 2H), 7.53-7.45 (m, 1H), 7.41-7.21 (m, 8H), 6.95-6.53 (m, 2H), 6.03 (s, 1H), 5.71-5.67 (m, 0.7H), 5.07 (m, 0.2H), 4.43-4.40 (m, 1H), 3.94 (m, 2H), 3.72-3.67 (m, 2H), 3.53-3.47 (m, 2H), 3.07-3.04 (m, 2H), 2.84 (m, 2H), 2.48-2.30 (m, 8H), 2.14-1.64 (m, 4H).

N-((2S,3R)-3-hydroxy-4-((5-methylisoxazol-3-yl)methylamino)-1-phenylbutan-2-yl)-3-((R)-2-(4-methylthiazol-2-yl)pyrrolidine-1-carbonyl)benzamide: $^1$H NMR (300 MHz, CDCl$_3$) δ 7.84 (m, 1H), 7.73-7.64 (m, 2H), 7.52-7.43 (m, 2H), 7.40-7.14 (m, 7H), 6.92 (m, 1H), 6.82 (s, 1H), 6.69-6.58 (m, 1H), 6.00 (s, 1H), 5.71-5.66 (m, 0.7H), 5.08 (m, 0.2H), 4.46-4.41 (m, 1H), 3.89 (m, 2H), 3.75-3.67 (m, 2H), 3.52-3.44 (m, 2H), 3.07-3.05 (m, 2H), 2.86-2.79 (m, 2H), 2.48-2.32 (m, 8H), 2.34-1.92 (m, 4H).

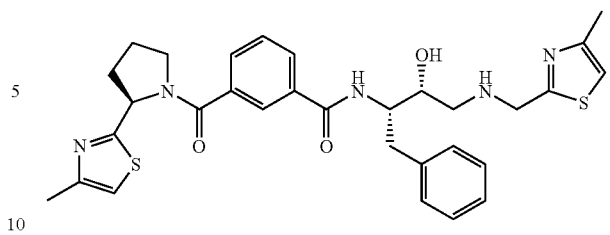

N-((2S,3R)-3-hydroxy-4-((4-methylthiazol-2-yl)methylamino)-1-phenylbutan-2-yl)-3-((R)-2-(4-methylthiazol-2-yl)pyrrolidine-1-carbonyl)benzamide: $^1$H NMR (300 MHz, CDCl$_3$) δ 7.85 (m, 1H), 7.73-7.64 (m, 2H), 7.54-7.46 (m, 1H), 7.36-7.23 (m, 7H), 6.95-6.82 (m, 2H), 5.71-5.67 (m, 0.6H), 5.10 (m, 0.2H), 4.50-4.46 (m, 1H), 4.21-4.09 (m, 2H), 3.74-3.69 (m, 2H), 3.49 (m, 1H), 3.08-3.06 (m, 2H), 2.94-2.93 (m, 2H), 2.48-2.32 (m, 8H), 2.32-1.93 (m, 4H).

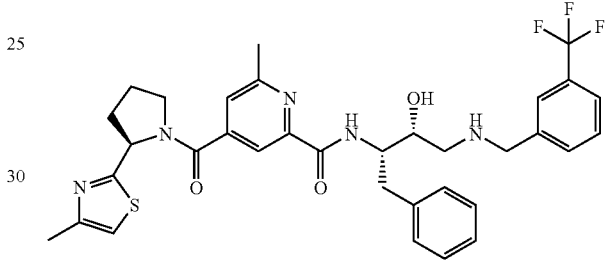

N-((2S,3R)-3-hydroxy-1-phenyl-4-(3-(trifluoromethyl) benzylamino)butan-2-yl)-6-methyl-4-((R)-2-(4-methylthiazol-2-yl)pyrrolidine-1-carbonyl)picolinamide: $^1$H NMR (300 MHz, CDCl$_3$) δ 8.27-8.30 (m, 1H), 8.062-8.064 (m, 1H), 7.63 (s, 1H), 7.43-7.65 (m, 4H), 7.21-7.35 (m, 5H), 6.82-6.83 (m, 1H), 5.65-5.69 (m, 1H), 4.23-4.40 (m, 1H), 3.90 (s, 2H), 3.83-4.00 (m, 1H), 3.59-3.77 (m, 2H), 3.43-3.51 (m, 1H), 3.07-3.16 (m, 2H), 2.68-2.86 (m, 2H), 2.61 (s, 3H), 2.37-2.49 (m, 4H), 2.06-2.29 (m, 2H), 1.92-2.06 (m, 1H).

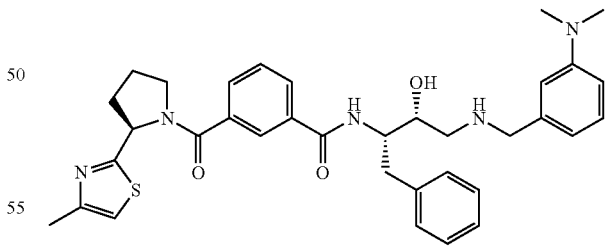

N-((2S,3R)-4-(3-(dimethylamino)benzylamino)-3-hydroxy-1-phenylbutan-2-yl)-3-((R)-2-(4-methylthiazol-2-yl) pyrrolidine-1-carbonyl)benzamide: $^1$H NMR (300 MHz, CDCl$_3$) δ 7.89 (m, 1H), 7.76-7.63 (m, 2H), 7.54-7.36 (m, 2H), 7.35-7.18 (m, 8H), 6.85-6.81 (m, 2H), 6.73-6.53 (m, 2H), 5.89-5.64 (m, 0.6H), 5.13 (m, 0.3H), 4.40 (m, 1H), 4.05-3.92 (m, 3H), 3.70-3.62 (m, 1H), 3.48-3.39 (m, 1H), 3.06-2.84 (m, 8H), 2.46-2.23 (m, 5H), 2.10-1.92 (m, 2H).

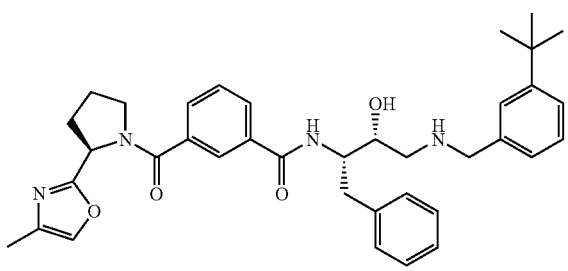

N-((2S,3R)-4-(3-tert-butylbenzylamino)-3-hydroxy-1-phenylbutan-2-yl)-3-((R)-2-(4-methyloxazol-2-yl)pyrrolidine-1-carbonyl)benzamide: ¹H NMR (300 MHz, CDCl₃): δ 1.24 (s, 9H), 1.92-2.42 (m, 7H), 2.86-3.05 (m, 4H), 3.42-3.52 (m, 1H), 3.68-3.97 (m, 4H), 4.34-4.43 (m, 1H), 5.32-5.42 (m, 1H), 7.16-7.41 (m, 11H), 7.63-7.77 (m, 2H), 7.91 (s, 1H).

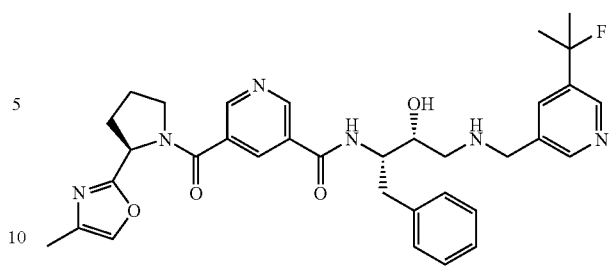

N-((2S,3R)-4-((5-(2-fluoropropan-2-yl)pyridin-3-yl)methylamino)-3-hydroxy-1-phenylbutan-2-yl)-5-((R)-2-(4-methyloxazol-2-yl)pyrrolidine-1-carbonyl)nicotinamide: ¹H NMR (300 MHz, CDCl₃): δ 1.68 (s, 3H), 1.75 (s, 3H), 1.80-2.04 (m, 2H), 2.04-2.24 (m, 1H), 2.17 (s, 3H), 2.24-2.44 (m, 1H), 2.80-2.86 (m, 2H), 2.90-3.16 (m, 2H), 3.42-3.60 (m, 1H), 3.74-3.96 (m, 4H), 4.34-4.46 (m, 1H), 5.36-5.42 (m, 1H), 7.16-7.40 (m, 6H), 7.76-7.78 (m, 1H), 8.20 (br s, 1H), 8.48-8.60 (m, 2H), 8.84 (br s, 2H).

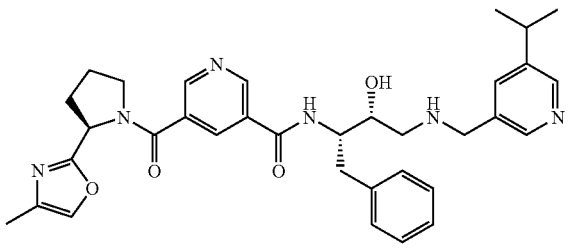

N-((2S,3R)-3-hydroxy-4-((5-isopropylpyridin-3-yl)methylamino)-1-phenylbutan-2-yl)-5-((R)-2-(4-methyloxazol-2-yl)pyrrolidine-1-carbonyl)nicotinamide: ¹H NMR (300 MHz, CDCl₃): δ 1.26 (d, J=7.2 Hz, 6H), 1.92-2.44 (m, 5H), 2.17 (s, 3H), 2.78-2.82 (m, 2H), 2.84-3.00 (m, 2H), 3.00-3.16 (m, 1H), 3.74-3.96 (m, 4H), 4.32-4.44 (m, 1H), 5.34-5.40 (m, 1H), 7.14-7.38 (m, 6H), 7.38-7.40 (m, 1H), 8.20-8.22 (m, 1H), 8.38-8.40 (m, 2H), 8.90-8.94 (m, 2H).

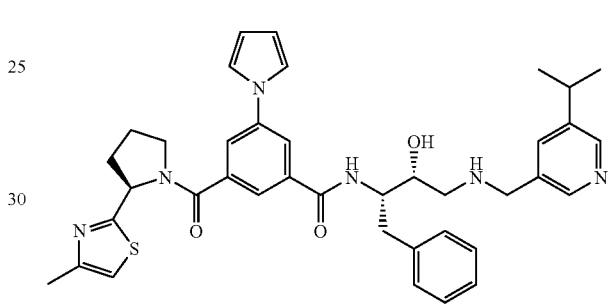

N-((2S,3R)-3-hydroxy-4-((5-isopropylpyridin-3-yl)methylamino)-1-phenylbutan-2-yl)-3-((R)-2-(4-methylthiazol-2-yl)pyrrolidine-1-carbonyl)-5-(1H-pyrrol-1-yl)benzamide: ¹H NMR (300 MHz, CDCl₃) δ 8.40-8.39 (m, 2H), 7.64-7.49 (m, 4H), 7.34-7.19 (m, 7H), 6.99-6.73 (m, 3H), 6.37-6.32 (m, 2H), 5.69-5.64 (m, 0.7H), 5.09-5.06 (m, 0.2H), 4.41 (m, 1H), 3.90-3.62 (m, 5H), 3.47-3.42 (m, 1H), 3.11-2.80 (m, 6H), 2.48-2.33 (m, 5H), 2.17-1.91 (m, 3H), 1.27 (d, 6H).

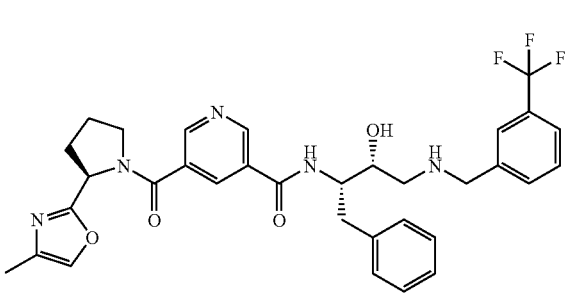

N-((2S,3R)-3-hydroxy-1-phenyl-4-(3-(trifluoromethyl)benzylamino)butan-2-yl)-5-((R)-2-(4-methyloxazol-2-yl)pyrrolidine-1-carbonyl)nicotinamide: ¹H NMR (300 MHz, CDCl₃): δ 1.80-2.46 (m, 4H), 2.17 (s, 3H), 2.80-2.88 (m, 2H), 2.90-3.14 (m, 2H), 3.42-3.58 (m, 1H), 3.72-3.80 (m, 2H), 3.80-3.96 (m, 2H), 4.34-4.46 (m, 1H), 5.34-5.42 (m, 1H), 7.12-7.38 (m, 6H), 7.40-7.62 (m, 4H), 8.20 (br s, 1H), 8.88 (br s, 2H).

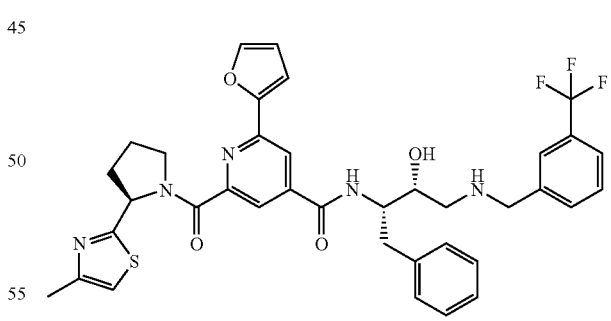

2-(furan-2-yl)-N-((2S,3R)-3-hydroxy-1-phenyl-4-(3-(trifluoromethyl)benzylamino)butan-2-yl)-6-((R)-2-(4-methylthiazol-2-yl)pyrrolidine-1-carbonyl)isonicotinamide: ¹H NMR (300 MHz, CDCl₃) δ 8.01-8.03 (m, 1H), 7.34-7.66 (m, 5H), 7.16-7.34 (m, 5H), 7.08-7.09 (m, 1H), 6.677-6.680 (m, 1H), 6.60-6.66 (m, 1H), 6.56-6.58 (m, 1H), 6.46-6.47 (m, 1H), 5.70-5.74 (m, 1H), 4.40-4.52 (m, 1H), 4.14-4.26 (m, 1H), 3.83-4.05 (m, 3H), 3.71-3.83 (m, 1H), 3.00-3.02 (m, 2H), 2.77-2.90 (m, 2H), 2.33-2.49 (m, 4H), 2.13-2.27 (m, 1H), 1.87-2.13 (m, 2H).

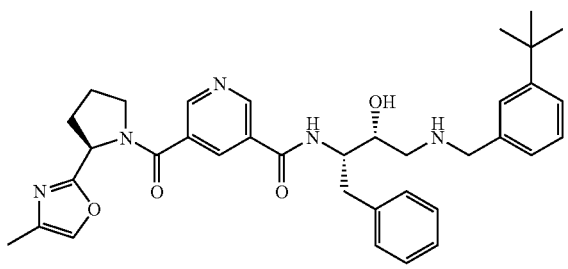

N-((2S,3R)-4-(3-tert-butylbenzylamino)-3-hydroxy-1-phenylbutan-2-yl)-5-((R)-2-(4-methyloxazol-2-yl)pyrrolidine-1-carbonyl)nicotinamide: ¹H NMR (300 MHz, CDCl₃): δ 1.24 (s, 9H), 1.92-2.43 (m, 7H), 2.83-3.05 (m, 4H), 3.45-3.53 (m, 1H), 3.70-3.98 (m, 4H), 4.36-4.45 (m, 1H), 5.34-5.39 (m, 1H), 7.18-7.40 (m, 10H), 8.24 (s, 1H), 8.83 (br s, 1H), 8.93 (br s, 1H).

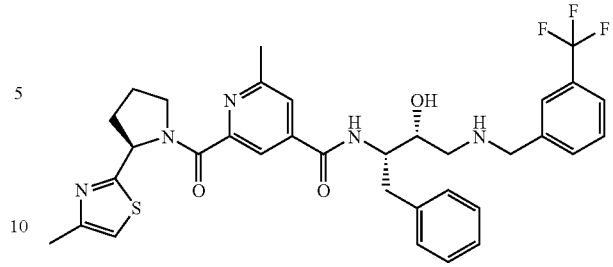

N-((2S,3R)-3-hydroxy-1-phenyl-4-(3-(trifluoromethyl)benzylamino)butan-2-yl)-2-methyl-6-((R)-2-(4-methylthiazol-2-yl)pyrrolidine-1-carbonyl)isonicotinamide: ¹H NMR (300 MHz, CDCl₃) δ 7.76-7.88 (m, 1H), 7.73 (s, 1H), 7.34-7.64 (m, 6H), 7.13-7.34 (m, 5H), 6.766-6.77 (m, 1H), 6.618-6.62 (m, 1H), 5.71-5.75 (m, 1H), 4.32-4.45 (m, 1H), 3.80-4.06 (m, 4H), 3.71-3.80 (m, 1H), 3.60-3.71 (m, 1H), 2.98-3.02 (m, 2H), 2.79-2.85 (m, 2H), 2.48 (s, 3H), 2.28-2.45 (m, 4H), 1.94-2.21 (m, 3H).

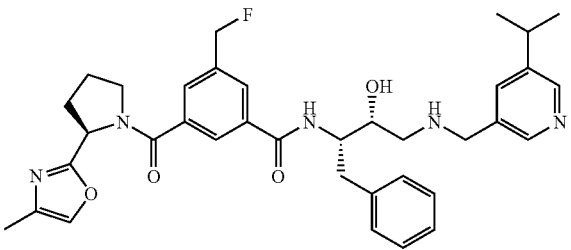

3-(fluoromethyl)-N-((2S,3R)-3-hydroxy-4-((5-isopropylpyridin-3-yl)methylamino)-1-phenylbutan-2-yl)-5-((R)-2-(4-methyloxazol-2-yl)pyrrolidine-1-carbonyl)benzamide: ¹H NMR (300 MHz, CDCl₃): δ 1.26 (d, J=7.2 Hz, 6H), 1.82-2.42 (m, 4H), 2.18 (s, 3H), 2.78-2.84 (m, 2H), 2.84-3.12 (m, 4H), 3.40-3.58 (m, 1H), 3.64-3.94 (m, 3H), 4.36-4.46 (m, 1H), 5.36-5.42 (m, 1H), 5.24 (s, 1H), 5.42 (s, 1H), 7.16-7.40 (m, 6H), 7.40-7.64 (m, 3H), 7.80 (br s, 1H), 8.39 (br s, 2H).

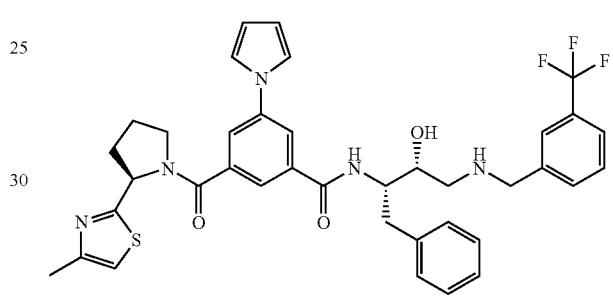

N-((2S,3R)-3-hydroxy-1-phenyl-4-(3-(trifluoromethyl)benzylamino)butan-2-yl)-3-((R)-2-(4-methylthiazol-2-yl)pyrrolidine-1-carbonyl)-5-(1H-pyrrol-1-yl)benzamide: ¹H NMR (300 MHz, CDCl₃) δ 7.64-7.42 (m, 7H), 7.34-7.19 (m, 7H), 6.96 (s, 2H), 6.83 (m, 1H), 6.37-6.32 (m, 2H), 5.68-5.64 (m, 0.7H), 5.07-5.05 (m, 0.3H), 4.40 (m, 1H), 3.98-3.61 (m, 5H), 3.50-3.40 (m, 1H), 3.15-2.97 (m, 2H), 2.85-2.74 (m, 2H), 2.48-2.33 (m, 6H), 2.20-1.91 (m, 3H).

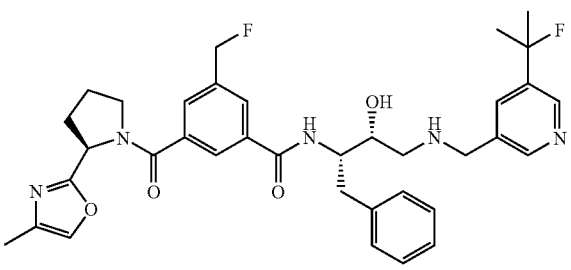

3-(fluoromethyl)-N-((2S,3R)-4-((5-(2-fluoropropan-2-yl)pyridin-3-yl)methylamino)-3-hydroxy-1-phenylbutan-2-yl)-5-((R)-2-(4-methyloxazol-2-yl)pyrrolidine-1-carbonyl)benzamide: ¹H NMR (300 MHz, CDCl₃): δ 1.67 (d, J=1.8 Hz, 3H), 1.74 (d, J=1.8 Hz, 3H), 1.84-2.44 (m, 4H), 2.18 (s, 3H), 2.70-2.84 (m, 2H), 2.90-3.16 (m, 2H), 3.40-3.58 (m, 1H), 3.62-3.96 (m, 4H), 4.36-4.43 (m, 1H), 5.36-5.42 (m, 1H), 5.24 (s, 1H), 5.42 (s, 1H), 7.08-7.40 (m, 6H), 7.40-7.82 (m, 4H), 8.50-8.56 (m, 2H).

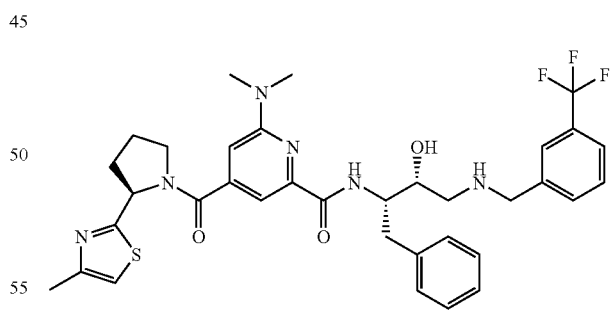

6-(dimethylamino)-N-((2S,3R)-3-hydroxy-1-phenyl-4-(3-(trifluoromethyl)benzylamino)butan-2-yl)-4-((R)-2-(4-methylthiazol-2-yl)pyrrolidine-1-carbonyl)picolinamide: ¹H NMR (300 MHz, CDCl₃) δ 8.02-8.05 (m, 1H), 7.42-7.65 (m, 5H), 7.21-7.34 (m, 5H), 6.80-6.82 (m, 2H), 5.64-5.68 (m, 1H), 4.22-4.37 (m, 1H), 3.90 (s, 2H), 3.87-3.93 (m, 1H), 3.68-3.79 (m, 1H), 3.55-3.66 (m, 1H), 3.47-3.54 (m, 1H), 3.10 (s, 3H), 2.99-3.23 (m, 2H), 2.91 (s, 3H), 2.75-2.85 (m, 1H), 2.66-2.75 (m, 1H), 2.47-2.473 (m, 3H), 2.35-2.45 (m, 1H), 2.05-2.28 (m, 2H), 1.90-2.05 (m, 1H).

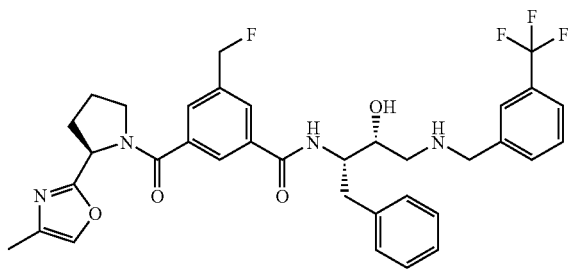

3-(fluoromethyl)-N-((2S,3R)-3-hydroxy-1-phenyl-4-(3-(trifluoromethyl)benzylamino)butan-2-yl)-5-((R)-2-(4-methyloxazol-2-yl)pyrrolidine-1-carbonyl)benzamide: $^1$H NMR (300 MHz, CDCl$_3$): δ 1.90-2.46 (m, 4H), 2.19 (s, 3H), 2.74-2.86 (m, 2H), 2.90-3.12 (m, 2H), 3.40-3.52 (m, 1H), 3.66-3.80 (m, 2H), 3.80-3.98 (m, 2H), 4.30-4.48 (m, 1H), 5.24 (s, 1H), 5.34-5.44 (m, 1H), 5.82 (s, 1H), 7.10-7.38 (m, 7H), 7.40-7.64 (m, 5H), 7.80 (br s, 1H).

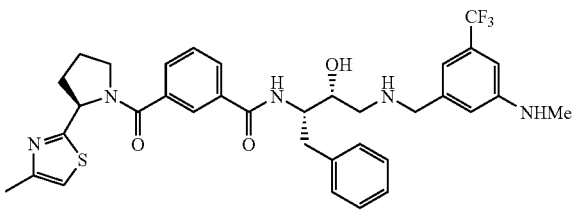

N-((2S,3R)-3-hydroxy-4-(3-(methylamino)-5-(trifluoromethyl)benzylamino)-1-phenylbutan-2-yl)-3-((R)-2-(4-methylthiazol-2-yl)pyrrolidine-1-carbonyl)benzamide: $^1$H NMR (300 MHz, CDCl$_3$): δ 1.90-1.96 (m, 1H), 2.04-2.10 (m, 1H), 2.30-2.45 (m, 5H), 2.80-3.01 (m, 7H), 3.39-3.47 (m, 1H), 3.62-3.87 (m, 5H), 4.32-4.42 (m, 1H), 5.63-5.67 (m, 1H), 6.67 (s, 1H), 6.75 (s, 1H), 6.79 (s, 1H), 6.85 (s, 1H), 7.18-7.37 (m, 6H), 7.60-7.65 (m, 2H), 7.85 (s, 1H).

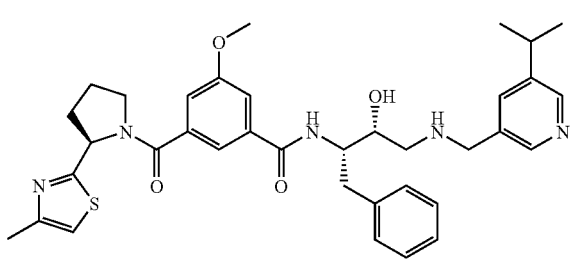

N-((2S,3R)-3-hydroxy-4-((5-isopropylpyridin-3-yl)methylamino)-1-phenylbutan-2-yl)-3-methoxy-5-((R)-2-(4-methylthiazol-2-yl)pyrrolidine-1-carbonyl)benzamide: $^1$H NMR (300 MHz, CDCl$_3$) δ 8.41 (s, 2H), 7.55-7.54 (m, 1H), 7.35-7.20 (m, 8H), 6.95-6.81 (m, 2H), 5.68-5.64 (m, 1H), 4.40-4.38 (m, 1H), 3.90-3.79 (m, 5H), 3.71-3.64 (m, 3H), 3.51-3.44 (m, 1H), 3.09-2.76 (m, 5H), 2.47-2.34 (m, 5H), 2.23-1.93 (m, 4H), 1.28 (m, 6H).

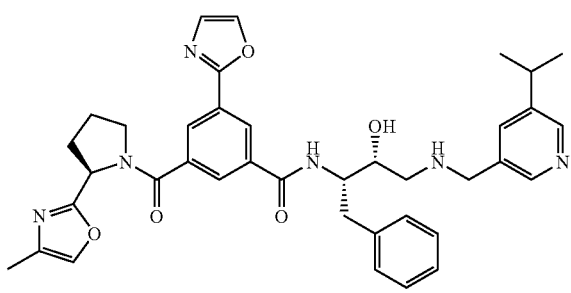

N-((2S,3R)-3-hydroxy-4-((5-isopropylpyridin-3-yl)methylamino)-1-phenylbutan-2-yl)-3-((R)-2-(4-methyloxazol-2-yl)pyrrolidine-1-carbonyl)-5-(oxazol-2-yl)benzamide: $^1$H NMR (300 MHz, CDCl$_3$): δ 1.26 (d, J=6.6 Hz, 6H), 1.92-2.44 (m, 4H), 2.18 (s, 3H), 2.78-2.88 (m, 3H), 2.88-3.02 (m, 2H), 3.48-3.60 (m, 1H), 3.62-3.88 (m, 4H), 4.32-4.46 (m, 1H), 5.38-5.42 (m, 1H), 7.14-7.38 (m, 7H), 7.40-7.52 (m, 1H), 7.56-7.62 (m, 1H), 7.70-7.80 (m, 1H), 7.82 (br s, 1H), 8.20-8.42 (m, 3H).

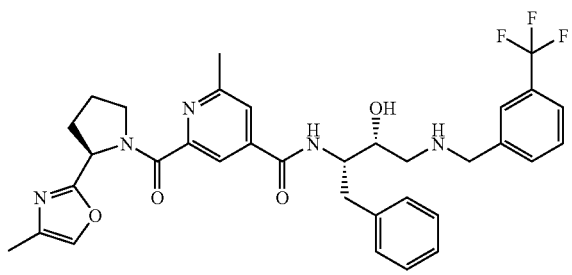

N-((2S,3R)-3-hydroxy-1-phenyl-4-(3-(trifluoromethyl)benzylamino)butan-2-yl)-2-methyl-6-((R)-2-(4-methyloxazol-2-yl)pyrrolidine-1-carbonyl)isonicotinamide: $^1$H NMR (300 MHz, CDCl$_3$) δ 7.76 (s, 1H), 7.40-7.65 (m, 5H), 7.13-7.40 (m, 8H), 5.39-5.43 (m, 1H), 4.34-4.46 (m, 1H), 3.93-4.10 (m, 1H), 3.70-3.93 (m, 4H), 2.91-3.08 (m, 2H), 2.77-2.83 (m, 2H), 2.27-2.42 (m, 4H), 2.12-2.27 (m, 2H), 1.95-2.12 (m, 4H).

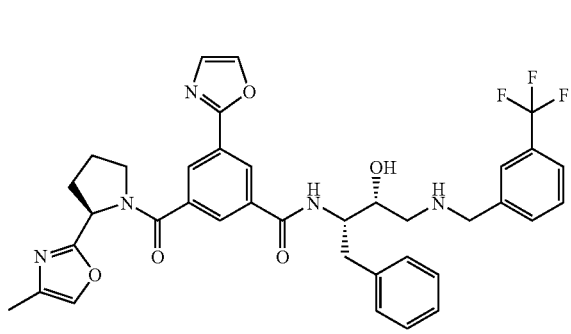

N-((2S,3R)-3-hydroxy-1-phenyl-4-(3-(trifluoromethyl)benzylamino)butan-2-yl)-3-((R)-2-(4-methyloxazol-2-yl)pyrrolidine-1-carbonyl)-5-(oxazol-2-yl)benzamide: $^1$H NMR (300 MHz, CDCl$_3$): δ 1.94-2.442 (m, 4H), 2.18 (s, 3H), 2.80-2.86 (m, 2H), 2.86-3.14 (m, 2H), 3.46-3.60 (m, 1H), 3.64-3.84 (m, 2H), 3.84-4.00 (m, 2H), 4.34-4.48 (m, 1H), 5.36-5.44 (m, 1H), 7.16-7.38 (m, 7H), 7.38-7.64 (m, 4H), 7.76 (br s, 1H), 7.92 (br s, 1H), 8.32 (br s, 2H).

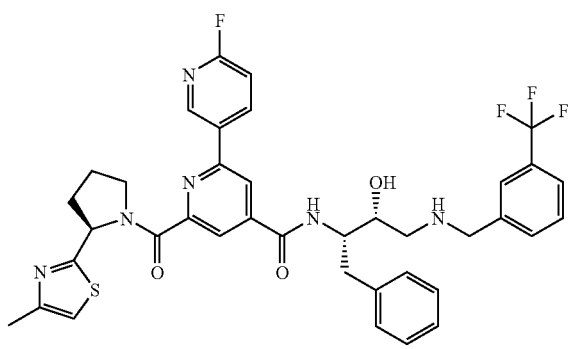

6'-fluoro-N-((2S,3R)-3-hydroxy-1-phenyl-4-(3-(trifluoromethyl)benzylamino)butan-2-yl)-6-((R)-2-(4-methylthiazol-2-yl)pyrrolidine-1-carbonyl)-2,3'-bipyridine-4-carboxamide: $^1$H NMR (300 MHz, CDCl$_3$) δ 8.76-8.82 (m, 1H), 7.98-8.11 (m, 2H), 7.92-7.93 (m, 1H), 7.72-7.91 (m, 1H), 7.49-7.72 (m, 4H), 7.41-7.49 (m, 1H), 7.15-7.34 (m, 5H), 6.79-6.84 (m, 2H), 5.72-5.75 (m, 1H), 4.40-4.54 (m, 1H), 4.22-4.33 (m, 1H), 4.02 (s, 2H), 3.84-4.08 (m, 2H), 3.74-3.84 (m, 1H), 2.93-3.09 (m, 2H), 2.77-2.93 (m, 2H), 2.30-2.49 (m, 4H), 2.12-2.30 (m, 1H), 1.89-2.12 (m, 2H).

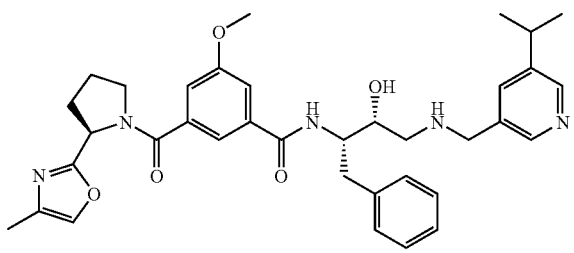

N-((2S,3R)-3-hydroxy-4-((5-isopropylpyridin-3-yl)methylamino)-1-phenylbutan-2-yl)-3-methoxy-5-((R)-2-(4-methyloxazol-2-yl)pyrrolidine-1-carbonyl)benzamide: $^1$H NMR (300 MHz, CDCl$_3$) δ 8.40 (m, 2H), 7.56 (m, 1H), 7.36-7.17 (m, 9H), 7.04-7.01 (m, 1H), 6.81-6.76 (m, 1H), 5.39-5.35 (m, 0.7H), 4.82-4.80 (m, 0.2H), 4.40-4.37 (m, 1H), 3.90-3.66 (m, 7H), 3.53-3.46 (m, 1H), 3.11-2.82 (m, 6H), 2.42-2.35 (m, 1H), 2.27-1.91 (m, 7H), 1.27 (d, 7H).

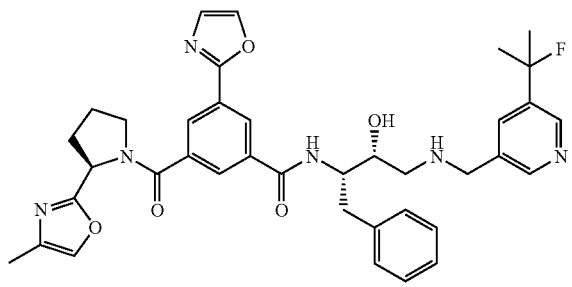

N-((2S,3R)-4-((5-(2-fluoropropan-2-yl)pyridin-3-yl)methylamino)-3-hydroxy-1-phenylbutan-2-yl)-3-((R)-2-(4-methyloxazol-2-yl)pyrrolidine-1-carbonyl)-5-(oxazol-2-yl)benzamide: $^1$H NMR (300 MHz, CDCl$_3$): δ 1.66 (d, J=2.7 Hz, 3H), 1.73 (d, J=2.7 Hz, 3H), 1.90-2.44 (m, 4H), 2.18 (s, 3H), 2.80-2.88 (m, 2H), 2.88-3.14 (m, 2H), 3.44-3.60 (m, 1H), 3.64-3.96 (m, 4H), 4.36-4.44 (m, 1H), 5.38-5.44 (m, 1H), 7.04-7.40 (m, 7H), 7.78 (br s, 2H), 7.86 (br s, 1H), 8.30-8.36 (m, 2H), 8.48-8.62 (m, 2H).

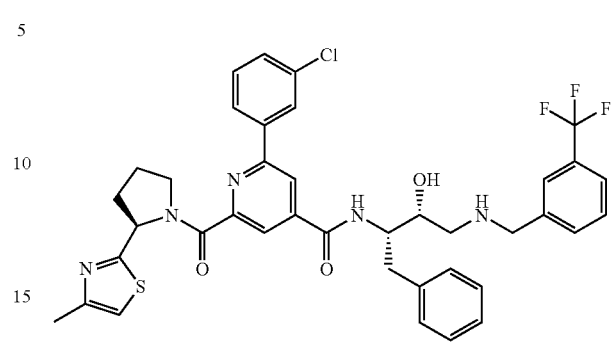

2-(3-chlorophenyl)-N-((2S,3R)-3-hydroxy-1-phenyl-4-(3-(trifluoromethyl)benzylamino)butan-2-yl)-6-((R)-2-(4-methylthiazol-2-yl)pyrrolidine-1-carbonyl)isonicotinamide: $^1$H NMR (300 MHz, CDCl$_3$) δ 8.02-8.03 (m, 1H), 7.89-7.99 (m, 2H), 7.77-7.89 (m, 1H), 7.36-7.77 (m, 8H), 7.19-7.36 (m, 5H), 6.790-6.793 (m, 1H), 5.71-5.76 (m, 1H), 4.40-4.54 (m, 1H), 4.18-4.28 (m, 1H), 3.83-4.05 (m, 3H), 3.74-3.83 (m, 2H), 2.95-3.10 (m, 2H), 2.79-2.92 (m, 2H), 2.27-2.44 (m, 4H), 1.89-2.27 (m, 3H).

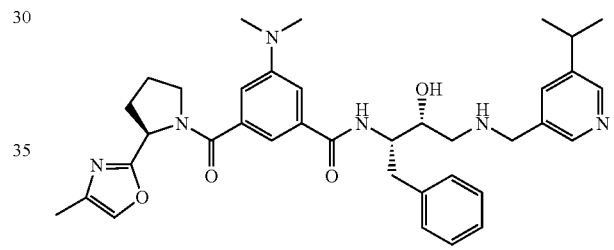

3-(dimethylamino)-N-((2S,3R)-3-hydroxy-4-((5-isopropylpyridin-3-yl)methylamino)-1-phenylbutan-2-yl)-5-((R)-2-(4-methyloxazol-2-yl)pyrrolidine-1-carbonyl)benzamide: $^1$H NMR (300 MHz, CDCl$_3$): δ 8.38 (m, 2H), 7.54 (m, 1H), 7.17-7.32 (m, 6H), 7.00-7.01 (m, 2H), 6.89 (s, 1H), 5.35 (m, 1H), 4.34 (m, 1H), 3.81 (s, 2H), 3.65 (m, 2H), 3.50 (m, 1H), 2.76-3.05 (m, 11H), 2.36 (m, 1H), 2.06-2.22 (m, 5H), 1.95 (m, 1H), 1.26 (m, 6H)

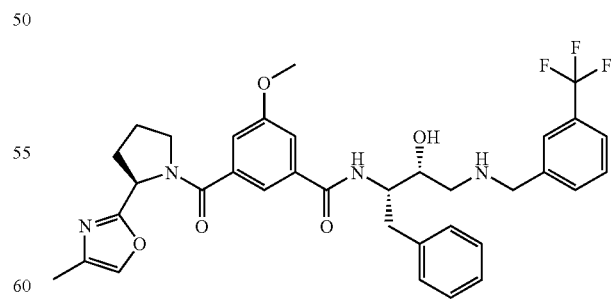

N-((2S,3R)-3-hydroxy-1-phenyl-4-(3-(trifluoromethyl)benzylamino)butan-2-yl)-3-methoxy-5-((R)-2-(4-methyloxazol-2-yl)pyrrolidine-1-carbonyl)benzamide: $^1$H NMR (300 MHz, CDCl$_3$) δ 7.64-7.43 (m, 4H), 7.37-7.15 (m, 10H), 7.04 (m, 1H), 6.813 (m, 1H), 5.38-5.34 (m, 0.7H), 4.80-4.79 (m, 0.2H), 4.40-4.37 (m, 1H), 3.94-3.65 (m, 8H), 3.52-3.45 (m, 1H), 3.11-2.80 (m, 6H), 2.41-2.35 (m, 1H), 2.24-1.90 (m, 7H).

1H), 3.03-3.17 (m, 2H), 2.69-2.85 (m, 2H), 2.59 (s, 3H), 2.29-2.43 (m, 1H), 2.08-2.29 (m, 5H), 1.91-2.08 (m, 1H).

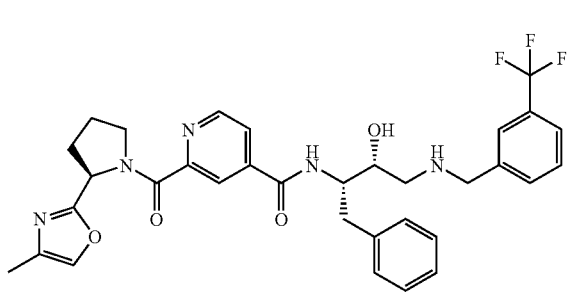

N-((2S,3R)-3-hydroxy-1-phenyl-4-(3-(trifluoromethyl)benzylamino)butan-2-yl)-2-((R)-2-(4-methyloxazol-2-yl)pyrrolidine-1-carbonyl)isonicotinamide: $^1$H NMR (300 MHz, CDCl$_3$) δ 8.61-8.62 (m, 1H), 8.19-8.28 (m, 2H), 7.43-7.65 (m, 4H), 7.18-7.36 (m, 6H), 7.127-7.13 (m, 1H), 5.37-5.42 (m, 1H), 4.27-4.43 (m, 1H), 3.89 (s, 2H), 3.80-3.99 (m, 1H), 3.62-3.80 (m, 2H), 3.46-3.54 (m, 1H), 3.13-3.19 (m, 1H), 2.95-3.11 (m, 1H), 2.70-2.86 (m, 2H), 2.31-2.46 (m, 1H), 2.08-2.31 (m, 5H), 1.92-2.08 (m, 1H).

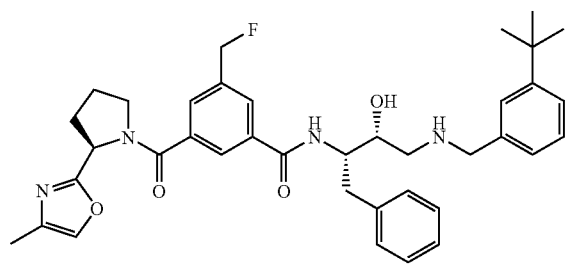

N-((2S,3R)-4-(3-tert-butylbenzylamino)-3-hydroxy-1-phenylbutan-2-yl)-3-(fluoromethyl)-5-((R)-2-(4-methyloxazol-2-yl)pyrrolidine-1-carbonyl)benzamide: $^1$H NMR (300 MHz, CDCl$_3$): δ 1.25 (s, 9H), 1.92-2.39 (m, 7H), 2.82-3.06 (m, 4H), 3.43-3.94 (m, 4H), 4.36-4.46 (m, 1H), 5.14-5.40 (m, 3H), 7.17-7.38 (m, 10H), 7.62 (s, 1H), 7.68 (s, 1H), 7.89 (s, 1H).

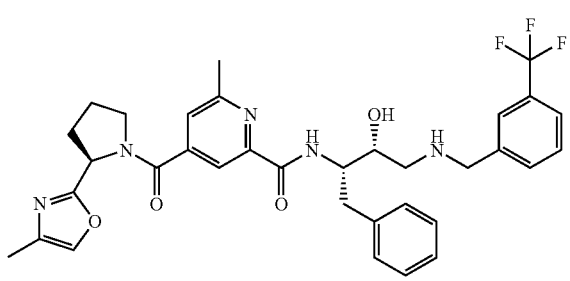

N-((2S,3R)-3-hydroxy-1-phenyl-4-(3-(trifluoromethyl)benzylamino)butan-2-yl)-6-methyl-4-((R)-2-(4-methyloxazol-2-yl)pyrrolidine-1-carbonyl)picolinamide: $^1$H NMR (300 MHz, CDCl$_3$) δ 8.27-8.30 (m, 1H), 8.057-8.06 (m, 1H), 7.63 (s, 1H), 7.43-7.60 (m, 4H), 7.16-7.36 (m, 5H), 7.005-7.009 (m, 1H), 5.37-5.41 (m, 1H), 4.24-4.39 (m, 1H), 3.89 (s, 2H), 3.78-3.98 (m, 1H), 3.60-3.78 (m, 2H), 3.45-3.53 (m,

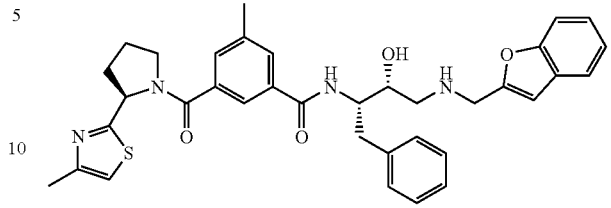

N-((2S,3R)-4-(benzofuran-2-ylmethylamino)-3-hydroxy-1-phenylbutan-2-yl)-3-methyl-5-((R)-2-(4-methylthiazol-2-yl)pyrrolidine-1-carbonyl)benzamide: $^1$H NMR (300 MHz, CDCl$_3$) δ 7.39-7.65 (m, 7H), 7.17-7.36 (m, 5H), 6.88-6.99 (m, 1H), 6.81 (s, 1H), 6.61 (s, 1H), 5.65-5.69 (m, 1H), 4.32-4.50 (m, 1H), 3.94-4.05 (m, 2H), 3.85-3.96 (m, 1H), 3.61-3.78 (m, 2H), 3.39-3.50 (m, 1H), 2.97-3.11 (m, 2H), 2.79-2.94 (m, 2H), 2.47 (s, 3H), 2.28-2.44 (m, 4H), 2.01-2.18 (m, 2H), 1.86-2.01 (m, 1H).

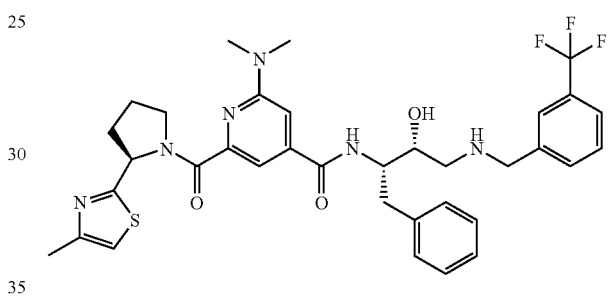

2-(dimethylamino)-N-((2S,3R)-3-hydroxy-1-phenyl-4-(3-(trifluoromethyl)benzylamino)butan-2-yl)-6-((R)-2-(4-methylthiazol-2-yl)pyrrolidine-1-carbonyl)isonicotinamide: $^1$H NMR (300 MHz, CDCl$_3$) δ 7.43-7.63 (m, 4H), 7.18-7.35 (m, 5H), 6.91 (s, 1H), 6.83-6.84 (m, 1H), 6.776-6.78 (m, 1H), 6.676-6.679 (m, 1H), 5.68-5.72 (m, 1H), 4.32-4.44 (m, 1H), 4.14-4.22 (m, 1H), 3.83-4.02 (m, 4H), 3.64-3.72 (m, 1H), 3.15 (s, 3H), 2.91-3.12 (m, 2H), 2.87 (s, 3H), 2.78-2.81 (m, 2H), 2.30-2.48 (m, 4H), 2.09-2.25 (m, 1H), 1.97-2.09 (m, 2H).

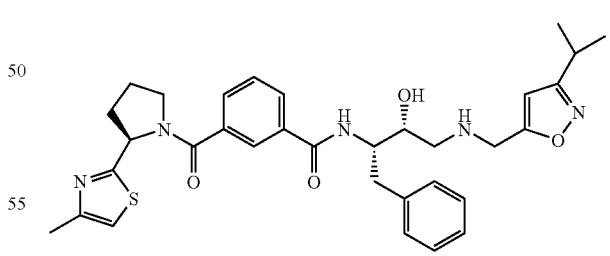

N-((2S,3R)-3-hydroxy-4-((3-isopropylisoxazol-5-yl)methylamino)-1-phenylbutan-2-yl)-3-((R)-2-(4-methylthiazol-2-yl)pyrrolidine-1-carbonyl)benzamide: $^1$H NMR (300 MHz, CDCl$_3$) δ 7.84 (s, 1H), 7.62-7.74 (m, 2H), 7.43-7.48 (m, 1H), 7.19-7.39 (m, 6H), 6.88-7.02 (m, 1H), 6.81 (s, 1H), 6.07 (s, 1H), 5.64-5.71 (m, 1H), 4.30-4.48 (m, 1H), 3.93 (s, 2H), 3.63-3.77 (m, 2H), 3.43-3.54 (m, 1H), 2.96-3.12 (m, 3H), 2.75-2.91 (m, 2H), 2.47 (s, 3H), 2.28-2.52 (m, 2H), 2.03-2.28 (m, 2H), 1.88-2.03 (m, 1H), 1.27-1.30 (m, 6H).

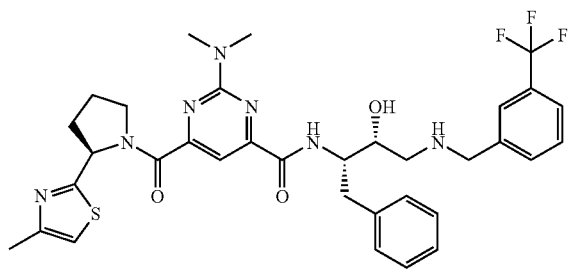

2-(dimethylamino)-N-((2S,3R)-3-hydroxy-1-phenyl-4-(3-(trifluoromethyl)benzylamino)butan-2-yl)-6-((R)-2-(4-methylthiazol-2-yl)pyrrolidine-1-carbonyl)pyrimidine-4-carboxamide: ¹H NMR (300 MHz, CDCl₃) δ 7.99-7.87 (m, 1H), 7.60-7.44 (m, 5H), 7.35-7.23 (m, 5H), 6.80-6.72 (m, 1H), 5.91-5.88 (m, 0.5H), 5.71-5.67 (m, 0.4H), 4.28 (m, 1H), 4.05-3.73 (m, 4H), 3.62-3.53 (m, 1H), 3.21-3.12 (m, 4H), 3.05-2.96 (m, 5H), 2.79-2.63 (m, 3H), 2.46-2.36 (m, 5H), 2.20-1.95 (m, 2H).

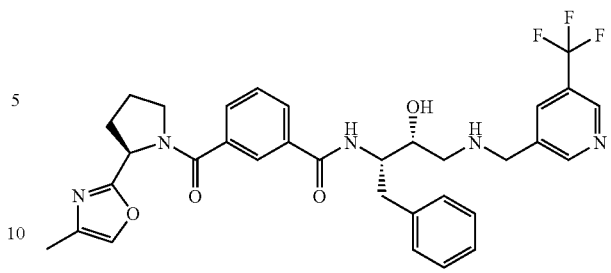

N-((2S,3R)-3-hydroxy-1-phenyl-4-(5-(trifluoromethyl)pyridin-3-yl)methylamino)butan-2-yl)-3-((R)-2-(4-methyloxazol-2-yl)pyrrolidine-1-carbonyl)benzamide: ¹H NMR (300 MHz, CDCl₃+CD₃OD) δ 8.752 (d, J=5.7 Hz, 2H), 7.980-7.146 (m, 11H), 5.339 (m, 0.73H), 4.810 (m, 0.27H), 4.362 (m, 1H), 3.898 (s, 2H), 3.787-3.651 (m, 2H), 3.463 (m, 1H), 3.160-2.733 (m, 4H), 2.414 (m, 2H), 2.161 (m, 4H), 1.966 (m, 1H).

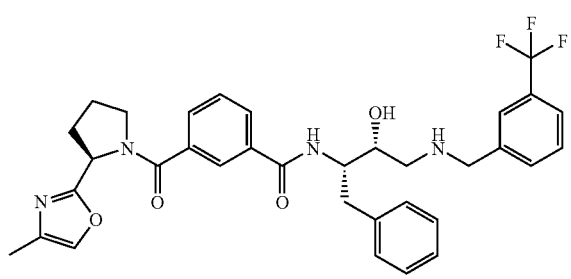

N-((2S,3R)-4-(3-(1,1-difluoroethyl)benzylamino)-3-hydroxy-1-phenylbutan-2-yl)-3-((R)-2-(4-methyloxazol-2-yl)pyrrolidine-1-carbonyl)benzamide: ¹H NMR (300 MHz, CDCl₃+CD₃OD), δ 7.901-7.124 (m, 14H), 5.332 (m, 0.77H), 4.811 (m, 0.23H), 4.369 (m, 1H), 3.887-3.680 (m, 4H), 3.452 (m, 1H), 3.083-2.798 (m, 4H), 2.369 (m, 1H), 2.146 (m, 5H), 1.903 (m, 4H).

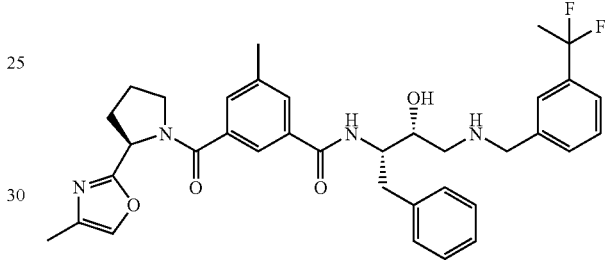

N-((2S,3R)-4-(3-(1,1-difluoroethyl)benzylamino)-3-hydroxy-1-phenylbutan-2-yl)-3-methyl-5-((R)-2-(4-methyloxazol-2-yl)pyrrolidine-1-carbonyl)benzamide: ¹H NMR (300 MHz, CDCl₃+CD₃OD) δ 7.642-7.147 (m, 13H), 5.329 (m, 0.75H), 4.755 (m, 0.25H), 4.354 (m, 1H), 3.879-3.654 (m, 4H), 3.455 (m, 1H), 3.097-2.779 (m, 4H), 2.316 (m, 4H), 2.148 (m, 5H), 1.901 (m, 4H).

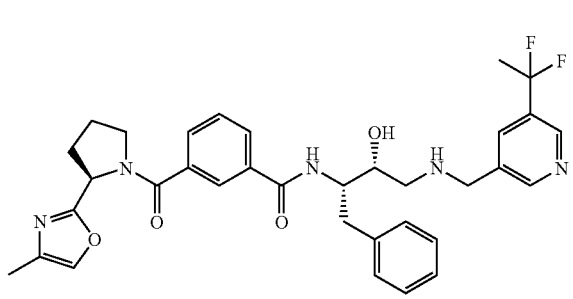

N-((2S,3R)-4-((5-(1,1-difluoroethyl)pyridin-3-yl)methylamino)-3-hydroxy-1-phenylbutan-2-yl)-3-((R)-2-(4-methyloxazol-2-yl)pyrrolidine-1-carbonyl)benzamide: ¹H NMR (300 MHz, CDCl₃+CD₃OD) δ 8.606 (d, J=9.3 Hz, 2H), 7.846 (d, J=6.0 Hz, 2H), 7.745-7.133 (m, 9H), 5.327 (m, 0.73H), 4.801 (m, 0.27H), 4.365 (m, 1H), 3.859 (s, 2H), 3.799-3.672 (m, 2H), 3.454 (m, 1H), 3.125-2.733 (m, 4H), 2.376 (m, 1H), 2.148 (m, 5H), 1.935 (m, 4H).

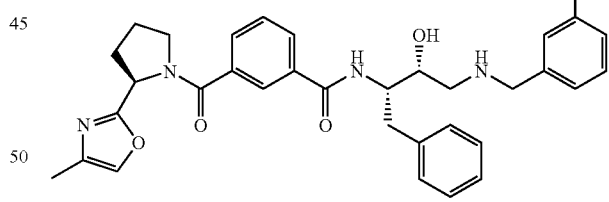

N-((2S,3R)-3-hydroxy-1-phenyl-4-(3-(prop-1-en-2-yl)benzylamino)butan-2-yl)-3-((R)-2-(4-methyloxazol-2-yl)pyrrolidine-1-carbonyl)benzamide.

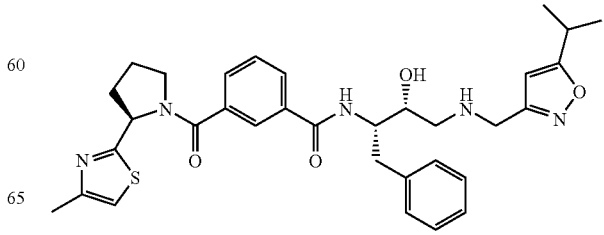

217

N-((2S,3R)-3-hydroxy-4-((5-isopropylisoxazol-3-yl)methylamino)-1-phenylbutan-2-yl)-3-((R)-2-(4-methylthiazol-2-yl)pyrrolidine-1-carbonyl)benzamide.

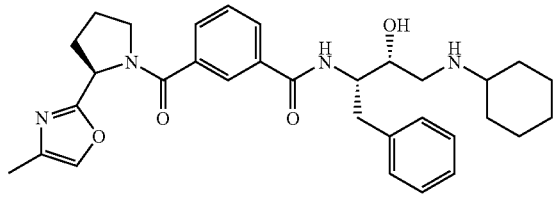

N-((2S,3R)-4-(cyclohexylamino)-3-hydroxy-1-phenylbutan-2-yl)-3-((R)-2-(4-methyloxazol-2-yl)pyrrolidine-1-carbonyl)benzamide.

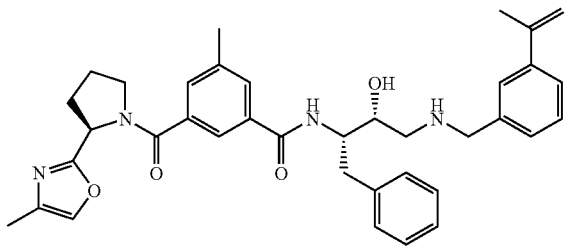

N-((2S,3R)-3-hydroxy-1-phenyl-4-(3-(prop-1-en-2-yl)benzylamino)butan-2-yl)-3-methyl-5-((R)-2-(4-methyloxazol-2-yl)pyrrolidine-1-carbonyl)benzamide.

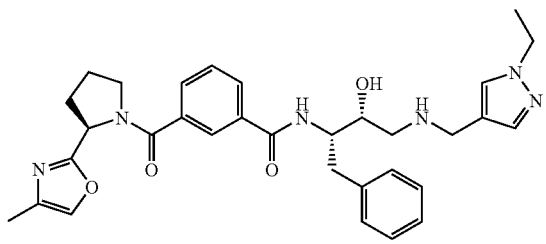

N-((2S,3R)-4-((1-ethyl-1H-pyrazol-4-yl)methylamino)-3-hydroxy-1-phenylbutan-2-yl)-3-((R)-2-(4-methyloxazol-2-yl)pyrrolidine-1-carbonyl)benzamide.

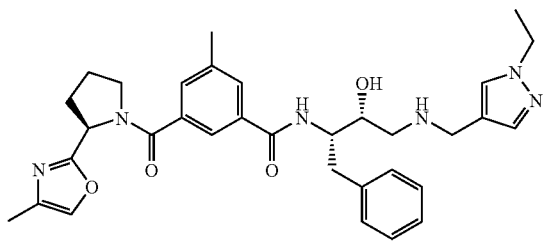

N-((2S,3R)-4-((1-ethyl-1H-pyrazol-4-yl)methylamino)-3-hydroxy-1-phenylbutan-2-yl)-3-methyl-5-((R)-2-(4-methyloxazol-2-yl)pyrrolidine-1-carbonyl)benzamide.

218

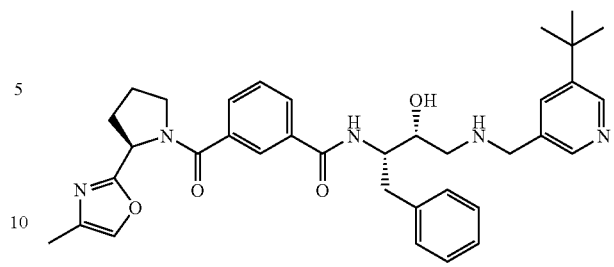

N-((2S,3R)-4-((5-tert-butylpyridin-3-yl)methylamino)-3-hydroxy-1-phenylbutan-2-yl)-3-((R)-2-(4-methyloxazol-2-yl)pyrrolidine-1-carbonyl)benzamide.

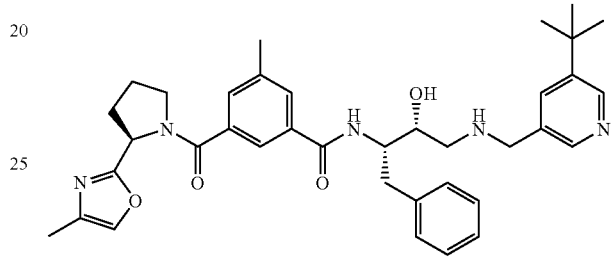

N-((2S,3R)-4-((5-tert-butylpyridin-3-yl)methylamino)-3-hydroxy-1-phenylbutan-2-yl)-3-methyl-5-((R)-2-(4-methyloxazol-2-yl)pyrrolidine-1-carbonyl)benzamide.

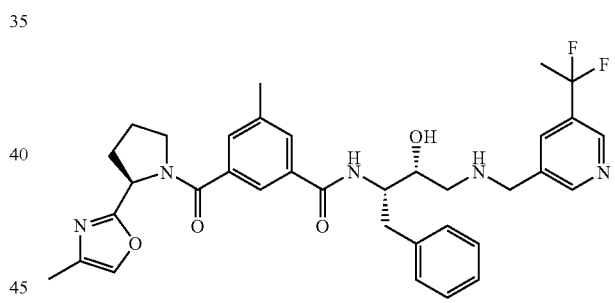

N-((2S,3R)-4-((5-(1,1-difluoroethyl)pyridin-3-yl)methylamino)-3-hydroxy-1-phenylbutan-2-yl)-3-methyl-5-((R)-2-(4-methyloxazol-2-yl)pyrrolidine-1-carbonyl)benzamide.

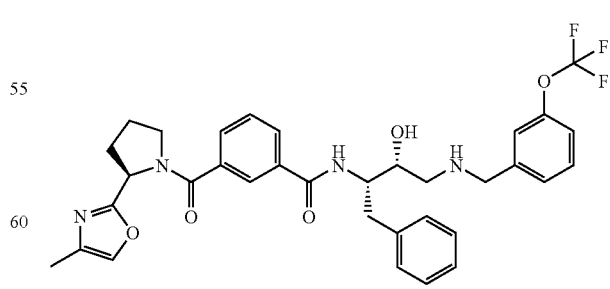

N-((2S,3R)-3-hydroxy-1-phenyl-4-(3-(trifluoromethoxy)benzylamino)butan-2-yl)-3-((R)-2-(4-methyloxazol-2-yl)pyrrolidine-1-carbonyl)benzamide.

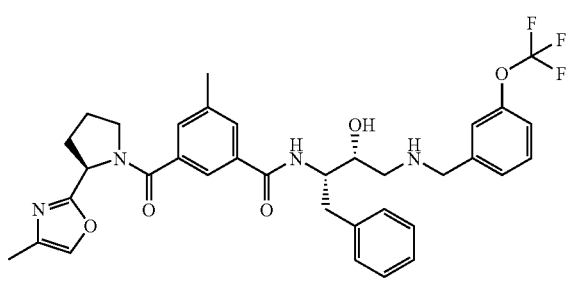

N-((2S,3R)-3-hydroxy-1-phenyl-4-(3-(trifluoromethoxy)benzylamino)butan-2-yl)-3-methyl-5-((R)-2-(4-methyloxazol-2-yl)pyrrolidine-1-carbonyl)benzamide.

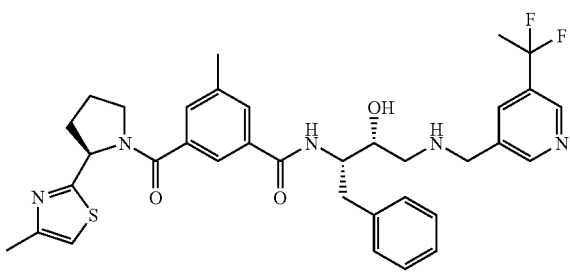

N-((2S,3R)-4-((5-(1,1-difluoroethyl)pyridin-3-yl)methylamino)-3-hydroxy-1-phenylbutan-2-yl)-3-methyl-5-((R)-2-(4-methylthiazol-2-yl)pyrrolidine-1-carbonyl)benzamide.

Example 4

Inhibition of Memapsin 1 Beta-Secretase Activity and Cathepsin D Activity

A substrate peptide $NH_3$-ELDLAVEFWHDR-$CO_2$ (SEQ ID NO.: 1) was dissolved at 2 mg/mL in 10% glacial acetic acid and diluted into 0.009M NaOH to obtain μM concentration at pH 4.1. After equilibration at 37 degrees C., the reactions were initiated by the addition of an aliquot of memapsin 2. Aliquots were removed at time intervals, and combined with an equal volume of MALDI-TOF matrix (α-hydroxycinnamic acid in acetone, 20 mg/mL) and immediately spotted in duplicate onto a stainless-steel MALDI sample plate. MALDI-TOF mass spectrometry was performed on a PE Biosystems Voyager DE. The instrument was operated at 25,000 accelerating volts in positive mode with a 150 ns delay. Ions with a mass-to-charge ratio (m/z) were detected in the range of 650-2000 atomic mass units. Data were analyzed by the Voyager Data Explorer module to obtain ion intensity data for mass species of substrates and corresponding products in a given mixture. Relative product formation was calculated as the ratio of signal intensity of the product to the sum of signal intensities of both product and the corresponding substrate. Relative product formed per unit time was obtained from non-linear regression analysis of the data representing the initial 15% formation of product using the model:

$$1-e^{-kT},$$

where k was the relative hydrolytic rate constant and T was time in seconds. Initial rates were expressed relative to uninhibited controls and fit to a tight-binding model of competitive inhibition as above. Results are shown in Table 1 above.

Example 5

Cellular AβIC50 Determinations

The potency of compounds against memapsin 2 activity was determined in a cellular assay of Aβ production. Compounds that successfully penetrate the cell membrane demonstrated their ability to inhibit memapsin 2 activity in endosomal compartments, thus blocking the production of Aβ. Chinese hamster ovary cells that over-express human APP695 with the London and Swedish mutations were seeded in multi-well plates at 10% confluency. Compounds are dissolved in DMSO to concentrations near 1 mM, and diluted into culture media to a final concentration near 4 μM (final 0.4% DMSO). Compounds were diluted serially and applied to cells in multi-well plates 48 h after seeding. Incubation was continued in 5% $CO_2$ at 37° C. for 24 h. Aliquots were removed and assayed for $Aβ_{40}$ content using a sandwich ELISA (BioSource International). Amount of $Aβ_{40}$ over the range of concentration of compounds, relative to control incubations, were fit to a 4-parameter $IC_{50}$ model. Results are provided in Table 1 above.

What is claimed is:

1. A compound having the formula:

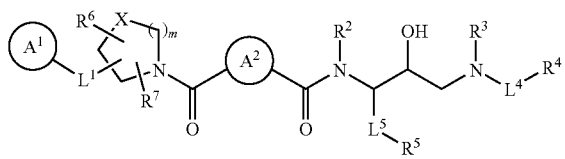

wherein
- $A^1$ is a substituted or unsubstituted cycloalkyl, substituted or unsubstituted heterocycloalkyl, substituted or unsubstituted aryl, or substituted or unsubstituted heteroaryl;
- $A^2$ is a substituted or unsubstituted cycloalkylene, substituted or unsubstituted heterocycloalkylene, substituted or unsubstituted arylene, or substituted or unsubstituted heteroarylene;
- X is —$CH_2$—, —O—, —N($R^8$)—, or —S(O)$_w$—;
  or where X is —CH— or —N—, and is the attachment point for $R^6$ or $R^7$;
- $L^1$ and $L^5$ are independently a bond, —N($R^{17}$)—, —S(O)$_q$—, or substituted or unsubstituted alkylene;
- $L^4$ is a bond, —C(O)—, —N($R^{17}$)—, —S(O)$_q$—, or substituted or unsubstituted alkylene;
- $R^2$ and $R^3$ are independently hydrogen, —S(O)$_2R^{11}$, —C(O)$R^{12}$, —N($R^8$)$R^9$, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl;
- $R^4$ and $R^5$ are independently hydrogen, halogen, —OH, —$NO_2$, —N($R^8$)$R^9$, —$OR^{10}$, —S(O)$_nR^{11}$, —C(O)$R^{12}$, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl;
- $R^6$ and $R^7$ are independently hydrogen, halogen, —OH, —$NO_2$, —N($R^8$)$R^9$, —$OR^{10}$, —S(O)$_nR^{11}$, —C(O)$R^{12}$, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl;
- $R^8$ is independently hydrogen, —C(O)$R^{13}$, —S(O)$_2R^{14}$, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl;
- $R^9$ is independently hydrogen, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl;
- $R^{10}$ is independently —C(O)$R^{13}$, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl;
- $R^{11}$ is independently hydrogen, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl, wherein if n is 2, then $R^{11}$ can also be $-NR^{15}R^{16}$, and wherein if n is 1 or 2, then $R^{11}$ is not hydrogen;

$R^{12}$ and $R^{13}$ are each independently hydrogen, $-N(R^{18})R^{19}$, $-OR^{19}$, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl;

$R^{14}$ is independently hydrogen, $-N(R^{18})R^{19}$, substituted or unsubstituted alkyl, substituted or unsubstituted cycloalkyl, substituted or unsubstituted cycloalkylalkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl;

$R^{15}$, $R^{16}$, $R^{17}$, $R^{18}$, and $R^{19}$ are each independently hydrogen, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl; and m, n, q, and w are each independently 0, 1, or 2;
or a pharmaceutically acceptable salt or solvate thereof.

2. The compound of claim 1, wherein $A^1$ is a substituted or unsubstituted heteroaryl; or a pharmaceutically acceptable salt or solvate thereof.

3. The compound of claim 1, wherein $A^1$ is a substituted or unsubstituted pyridyl, substituted or unsubstituted phenyl, substituted or unsubstituted thiazolyl, substituted or unsubstituted oxazolyl, substituted or unsubstituted imidazolyl, substituted or unsubstituted pyrazolyl, substituted or unsubstituted isoxazolyl, substituted or unsubstituted pyrimidyl, substituted or unsubstituted oxadiazolyl, substituted or unsubstituted pyranyl, or substituted or unsubstituted furanyl; or a pharmaceutically acceptable salt or solvate thereof.

4. The compound of claim 1, wherein $A^1$ is a substituted or unsubstituted thiazolyl; or a pharmaceutically acceptable salt or solvate thereof.

5. The compound of claim 1, wherein $A^1$ is a substituted or unsubstituted oxazolyl; or a pharmaceutically acceptable salt or solvate thereof.

6. The compound of claim 1, wherein $A^1$ is a substituted or unsubstituted 2-thiazolyl; or a pharmaceutically acceptable salt or solvate thereof.

7. The compound of claim 1, wherein $A^1$ is a substituted or unsubstituted 2-oxazoyl; or a pharmaceutically acceptable salt or solvate thereof.

8. The compound of claim 1, wherein $A^2$ has the formula:

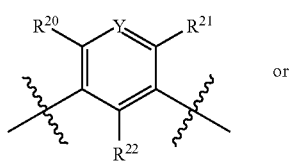

or

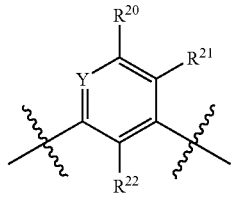

wherein
$R^{20}$, $R^{21}$, and $R^{22}$ are independently hydrogen, $-N(R^{24})R^{25}$, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl; and Y is $-N=$ or $-C(R^{23})=$, wherein $R^{23}$ is hydrogen, halogen, $-NO_2$, $-N(R^{24})R^{25}$, $-OR^{26}$, $-S(O)_tR^{27}$, or $-C(O)R^{28}$, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl;

wherein
t is an integer from 0 to 2;
$R^{24}$ and $R^{25}$ are independently hydrogen, $-C(O)R^{29}$, or $-S(O_2)R^{30}$, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl;

wherein
$R^{29}$ is independently hydrogen, $-N(R^{31})R^{32}$, or $-OR^{33}$, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl;

wherein
$R^{31}$, $R^{32}$, and $R^{33}$ are independently hydrogen, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl; and $R^{30}$ is hydrogen, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl;

$R^{26}$ is hydrogen, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl;

$R^{27}$ is —$N(R^{34})R^{35}$, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl;

wherein
$R^{34}$ and $R^{35}$ are independently hydrogen, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl; and $R^{28}$ is —$OR^{36}$, —$N(R^{37})R^{38}$, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl;

wherein
$R^{36}$, $R^{37}$, and $R^{38}$ are independently hydrogen, substituted or unsubstituted alkyl, substituted or unsubstituted cycloalkyl, substituted or unsubstituted cycloalkyl-alkyl, substituted or unsubstituted heterocycloalkyl, substituted or unsubstituted heterocycloalkyl-alkyl, substituted or unsubstituted aryl, substituted or unsubstituted aralkyl, substituted or unsubstituted heteroaryl, or substituted or unsubstituted heteroaralkyl;

or a pharmaceutically acceptable salt or solvate thereof.

9. The compound of claim 8, wherein $A^2$ has the formula:

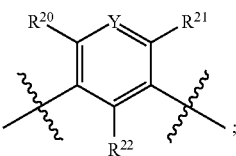

or a pharmaceutically acceptable salt or solvate thereof.

10. The compound of claim 8, wherein Y is —$C(R^{23})$=; or a pharmaceutically acceptable salt or solvate thereof.

11. The compound of claim 8, wherein $R^{23}$ is hydrogen or —$N(R^{24})R^{25}$; or a pharmaceutically acceptable salt or solvate thereof.

12. The compound of claim 8, wherein $R^{23}$ is substituted or unsubstituted $C_1$-$C_6$ alkyl; or a pharmaceutically acceptable salt or solvate thereof.

13. The compound of claim 12, wherein $R^{23}$ is substituted by halogen; or a pharmaceutically acceptable salt or solvate thereof.

14. The compound of claim 8, wherein $R^{23}$ is a substituted or unsubstituted pyridyl, substituted or unsubstituted phenyl, substituted or unsubstituted thiazolyl, substituted or unsubstituted oxazolyl, substituted or unsubstituted oxadiazolyl, substituted or unsubstituted imidazolyl, substituted or unsubstituted pyrazolyl, substituted or unsubstituted isoxazolyl, substituted or unsubstituted pyrimidyl, or substituted or unsubstituted furanyl; or a pharmaceutically acceptable salt or solvate thereof.

15. The compound of claim 8, wherein $R^{23}$ is a substituted or unsubstituted oxazolyl; or a pharmaceutically acceptable salt or solvate thereof.

16. The compound of claim 8, wherein $R^{23}$ is a substituted or unsubstituted pyrazolyl; or a pharmaceutically acceptable salt or solvate thereof.

17. The compound of claim 8, wherein $R^{24}$ and $R^{25}$ are independently hydrogen, or substituted or unsubstituted alkyl; or a pharmaceutically acceptable salt or solvate thereof.

18. The compound of claim 8, wherein $R^{20}$, $R^{21}$, and $R^{22}$ are hydrogen; or a pharmaceutically acceptable salt or solvate thereof.

19. The compound of claim 1, wherein X is —$CH_2$—; or a pharmaceutically acceptable salt or solvate thereof.

20. The compound of claim 1, wherein $R^6$ and $R^7$ are independently hydrogen, halogen, —$OR^{10}$, substituted or unsubstituted alkyl, substituted or unsubstituted cycloalkyl, substituted or unsubstituted heterocycloalkyl, substituted or unsubstituted aryl, or substituted or unsubstituted heteroaryl; or a pharmaceutically acceptable salt or solvate thereof.

21. The compound of claim 1, wherein $R^6$ and $R^7$ are independently hydrogen, or substituted or unsubstituted alkyl; or a pharmaceutically acceptable salt or solvate thereof.

22. The compound of claim 1, wherein $R^2$ is hydrogen or substituted or unsubstituted $C_1$-$C_6$ alkyl; or a pharmaceutically acceptable salt or solvate thereof.

23. The compound of claim 1, wherein $R^4$ is a substituted or unsubstituted aryl, or substituted or unsubstituted heteroaryl; or a pharmaceutically acceptable salt or solvate thereof.

24. The compound of claim 1, wherein $R^4$ is a substituted or unsubstituted aryl; or a pharmaceutically acceptable salt or solvate thereof.

25. The compound of claim 1, wherein $R^4$ is a substituted or unsubstituted pyridyl, or substituted or unsubstituted phenyl; or a pharmaceutically acceptable salt or solvate thereof.

26. The compound of claim 1, wherein $R^4$ is a substituted or unsubstituted phenyl; or a pharmaceutically acceptable salt or solvate thereof.

27. The compound of claim 1, wherein $R^4$ is phenyl or pyridyl, substituted with $C_1$-$C_6$ alkyl or $C_1$-$C_6$ alkoxy; and wherein each $C_1$-$C_6$ alkyl and $C_1$-$C_6$ alkoxy is optionally substituted with 1-3 halogens; or a pharmaceutically acceptable salt or solvate thereof.

28. The compound of claim 1, wherein $R^4$ is phenyl, substituted with $C_1$-$C_6$ alkyl or $C_1$-$C_6$ alkoxy; and wherein each $C_1$-$C_6$ alkyl and $C_1$-$C_6$ alkoxy is optionally substituted with 1-3 halogens; or a pharmaceutically acceptable salt or solvate thereof.

29. The compound of claim 1, wherein $R^4$ is phenyl, substituted with one or more groups selected from —$CF_3$, —$CHF_2$, and —$CH_2F$; or a pharmaceutically acceptable salt or solvate thereof.

30. The compound of claim 1, wherein $R^5$ is substituted or unsubstituted aryl; or a pharmaceutically acceptable salt or solvate thereof.

31. The compound of claim 1, wherein $R^5$ is phenyl, optionally substituted with one or more halogens; or a pharmaceutically acceptable salt or solvate thereof.

32. The compound of claim 1 wherein $L^1$ is a bond; or a pharmaceutically acceptable salt or solvate thereof.

33. The compound of claim 1, wherein $L^4$ is a bond, or substituted or unsubstituted alkylene; or a pharmaceutically acceptable salt or solvate thereof.

34. The compound of claim 1, wherein $L^4$ is a substituted or unsubstituted $C_1$-$C_6$ alkylene; or a pharmaceutically acceptable salt or solvate thereof.

35. The compound of claim 1, wherein $L^4$ is methylene; or a pharmaceutically acceptable salt or solvate thereof.

36. The compound of claim 1, wherein $L^5$ is a substituted or unsubstituted $C_1$-$C_6$ alkylene; or a pharmaceutically acceptable salt or solvate thereof.

37. The compound of claim 1, wherein $L^5$ is methylene; or a pharmaceutically acceptable salt or solvate thereof.

38. The compound of claim 1, wherein m is 1; or a pharmaceutically acceptable salt or solvate thereof.

39. The compound of claim 1, wherein $A^1$ is a substituted or unsubstituted 5 membered heteroaryl; $A^2$ is substituted or unsubstituted arylene, or substituted or unsubstituted heteroarylene; X is —$CH_2$—; $L^1$ is a bond; $L^4$, and $L^5$ are independently substituted or unsubstituted alkylene; $R^2$ and $R^3$ are independently hydrogen, or substituted or unsubstituted alkyl; $R^4$ and $R^5$ are independently substituted or unsubstituted aryl, or substituted or unsubstituted heteroaryl; $R^6$ and $R^7$ are hydrogen; and m is 1.

40. The compound of claim 1, wherein $A^1$ is a substituted or unsubstituted thiazolyl; $A^2$ is substituted or unsubstituted phenyl, X is —$CH_2$—; $L^1$ is a bond; $L^4$ and $L^5$ are methylene; $R^2$ and $R^3$ are hydrogen; $R^4$ is substituted or unsubstituted aryl, or substituted or unsubstituted heteroaryl; $R^5$ is substituted or unsubstituted aryl; $R^6$ and $R^7$ are hydrogen; and m is 1.

41. The compound of claim 1, wherein the compound is selected from the group consisting of:
N-((2S,3R)-3-hydroxy-1-phenyl-4-(3-(trifluoromethyl) benzylamino)butan-2-yl)-3-((R)-2-(4-methyloxazol-2-yl)pyrrolidine-1-carbonyl)benzamide;
N-((2S,3R)-3-hydroxy-1-phenyl-4-(3-(trifluoromethyl) benzylamino)butan-2-yl)-3-methyl-5-((R)-2-(4-methylthiazol-2-yl)pyrrolidine-1-carbonyl)benzamide;
N-((2S,3R)-3-hydroxy-4-(3-methoxybenzylamino)-1-phenylbutan-2-yl)-3-((R)-2-(4-methylthiazol-2-yl)pyrrolidine-1-carbonyl)benzamide;
N-((2S,3R)-3-hydroxy-4-((5-isopropylpyridin-3-yl)methylamino)-1-phenylbutan-2-yl)-3-((R)-2-(4-methylthiazol-2-yl)pyrrolidine-1-carbonyl)benzamide;
N-((2S,3R)-3-hydroxy-4-(3-methoxybenzylamino)-1-phenylbutan-2-yl)-3-((S)-2-(4-methylthiazol-2-yl)pyrrolidine-1-carbonyl)benzamide;
N-((2S,3R)-3-hydroxy-4-(3-methoxybenzylamino)-1-phenylbutan-2-yl)-3-((R)-2-(4-methylthiazol-2-yl)piperidine-1-carbonyl)benzamide;
N-((2S,3R)-3-hydroxy-4-(3-methoxybenzylamino)-1-phenylbutan-2-yl)-3-methyl-5-((R)-2-(4-methylthiazol-2-yl)pyrrolidine-1-carbonyl)benzamide;
N-((2S,3R)-3-hydroxy-4-(3-methoxybenzylamino)-1-phenylbutan-2-yl)-3-((2R,4R)-4-methoxy-2-(4-methylthiazol-2-yl)pyrrolidine-1-carbonyl)benzamide;
N-((2S,3R)-3-hydroxy-4-(3-methoxybenzylamino)-1-phenylbutan-2-yl)-3-((R)-4-(4-methylthiazol-2-yl)thiazolidine-3-carbonyl)benzamide;
N-((2S,3R)-3-hydroxy-1-phenyl-4-(3-(trifluoromethyl) benzylamino)butan-2-yl)-3-((R)-2-(4-methylthiazol-2-yl)pyrrolidine-1-carbonyl)benzamide;
N-((2S,3R)-4-(3-tert-butylbenzylamino)-3-hydroxy-1-phenylbutan-2-yl)-3-((R)-2-(4-methylthiazol-2-yl)pyrrolidine-1-carbonyl)benzamide;
N-((2S,3R)-3-hydroxy-4-(3-methoxybenzylamino)-1-phenylbutan-2-yl)-3-methoxy-5-((R)-2-(4-methylthiazol-2-yl)pyrrolidine-1-carbonyl)benzamide;
N-((2S,3R)-3-hydroxy-4-(3-methoxybenzylamino)-1-phenylbutan-2-yl)-3-((R)-4-(4-methylthiazol-2-yl)thiazolidine-5-dioxide-3-carbonyl)benzamide;
N-((2S,3R)-4-(3-tert-butylbenzylamino)-3-hydroxy-1-phenylbutan-2-yl)-3-methyl-5-((R)-2-(4-methylthiazol-2-yl)pyrrolidine-1-carbonyl)benzamide;
N-((2S,3R)-3-hydroxy-4-(3-methoxybenzylamino)-1-phenylbutan-2-yl)-3-((R)-4-(4-methylthiazol-2-yl)oxazolidine-3-carbonyl)benzamide;
N-((2S,3R)-4-(3-tert-butylbenzylamino)-3-hydroxy-1-phenylbutan-2-yl)-3-methoxy-5-((R)-2-(4-methylthiazol-2-yl)pyrrolidine-1-carbonyl)benzamide;
N-((2S,3R)-4-(3-chlorobenzylamino)-3-hydroxy-1-phenylbutan-2-yl)-3-((R)-2-(4-methylthiazol-2-yl)pyrrolidine-1-carbonyl)benzamide;
N-((2S,3R)-4-(3-chlorobenzylamino)-3-hydroxy-1-phenylbutan-2-yl)-3-methoxy-5-((R)-2-(4-methylthiazol-2-yl)pyrrolidine-1-carbonyl)benzamide;
N-((2S,3R)-4-(cyclopropylamino)-3-hydroxy-1-phenylbutan-2-yl)-3-((R)-2-(4-methylthiazol-2-yl)pyrrolidine-1-carbonyl)benzamide;
N-((2S,3R)-3-hydroxy-4-((S)-1-(3-methoxyphenyl)ethylamino)-1-phenylbutan-2-yl)-3-methoxy-5-((R)-2-(4-methylthiazol-2-yl)pyrrolidine-1-carbonyl)benzamide;
N-((2S,3R)-3-hydroxy-4-((S)-1-(3-methoxyphenyl)ethylamino)-1-phenylbutan-2-yl)-3-((R)-2-(4-methylthiazol-2-yl)pyrrolidine-1-carbonyl)benzamide;
N-((2S,3R)-3-hydroxy-4-(3-hydroxy-5-isopropylbenzylamino)-1-phenylbutan-2-yl)-3-((R)-2-(4-methylthiazol-2-yl)pyrrolidine-1-carbonyl)benzamide;
N-((2S,3R)-3-hydroxy-4-((5-isopropylpyridin-3-yl)methylamino)-1-phenylbutan-2-yl)-3-((R)-2-(4-methylthiazol-2-yl)pyrrolidine-1-carbonyl)-5-(oxazol-2-yl) benzamide;
N-((2S,3R)-3-hydroxy-1-phenyl-4-(3-(trifluoromethyl) benzylamino)butan-2-yl)-3-((R)-4-(4-methylthiazol-2-yl)oxazolidine-3-carbonyl)benzamide;
N-((2S,3R)-3-hydroxy-4-((5-isopropylpyridin-3-yl)methylamino)-1-phenylbutan-2-yl)-5-((R)-2-(4-methylthiazol-2-yl)pyrrolidine-1-carbonyl)nicotinamide;
N-((2S,3R)-3-hydroxy-1-phenyl-4-(3-(trifluoromethyl) benzylamino)butan-2-yl)-3-((R)-2-(4-methylthiazol-2-yl)pyrrolidine-1-carbonyl)-5-(oxazol-2-yl)benzamide;
3-(dimethylamino)-N-((2S,3R)-3-hydroxy-4-((5-isopropylpyridin-3-yl)methylamino)-1-phenylbutan-2-yl)-5-((R)-2-(4-methylthiazol-2-yl)pyrrolidine-1-carbonyl) benzamide;
3-(dimethylamino)-N-((2S,3R)-3-hydroxy-1-phenyl-4-(3-(trifluoromethyl)benzylamino)butan-2-yl)-5-((R)-2-(4-methylthiazol-2-yl)pyrrolidine-1-carbonyl)benzamide;
N-((2S,3R)-3-hydroxy-1-phenyl-4-(3-(trifluoromethyl) benzylamino)butan-2-yl)-5-((R)-2-(4-methylthiazol-2-yl)pyrrolidine-1-carbonyl)nicotinamide;

N-((2S,3R)-4-(3-tert-butylbenzylamino)-3-hydroxy-1-phenylbutan-2-yl)-5-((R)-2-(4-methylthiazol-2-yl)pyrrolidine-1-carbonyl)nicotinamide;

N-((2S,3R)-3-hydroxy-4-((5-isopropylpyridin-3-yl)methylamino)-1-phenylbutan-2-yl)-3-((R)-2-(4-methylthiazol-2-yl)pyrrolidine-1-carbonyl)-5-(oxazol-5-yl)benzamide;

N-((2S,3R)-3-hydroxy-4-((5-isopropylpyridin-3-yl)methylamino)-1-phenylbutan-2-yl)-3-((R)-2-(4-methyloxazol-2-yl)pyrrolidine-1-carbonyl)benzamide;

3-(dimethylamino)-N-((2S,3R)-4-((5-(2-fluoropropan-2-yl)pyridin-3-yl)methylamino)-3-hydroxy-1-phenylbutan-2-yl)-5-((R)-2-(4-methylthiazol-2-yl)pyrrolidine-1-carbonyl)benzamide;

N-((2S,3R)-4-(3-tert-butylbenzylamino)-3-hydroxy-1-phenylbutan-2-yl)-3-((R)-2-(4-methylthiazol-2-yl)pyrrolidine-1-carbonyl)-5-(oxazol-2-yl)benzamide;

N-((2S,3R)-4-((5-(2-fluoropropan-2-yl)pyridin-3-yl)methylamino)-3-hydroxy-1-phenylbutan-2-yl)-3-((R)-2-(4-methylthiazol-2-yl)pyrrolidine-1-carbonyl)-5-(oxazol-2-yl)benzamide;

N-((2S,3R)-4-((5-(2-fluoropropan-2-yl)pyridin-3-yl)methylamino)-3-hydroxy-1-phenylbutan-2-yl)-3-((R)-2-(4-methyloxazol-2-yl)pyrrolidine-1-carbonyl)benzamide;

N-((2S,3R)-4-((5-(1,1-difluoroethyl)pyridin-3-yl)methylamino)-3-hydroxy-1-phenylbutan-2-yl)-3-(dimethylamino)-5-((R)-2-(4-methylthiazol-2-yl)pyrrolidine-1-carbonyl)benzamide;

N-((2S,3R)-4-(3-tert-butylbenzylamino)-3-hydroxy-1-phenylbutan-2-yl)-3-(dimethylamino)-5-((R)-2-(4-methylthiazol-2-yl)pyrrolidine-1-carbonyl)benzamide;

N-((2S,3R)-4-((5-(2-fluoropropan-2-yl)pyridin-3-yl)methylamino)-3-hydroxy-1-phenylbutan-2-yl)-3-methyl-5-((R)-2-(4-methylthiazol-2-yl)pyrrolidine-1-carbonyl)benzamide;

N-((2S,3R)-3-hydroxy-4-((5-isopropylpyridin-3-yl)methylamino)-1-phenylbutan-2-yl)-3-((R)-2-(4-methylthiazol-2-yl)pyrrolidine-1-carbonyl)-5-(pyrazin-2-yl)benzamide;

N-((2S,3R)-4-((5-(2-fluoropropan-2-yl)pyridin-3-yl)methylamino)-3-hydroxy-1-phenylbutan-2-yl)-5-((R)-2-(4-methylthiazol-2-yl)pyrrolidine-1-carbonyl)nicotinamide;

N-((2S,3R)-4-((5-(2-fluoropropan-2-yl)pyridin-3-yl)methylamino)-3-hydroxy-1-phenylbutan-2-yl)-3-((R)-2-(4-methylthiazol-2-yl)pyrrolidine-1-carbonyl)benzamide;

N-((2S,3R)-3-hydroxy-4-((R)-1-(5-isopropylpyridin-3-yl)ethylamino)-1-phenylbutan-2-yl)-3-((R)-2-(4-methylthiazol-2-yl)pyrrolidine-1-carbonyl)benzamide;

N-((2S,3R)-4-(3-chlorobenzylamino)-3-hydroxy-1-phenylbutan-2-yl)-3-(dimethylamino)-5-((R)-2-(4-methylthiazol-2-yl)pyrrolidine-1-carbonyl)benzamide;

N-((2S,3R)-4-(3,5-dichlorobenzylamino)-3-hydroxy-1-phenylbutan-2-yl)-3-(dimethylamino)-5-((R)-2-(4-methylthiazol-2-yl)pyrrolidine-1-carbonyl)benzamide;

N-((2S,3R)-3-hydroxy-1-phenyl-4-(3-(trifluoromethyl)benzylamino)butan-2-yl)-3-((R)-2-(4-methylthiazol-2-yl)pyrrolidine-1-carbonyl)-5-(pyrazin-2-yl)benzamide;

3-(fluoromethyl)-N-((2S,3R)-4-((5-(2-fluoropropan-2-yl)pyridin-3-yl)methylamino)-3-hydroxy-1-phenylbutan-2-yl)-5-((R)-2-(4-methylthiazol-2-yl)pyrrolidine-1-carbonyl)benzamide;

3-(fluoromethyl)-N-((2S,3R)-3-hydroxy-1-phenyl-4-(5-(trifluoromethyl)pyridin-3-yl)methylamino)butan-2-yl)-5-((R)-2-(4-methylthiazol-2-yl)pyrrolidine-1-carbonyl)benzamide;

N-((2S,3R)-3-hydroxy-4-((5-isopropylpyridin-3-yl)methylamino)-1-phenylbutan-2-yl)-3-methyl-5-((R)-2-(4-methylthiazol-2-yl)pyrrolidine-1-carbonyl)benzamide;

3-(dimethylamino)-N-((2S,3R)-3-hydroxy-4-((S)-1-(3-methoxyphenyl)ethylamino)-1-phenylbutan-2-yl)-5-((R)-2-(4-methylthiazol-2-yl)pyrrolidine-1-carbonyl)benzamide;

N-((2S,3R)-4-(3,5-dichlorobenzylamino)-3-hydroxy-1-phenylbutan-2-yl)-3-methoxy-5-((R)-2-(4-methylthiazol-2-yl)pyrrolidine-1-carbonyl)benzamide;

N-((2S,3R)-3-hydroxy-1-phenyl-4-(3-(trifluoromethyl)benzylamino)butan-2-yl)-3-methyl-5-((R)-2-(4-methyloxazol-2-yl)pyrrolidine-1-carbonyl)benzamide;

N-((2S,3R)-3-hydroxy-4-((5-isopropylpyridin-3-yl)methylamino)-1-phenylbutan-2-yl)-3-methyl-5-((R)-2-(4-methyloxazol-2-yl)pyrrolidine-1-carbonyl)benzamide;

3-(difluoromethyl)-N-((2S,3R)-3-hydroxy-1-phenyl-4-(3-(trifluoromethyl)benzylamino)butan-2-yl)-5-((R)-2-(4-methylthiazol-2-yl)pyrrolidine-1-carbonyl)benzamide;

3-(difluoromethyl)-N-((2S,3R)-4-((5-(2-fluoropropan-2-yl)pyridin-3-yl)methylamino)-3-hydroxy-1-phenylbutan-2-yl)-5-((R)-2-(4-methylthiazol-2-yl)pyrrolidine-1-carbonyl)benzamide;

N-((2S,3R)-4-((5-(2-fluoropropan-2-yl)pyridin-3-yl)methylamino)-3-hydroxy-1-phenylbutan-2-yl)-3-methyl-5-((R)-2-(4-methyloxazol-2-yl)pyrrolidine-1-carbonyl)benzamide;

N-((2S,3R)-4-(3,5-dichlorobenzylamino)-3-hydroxy-1-phenylbutan-2-yl)-5-((R)-2-(4-methylthiazol-2-yl)pyrrolidine-1-carbonyl)nicotinamide;

N-((2S,3R)-4-(3-cyano-5-isopropylbenzylamino)-3-hydroxy-1-phenylbutan-2-yl)-5-((R)-2-(4-methylthiazol-2-yl)pyrrolidine-1-carbonyl)nicotinamide;

3-(difluoromethyl)-N-((2S,3R)-3-hydroxy-4-((5-isopropylpyridin-3-yl)methylamino)-1-phenylbutan-2-yl)-5-((R)-2-(4-methylthiazol-2-yl)pyrrolidine-1-carbonyl)benzamide;

3-(difluoromethyl)-N-((2S,3R)-3-hydroxy-4-((S)-1-(3-methoxyphenyl)ethylamino)-1-phenylbutan-2-yl)-5-((R)-2-(4-methylthiazol-2-yl)pyrrolidine-1-carbonyl)benzamide;

N-((2S,3R)-3-hydroxy-1-phenyl-4-(3-(trifluoromethyl)benzylamino)butan-2-yl)-2-((R)-2-(4-methylthiazol-2-yl)pyrrolidine-1-carbonyl)isonicotinamide;

N-((2S,3R)-3-hydroxy-4-((3-methylisoxazol-5-yl)methylamino)-1-phenylbutan-2-yl)-3-((R)-2-(4-methylthiazol-2-yl)pyrrolidine-1-carbonyl)benzamide;

N-((2S,3R)-3-hydroxy-4-((5-methylisoxazol-3-yl)methylamino)-1-phenylbutan-2-yl)-3-((R)-2-(4-methylthiazol-2-yl)pyrrolidine-1-carbonyl)benzamide;

N-((2S,3R)-3-hydroxy-4-((4-methylthiazol-2-yl)methylamino)-1-phenylbutan-2-yl)-3-((R)-2-(4-methylthiazol-2-yl)pyrrolidine-1-carbonyl)benzamide;

N-((2S,3R)-3-hydroxy-1-phenyl-4-(3-(trifluoromethyl)benzylamino)butan-2-yl)-6-methyl-4-((R)-2-(4-methylthiazol-2-yl)pyrrolidine-1-carbonyl)picolinamide;

N-((2S,3R)-4-(3-(dimethylamino)benzylamino)-3-hydroxy-1-phenylbutan-2-yl)-3-((R)-2-(4-methylthiazol-2-yl)pyrrolidine-1-carbonyl)benzamide;

N-((2S,3R)-4-(3-tert-butylbenzylamino)-3-hydroxy-1-phenylbutan-2-yl)-3-((R)-2-(4-methyloxazol-2-yl)pyrrolidine-1-carbonyl)benzamide;

N-((2S,3R)-3-hydroxy-4-((5-isopropylpyridin-3-yl)methylamino)-1-phenylbutan-2-yl)-5-((R)-2-(4-methyloxazol-2-yl)pyrrolidine-1-carbonyl)nicotinamide;

N-((2S,3R)-3-hydroxy-1-phenyl-4-(3-(trifluoromethyl)benzylamino)butan-2-yl)-5-((R)-2-(4-methyloxazol-2-yl)pyrrolidine-1-carbonyl)nicotinamide;

N-((2S,3R)-4-((5-(2-fluoropropan-2-yl)pyridin-3-yl)methylamino)-3-hydroxy-1-phenylbutan-2-yl)-5-((R)-2-(4-methyloxazol-2-yl)pyrrolidine-1-carbonyl)nicotinamide;

N-((2S,3R)-3-hydroxy-4-((5-isopropylpyridin-3-yl)methylamino)-1-phenylbutan-2-yl)-3-((R)-2-(4-methylthiazol-2-yl)pyrrolidine-1-carbonyl)-5-(1H-pyrrol-1-yl)benzamide;

2-(furan-2-yl)-N-((2S,3R)-3-hydroxy-1-phenyl-4-(3-(trifluoromethyl)benzylamino)butan-2-yl)-6-((R)-2-(4-methylthiazol-2-yl)pyrrolidine-1-carbonyl)isonicotinamide;

N-((2S,3R)-4-(3-tert-butylbenzylamino)-3-hydroxy-1-phenylbutan-2-yl)-5-((R)-2-(4-methyloxazol-2-yl)pyrrolidine-1-carbonyl)nicotinamide;

3-(fluoromethyl)-N-((2S,3R)-3-hydroxy-4-((5-isopropylpyridin-3-yl)methylamino)-1-phenylbutan-2-yl)-5-((R)-2-(4-methyloxazol-2-yl)pyrrolidine-1-carbonyl)benzamide;

3-(fluoromethyl)-N-((2S,3R)-4-((5-(2-fluoropropan-2-yl)pyridin-3-yl)methylamino)-3-hydroxy-1-phenylbutan-2-yl)-5-((R)-2-(4-methyloxazol-2-yl)pyrrolidine-1-carbonyl)benzamide;

N-((2S,3R)-3-hydroxy-1-phenyl-4-(3-(trifluoromethyl)benzylamino)butan-2-yl)-2-methyl-6-((R)-2-(4-methylthiazol-2-yl)pyrrolidine-1-carbonyl)isonicotinamide;

N-((2S,3R)-3-hydroxy-1-phenyl-4-(3-(trifluoromethyl)benzylamino)butan-2-yl)-3-((R)-2-(4-methylthiazol-2-yl)pyrrolidine-1-carbonyl)-5-(1H-pyrrol-1-yl)benzamide;

6-(dimethylamino)-N-((2S,3R)-3-hydroxy-1-phenyl-4-(3-(trifluoromethyl)benzylamino)butan-2-yl)-4-((R)-2-(4-methylthiazol-2-yl)pyrrolidine-1-carbonyl)picolinamide;

3-(fluoromethyl)-N-((2S,3R)-3-hydroxy-1-phenyl-4-(3-(trifluoromethyl)benzylamino)butan-2-yl)-5-((R)-2-(4-methyloxazol-2-yl)pyrrolidine-1-carbonyl)benzamide;

N-((2S,3R)-3-hydroxy-4-((5-isopropylpyridin-3-yl)methylamino)-1-phenylbutan-2-yl)-3-methoxy-5-((R)-2-(4-methylthiazol-2-yl)pyrrolidine-1-carbonyl)benzamide;

N-((2S,3R)-3-hydroxy-1-phenyl-4-(3-(trifluoromethyl)benzylamino)butan-2-yl)-2-methyl-6-((R)-2-(4-methyloxazol-2-yl)pyrrolidine-1-carbonyl)isonicotinamide;

N-((2S,3R)-3-hydroxy-4-(3-(methylamino)-5-(trifluoromethyl)benzylamino)-1-phenylbutan-2-yl)-3-((R)-2-(4-methylthiazol-2-yl)pyrrolidine-1-carbonyl)benzamide;

N-((2S,3R)-3-hydroxy-4-((5-isopropylpyridin-3-yl)methylamino)-1-phenylbutan-2-yl)-3-((R)-2-(4-methyloxazol-2-yl)pyrrolidine-1-carbonyl)-5-(oxazol-2-yl)benzamide;

N-((2S,3R)-3-hydroxy-1-phenyl-4-(3-(trifluoromethyl)benzylamino)butan-2-yl)-3-((R)-2-(4-methyloxazol-2-yl)pyrrolidine-1-carbonyl)-5-(oxazol-2-yl)benzamide;

6'-fluoro-N-((2S,3R)-3-hydroxy-1-phenyl-4-(3-(trifluoromethyl)benzylamino)butan-2-yl)-6-((R)-2-(4-methylthiazol-2-yl)pyrrolidine-1-carbonyl)-2,3'-bipyridine-4-carboxamide;

N-((2S,3R)-3-hydroxy-4-((5-isopropylpyridin-3-yl)methylamino)-1-phenylbutan-2-yl)-3-methoxy-5-((R)-2-(4-methyloxazol-2-yl)pyrrolidine-1-carbonyl)benzamide;

N-((2S,3R)-4-((5-(2-fluoropropan-2-yl)pyridin-3-yl)methylamino)-3-hydroxy-1-phenylbutan-2-yl)-3-((R)-2-(4-methyloxazol-2-yl)pyrrolidine-1-carbonyl)-5-(oxazol-2-yl)benzamide;

2-(3-chlorophenyl)-N-((2S,3R)-3-hydroxy-1-phenyl-4-(3-(trifluoromethyl)benzylamino)butan-2-yl)-6-((R)-2-(4-methylthiazol-2-yl)pyrrolidine-1-carbonyl)isonicotinamide;

3-(dimethylamino)-N-((2S,3R)-3-hydroxy-4-((5-isopropylpyridin-3-yl)methylamino)-1-phenylbutan-2-yl)-5-((R)-2-(4-methyloxazol-2-yl)pyrrolidine-1-carbonyl)benzamide;

N-((2S,3R)-3-hydroxy-1-phenyl-4-(3-(trifluoromethyl)benzylamino)butan-2-yl)-3-methoxy-5-((R)-2-(4-methyloxazol-2-yl)pyrrolidine-1-carbonyl)benzamide;

N-((2S,3R)-3-hydroxy-1-phenyl-4-(3-(trifluoromethyl)benzylamino)butan-2-yl)-2-((R)-2-(4-methyloxazol-2-yl)pyrrolidine-1-carbonyl)isonicotinamide;

N-((2S,3R)-4-(3-tert-butylbenzylamino)-3-hydroxy-1-phenylbutan-2-yl)-3-(fluoromethyl)-5-((R)-2-(4-methyloxazol-2-yl)pyrrolidine-1-carbonyl)benzamide;

N-((2S,3R)-3-hydroxy-1-phenyl-4-(3-(trifluoromethyl)benzylamino)butan-2-yl)-6-methyl-4-((R)-2-(4-methyloxazol-2-yl)pyrrolidine-1-carbonyl)picolinamide;

N-((2S,3R)-4-(benzofuran-2-ylmethylamino)-3-hydroxy-1-phenylbutan-2-yl)-3-methyl-5-((R)-2-(4-methylthiazol-2-yl)pyrrolidine-1-carbonyl)benzamide;

2-(dimethylamino)-N-((2S,3R)-3-hydroxy-1-phenyl-4-(3-(trifluoromethyl)benzylamino)butan-2-yl)-6-((R)-2-(4-methylthiazol-2-yl)pyrrolidine-1-carbonyl)isonicotinamide;

N-((2S,3R)-3-hydroxy-4-((3-isopropylisoxazol-5-yl)methylamino)-1-phenylbutan-2-yl)-3-((R)-2-(4-methylthiazol-2-yl)pyrrolidine-1-carbonyl)benzamide;

2-(dimethylamino)-N-((2S,3R)-3-hydroxy-1-phenyl-4-(3-(trifluoromethyl)benzylamino)butan-2-yl)-6-((R)-2-(4-methylthiazol-2-yl)pyrrolidine-1-carbonyl)pyrimidine-4-carboxamide;

N-((2S,3R)-4-(3-(1,1-difluoroethyl)benzylamino)-3-hydroxy-1-phenylbutan-2-yl)-3-((R)-2-(4-methyloxazol-2-yl)pyrrolidine-1-carbonyl)benzamide;

N-((2S,3R)-4-((5-(1,1-difluoroethyl)pyridin-3-yl)methylamino)-3-hydroxy-1-phenylbutan-2-yl)-3-((R)-2-(4-methyloxazol-2-yl)pyrrolidine-1-carbonyl)benzamide;

N-((2S,3R)-3-hydroxy-1-phenyl-4-((5-(trifluoromethyl)pyridin-3-yl)methylamino)butan-2-yl)-3-((R)-2-(4-methyloxazol-2-yl)pyrrolidine-1-carbonyl)benzamide;

N-((2S,3R)-4-(3-(1,1-difluoroethyl)benzylamino)-3-hydroxy-1-phenylbutan-2-yl)-3-methyl-5-((R)-2-(4-methyloxazol-2-yl)pyrrolidine-1-carbonyl)benzamide;

N-((2S,3R)-3-hydroxy-1-phenyl-4-(3-(prop-1-en-2-yl)benzylamino)butan-2-yl)-3-((R)-2-(4-methyloxazol-2-yl)pyrrolidine-1-carbonyl)benzamide;

N-((2S,3R)-3-hydroxy-4-((5-isopropylisoxazol-3-yl)methylamino)-1-phenylbutan-2-yl)-3-((R)-2-(4-methylthiazol-2-yl)pyrrolidine-1-carbonyl)benzamide;

N-((2S,3R)-4-(cyclohexylamino)-3-hydroxy-1-phenylbutan-2-yl)-3-((R)-2-(4-methyloxazol-2-yl)pyrrolidine-1-carbonyl)benzamide;

N-((2S,3R)-3-hydroxy-1-phenyl-4-(3-(prop-1-en-2-yl)benzylamino)butan-2-yl)-3-methyl-5-((R)-2-(4-methyloxazol-2-yl)pyrrolidine-1-carbonyl)benzamide;

N-((2S,3R)-4-((1-ethyl-1H-pyrazol-4-yl)methylamino)-3-hydroxy-1-phenylbutan-2-yl)-3-((R)-2-(4-methyloxazol-2-yl)pyrrolidine-1-carbonyl)benzamide;

N-((2S,3R)-4-((1-ethyl-1H-pyrazol-4-yl)methylamino)-3-hydroxy-1-phenylbutan-2-yl)-3-methyl-5-((R)-2-(4-methyloxazol-2-yl)pyrrolidine-1-carbonyl)benzamide;

N-((2S,3R)-4-((5-tert-butylpyridin-3-yl)methylamino)-3-hydroxy-1-phenylbutan-2-yl)-3-((R)-2-(4-methyloxazol-2-yl)pyrrolidine-1-carbonyl)benzamide;

N-((2S,3R)-4-((5-tert-butylpyridin-3-yl)methylamino)-3-hydroxy-1-phenylbutan-2-yl)-3-methyl-5-((R)-2-(4-methyloxazol-2-yl)pyrrolidine-1-carbonyl)benzamide;

N-((2S,3R)-4-((5-(1,1-difluoroethyl)pyridin-3-yl)methylamino)-3-hydroxy-1-phenylbutan-2-yl)-3-methyl-5-((R)-2-(4-methyloxazol-2-yl)pyrrolidine-1-carbonyl)benzamide;

N-((2S,3R)-3-hydroxy-1-phenyl-4-(3-(trifluoromethoxy)benzylamino)butan-2-yl)-3-((R)-2-(4-methyloxazol-2-yl)pyrrolidine-1-carbonyl)benzamide;

N-((2S,3R)-3-hydroxy-1-phenyl-4-(3-(trifluoromethoxy)benzylamino)butan-2-yl)-3-methyl-5-((R)-2-(4-methyloxazol-2-yl)pyrrolidine-1-carbonyl)benzamide;

N-((2S,3R)-4-((5-(1,1-difluoroethyl)pyridin-3-yl)methylamino)-3-hydroxy-1-phenylbutan-2-yl)-3-methyl-5-((R)-2-(4-methylthiazol-2-yl)pyrrolidine-1-carbonyl)benzamide;

or a pharmaceutically acceptable salt or solvate thereof.

42. The compound of claim 1, which is N-((2S,3R)-3-hydroxy-1-phenyl-4-(3-(trifluoromethyl)benzylamino)butan-2-yl)-3-((R)-2-(4-methylthiazol-2-yl)pyrrolidine-1-carbonyl)-5-(oxazol-2-yl)benzamide or a pharmaceutically acceptable salt or solvate thereof.

43. The compound of claim 1, which is N-((2S,3R)-3-hydroxy-1-phenyl-4-(3-(trifluoromethyl)benzylamino)butan-2-yl)-3-((R)-2-(4-methylthiazol-2-yl)pyrrolidine-1-carbonyl)-5-(pyrazin-2-yl)benzamide or a pharmaceutically acceptable salt or solvate thereof.

44. The compound of claim 1, wherein the compound has an apparent memapsin 2 Ki of less than about 100 nM as measured by inhibition of memapsin 2 catalytic activity toward the fluorogenic substrate FS-2 (MCA-SEVNLDAEFK-DNP; SEQ ID NO.: 2); or a pharmaceutically acceptable salt or solvate thereof.

45. The compound of claim 1, wherein the compound (a) has a memapsin 2 Ki of less than about 100 nM; (b) is capable of inhibiting cellular Aβ production with an $IC_{50}$ of less than about 100 nM; and (c) is capable of selectively reducing memapsin 2 catalytic activity relative to memapsin 1 or cathepsin D catalytic activity by greater than about 10-fold; or a pharmaceutically acceptable salt or solvate thereof.

46. A formulation comprising a compound of claim 1 or a pharmaceutically acceptable salt or solvate thereof, and a pharmaceutically acceptable carrier.

47. A method of reducing memapsin 2 catalytic activity, the method comprising contacting, in vitro, a memapsin 2 protein with an effective amount of a compound of claim 1 or a pharmaceutically acceptable salt or solvate thereof.

48. A method of selectively reducing memapsin 2 catalytic activity relative to memapsin 1 catalytic activity, the method comprising contacting a memapsin 2 protein with an effective amount of a compound of claim 1 in the presence of memapsin 1 beta-secretase.

49. A method of selectively reducing memapsin 2 catalytic activity relative to cathepsin D catalytic activity, the method comprising contacting a memapsin 2 protein with a therapeutically effective amount of a compound of claim 1 in the presence of cathepsin D.

50. A method for treating a condition characterized by memapsin 2 catalytic activity in a patient comprising administering to the patient a therapeutically effective amount of a compound of claim 1 or a pharmaceutically acceptable salt or solvate thereof.

51. The method of claim 49, wherein the condition is Alzheimer's disease.

52. A kit for the treatment of Alzheimer's disease in an individual, comprising:
(a) a compound of claim 1; and
(b) packaging.

* * * * *